US012788935B2

(12) United States Patent
Malchano et al.

(10) Patent No.: US 12,788,935 B2
(45) Date of Patent: Nov. 10, 2026

(54) METHODS OF ENHANCING NEUROSTIMULATION DURING ACTIVITIES

(71) Applicant: Cognito Therapeutics, Inc., Cambridge, MA (US)

(72) Inventors: Zachary Malchano, Cambridge, MA (US); Brent Vaughan, Cambridge, MA (US); Martin Williams, Cambridge, MA (US); Mihály Hajós, Cambridge, MA (US); Edward Boyden, Cambridge, MA (US); Aylin Cimenser, Cambridge, MA (US); Xiao Da, Cambridge, MA (US)

(73) Assignee: Cognito Therapeutics, Inc., Cambridge, MA (US)

( * ) Notice: Subject to any disclaimer, the term of this patent is extended or adjusted under 35 U.S.C. 154(b) by 984 days.

(21) Appl. No.: 17/953,260

(22) Filed: Sep. 26, 2022

(65) Prior Publication Data

US 2023/0111776 A1 Apr. 13, 2023

Related U.S. Application Data

(63) Continuation of application No. PCT/US2022/044760, filed on Sep. 26, 2022.

(Continued)

(51) Int. Cl.
*A61M 21/00* (2006.01)

(52) U.S. Cl.
CPC ..... *A61M 21/00* (2013.01); *A61M 2021/0022* (2013.01); *A61M 2021/0027* (2013.01);

(Continued)

(58) Field of Classification Search
CPC ................ A61M 21/00–02; A61B 5/165–168
See application file for complete search history.

(56) References Cited

U.S. PATENT DOCUMENTS

| | | | |
|---|---|---|---|
| 4,315,502 | A | 2/1982 | Gorges |
| 4,449,047 | A | 5/1984 | Monroe |

(Continued)

FOREIGN PATENT DOCUMENTS

| | | | |
|---|---|---|---|
| CA | 3156908 | A1 | 7/2016 |
| CA | 2979687 | A1 | 9/2016 |

(Continued)

OTHER PUBLICATIONS

Agosta F, et al. White matter damage in Alzheimer disease and its relationship to gray matter atrophy. Radiology. Mar. 2011;258(3):853-63. Epub Dec. 21, 2010.

(Continued)

*Primary Examiner* — Thaddeus B Cox
(74) *Attorney, Agent, or Firm* — Wilson Sonsini Goodrich & Rosati

(57) ABSTRACT

Systems and methods of the present disclosure are directed to neural stimulation via non-invasive sensory stimulation. Non-invasive sensory stimulations can comprise audio stimulation, visual stimulation, mechanical stimulation, or a combination thereof. The combination and/or sequence of one or more of audio, visual, and mechanical brain stimulations can adjust, control or otherwise manage the frequency of the neural oscillations to provide beneficial effects to one or more cognitive states or cognitive functions of the brain, while mitigating or preventing adverse consequences on a cognitive state or cognitive function that stems from, for example, sleep deprivation, stress, hormonal imbalance, or other physical, physiological, or psychological conditions. In doing so, the present systems and methods can improve the cognitive potential of a person.

20 Claims, 72 Drawing Sheets

Related U.S. Application Data

(60) Provisional application No. 63/248,880, filed on Sep. 27, 2021.

(52) U.S. Cl.
CPC ............... *A61M 2021/0044* (2013.01); *A61M 2021/0077* (2013.01)

(56) References Cited

U.S. PATENT DOCUMENTS

| | | | |
|---|---|---|---|
| 4,456,910 | A | 6/1984 | DiMassimo et al. |
| 4,674,852 | A | 6/1987 | Tanaka |
| 5,151,687 | A | 9/1992 | Younger |
| 5,534,953 | A | 7/1996 | Schmielau |
| 5,659,287 | A | 8/1997 | Donati et al. |
| 5,923,398 | A | 7/1999 | Goldman |
| 5,934,967 | A | 8/1999 | Brown et al. |
| 6,066,163 | A | 5/2000 | John |
| 6,071,229 | A | 6/2000 | Rubins |
| 6,113,537 | A | 9/2000 | Castano |
| 6,167,298 | A | 12/2000 | Levin |
| 6,206,537 | B1 | 3/2001 | Hauck |
| 6,234,953 | B1 | 5/2001 | Thomas et al. |
| 6,443,977 | B1 | 9/2002 | Jaillet |
| 6,463,328 | B1 | 10/2002 | John |
| 6,539,263 | B1 | 3/2003 | Schiff et al. |
| 6,733,490 | B1 | 5/2004 | Falsini et al. |
| 7,010,356 | B2 | 3/2006 | Jog et al. |
| 7,361,074 | B1 | 4/2008 | Periman et al. |
| 7,446,785 | B1 | 11/2008 | Hewlett et al. |
| 7,569,545 | B2 | 8/2009 | Li et al. |
| 7,645,226 | B2 | 1/2010 | Shealy et al. |
| 7,715,910 | B2 | 5/2010 | Hargrove et al. |
| 7,748,846 | B2 | 7/2010 | Todd |
| 7,769,439 | B2 | 8/2010 | Vesely et al. |
| 8,070,669 | B2 | 12/2011 | Brunelle et al. |
| 8,083,392 | B2 | 12/2011 | Chien |
| 8,121,694 | B2 | 2/2012 | Molnar et al. |
| 8,239,030 | B1 | 8/2012 | Hagedorn et al. |
| 8,267,851 | B1 | 9/2012 | Kroll |
| 8,280,502 | B2 | 10/2012 | Hargrove et al. |
| 8,328,420 | B2 | 12/2012 | Abreu |
| 8,380,314 | B2 | 2/2013 | Panken et al. |
| 8,396,545 | B2 | 3/2013 | Berridge et al. |
| 8,423,144 | B2 | 4/2013 | Tass et al. |
| 8,543,219 | B2 | 9/2013 | Tass |
| 8,577,470 | B2 | 11/2013 | Assaf et al. |
| 8,579,793 | B1 | 11/2013 | Honeycutt et al. |
| 8,591,392 | B2 | 11/2013 | Bentwich et al. |
| 8,636,640 | B2 | 1/2014 | Chang |
| 8,700,167 | B2 | 4/2014 | Sabel |
| 8,845,704 | B2 | 9/2014 | Dunning et al. |
| 8,892,207 | B2 | 11/2014 | Nelson et al. |
| 8,894,696 | B2 | 11/2014 | Hurst |
| 8,914,119 | B2 | 12/2014 | Wu et al. |
| 8,932,218 | B1 | 1/2015 | Thompson |
| 8,942,809 | B2 | 1/2015 | Assaf et al. |
| 9,119,583 | B2 | 9/2015 | Tass |
| 9,272,118 | B1 | 3/2016 | Acton |
| 9,302,069 | B2 | 4/2016 | Tass et al. |
| 9,629,976 | B1 | 4/2017 | Acton |
| 10,159,816 | B2 | 12/2018 | Tsai et al. |
| 10,265,487 | B2 | 4/2019 | Booth Wise et al. |
| 10,265,497 | B2 | 4/2019 | Tsai et al. |
| 10,279,192 | B2 | 5/2019 | Malchano et al. |
| 10,293,177 | B2 | 5/2019 | Malchano et al. |
| 10,307,611 | B2 | 6/2019 | Malchano et al. |
| 10,518,063 | B1 | 12/2019 | Noftsker |
| 10,682,490 | B2 | 6/2020 | Tsai et al. |
| 10,702,705 | B2 | 7/2020 | Malchano et al. |
| 10,745,479 | B2 | 8/2020 | Jaminet et al. |
| 10,843,006 | B2 | 11/2020 | Malchano et al. |
| 11,141,604 | B2 | 10/2021 | Malchano et al. |
| 11,241,586 | B2 | 2/2022 | Tsai et al. |
| 12,296,106 | B2 | 5/2025 | Tsai et al. |
| 12,311,194 | B2 | 5/2025 | Tsai et al. |
| 12,318,549 | B2 | 6/2025 | Tsai et al. |
| 12,383,759 | B2 | 8/2025 | Malchano et al. |
| 12,434,072 | B2 | 10/2025 | Malchano et al. |
| 12,515,069 | B2 | 1/2026 | Adaikkan et al. |
| 2001/0027278 | A1 | 10/2001 | Kaufman et al. |
| 2001/0039012 | A1 | 11/2001 | Lapidus |
| 2004/0097841 | A1 | 5/2004 | Saveliev et al. |
| 2004/0158119 | A1 | 8/2004 | Osorio et al. |
| 2005/0070977 | A1 | 3/2005 | Molina |
| 2005/0234286 | A1 | 10/2005 | Riehl et al. |
| 2006/0173510 | A1 | 8/2006 | Besio et al. |
| 2007/0038142 | A1 | 2/2007 | Todd et al. |
| 2007/0156182 | A1 | 7/2007 | Castel et al. |
| 2007/0179557 | A1 | 8/2007 | Maschino et al. |
| 2007/0191727 | A1 | 8/2007 | Fadem |
| 2007/0218994 | A1 | 9/2007 | Goto et al. |
| 2007/0225773 | A1 | 9/2007 | Shen et al. |
| 2007/0253561 | A1 | 11/2007 | Williams et al. |
| 2008/0055541 | A1 | 3/2008 | Coulter et al. |
| 2008/0181882 | A1 | 7/2008 | Hahn |
| 2008/0227139 | A1 | 9/2008 | Deisseroth et al. |
| 2008/0255949 | A1 | 10/2008 | Genco et al. |
| 2008/0269629 | A1 | 10/2008 | Reiner |
| 2009/0005837 | A1 | 1/2009 | Olmstead |
| 2009/0018419 | A1 | 1/2009 | Torch |
| 2009/0023977 | A1 | 1/2009 | Sperling et al. |
| 2009/0030476 | A1 | 1/2009 | Hargrove |
| 2009/0093403 | A1 | 4/2009 | Zhang et al. |
| 2009/0153800 | A1 | 6/2009 | Bassi et al. |
| 2009/0237563 | A1 | 9/2009 | Doser |
| 2009/0270776 | A1 | 10/2009 | Chang |
| 2010/0013402 | A1 | 1/2010 | Chaffai et al. |
| 2010/0109541 | A1 | 5/2010 | Roberts et al. |
| 2010/0174344 | A1 | 7/2010 | Dadd et al. |
| 2010/0190129 | A1 | 7/2010 | Paz |
| 2010/0217358 | A1 | 8/2010 | Hebert et al. |
| 2010/0241021 | A1 | 9/2010 | Morikawa et al. |
| 2010/0274329 | A1 | 10/2010 | Bradley et al. |
| 2011/0066586 | A1 | 3/2011 | Sabel et al. |
| 2011/0105998 | A1 | 5/2011 | Zhang et al. |
| 2011/0122396 | A1 | 5/2011 | Ivaldi et al. |
| 2011/0152967 | A1 | 6/2011 | Simon et al. |
| 2011/0280932 | A1 | 11/2011 | Garcia et al. |
| 2012/0016174 | A1 | 1/2012 | De Taboada et al. |
| 2012/0065709 | A1 | 3/2012 | Dunning et al. |
| 2012/0150545 | A1 | 6/2012 | Simon |
| 2012/0251989 | A1 | 10/2012 | Wetmore et al. |
| 2012/0289869 | A1 | 11/2012 | Tyler |
| 2013/0021138 | A1 | 1/2013 | Ezzat et al. |
| 2013/0066392 | A1 | 3/2013 | Simon et al. |
| 2013/0066395 | A1 | 3/2013 | Simon et al. |
| 2013/0083173 | A1 | 4/2013 | Geisner et al. |
| 2013/0084299 | A1 | 4/2013 | Maze et al. |
| 2013/0211238 | A1 | 8/2013 | Decharms |
| 2013/0216055 | A1 | 8/2013 | Wanca |
| 2013/0253338 | A1 | 9/2013 | Kang et al. |
| 2013/0267759 | A1 | 10/2013 | Jin |
| 2013/0317569 | A1 | 11/2013 | Deisseroth et al. |
| 2013/0328490 | A1 | 12/2013 | Chen |
| 2013/0338738 | A1 | 12/2013 | Garcia Molina et al. |
| 2014/0081347 | A1 | 3/2014 | Nelson et al. |
| 2014/0135680 | A1 | 5/2014 | Peyman |
| 2014/0194957 | A1 | 7/2014 | Rubinfeld et al. |
| 2014/0200432 | A1 | 7/2014 | Banerji et al. |
| 2014/0257438 | A1 | 9/2014 | Simon et al. |
| 2014/0303025 | A1 | 10/2014 | Van Keuren-Jensen et al. |
| 2014/0303424 | A1 | 10/2014 | Glass |
| 2014/0316192 | A1 | 10/2014 | De Zambotti et al. |
| 2014/0324138 | A1 | 10/2014 | Wentz et al. |
| 2014/0330335 | A1 | 11/2014 | Errico et al. |
| 2014/0336514 | A1 | 11/2014 | Peyman |
| 2014/0347265 | A1 | 11/2014 | Aimone et al. |
| 2015/0002025 | A1 | 1/2015 | Maricic et al. |
| 2015/0088212 | A1 | 3/2015 | De Ridder |
| 2015/0157604 | A1 | 6/2015 | Morozova et al. |
| 2015/0196762 | A1 | 7/2015 | Amurthur et al. |
| 2015/0235597 | A1 | 8/2015 | Meng et al. |
| 2015/0305667 | A1 | 10/2015 | Durand |

(56) References Cited

U.S. PATENT DOCUMENTS

| | | | | |
|---|---|---|---|---|
| 2015/0337030 | A1 | 11/2015 | Abeliovich | |
| 2015/0342495 | A1 | 12/2015 | Davis et al. | |
| 2016/0067087 | A1 | 3/2016 | Tedford et al. | |
| 2016/0091758 | A1 | 3/2016 | Yoneyama | |
| 2016/0220821 | A1 | 8/2016 | O'Connell et al. | |
| 2016/0235980 | A1 | 8/2016 | Berman et al. | |
| 2016/0242995 | A1 | 8/2016 | Karkkainen | |
| 2017/0072162 | A1 | 3/2017 | Kim et al. | |
| 2017/0082255 | A1 | 3/2017 | Bentley et al. | |
| 2017/0143934 | A1 | 5/2017 | Tsai et al. | |
| 2017/0143966 | A1 | 5/2017 | Reymers et al. | |
| 2017/0151436 | A1 | 6/2017 | Flaherty et al. | |
| 2017/0182285 | A1 | 6/2017 | Tyler et al. | |
| 2017/0266443 | A1 | 9/2017 | Rajguru et al. | |
| 2018/0126062 | A1 | 5/2018 | Solem et al. | |
| 2018/0133507 | A1* | 5/2018 | Malchano | A61B 5/377 |
| 2018/0236202 | A1 | 8/2018 | Weiss et al. | |
| 2018/0236262 | A1 | 8/2018 | Morries et al. | |
| 2018/0333590 | A1 | 11/2018 | Millard et al. | |
| 2019/0030190 | A1 | 1/2019 | Peyman | |
| 2019/0076670 | A1 | 3/2019 | Vyshedskiy | |
| 2019/0126056 | A1 | 5/2019 | Vlădila Bogdan | |
| 2019/0151192 | A1* | 5/2019 | Yamashita | A61N 7/00 |
| 2019/0388020 | A1 | 12/2019 | Stauch et al. | |
| 2020/0038658 | A1 | 2/2020 | Tyler et al. | |
| 2020/0069808 | A1 | 3/2020 | Luehr et al. | |
| 2020/0139112 | A1* | 5/2020 | Aharonovitch | A61B 5/389 |
| 2020/0164220 | A1 | 5/2020 | Broeng et al. | |
| 2020/0171267 | A1 | 6/2020 | Millard et al. | |
| 2020/0246579 | A1 | 8/2020 | Cohen | |
| 2020/0269065 | A1 | 8/2020 | Broeng et al. | |
| 2020/0360715 | A1* | 11/2020 | Lim | A61N 5/0622 |
| 2021/0030998 | A1 | 2/2021 | Wong | |
| 2021/0121713 | A1 | 4/2021 | Malchano et al. | |
| 2021/0339043 | A1 | 11/2021 | Malchano et al. | |
| 2022/0008746 | A1 | 1/2022 | Malchano et al. | |
| 2022/0134047 | A1* | 5/2022 | Carstensen | A61M 21/02<br>600/27 |
| 2023/0022546 | A1 | 1/2023 | Malchano et al. | |
| 2023/0095907 | A1* | 3/2023 | Venturino | A61K 31/135<br>514/647 |
| 2023/0166072 | A1 | 6/2023 | Malchano et al. | |
| 2023/0173295 | A1 | 6/2023 | Kim et al. | |
| 2024/0269481 | A1 | 8/2024 | Malchano et al. | |
| 2024/0293680 | A1 | 9/2024 | Malchano et al. | |
| 2024/0325780 | A1 | 10/2024 | Malchano et al. | |
| 2025/0001203 | A1 | 1/2025 | Malchano et al. | |
| 2025/0288771 | A1 | 9/2025 | Tsai et al. | |
| 2025/0360285 | A1 | 11/2025 | Malchano et al. | |
| 2025/0360334 | A1 | 11/2025 | Malchano et al. | |

FOREIGN PATENT DOCUMENTS

| | | | |
|---|---|---|---|
| CN | 102791332 | A | 11/2012 |
| CN | 103298480 | A | 9/2013 |
| CN | 103492564 | A | 1/2014 |
| CN | 104039353 | A | 9/2014 |
| CN | 104783788 | A | 7/2015 |
| CN | 103932701 | B | 9/2015 |
| CN | 105278387 | A | 1/2016 |
| CN | 106103711 | A | 11/2016 |
| CN | 106725462 | A | 5/2017 |
| CN | 107002076 | A | 8/2017 |
| CN | 108697889 | A | 10/2018 |
| CN | 108725462 | A | 11/2018 |
| EP | 0911398 | A3 | 2/2003 |
| EP | 1642609 | A1 | 4/2006 |
| EP | 2075035 | A1 | 7/2009 |
| EP | 2489402 | A2 | 8/2012 |
| EP | 4188226 | A4 | 10/2024 |
| IT | RM20090027 | A1 | 7/2010 |
| JP | H08150210 | A | 6/1996 |
| JP | 2003038603 | A * | 2/2003 |
| JP | 2006525039 | A | 11/2006 |
| JP | 2008520280 | A | 6/2008 |
| JP | 2011514194 | A | 5/2011 |
| JP | 2014071825 | A | 4/2014 |
| JP | 2015519096 | A | 7/2015 |
| JP | 2018525754 | A | 9/2018 |
| JP | 2020507414 | A | 3/2020 |
| JP | 2020171267 | A | 10/2020 |
| JP | 2020536643 | A | 12/2020 |
| JP | 2020536653 | A | 12/2020 |
| KR | 20020025884 | A | 4/2002 |
| KR | 20130101596 | A | 9/2013 |
| KR | 20140144272 | A | 12/2014 |
| KR | 20160017099 | A | 2/2016 |
| KR | 20160129752 | A | 11/2016 |
| WO | WO-9716196 | A1 | 5/1997 |
| WO | WO-0184141 | A1 | 11/2001 |
| WO | WO-2006055582 | A2 | 5/2006 |
| WO | WO-2007062367 | A2 | 5/2007 |
| WO | WO-2008041129 | A2 | 4/2008 |
| WO | WO-2008101128 | A1 | 8/2008 |
| WO | WO-2008147958 | A1 | 12/2008 |
| WO | WO-2010123577 | A2 | 10/2010 |
| WO | WO-2011042908 | A1 | 4/2011 |
| WO | WO-2011057028 | A1 | 5/2011 |
| WO | WO-2012024243 | A1 | 2/2012 |
| WO | WO-2013061597 | A1 | 5/2013 |
| WO | WO-2013152348 | A1 | 10/2013 |
| WO | WO-2014040175 | A1 | 3/2014 |
| WO | WO-2014107795 | A1 | 7/2014 |
| WO | WO-2014130960 | A1 | 8/2014 |
| WO | WO-2014162271 | A2 | 10/2014 |
| WO | WO-2014179331 | A2 | 11/2014 |
| WO | WO-2015034673 | A1 | 3/2015 |
| WO | WO-2015066679 | A2 | 5/2015 |
| WO | WO-2015149170 | A1 | 10/2015 |
| WO | WO-2016179240 | A1 | 11/2016 |
| WO | WO-2017091698 | A1 | 6/2017 |
| WO | WO-2017091758 | A1 | 6/2017 |
| WO | WO-2017172728 | A1 | 10/2017 |
| WO | WO-2018094226 | A1 | 5/2018 |
| WO | WO-2018152255 | A1 | 8/2018 |
| WO | WO-2019046338 | A1 | 3/2019 |
| WO | WO-2019241430 | A2 | 12/2019 |
| WO | WO-2021074448 | A1 | 4/2021 |
| WO | WO-2021221879 | A1 | 11/2021 |
| WO | WO-2022192277 | A1 | 9/2022 |

OTHER PUBLICATIONS

Koenig SH. Cholesterol of myelin is the determinant of gray-white contrast in MRI of brain. Magn Reson Med. Aug. 1991;20(2):285-91.

Y Cajal Sr. Degeneration & regeneration of the nervous system. Oxford University Press, Humphrey Milford; 1928.

PCT/US2022/044760 International Search Report and Written Opinion mailed Dec. 23, 2022.

Adaikkan, Chinnakkaruppan et al.: Gamma Entrainment: Impact on Neurocircuits, Glia, and Therapeutic Opportunities. Trends in neurosciences 43(1):24-41 (2020). Published online Dec. 10, 2019.

Adaikkan et al.: Gamma Entrainment Binds Higher-Order Brain Regions and Offers Neuroprotection. Neuron 102(5): 929-943 e928 (2019).

Alawode, Deborah OT. et al.: Transitioning from cerebrospinal fluid to blood tests to facilitate diagnosis and disease monitoring in Alzheimer's disease. Journal of Internal Medicine 290(3):583-601 (2021).

Amazon-listed product. "Mindplace Kasina DeepVision Bundle—Light and Sound Meditation Aid"; https://a.co/d/6nu7NcP; Date First Available: Nov. 6, 2015.

Bartos, M. et al.: Synaptic mechanisms of synchronized gamma oscillations in inhibitory interneuron networks. Nature Reviews Neuroscience 8:45-56 (Jan. 2007).

Benedet, Andrea L. et al.: Differences Between Plasma and Cerebrospinal Fluid Glial Fibrillary Acidic Protein Levels Across the Alzheimer Disease Continuum. JAMA Neurology 78(12):1471-1483 (2021).

(56) References Cited

OTHER PUBLICATIONS

Doody, Rachelle S. et al. Phase 3 Trials of Solanezumab for Mild-to-Moderate Alzheimer's Disease. The New England Journal of Medicine 370(4):311-321 (2014).
Extended European Search Report dated Mar. 21, 2025 issued in European Patent Application No. 22767816.6.
Herrmann, Christoph S.: Human EEG responses to 1-100 Hz flicker: resonance phenomena in visual cortex and their potential correlation to cognitive phenomena. Experimental Brain Research 137(3-4):346-353 (2001).
Kasteleijn-Nolst Trenite, Dorothee. et al. Methodology of photic stimulation revisited: updated European algorithm for visual stimulation in the EEG laboratory. Epilepsia 53(1):16-24 (2012).
Mcfadden; Kristina L. et al.: Test-Retest Reliability of the 40 Hz EEG Auditory Steady-State Response. PLOS ONE, Published: Jan. 22, 2014. https://doi.org/10.1371/journal.pone.0085748.
Summary: *Cognito Therapeutics & MIT* v. *OptoCeutics* (D. Del. 1:26-cv-00011-JLH), filed Feb. 27, 2026, 42 pages Case.
U.S. Appl. No. 19/292,383 Office Action dated Apr. 13, 2026.
U.S. Appl. No. 19/292,383 Office Action dated Dec. 18, 2025.
Adduru et al.: A method to estimate brain volume from head CT images and application to detect brain atrophy in Alzheimer disease. American Journal of Neuroradiology DOI:https://doi.org/10.3174/ajnr.A6402 [1-7](2020).
Ancoli-Israel et al.: Cognitive Effects of Treating Obstructive Sleep Apnea in Alzheimer's Disease: A Randomized Controlled Study. J Am Geriatr Soc. 56(11): 2076-2081 (2008). doi:10.1111/j.1532-5415.2008.01934.x.
Aronov, D. et al., "Engagement of neural circuits underlying 2D spatial navigation in a rodent virtual reality system," Neuron, vol. 84 (Oct. 2014): 442-456.
Barton, A., "Sound vibration treatment may boost brain activity in Alzheimer's patients," The Globe and Mail (2016): http://www.theglobeandmail.com/life/health-and-fitness/health/sound-vibration-treatment-may-boost-brain-activity-in-alzheimers-patients/article29771676/.
Basar, E. et al., "Delay of cognitive gamma responses in Alzheimer's disease," NeuroImage: Clinical, vol. 11 (2016): 106-115.
Bero, A. et al., "Neuronal activity regulates the regional vulnerability to amyloid-β deposition," Nature Neuroscience, vol. 14 (May 2011): 750-756.
Boissonneault, V. et al., "Powerful beneficial effects of macrophage colony-stimulating factor on beta-amyloid deposition and cognitive impairment in Alzheimer's disease," Brain, vol. 132 (Apr. 2009): 1078-1092.
Boublay et al.: Brain volume predicts behavioral and psychological symptoms in Alzheimer's disease. J. Alzheimers Dis. 73(4):1343-1353 (2020).
Bragin, A. et al., "Gamma (40-100 Hz) oscillation in the hippocampus of the behaving rat," Journal of Neuroscience, vol. 15 (Jan. 1995): 47-60.
"Brainsway: Deep TMS Therapy," Brainsway (2014): http://www.brainsway.com/us.
Briones et al., "Dysregulation in myelination mediated by persistent neuroinflammation: possible mechanisms in chemotherapy-related cognitive impairment" Brain, behavior, and immunity 35 (2014): 23-32.
Busche, M. et al., "Decreased amyloid-β and increased neuronal hyperactivity by immunotherapy in Alzheimer's models," Nature Neuroscience, vol. 18 (Dec. 2015): 1725-1727.
Buzsaki et al., "Mechanisms of Gamma Oscillations," Rev. Neurosci. 35, 203-25 (2012).
Buzsaki, G. et al., "Scaling brain size, keeping timing: evolutionary preservation of brain rhythms," Neuron, vol. 80 (Oct. 2013): 751-764.
Buzsaki, G. et al., "Hippocampal network patterns of activity in the mouse," Neuroscience, vol. 116 (2003): 201-211.
Buzsaki, G.: Theta oscillations in the hippocampus. Neuron 33:325-340 (2002).
Buzsaki: Rhythms of the Brain. New York: Oxford University Press. (465 pgs) (2006).
Callaghan, et al., "Long-term cognitive dysfunction in the rat following docetaxel treatment is ameliorated by the phosphodiesterase-4 inhibitor, rolipram." Behavioural brain research 290 (2015): 84-89, 6 pages.
Cardin, Jessica A. et al.: Driving fast-spiking cells induces gamma rhythm and controls sensory responses. Nature 459(7247):663-667 (2009).
Carr, M. et al., "Hippocampal replay in the awake state: a potential substrate for memory consolidation and retrieval," Nature Neuroscience, vol. 14 (Feb. 2011): 147-153.
Carr, M. et al., "Transient slow gamma synchrony underlies hippocampal memory replay," Neuron, vol. 75 (Aug. 2012): 700-713.
Cataldo et al.: Endocytic pathway abnormalities precede amyloid beta deposition in sporadic Alzheimer's disease and Down syndrome: differential effects of APOE genotype and presenilin mutations. Am J Pathol. 157(1):277-286 (2000).
CDR(R) Dementia Staging Instrument [1-4] https://knightadrc.wustl.edu/cdr/cdr.htm.
Chitu, V. et al., "Colony-stimulating factor-1 in immunity and inflammation," Current Opinion in Immunology, vol. 18 (Feb. 2006): 39-48.
Chiu, et al.: A neurodegeneration-specific gene-expression signature of acutely isolated microglia from an amyotrophic lateral sclerosis mouse model. Cell Rep. 4:385-401 (2013).
Cholerton et al.: Total brain and hippocampal volumes and cognition in older American Indians: The strong heart study. Alzheimer Dis Assoc Disord. 31(2):94-100 (2017).
Chung, et al.: Structural and molecular interrogation of intact biological systems. Nature. May 16, 2013; 497(7449):332-7. doi: 10.1038/nature12107. Epub Apr. 10, 2013.
Cirrito, J. et al., "In vivo assessment of brain interstitial fluid with microdialysis reveals plaque-associated changes in amyloid-beta metabolism and half-life," The Journal of Neuroscience, vol. 23 (Oct. 2003): 8844-8853.
Clements-Cortes, A. "Sound Stimulation in Patients With Alzheimer's Disease," Annals of Long-Term Care: Clinical Care and Aging, vol. 23 (May 2015): 10-16.
Clements-Cortes et al., "Short-term effects of rhythmic sensory stimulation in Alzheimer's disease: An exploratory pilot study." Journal of Alzheimer's Disease 52.2 (2016): 651-660.
Cognito Therapeutics to advance digital therapeutic for Alzheimer's into pivotal studies based on positive clinical results announced at AD/PD 2021. Business Wire (2021).
Colgin, L. et al., "Frequency of gamma oscillations routes flow of information in the hippocampus," Nature, vol. 462 (Nov. 2009): 353-357.
Colgin, L. et al., "Gamma oscillations in the hippocampus," Physiology, vol. 25 (Oct. 2010): 319-329.
Correa et al., "A prospective evaluation of changes in brain structure and cognitive functions in adult stem cell transplant recipients." Brain imaging and behavior 7.4 (2013): 478-490.
Cronk, J. et al., "Methyl-CpG binding protein 2 regulates microglia and macrophage gene expression in response to inflammatory stimuli," Immunity, vol. 42 (Apr. 2015): 679-691.
Crotti et al., Mutant Huntingtin Promotes Autonomous Microglia Activation via Myeloid Lineage-Determining Factors, Nature Neuroscience, vol. 17, pp. 513-521, 2014.
Das, U. et al., "Activity-induced convergence of App and Bace-1 in acidic microdomains via an endocytosis-dependent pathway," Neuron, vol. 79 (Aug. 2013): 447-460.
Deschenes, Cynthia L. et al. Current Treatments for Sleep Disturbances in Individuals With Dementia. Curr Psychiatry Rep. 11(1):20-26 (2009).
Doody, Rachelle S. et al.: A Phase 3 Trial of Semagacestat for Treatment of Alzheimer's Disease. The New England Journal of Medicine 369(4):341-350 (2013).
Eckhorn, R. et al., "Coherent Oscillations: a Mechanism of Feature Linking in the Visual Cortex," Biological Cybernetics, vol. 60 (1988): 121-130.

(56) References Cited

OTHER PUBLICATIONS

Elbeltagy, et al., "Fluoxetine improves the memory deficits caused by the chemotherapy agent 5-fluorouracil." Behavioural brain research 208.1 (2010): 112-117.
Erny et al.: Host Microbiota Constantly Control Maturation and Function of Microglia in the CNS. Nature Neuroscience 18:965-977 (2015).
Erum, Jan Van et al.: Sleep and Alzheimer's disease: A pivotal Role for the Suprachiasmatic Nucleus. Sleep Medicine Reviews 40:17-27 (2018).
Fardell, et al., "Cognitive impairments caused by oxaliplatin and 5-fluorouracil chemotherapy are ameliorated by physical activity." Psychopharmacology 220 (2012): 183-193, 12 pages.
Foster, D. et al., "Reverse replay of behavioural sequences in hippocampal place cells during the awake state," Nature, vol. 440 (Mar. 2006):680-683.
Fries, P. et al., "The gamma cycle," Trends in Neurosciences, vol. 30 (Jul. 2007): 309-316.
Gibson et al., "Neuronal activity promotes oligodendrogenesis and adaptive myelination in the mammalian brain." Science 344.6183 (2014). 27 pages.
Gillepsie, A. et al., "Apolipoprotein E4 Causes Age-Dependent Disruption of Slow Gamma Oscillations during Hippocampal Sharp-Wave Ripples," Neuron, vol. 90 (May 2016): 740-751.
Gjoneska, E. et al., "Conserved epigenomic signals in mice and humans reveal immune basis of Alzheimer's disease," Nature, vol. 518 (Feb. 2015): 365-369.
Good Vibrations Can Help Alzheimer's Patients, Awakening from Alzheimer's http://www.awakeningfromalzheimers.com/good-vibrations-can-help-alzheimers-patients/, Internet Archive Wayback Machine earliest Internet archived date Nov. 2, 2016.
Gosselin et al., Environment Drives Selection and Function of Enhancers Controlling Tissue-Specific Macrophage Identities, Cell, vol. 159, pp. 1327-1340, 2014.
Goutagny, R. et al., "Alterations in hippocampal network oscillations and theta-gamma coupling arise before Aβ overproduction in a mouse model of Alzheimer's disease," European Journal of Neuroscience, vol. 37 (Jun. 2013): 1896-1902.
Gray, C. et al., "Chattering cells: superficial pyramidal neurons contributing to the generation of synchronous oscillations in the visual cortex," Science, vol. 274 (Oct. 1996): 109-113.
Gray, C. et al., "Oscillatory responses in cat visual cortex exhibit inter-columnar synchronization which reflects global stimulus properties," Nature, vol. 338 (Mar. 1989): 334-337.
Gray et al.: Full-length human mutant huntingtin with a stable polyglutamine repeat can elicit progressive and selective neuropathogenesis in BACHD mice. Journal of Neuroscience 28(24):6182-6195 (2008).
Gunter et al.: Methodological considerations for measuring rates of brain atrophy. J. Magn. Reson. Imaging 18(1):16-24 (2003).
Hale: Cognito's light-and-sound therapy slows Alzheimer's declines in clinical study. Fierce Biotech: MedTech [1-4] (2021).
Harris et al.: The shrinking brain: Cerebral atrophy following traumatic brain injury. Ann Biomed Eng. 47(9):1941-1959 (2019).
Harvey, C. et al., "Intracellular dynamics of hippocampal place cells during virtual navigation," Nature, vol. 461 (Oct. 2009): 941-946.
Helwig, M. et al.: The neuroendocrine protein 7B2 suppresses the aggregation of neurodegenerative disease-related proteins. The Journal of Biological Chemistry 288:1114-1124 (2013).
Heneka, M. et al., "Innate immune activation in neurodegenerative disease," Nature Reviews Immunology, vol. 14 (Jul. 2014): 463-477.
Hermelink, "Chemotherapy and cognitive function in breast cancer patients: the so-called chemo brain." Journal of the National Cancer Institute Monographs 2015.51 (2015): 67-69.
Herring, W Joseph et al.: Polysomnographic Assessment of Suvorexant in Patients with Probable Alzheimer's Disease Dementia and Insomnia: a Randomized Trial. The Journal of the Alzheimer's Association 16(3):541-551 (2019).
Herrmann, C. et al., "Human EEG gamma oscillations in neuropsychiatric disorders," Clinical Neurophysiology, vol. 116 (Dec. 2005): 2719-2733. Epub Oct. 25, 2005.
Hsiao, F. et al., "Altered Oscillation and Synchronization of Default-Mode Network Activity in Mild Alzheimer's Disease Compared to Mild Cognitive Impairment: an Electrophysiological Study," PLOS One, vol. 8 (Jul. 2013): 1-10.
Huang, S. et al., "Cell-intrinsic lysosomal lipolysis is essential for alternative activation of macrophages," Nature Immunology, vol. 15 (Sep. 2014): 846-855.
Iaccarino, Hannah F. et al.: Gamma Frequency Entrainment Attenuates Amyloid Load and Modifies Microglia. Nature 540(7632):230-235 (2016).
Iliff, J. et al., "A Paravascular Pathway Facilitates CSF Flow Through the Brain Parenchyma and the Clearance of Interstitial Solutes, Including Amyloid β," Science Translational Medicine, vol. 4 (Aug. 2012): 147.
Israel, M. et al., "Probing sporadic and familial Alzheimer's disease using induced pluripotent stem cells," Nature, vol. 482 (Jan. 2012): 216-220.
Jeong, J., "EEG dynamics in patients with Alzheimer's disease," Clinical Neurophysiology, vol. 115 (Aug. 2004): 1490-1505.
Kang, Seong Su et al.: Norepinephrine Metabolite Dopegal Activates AEP and Pathological Tau Aggregation in Locus Coeruleus. J Clin Invest. 130(1):422-437 (2020).
Kasina Manual. MindPlace. Updated: Jan. 2020. [Online]. Available: https://mindplacesupport.com/download/1244/?tmstv=1687473751.
Koenig, T. et al., "Decreased EEG synchronization in Alzheimer's disease and mild cognitive impairment," Neurobiology of Aging, vol. 26 (Feb. 2005): 165-171.
Kreutzberg, G., "Microglia: a sensor for pathological events in the CNS," Trends in Neurosciences, vol. 19 (Sep. 1996): 312-318.
Krynetskiy et al., "Establishing a model for assessing DNA damage in murine brain cells as a molecular marker of chemotherapy-associated cognitive impairment." Life sciences 93.17 (2013): 605-610.
Kurudenkandy, F. et al., "Amyloid-β-Induced Action Potential Desynchronization and Degradation of Hippocampal Gamma Oscillations Is Prevented by Interference with Peptide Conformation Change and Aggregation," The Journal of Neuroscience, vol. 34 (Aug. 2014): 11416-11425.
Leinenga, G. et al., "Scanning ultrasound removes amyloid-β and restores memory in an Alzheimer's disease mouse model," Science Translational Medicine, vol. 7 (Mar. 2015): 278.
Li, F. et al., "Effect of electroacupuncture stimulation of "Baihui" (GV 20) and "Yongquan" (KI 1) on expression of hippocampal amyloid-β and low density lipoprotein receptor-related protein-1 in APP/PS 1 transgenic mice," Zhen Ci Yan Jiu, vol. 40 (Feb. 2015). Abstract.
Lim, et al., "PET evidence of the effect of donepezil on cognitive performance in an animal model of chemobrain." BioMed research international 2016 (2016), 8 pages.
Lok, K. et al., "Characterization of the APP/PS1 mouse model of Alzheimer's disease in senescence accelerated background," Neuroscience Letters, vol. 557 (Dec. 2013): 84-89.
Loy, C and Schneider L. Galantamine for Alzheimer's disease and mild cognitive impairment. Cochrane Database Syst Rev. 2006(1):CD001747, 1-85 (2006).
Lyons, et al., "Fluoxetine counteracts the cognitive and cellular effects of 5-fluorouracil in the rat hippocampus by a mechanism of prevention rather than recovery." PloS one 7.1 (2012): e30010, 8 pages.
Marasco: Current and evolving treatment strategies for the Alzheimer disease continuum. Am J Manag Care 26(8Suppl):S167-S176 (2020).
Martorell, Anthony J. et al.: Multi-sensory gamma stimulation ameliorates Alzheimer's-associated pathology and improves cognition. Cell 177(2):256-271_e1-e22 (2019).
Mastrangelo, M. et al., "Detailed immunohistochemical characterization of temporal and spatial progression of Alzheimer's disease-related pathologies in male triple-transgenic mice," BMC Neuroscience, vol. 9 (Aug. 2008): 1-31.

(56) References Cited

OTHER PUBLICATIONS

Mcdougall et al.: Psychometric properties of the clinical dementia rating—sum of boxes and other cognitive and functional outcomes in a prodromal Alzheimer's disease population. J. Prev Alzheimers Dis. 8(2):151-160 (2021).
Meyers, "How chemotherapy damages the central nervous system." Journal of biology 7.4 (2008): 11. 3 pages.
Mind Alive Inc. http://mindalive.com/ Internet Archive Wayback Machine earliest Internet archived date Mar. 2, 2001, 2 pages.
Mind Machines http://www.mindmachines.com/: Internet Archive Wayback Machine earliest Internet archived date Dec. 7, 1998, 6 pages.
Mind Mods http://www.mindmods.com/, Internet Archive Wayback Machine earliest. Internet archived date Mar. 12, 2008, 2 pages.
Mitrasinovic, O. et al., "Microglial overexpression of the M-CSF receptor augments phagocytosis of opsonized Aβ," Neurobiology of Aging, vol. 24 (Oct. 2003): 807-815.
Most et al.: Discrepancy Between Subjective and Objective Sleep Disturbances in Early- and Moderate-Stage Alzheimer Disease. The American Journal of Geriatric Psychiatry 20(6): 460-467 (2012). https://doi.org/10.1097/JGP.0b013e318252e3ff.
Neuropsychiatric Inventory (NPI): Construct: Behavioral disturbances in dementia patients. APA [1-3] (2011).
Nguyen et al.: Behavioral abnormalities precede neuropathological markers in rats transgenic for Huntington's disease. Hum Mol Genet. 15(21):3177-3194 (2006).
Notice of Allowance issued in U.S. Appl. No. 16/135,938 dated Sep. 21, 2021.
Notice of Allowance issued in U.S. Appl. No. 16/156,833 dated Feb. 3, 2021.
Oakley, H. et al., "Intraneuronal beta-amyloid aggregates, neurodegeneration, and neuron loss in transgenic mice with five familial Alzheimer's disease mutations: potential factors in amyloid plaque formation," Journal of Neuroscience, vol. 26 (Oct. 2006): 10129-10140.
O'Connor et al., "The use of the puzzle box as a means of assessing the efficacy of environmental enrichment." JoVE (Journal of Visualized Experiments) 94 (2014): e52225. 8 pages.
Office Action issued in U.S. Appl. No. 16/901,628 dated May 23, 2024.
Office Action issued in U.S. Appl. No. 17/666,153 dated Sep. 16, 2024.
Ohmi et al.: Defects in the medial entorhinal cortex and dentate gyrus in the mouse model of Sanfilippo syndrome type B. PLoS One 6:e27461 (2011).
Ooms, Sharon et al.: Treatment of sleep disorders in dementia. Current Treatment Options in Neurology 18(9):40 (2016).
Osmand et al.: Imaging polyglutamine deposits in brain tissue. Methods Enzymol. 412:106-122 (2006).
Ouslander, Joseph et al.: A Nonpharmacological Intervention to Improve Sleep in Nursing Home Patients: Results of a Controlled Clinical Trial. Journal of the American Geriatrics Society 54(1):38-47 (2005).
Palop et al.: Aberrant Excitatory Neuronal Activity and Compensatory Remodeling of Inhibitory Hippocampal Circuits in Mouse Models of Alzheimer's Disease, Neuron, 55: 697-711 (2007).
Paro Therapeutic Robot http://www.parorobots.com/: Internet Archive Wayback Machine earliest Internet Archived date Dec. 4, 2008, 2 pages.
Pastor et al., "Activation of human cerebral and cerebellar cortex by auditory stimulation at 40 Hz." Journal of Neuroscience 22.23 (2002): 10501-10506.
Paxinos et al.: The rat brain in stereotaxic coordinates. Elsevier Sixth Edition, 2006 (286 pages).
Pericic, D. et al., "Sex differences in the response to GABA antagonists depend on the route of drug administration," Experimental Brain Research, vol. 115 (Jun. 1997): 187-190.
Peskind, Elaine R. et al.: Memantine Treatment in Mild to Moderate Alzheimer Disease: a 24-week randomized, controlled trial. The American Journal of Geriatric Psychiatry 14(8): 704-715 (2006).
Petrasch-Parwez et al.: Cellular and subcellular localization of Huntington aggregates in the brain of a rat transgenic for Huntington disease. J Comp Neurol. 501(5):716-730 (2007).
Poza et al.: Analysis of spontaneous MEG activity in patients with Alzheimer's disease using spectral entropies. 2007 29th Annual International Conference of the IEEE Engineering in Medicine and Biology Society. IEEE, 2007, 4 pages.
Product Comparison. (Jan. 2020). MindPlace. https://mindplace.com/pages/product.
"PSiO Manual," PSiO http://www.psioplanet.com/download/manuals/manuel-psio-1.1-EN.pdf, http://www.psoplanet.com/, Internet Archive Wayback Machine earliest Internet archived date Mar. 2, 2013, 16 pages.
Raivich, G. et al., "Neuroglial activation repertoire in the injured brain: graded response, molecular mechanisms and cues to physiological function," Brain Research Reviews, vol. 30 (Aug. 1999): 77-105.
Ravassard, P. et al., "Multisensory control of hippocampal spatiotemporal selectivity," Science, vol. 340 (Jun. 2013): 1342-1346.
Richard et al.: Steady-state visual evoked potential temporal dynamics reveal correlates of cognitive decline. Clinical Neurophysiology 131(4): 836-846 (2020).
Santarnecchi, "Individual differences and specificity of prefrontal gamma frequency-tACS on fluid intelligence capabilities." Cortex 75 (2016): 33-43.
Sauer et al.: Impaired fast-spiking interneuron function in a genetic mouse model of depression. eLIFE 4:1-20 (2015).
Schwarz et al.: Magnetic resonance imaging measures of brain atrophy from the Expedition3 trial in mild Alzheimer's disease. Alzheimers Dement (NY) 5:328-337 (2019).
Seibenhener et al., "Use of the open field maze to measure locomotor and anxiety-like behavior in mice." JoVE (Journal of Visualized Experiments) 96 (2015): e52434. 9 pages.
Selkoe, D. et al., "The role of APP processing and trafficking pathways in the formation of amyloid beta-protein," Annals of the New York Academy of Sciences (Jan. 1996): 57-64.
Shop 40 Hertz Light & Sound at MindPlace. (Jan. 2020). MindPlace. https://mindplace.com/collections/light-sound/40-hertz.
Siegle, J. et al., "Enhancement of Encoding and retrieval functions through theta phase-specific manipulation of hippocampus," ELife Sciences Publications (Jul. 2014).
Siemers et al.: Phase 3 solanezumab trials: Secondary outcomes in mild Alzheimer's disease patients. Alzheimers Dement. 12(2):110-120 (2016).
Smeets et al.: Reliable measurements of brain atrophy in individual patients with multiple sclerosis. Brain Behav. 6(9):e00518 [1-12] doi:10.1002/brb3.518 (2016).
Smith et al., "The validity of neuropathy and neuropathic pain measures in patients with cancer receiving taxanes and platinums." Oncology nursing forum. vol. 38. No. 2. 2011. 10 pages.
Stam, C. et al., "Generalized synchronization of MEG recordings in Alzheimer's Disease: evidence for involvement of the gamma band," Journal of Clinical Neurophysiology, vol. 19 (Dec. 2002): 562-574.
Storelli et al.: Measurement of whole-brain and gray matter atrophy in multiple sclerosis: assessment with MR imaging. Radiology 288(2):554-564 (2018).
Subramanian, Aravind, et al., Gene Set Enrichment Analysis: a Knowledge-based Approach for Interpreting Genome-wide Expression Profiles. Proceedings of the National Academy of Sciences of the United States of America 102(43):15545-15550 (2005).
Sudol, K. et al., "Generating Differentially Targeted Amyloid-β Specific Intrabodies as a Passive Vaccination Strategy for Alzheimer's Disease," Molecular Therapy, vol. 17 (Dec. 2009): 2031-2040.
Sur et al.: BACE inhibition causes rapid, regional, and non-progressive volume reduction in Alzheimer's disease brain. Brain 143(12):3816-3826 (2020).
Tada et al.: Gamma-Band Auditory Steady-State Response as a Neurophysiological Marker for Excitation and Inhibition Balance: A Review for Understanding Schizophrenia and Other Neuropsychiatric Disorders. Clinical EEG and Neuroscience 51:4 (2019) .https://doi.org/10.1177/1550059419868872.

(56) References Cited

OTHER PUBLICATIONS

Thakurela, S. et al., "Dynamics and function of distal regulatory elements during neurogenesis and neuroplasticity," Genome Research, vol. 25 (Sep. 2015): 1309-1324.
Tiepolt, Solveig et al.: Current Radiotracers to Image Neurodegenerative Diseases. EJNMMI Radiopharmacy and Chemistry 4(1):17, 1-23 (2019).
Trapnell et al.: Differential gene and transcript expression analysis of RNA-seq experiments with TopHat and Cufflinks. Nature protocols 7:562-578 (2012).
Trapnell, et al.: Transcript assembly and quantification by RNA-Seq reveals unannotated transcripts and isoform switching during cell differentiation. Nat Biotechnol. May 2010;28(5):511-5. doi: 10.1038/nbt.1621. Epub May 2, 2010.
Traub, R. et al., "Analysis of gamma rhythms in the rat hippocampus in vitro and in vivo," the Journal of Physiology, vol. 493 (Jun. 1996): 471-484.
U.S. Appl. No. 16/901,628 Notice of Allowance dated Jun. 13, 2024.
U.S. Appl. No. 15/360,637 Office Action dated Sep. 8, 2017.
U.S. Appl. No. 15/647,157 Notice of Allowance dated Sep. 24, 2018.
U.S. Appl. No. 15/647,157 Office Action dated Sep. 11, 2017.
U.S. Appl. No. 16/135,938 Office Action dated Mar. 18, 2021.
U.S. Appl. No. 16/901,592 Notice of Allowance issued Aug. 8, 2024.
U.S. Appl. No. 16/901,592 Office Action dated Mar. 29, 2024.
U.S. Appl. No. 16/901,592 Office Action dated Oct. 6, 2023.
U.S. Appl. No. 16/901,628 Office Action dated Dec. 15, 2023.
U.S. Appl. No. 17/217,789 Notice of Allowance dated Jul. 31, 2023.
U.S. Appl. No. 17/217,789 Notice of Allowance dated Jun. 14, 2024.
U.S. Appl. No. 17/217,789 Notice of Allowance dated Mar. 13, 2024.
U.S. Appl. No. 17/217,789 Notice of Allowance dated Oct. 18, 2023.
U.S. Appl. No. 17/217,789 Office Action dated Dec. 22, 2022.
U.S. Appl. No. 17/300,314 Office Action dated Apr. 25, 2024.
U.S. Appl. No. 17/666,153 Office Action dated Dec. 21, 2023.
U.S. Appl. No. 17/666,153 Office Action dated Sep. 16, 2024.
Van De Weijer et al.: The Parkin'Play study: protocol of a phase II randomized controlled trial to assess the effects of a health game on cognition in Parkinson's disease. BMC Neurol. 16(1):209 [1-11] (2016).
Verret, L. et al.: Inhibitory Interneuron Deficit Links Altered Network Activity and Cognitive Dysfunction in Alzheimer Model. Cell 149(3): 708-721 (2012).
Vialatte et al.: Steady-state visually evoked potentials: Focus on essential paradigms and future perspectives. Progress in Neurobiology 90(4): 418-438 (2010).
Vijayanathan, Veena et al.: Persistent cognitive deficits, induced by intrathecal methotrexate, are associated with elevated CSF concentrations of excitotoxic glutamate analogs and can be reversed by an NMDA antagonist. Behavioural brain research 225(2):491-497 (2011).
Vitiello, M.V. et al.: Sleep Disturbances in Patients with Alzheimer's Disease. CNS Drugs 15(10):777-796 (2001).
Vonsattel et al.: Huntington disease. J Neuropathol Exp Neurol. 57(5):369-384 (1998).
Walsh et al.: The open-field test: a critical review. Psychological bulletin 83.3:482-504 (1976). DOI:10.1037/0033-2909.83.3.482.
Wang, et al.: TREM2 lipid sensing sustains the microglial response in an Alzheimer's disease model. Cell 160:1061-1071 (2015).
Wang et al.: ADCOMS: a composite clinical outcome for prodromal Alzheimer's disease trials. J. Neurol Neurosurg Psychiatry. 87(9):993-999 (2016).
Wang et al., "The gamma frequency band neural oscillation: generation mechanisms and functions." Progress in Biochemistry and Biophysics 38.8 (2011): 688-693. English Abstract.
Wang: Neurophysiological and computational principles of cortical rhythms in cognition. Physiol Rev 90:1195-268 (2010).
Wessels, A.M. et al.: A Combined Measure of Cognition and Function for Clinical Trials: The Integrated Alzheimer's Disease Rating Scale (iADRS). The journal of prevention of Alzheimer's disease 2(4):227-241 (2015).
Whitwell et al.: Rates of cerebral atrophy differ in different degenerative pathologies. Brain 130(Pt4):1148-1158 (2007).
Winocur, Gordon et al.: Donepezil reduces cognitive impairment associated with anti-cancer drugs in a mouse model. Neuropharmacology 61(8):1222-1228 (2011).
Winocur, Gordon et al.: Environmental enrichment protects against cognitive impairment following chemotherapy in an animal model. Behavioral neuroscience 130(4):428-436 (2016).
Winocur, Gordon et al.: Physical exercise prevents suppression of hippocampal neurogenesis and reduces cognitive impairment in chemotherapy-treated rats. Psychopharmacology 231(11):2311-2320 (2014). Published online Dec. 17, 2013.
Wujek et al.: Axon loss in the spinal cord determines permanent neurological disability in an animal model of multiple sclerosis. J Neuropathol Exp Neurol. 61(1):23-32 (2002).
Ylinen, A. et al., "Sharp wave-associated high-frequency oscillation (200 Hz) in the intact hippocampus: network and intracellular mechanisms," Journal of Neuroscience, vol. 15 (Jan. 1995): 30-46.
Yoshiyama et al.: Synapse loss and microglial activation precede tangles in a P301S tauopathy mouse model. Neuron 53(3):337-351 (2007).
Young: Brain Changes Speak Volumes About Normal Aging and Dementia. Alzforum [1-5] (2013).
Yu et al.: Interferon-β inhibits progression of relapsing-remitting experimental autoimmune encephalomyelitis. Journal of Neuroimmunology 64(1):91-100 (1996).
Yu, H. et al., "Tet3 regulates synaptic transmission and homeostatic plasticity via Dna oxidation and repair," Nature Neuroscience, vol. 18 (Jun. 2015): 836-843.
Yu-Taeger et al.: A Novel BACHD Transgenic Rat Exhibits Characteristic Neuropathological Features of Huntington Disease. J Neurosci. 32(44):15426-15438 (2012).
Zhang et al.: An RNA-Sequencing Transcriptome and Splicing Database of Glia, Neurons, and Vascular Cells of the Cerebral Cortex, Journal of Neuroscience Research 34:11929-11947 (2014).
Zhou, Wenjun et al.: Metformin Prevents Cisplatin-Induced Cognitive Impairment and Brain Damage in Mice. PloS one 11(3):e0151890, 1-15 (2016).

* cited by examiner

100

900

Efficacy summary (mITT population)

| | P-value | Difference | CI |
|---|---|---|---|
| MADCOMS | 0.3900 | 0.62 | (-1.35,2.58) |
| ADAS-Cog14 | 0.7920 | -0.6 | (-7.25,6.04) |
| CDR-sb | 0.4850 | 0.43 | (-1.12,1.97) |
| ADCS-ADL** | 0.0009 | 7.59 | (3.15,12.04) |
| MMSE** | 0.0127 | 2.42 | (0.54,4.3) |
| Whole Brain Vol.** | 0.0154 | 9.34 | (1.88,16.79) |
| Hippocampal Vol.** | 0.7678 | -0.02 | (-0.12,0.09) |

**Differences inverted for visual consistency.

| Scale | p-value | Difference | CI | %Slowing* |
|---|---|---|---|---|
| ADAS-cog14 | 0.792 | 0.6 | -6.0,7.2 | -15% |
| MADCOMS | 0.390 | -0.6 | -2.6, 1.3 | 35% |
| CDR-sb | 0.485 | -0.4 | -2.0,1.1 | 27% |
| ADCS-ADL | 0.0009 | 7.6 | 3.1, 12.0 | 84% |
| MMSE | 0.013 | 2.58 | 0.5, 4.3 | 83% |
| Whole Brain Volume | 0.015 | 9.3 | 1.9, 16.8 | 61% |
| Hippocampal Volume | 0.768 | 0.0 | -0.1, 0.1 | -16% |

*Positive % slowing is in favor of active, negative is in favor of sham.

FIG. 26

METHODS OF ENHANCING NEUROSTIMULATION DURING ACTIVITIES

CROSS-REFERENCE

This application is a continuation of International Application No. PCT/US2022/44760, filed Sep. 26, 2022, which claims the benefit of U.S. Provisional Application No. 63/248,880 filed Sep. 27, 2021, which is incorporated herein by reference in its entirety.

INCORPORATION BY REFERENCE

Each patent, publication, and non-patent literature cited in the application is hereby incorporated by reference in its entirety as if each was incorporated by reference individually.

BACKGROUND

Neural oscillation occurs in humans or animals and includes rhythmic or repetitive neural activity in the central nervous system. Neural tissue can generate oscillatory activity by mechanisms within individual neurons or by interactions between neurons. Oscillations can appear as either oscillations in membrane potential or as rhythmic patterns of action potentials, which can produce oscillatory activation of post-synaptic neurons. Synchronized activity of a group of neurons can give rise to macroscopic oscillations, which can be observed by electroencephalography ("EEG"). Neural oscillations can be characterized by their frequency, amplitude, and phase. Neural oscillations can give rise to electrical impulses that form a brainwave. These signal properties can be observed from neural recordings using time-frequency analysis.

SUMMARY

In some embodiments, the present disclosure provides a method comprising: identifying an activity being performed by a subject; and administering sensory stimulation to the subject during the activity to induce gamma oscillations in a brain region of the subject.

In some embodiments, the subject has a disease or disorder associated with white brain matter atrophy, demyelination, or a combination thereof. In some embodiments, the method further comprises administering one or more of an active agent to treat the disease or disorder.

In some embodiments, the sensory stimulation comprises one or more of: mechanical stimulation, auditory stimulation, and visual stimulation. In some embodiments, the sensory stimulation comprises a frequency of between 10 and 100 Hertz.

In some embodiments, the activity involves a cognitive process. For example, in some cases, the cognitive process comprises one or more of an executive function. In some cases, the executive function comprises emotional control, cognitive flexibility, goal-directed persistence, metacognition, organization, planning/prioritization, response inhibition, stress tolerance, sustained attention, task initiation, time management, working memory, or a combination thereof.

In certain embodiments, the activity being performed involves one or more cognitive processes selected from: memory encoding, memory consolidation, memory recall, perception, attention, knowledge formation, problem solving, concept formation, pattern recognition, association, decision making, motor coordination, task planning, language expression, or language comprehension.

In some cases, administering comprises slowing neurodegeneration.

In some cases, the administering causes a change in neurotic behavior, anxious behavior, depressive behavior, addictive behavior, food-seeking behavior, or sleeping behavior of the subject. In some cases, the administering improves a cognitive skill. For example, in some cases, the cognitive skill comprises: perceptual reasoning, sustained attention, selective attention, divided attention, long-term memory, working memory, logic and reasoning, auditory processing, visual processing, visual-motor planning and processing, visual spatial planning and processing, auditory memory, visual memory, task planning, task sequencing, task initiation, task completion, visual encoding and decoding, auditory encoding and decoding, sensory encoding and decoding, language expression, language comprehension, processing speed, cognitive control, cognitive inhibition, declarative memory, procedural memory, episodic memory, auditory memory, visual memory, semantic memory, or autobiographical memory. In some cases, the processing speed comprises one or more of: visual processing speed, language processing speed, auditory processing speed, and motor processing speed.

In some cases, the activity being performed comprises meditating, sleeping, reading, or consuming a substance. In some cases, the consumed substance promotes blood flow. In some cases, the substance promotes blood flow. In some cases, the substance comprises a stimulant or a depressant.

In some cases, the activity performed comprises a physical activity. In some cases, the activity comprises bathing or showering. For example, in some embodiments, the sensory stimulation comprises auditory stimulation and mechanical stimulation, and wherein administering the sensory stimulation comprises turning on a source of water, the source of water capable of causing water pressure to fluctuate, thereby administering the sensory stimulation to the subject during the activity. In some cases, the activity comprises operating heavy machinery. In some cases, the operating heavy machinery comprises an automobile or an aircraft.

The present disclosure further provides a system for slowing neurodegeneration in a subject in need thereof, the system comprising a stimulus-emitting component and one or more processors configured to: a) receive an indication of a subject; b) generate an output signal based on the indication; and c) provide the output signal to the stimulus-emitting component to cause the stimulus-emitting component to provide stimulation in accordance with the generated output signal, thereby slowing neurodegeneration in the subject. In some embodiments, the stimulus-emitting component comprises a display device. In some cases, slowing neurodegeneration comprises reducing white matter brain atrophy experienced by the subject. In some embodiments, slowing neurodegeneration comprises reducing a rate of demyelination experienced by the subject.

In some embodiments, the indication is associated with an activity performed by the subject. In some cases, the activity is selected from a group consisting of learning, studying, presenting, speaking, focusing, analyzing, or listening. In some cases, the activity comprises relocating the subject's position or location. In some cases, the activity comprises walking, jogging, skipping, running, hopping, marching, swimming, or any combination thereof. In some cases, the activity comprises engaging in a mental effort, a physical effort, or a combination thereof. In some embodiments, the activity comprises playing a logic game, a board game, a videogame.

In some embodiments of the systems provided herein, the system further comprises a feedback monitor configured to provide the indication of the subject. In some embodiments of the systems provided herein, the system further comprises a profile manager configured to provide the indication of the subject.

BRIEF DESCRIPTION OF THE DRAWINGS

FIG. 26 is a table depicting a summary of efficacy findings resulting from the human clinical trial, including p-values, treatment differences, CI values and the percentage of slowing of brain atrophy.

FIG. 33) of Stimulus Delivery System (170; FIG. 33). Numbers and relative dimensions of elements in FIG. 31 are adjusted for presentation and may not represent those for actual embodiments.

FIG. 33 provides a block diagram of an exemplary stimulus delivery system and analysis and monitoring system, said analysis and monitoring system comprising modules specific to sleep-related monitoring and/or analysis.

FIG. 36). In FIG. 37, terms in italics in braces refer to MATLAB (R2020a) APIs employed in the corresponding steps in an exemplary embodiment, e.g., "medfilt1" refers to 1-D median filtering. In some embodiments, alternate APIs, methods, or processes, with equivalent function are employed (e.g., Wolfram Language's "ButterworthFilterModel" may be substituted for "butter").

FIG. 40 demonstrates a reduction in duration of active periods for the treatment group and, consequently, a reduction in sleep fragmentation leading to increased sleep quality. In contrast, the opposite effect was seen with the sham group, which is represented by the line closest to the gray arrow. Panel A of FIG. 40 shows the relative change based on the duration of active periods, and Panel B of FIG. 40 shows the normalized nighttime active durations, calculated by dividing the duration of each active period by the duration of the matching entire nighttime period.

FIG. 46A provides the results for entorhinal region, left cingulate lobe, parstriangularis region, cuneus region, lateral occipital region, postcentral region, left occipital lobe, left frontal lobe, left parietal lobe, occipital lobe, left temporal lobe and caudal middle frontal region (sorted in ascending order by p value) for the treatment group after 6 months of treatment. FIG. 46B provides the results for the precentral region, paracentral region, lingual region, fusiform region, frontal lobe, rostral anterior cingulate region, inferior temporal region, right occipital lobe, parietal lobe, rostral middle frontal, precuneus region, medial orbitofrontal region and temporal lobe (sorted in ascending order by p value).

FIG. 47A provides the results for the entorhinal region, parstriangularis region, postcentral region, left parietal lobe, lateral occipital region, paracentral region, rostral middle frontal region, supramarginal region, precentral region, parietal lobe, right occipital lobe, fusiform region, occipital lobe, left frontal lobe, cuneus region, precuneus region, inferior parietal region, frontal lobe, lingual region, left occipital lobe, left temporal lobe, right parietal lobe and parsorbitalis region, with white matter structures sorted in ascending order by p value. FIG. 47B provides the results for the right frontal lobe, caudal middle frontal region, rostral anterior cingulate region, superior frontal region, temporal lobe, medial orbitofrontal region, posterior cingulate region, superior parietal region, left cingulate lobe, superior temporal region, cingulate lobe and temporal pole region, with white matter structures sorted in ascending order by p value.

Figure 1:
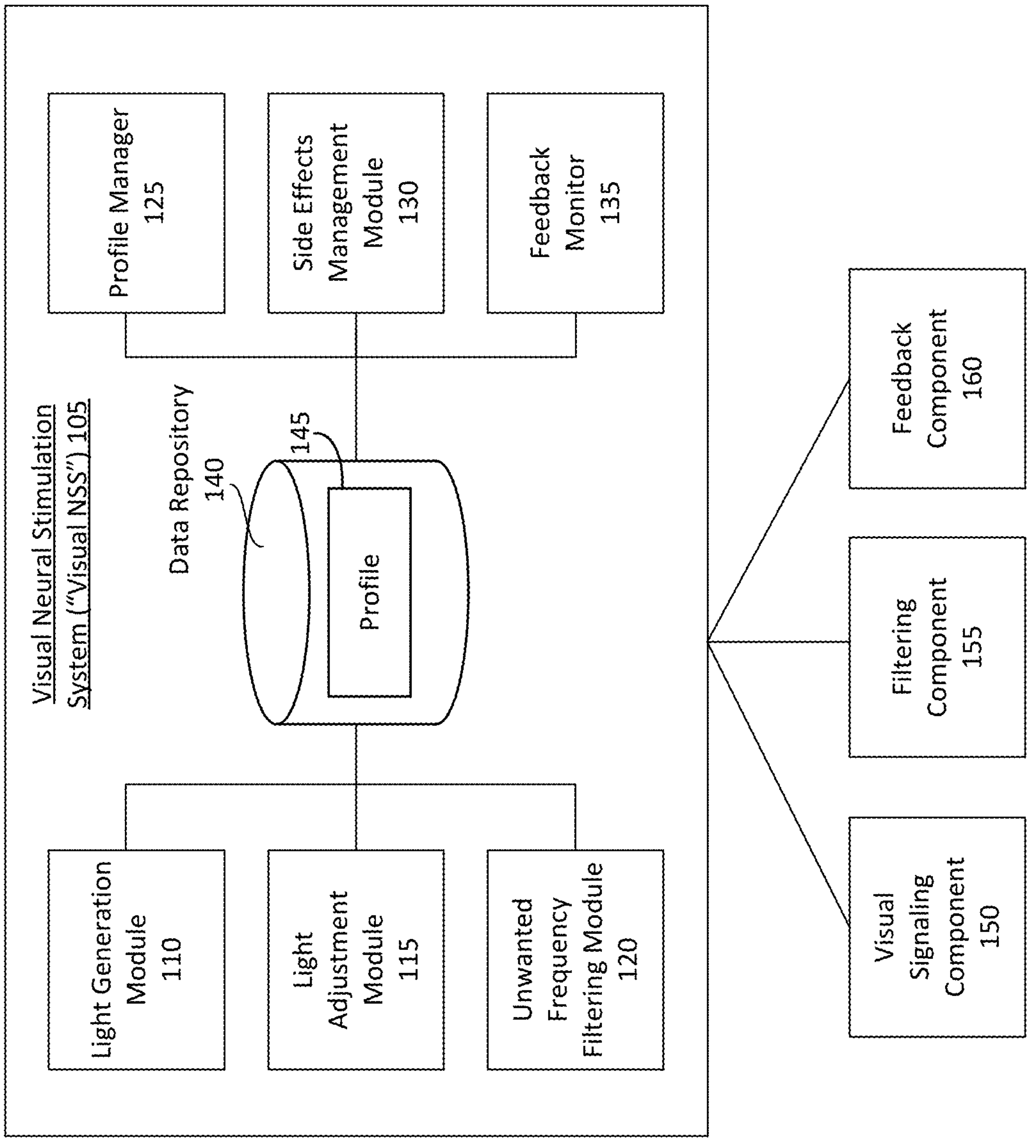
FIG. 1 illustrates a block diagram depicting a system to perform neural stimulation via visual stimulation in accordance with an embodiment

The features and advantages of the present solution will become more apparent from the detailed description set forth below when taken in conjunction with the drawings, in which like reference characters identify corresponding elements throughout. In the drawings, like reference numbers generally indicate like elements.

DETAILED DESCRIPTION OF THE INVENTION

Described herein are systems and methods for using non-invasive stimulation to a human subject and/or producing gamma wave oscillations in the brain of a human subject, which may improve one or more cognitive functions of a subject. In particular, the present disclosure uses non-invasive stimulation to generate sensory-evoked potentials in at least one region of the brain and, as a result, causes a neuromodulatory effect on a brain of a subject. The present disclosure achieves improvement in mood, behavior, cognitive processing, memory, executive functioning, focus, and neurostimulation.

Systems and methods described herein may influence one or more of a cognitive process. For example, systems and methods described herein may cause an improvement in emotional control, perceptual reasoning, cognitive flexibility, goal-directed persistence, metacognition, organization, planning/prioritization, response inhibition, stress tolerance, sustained attention, task initiation, time management, working memory, or a combination thereof. Other cognitive processes that may benefit from the systems and methods described herein include sensory register, short-term memory formation, long-term memory formation, memory encoding, memory consolidation, molecular or cellular memory consolidation, memory recall, perception, attention, knowledge formation, problem solving, concept formation, pattern recognition, association, decision making, motor coordination, decision making, planning, language production, or language comprehension. Further mental processes that may benefit from the technology described herein may also comprise mental calculation, visual encoding and decoding, auditory coding and decoding, sensory encoding and decoding, visual processing, visual-motor planning and processing, visual-spatial planning and processing, auditory memory, visual memory, and task planning, sequencing, initiation, and completion.

The present disclosure is also directed towards improving cognitive skills. Cognitive skills may include one or more of sustained attention, selective attention, divided attention, long-term memory, working memory, logic and reasoning, auditory processing, visual processing, processing speed, cognitive control, cognitive inhibition, declarative memory, procedural memory, episodic memory, semantic memory, autobiographical memory.

The present technological solution achieves the entrainment of gamma wave oscillations in the brain through a variety of methods and systems, and includes aspects covering the monitoring and analysis of patient activity, motivation and feedback to users and/or third parties, and specific stimulation parameters targeted at improving cognition and cognitive functioning. Entrainment of gamma wave oscillations in the brain can be done using non-invasive sensory stimulation, which can include haptic or mechanical stimulation, peripheral nerve stimulation, visual stimulation, auditory stimulation, or a combination thereof. The disclosure further achieves improved brain wave coherence, measured through increased power in alpha and other frequency bands and other methods for assessing functional connectivity, which are associated with cognitive function, brain health, and general wellbeing.

Systems and methods of the present disclosure may be directed to improving the cognitive capacity of a person. In some embodiments, the present disclosure can improve or maintain cognitive functioning of an individual. Any individual may use the systems and methods of the present disclosure. The individual can be neurotypical or neurodivergent. In some embodiments, the individual has a neurodegenerative disease. In some embodiments, the individual has a physiological disorder, a psychological disorder, a psychosomatic disorder, or a psychiatric disorder.

In some embodiments, the present disclosure provides systems and methods for alleviating symptoms associated with a microglial-mediated disease or disorder associated with brain atrophy. For example, the microglial-mediated disease or disorder may comprise a neurodegenerative disease associated with tauopathy, including but not limited to chronic traumatic encephalopathy, frontotemporal dementia, and corticobasilar degeneration. The microglial-mediated disease or disorder may comprise a genetic disorder, such as an inherited ataxia associated with brain atrophy. The microglial-mediated disease or disorder may also comprise a neuropsychiatric disorder associated with brain atrophy, such as depression or schizophrenia; brain injury, such as stroke; or demyelinating diseases, such as Multiple Sclerosis and Acute disseminated encephalomyelitis.

Neurodegenerative Diseases Causing Tauopathy: Alzheimer's Disease, Frontotemporal Dementia, Chronic Traumatic Encephalopathy, and Corticobasilar Degeneration In some embodiments, the microglial-mediated disease or disorder may comprise a neurodegenerative disease associated with tauopathy, including but not limited to Alzheimer's disease, frontotemporal dementia, chronic traumatic encephalopathy (CTE), and corticobasilar degeneration.

Alzheimer's disease (AD) is a progressive neurodegenerative disease characterized by a decline in memory, orientation, and reasoning. AD may be characterized by the accumulation of amyloid plaques comprising the amyloid-β (AB) peptide and neurofibrillary tangles (NFTs) made of the tau protein. Under normal conditions, the soluble Aβ peptide is produced and secreted by neurons and subsequently cleared from the brain via cerebral spinal fluid (CSF) pathways. However, in subjects with AD, the Aβ peptide appears to aggregate into higher-order species to form soluble oligomers and insoluble plaques in a concentration-dependent manner. This aggregation may initiate many neurotoxic events including disrupted brain metabolism, neuroinflammation, reduced functional connectivity, synaptic and neuronal loss, and/or formation of NFTs.

Frontotemporal dementia (FTD) is a group of disorders that result from damage to the frontal and temporal lobes of the brain. Depending on the location of the damage, the disorder causes changes in social behavior, personality, and/or loss of language skills. In some people, FTD may also lead to neuromuscular disorder, such as parkinsonism. Frontotemporal dementia occurs where abnormal proteins build up in the brain, leading to death of brain cells and atrophy of the frontal and temporal lobes of the brain. Frontotemporal dementia occurs in Alzheimer's disease, although it may be caused by other neurodegenerative diseases as well.

Chronic traumatic encephalopathy (CTE) is characterized by symptoms that may include memory loss, confusion, impaired judgment, impulse control problems, aggression, depression, anxiety, suicidality, parkinsonism, and progressive dementia. CTE results from traumatic injury to the head triggers microglia, leading to tau proteins becoming phosphorylated at progressively higher rates and, accordingly, accumulation of hyperphosphorylated tau deposits. The buildup of phosphorylated tau proteins can lead to axonal transport defects, neuroinflammation, and synapse loss.

Corticobasal degeneration (CBD) is characterized by cell loss and deterioration of specific areas of the brain. In corticobasal degeneration, abnormal levels of tau accumulate in certain brain cells, eventually causing their deterioration. Symptoms often initially include experiencing motor abnormalities in one limb that progressively spreads to all limbs. Such motor abnormalities include, for example, progressive stiffening or tightening of muscles in the limb (progressive asymmetric rigidity) and the inability to perform purposeful or voluntary movements (apraxia). Trouble with speech and language, including aphasia, apraxia of speech, dysarthria, dysphagia. Symptoms may also be reflected in physical movements and tremors, such as experiencing action tremor, postural tremor, bradykinesia, akinesia, myoclonus, and ataxic gait. The severity and type of symptoms depend on the area of the brain affected by the disease, which is most commonly the cerebral cortex and basal ganglia.

Genetic Disorders: Inherited Ataxias.

As stated above, the present systems and methods may be used to alleviate symptoms associated with inherited ataxias. Hereditary ataxias are characterized by slowly progressive incoordination of gait and are often associated with poor coordination of hands, speech, and eye movements. Hereditary ataxias frequently cause atrophy of the cerebellum as a result of impaired circuitry and function of the cerebellar cortex, a result of neurodegeneration of cellular afferents and the Prukinje cells, which have long axonal projections that comprise the only sources of output from the cerebellar cortex to deep cerebellar nuclei.

Neuropsychiatric Disorders: Schizophrenia, Depression, Chronic Stress

In other embodiments, the present disclosure provides system and methods for treating neuropsychiatric disorders associated with brain atrophy, which is mediated by microglial cells. For example, individuals with schizophrenia often show reduced postmortem cortical tissue. This phenomenon is caused by synaptic pruning, which reflects abnormalities in microglia-like cells and synaptic function. In other embodiments, the present disclosure provides methods and systems for alleviating symptoms of depression. Stress, impaired neurogenesis, and defects in synaptic plasticity are associated with depression. Chronic stress promotes microglial hyper-ramification and astroglial atrophy. Thus, in some embodiments, the system and methods disclosed may alleviate symptoms associated with chronic stress or depression by improving synaptic plasticity and stimulating neural networking, along with improving microglial-mediated clearance.

Brain Injury: Stroke and Related Cerebrovascular Diseases

In some embodiments, the present disclosure provides systems and methods for alleviating symptoms associated with a stroke. For example, the stroke may be an ischemic stroke, which causes a neuroinflammatory response and activates microglia to help repair the brain. Ischemic stroke is associated with disappearance of synaptic activity. As a result, brain tissue within the penumbra during an ischemic stroke is structurally intact, but functionally silent. Failure to reperfused this penumbral region or resupply glucose and oxygen in time may lead to atrophy of brain cells located in the penumbra. In contrast, activating synapses in this region may delay cell death and salvage brain tissue. By improving synaptic plasticity and stimulating neural networking, the present systems and methods can reduce brain atrophy and related symptoms associated with ischemic stroke. Other forms cerebrovascular diseases with similar symptoms—e.g., neuroimmune modulation, synaptic function—may also be treated by the present disclosure, including but not limited to: transient ischemic attack (TIA), hemorrhagic stroke, arteriovenous malformation, intracranial atherosclerosis (ICAD), and Moyamoya.

Demyelinating Diseases: Multiple Sclerosis and Acute Disseminated Encephalomyelitis In some embodiments, the present disclosure provides systems and methods for alleviating symptoms of demyelinating diseases associated with brain atrophy. For example, the demyelinating disease may comprise Multiple Sclerosis or Acute disseminated encephalomyelitis, both of which may cause neuroinflammation and cerebral atrophy. In multiple sclerosis (MS), brain or cerebral atrophy is common due to demyelination and destruction of nerve cells. Widespread myelin damage occurs, causing damage to the myelin-rich white matter of the brain, occurs as a result of a number of attacks which occur over time. In acute disseminated encephalomyelitis, similar symptoms are seen, but the onset of widespread myelin damage is often due to a single episode or attack. By reducing neuroinflammation and stimulating neural networking, the present disclosure provides systems and methods for slowing brain atrophy associated with demyelinating diseases and related symptoms.

In some embodiments, the present system and methods aim to reduce interference in cognitive functioning. Interference in cognitive function severely impacts cognitive performance across a range of functions, including perception, attention, and memory. People are susceptible to interference or are exposed to interference in daily life. Accordingly, there are many potential populations that would benefit from a system or method that specifically aims to enhance the ability to deal with interference. Additionally, many individuals, though not experiencing a perceptible decline in cognitive function, may desire to increase their current cognitive abilities. One example is to improve the performance of everyday tasks (e.g., multitasking, focus, memory, social skills, such as conversational skills, decision-making abilities, creativity, or reaction times to specific task). Another example is to improve general metrics of cognitive ability (e.g., to “enhance IQ”).

The present disclosure may be directed at improving cognitive abilities in those who are not necessarily experiencing a cognitive decline or impairment. Secondary effects of improving cognitive function may also be motivate use of the present technology. For examples, populations whose activities involve multitasking could increase performance in carrying out their professional duties or hobbies through use of the systems and methods described herein. Examples of such populations include, but are not limited to, athletes, airline pilots, military personnel, doctors, call center attendees, teachers, and drivers of vehicles.

In other embodiments, the present disclosure provides methods and systems for improving the cognitive potential of a user. In some embodiments, the present disclosure provides systems and methods of increasing the cognitive capacity of a general population. In other embodiments, the systems and methods described herein may be used to improve cognitive processing during a certain time frame or activity. For example, the systems and methods may be used to momentarily increase a user’s focus during a presentation, or the systems and methods may be used to help reinforce learned materials, with gamma therapy being administered one or more of: before learning the material, during learning of the material, and after learning the material.

Systems and methods of the present disclosure may be used during a range of activities. They may also be used to improve performance of an activity. Improved performance may be achieved in an activity, function, or process that is independent of the activity involved in use of the present systems and methods. Alternatively, or additionally, the improved performance may relate directly to the activity during which a person engages in or with the systems and methods described herein. Activities might involve leisure, work, physical effort, mental effort, or all of the above. Cognitive processes that may be involved in such an activity include but are not limited to memory consolidation or recall, emotional control, cognitive flexibility, goal-directed persistence, metacognition, organization, planning/prioritization, response inhibition, stress tolerance, sustained attention, task initiation, time management, working memory, or a combination thereof.

In some embodiments, the systems and methods of the present disclosure may improve cognitive capacity by slowing brain atrophy. A subject with brain atrophy may experience this as a normal part of aging, or may experience brain atrophy as a cause or result of a variety of conditions, disorders, or diseases, including but not limited to: Alzheimer’s Disease (AD), dementia, Parkinson’s disease, seizure, cerebral palsy, senile dementia, pick’s disease, Huntington’s disease, Krabbe disease, leukodystrophies, multiple sclerosis, epilepsy, anorexia nervosa, aphasia, learning disability, frontotemporal dementia, expressive aphasia, receptive aphasia, Lewy body dementia, chronic traumatic encephalopathy (CTE), and others.

In some embodiments, the systems and methods of the present disclosure may improve cognitive capacity by alleviating symptoms of brain atrophy. Symptoms may include a loss of neurons, memory loss, blurred vision, aphasia, impaired balance, paralysis, decreases in cortical volume, increases in CSF volume, loss of motor control, difficulty speaking, comprehension, reading comprehension, memory, decrease in gray and/or white matter, decrease in neuronal size, loss of neuronal cytoplasmic proteins, or any combination thereof. In some embodiments, the present disclosure describes systems and methods which act to slow the onset of symptoms of brain atrophy. The present disclosure provides systems and methods for treating any of the above-listed diseases and disorders by reducing any of the above-listed symptoms associated with brain atrophy.

For example, the methods and systems described herein may alleviate symptoms of depression. Stress, impaired neurogenesis, and defects in synaptic plasticity are associated with depression. Chronic stress promotes microglial hyper-ramification and astroglial atrophy. Thus, in some embodiments, the system and methods disclosed may alleviate symptoms associated with chronic stress or depression by improving synaptic plasticity and stimulating neural networking, along with improving microglial-mediated clearance.

Systems and methods described herein use sensory evoked potentials to slow brain atrophy, and thus mediate symptoms associated with brain atrophy through a variety of mechanisms. For example, the present disclosure describes systems and methods for reducing neuroinflammation, improving synaptic plasticity and stimulating neural networking, and improving microglial-mediated clearance of cerebral insults, all of which may contribute to the progression of brain atrophy, by inducing synchronized gamma oscillations in at least one region of a brain in a subject. The at least one brain region, for example, can include a visual cortex, a somatosensory cortex, an insular cortex, and/or a hippocampus of the subject. The present disclosure also describes systems and methods for alleviating symptoms of diseases and disorders associated with brain atrophy through non-invasive stimulation of gamma oscillations.

Atrophy of brain tissue describes the loss of volume within neurons, extracellular space, or glia. Atrophy may occur at different rates in different areas or regions of the brain, and it may be reflected by changes in whole brain volume. For an adult, whole brain volume can be, for example, between around 950 ml and 1550 ml. For an adult female, average whole brain volume can be around 1130 ml. For an adult male, average brain volume can be around 1260 ml. For a child of an age between around 4 years old and 16 years old, whole brain volume can be, for example, between 60 ml and 120 ml.

Brain volume can be measured using magnetic resonance imaging (MRI) or computerized tomography (CT) scans. Loss of brain volume may be measured by comparing brain volume over time. Various methods can be used to measure brain volume or changes in brain volume, which indicate brain atrophy. Most commonly, brain volume or brain volume loss can be measured using cross-sectional methods or longitudinal methods. Cross-sectional methods can use a single MRI scan to segment particular tissues or structures and calculate the volume of these tissue types and/or structures. Longitudinal methods can use at least two MRI scans of the same subject at different points in time to calculate brain volume changes or atrophy. Longitudinal methods may seek to match the two MRI scans using warping techniques and, from this process, directly extract small changes in brain volume.

Various tools and algorithms may be employed to determine brain volume through CT or MRI scans. Of the various toolkits available for determining brain volume and changes in brain volume based on the scanned images, examples include, but are not limited to, the following tools: Atropos, an opensource tissue segmentation algorithm; CIVET, a web-based image-processing tool for volumetric analysis with different human brain images; the Structural Image Evaluation using Normalization of Atrophy (SIENA and SIENAX), a software that applies a Brain Extraction Tool (BET) to determine cross-sectional volumes; MSmetrix, a fully-automatic tool that detects brain lesions and calculates lesion volume and measures whole-brain and gray matter atrophy; and Statistical Parametric Mapping (SPM), which for analysis of images in a MATLAB environment.

A subject with brain atrophy may experience this as a cause or result of a variety of conditions, disorders, or diseases, including but not limited to: Alzheimer's Disease (AD), dementia, Parkinson's disease, seizure, cerebral palsy, senile dementia, pick's disease, Huntington's disease, Krabbe disease, leukodystrophies, multiple sclerosis, epilepsy, anorexia nervosa, aphasia, learning disability, frontotemporal dementia, expressive aphasia, receptive aphasia, Lewy body dementia, chronic traumatic encephalopathy (CTE), and others.

The change in brain volume can be a reduction of around: 0.3 cm3 per month, 0.5 cm3 per month, 1 cm3 per month, 2 cm3 per month, 0.3 cm3 per year, 0.5 cm3 per year, 1 cm3 per year, 2 cm3 per year, 3 cm3 per year, 4 cm3 per year, 5 cm3 per year, 6 cm3 per year, 7 cm3 per year, 8 cm3 per year, 9 cm3 per year, 10 $cm^3$ per year, 11 cm3 per year, 12 cm3 per year, 13 cm3 per year, 14 cm3 per year, or 15 cm3 per year, or 16 cm3 per year. The rate of brain atrophy can differ between individuals. Exemplary rates of brain atrophy can include, but are not limited to, rates around: between 0.1% and 0.5% per year, between 0.5% and 1.5% per year, between 1.0% and 3.0% per year, or between 3.0% and 6.0% per year. The rate of brain atrophy can vary based on the cause of atrophy. For example, a healthy individual can experience an average brain atrophy rate of 0.1% and 0.4% per year. In contrast, for subjects with Multiple Sclerosis (MS), the average brain atrophy rate can be between 0.5% and 1.3% per year. The average rate of whole brain atrophy for a patient with Alzheimer's Disease can be, for example, between 1.0% and 4.0% per year. Aging can also cause brain atrophy rates to increase. For example, an individual in their mid-thirties can experience a rate of brain atrophy that is around 0.2% per year, and an individual at around age sixty can experience a rate of brain atrophy that is around 0.5% per year.

The systems and methods of the present disclosure are also directed to alleviating symptoms of brain atrophy. Symptoms may include a loss of neurons, memory loss, blurred vision, aphasia, impaired balance, paralysis, decreases in cortical volume, increases in CSF volume, loss of motor control, difficulty speaking, comprehension, reading comprehension, memory, decrease in gray and/or white matter, decrease in neuronal size, loss of neuronal cytoplasmic proteins, or any combination thereof. In some embodiments, the present disclosure describes systems and methods which act to slow the onset of symptoms of brain atrophy. The present disclosure provides systems and methods for treating any of the above-listed diseases and disorders by reducing any of the above-listed symptoms associated with brain atrophy.

The present disclosure is also directed towards improving a brain's executive functions. Executive functions may include perception, attention, knowledge formation, problem solving, concept formation, pattern recognition, association, decision making, comprehension, motor coordination, decision making, planning, or language production.

In some embodiments, the systems and methods of the present disclosure may improve cognitive capacity by improving microglial clearance, reducing amyloid-beta burden, reduce tau tangles, or promoting other neuroprotective physiological responses. For example, the systems and methods of the present disclosure may improve cognitive capacity by reducing a level (e.g., an amount or rate) of Aβ peptide in at least one brain region of a subject. In some embodiments, the systems and methods of the present disclosure may reduce production of AB peptide in the at least one brain region of the subject by, for example, reducing a level (e.g., an amount or rate) of C-terminal fragments (CTFs) and/or N-terminal fragments (NTFs) of APP in the at least one brain region of the subject. The synchronized gamma oscillations may reduce cleavage of APP into CTFs and NTFs by BACE1 and/or γ-secretase in the at least one brain region of the subject. The synchronized gamma oscillations may reduce a level (e.g., a number or rate) of endosomes in the at least one brain region of the subject. For example, the endosomes may be positive for early endosomal antigen 1 (EEA1) and/or Ras-related protein encoded by the RAB5A gene (Rab5). In some embodiments, the synchronized gamma oscillations may improve cognitive capacity by promoting clearance of Aβ peptide in the at least one brain region of the subject. The synchronized gamma oscillations may increase uptake of Aβ peptide by microglia in the at least one brain region of the subject.

The systems and methods of the present disclosure may also improve cognitive capacity by increasing a level (e.g., a number or rate) of microglial cells, a morphologic change in the microglial cells consistent with a neuroprotective state, and/or an activity of the microglial cells in at least one brain region of a subject comprising inducing synchronized gamma oscillations in the at least one brain region of the subject. The synchronized gamma oscillations may upregulate at least one differentially expressed gene, such as Nr4a1, Arc, Npas4, Cd68, B2m, Bsr2, Icam1, Lyz2, Irf7, Spp1, Csf1r, and/or Csf2ra, involved in the microglia activity in the at least one brain region of the subject. The morphologic change in the microglial cells consistent with the neuroprotective state may include an increase in cell body size and/or a decrease in process length.

In some embodiments, the systems and methods of the present disclosure may improve cognitive capacity by reducing a level (e.g., an amount or rate) of Aβ peptide in a hippocampus of a subject by optogenetically stimulating FS-PV-interneurons in the hippocampus with a plurality of light pulses, the FS-PV-interneurons expressing an optogenetic actuator, thereby entraining in vivo synchronized gamma oscillations measured by local field potentials in the excitatory neurons (e.g., FS-PV-interneurons) that reduce the level of AB peptide in the hippocampus. The light pulses may have a pulse frequency of about 40 pulses/s. Each light pulse may have a duration of about 1 ms. At least one light pulse may have a wavelength of about 473 nm. The optogenetic actuator may include channelrhodopsin, halorhodopsin, and/or archaerhodopsin. For example, the optogenetic actuator may be channelrhodopsin-2 (ChR2).

In some embodiments, the systems and methods of the present disclosure may improve cognitive capacity by reducing a level (e.g., an amount or rate) soluble and/or insoluble Aβ peptide in a visual cortex of a subject includes stimulating the subject with a plurality of light pulses at a pulse frequency of about 40 pulses/s, thereby inducing in vivo synchronized gamma oscillations in the visual cortex that reduce the level of the soluble and/or insoluble Aβ peptide in the visual cortex. In some embodiments, the systems and methods of the present disclosure may also improve cognitive capacity by reducing a level of (e.g., an amount or rate) tau phosphorylation in a visual cortex of a subject.

Methods and systems of the present disclosure may involve evaluating the likelihood of a subject to successfully respond to sensory stimulation promoting entrainment of gamma oscillations. For example, a successful response can comprise a subject indicating a willingness to engage in sensory stimulation that promotes entrainment of gamma oscillations in one or more brain regions. In some embodiments, the neural stimulation system may identify a high likelihood of a successful response and, in response, provide a prompt to the subject asking the subject to accept or decline administration of the gamma stimulation. In some embodiments, a successful response can comprise a greater degree of gamma oscillations in a brain region than before the sensory stimulation is administered.

The present disclosure also describes technologies for monitoring a person's activity, identifying whether gamma stimulation may be administered during said activity, and if so, presenting the person with a prompt encouraging initiating gamma stimulation. In some embodiments, the present disclosure describes technologies for monitoring a person's activity, identifying whether gamma stimulation may be administering during said activity, and if identified as appropriate, providing the gamma stimulation. In some embodiments, the described technology involves a sensor operatively coupled to a device. Devices can include any device capable of input and output functions.

The sensor operatively coupled to a device may inform whether a subject can benefit from administration of gamma stimulation. For example, the benefit from administration of gamma stimulation can be one or more of: (a) maintaining and/or reducing a blood level (e.g., an amount) of a glucocorticoid involved in a stress response in a subject; (b) preventing and/or reducing anxiety in a subject; (c) maintaining and/or enhancing memory association in a subject; (d) a maintaining and/or enhancing cognitive flexibility; (e) maintaining and/or reducing changes to anatomy and/or morphology in at least one brain region of the subject; (f) maintaining and/or reducing changes to a number of neurons, a quality of DNA in the neurons, and/or a synaptic puncta density. In some embodiments, the device that induces synchronized gamma oscillations in at least one brain region of a subject can prevent, mitigate, and/or treat dementia and/or anxiety in the subject, maintain and/or enhance a memory association and/or cognitive flexibility of the subject, and/or maintain and/or reduce changes to anatomy, morphology, cells, and molecules in the at least one brain region of the subject.

For example, the benefit may comprise (c) maintaining and/or enhancing memory association in a subject. In one aspect, maintaining and/or enhancing memory association comprises maintaining and/or enhancing spatial memory. In one aspect, the benefit comprises (d) maintaining and/or enhancing cognitive flexibility. In one aspect, the benefit comprises (e) maintaining and/or reducing changes in at least one brain region. For example, the changes in anatomy and/or morphology may include changes in one or more of: brain weight, lateral ventricle size, a thickness of a cortical layer, a thickness of a neuronal layer, and/or a blood vessel diameter. The at least one brain region may include, for example, a visual cortex, a somatosensory cortex, and/or an insular cortex. In another embodiment, the benefit comprises (f) maintaining and/or reducing changes to a number of neurons, a quality of DNA in the neurons, and/or a synaptic puncta density in at least one brain region of a subject, such as a visual cortex, a somatosensory cortex, an insular cortex, and/or a hippocampus of the subject.

In some embodiments, the present technological solution provides methods and systems directed at monitoring and/or observing and/or recording aspects related to non-invasive sensory stimulus. In some embodiments, monitoring and/or observing and/or recording is implemented and/or provided by the neural stimulation system. In some embodiments, monitoring is provided via a separate, operatively coupled device, such as a personal tablet or mobile phone. In some embodiments, monitoring of the context or setting in which therapy is taking place, or more generally monitoring context of a therapy user or others associated with the user or delivery of therapy may usefully inform the scheduling and selection of devices through which therapy is delivered, the scheduling and dosing of therapy, or other aspects of the management and delivery of therapy and related activities and interactions. In such scenarios monitoring of context or setting may also usefully inform analysis of the effectiveness of therapy and the identification of more or less effective opportunities for therapy delivery, or the configuration and management of other aspects related to therapy delivery and therapeutic outcomes, including engagement and burdens related to therapy.

In some embodiments, aspects related to non-invasive sensory stimulus include but are not limited to one or more of: user context, social context, events, environment, ambient conditions, device environment, device capabilities, location, weather, activities. In some embodiments monitoring and/or observing and/or recording is directed at improving therapeutic effectiveness and/or outcomes and/or engagement and/or compliance of one or more users and/or third parties. In some embodiments monitoring and/or observing and/or recording is directed at one or more of: stimulus delivery management, stimulus configuration, identifying opportunities for therapy delivery, scheduling therapy delivery, configuring therapy delivery. In some embodiments one or more of the following are responsive to monitoring and/or observing and/or recording: therapy dispatch, therapy distribution, therapy configuration, feedback, motivation, analysis, combination.

In some embodiments, the present technological solution performs monitoring of social aspects. In some embodiments, social aspects include, but are not limited to one or more of: presence of one or more users and/or third parties, one or more relationship between one or more user and/or third party, social calendar, social context, social event, social network information, social network activity, interactions between one or more users and/or third party, propinquity, proximity among two or more users and/or third parties, contacts and/or contact and/or proximity histories among two or more users and/or third parties. In some embodiments, monitoring of social aspects is directed at one or more of: identifying one or more social relationships, recording one or more social network, confirming one or more social aspect, identifying one or more social aspect. In some embodiments, monitoring of social aspects is directed at one or more of: identifying a current and/or potential care partner, locating a current and/or potential care partner, locating and/or identifying a friend, relative, caregiver, clinician, or other third party. In some embodiments, monitoring of social aspects is performed by the neural stimulation system. In other embodiments, monitoring of social aspects is performed by a computer processor. In some embodiments, monitoring of social aspects is performed by operatively coupling a personal device, such as a tablet or smartphone, to the neural stimulation system. In other systems, a cloud-based system for transferring data and information is used.

In an exemplary embodiment, monitoring of social aspects is directed at one or more of: recording and/or characterizing involvement and/or participation of one or more third party in one or more administrations of non-invasive sensory stimulus. In an exemplary embodiment, monitoring of social aspects is directed at distributing and/or reducing and/or assigning one or more burden and/or workload and/or task associated with non-invasive sensory stimulation. For example, monitoring of social aspects may include monitoring the distribution among care partners or caregivers of a workload associated with non-invasive sensory stimulation over the course of a period of time. In such an example, in some embodiments, scheduling or locations or dosing of the is formulated or modified responsive to such monitoring directed at more evenly distributing the workload among care partners or caregivers and/or identifying alternative or substitute care partners or caregivers. In some embodiments, monitoring of social aspects identifies two or more caregivers or care partners characterized by a social relationship with one or more of: each other, a user, a third party. In some embodiments, identification of two or more caregivers or care partners characterized by a social relationship is directed at coordinating the therapy related activities of two or more care givers or care partners. For example, identification of a relationship such as kinship, friendship, or frequent contact or communication among two or more people participating in supporting the administration of non-invasive sensory stimulation or associated activities may be used in part to schedule therapy sessions so that two or more such people are available whenever care is administered, or to provide the option for two or more such people to assist in therapy delivery. Conversely, in some embodiments, monitoring of social aspects, in particular monitoring of contacts or contact histories of one or more individuals, is used in part (e.g., in conjunction with infection testing, epidemiological data, or other health information), to restrict and/or select individuals and/or constrain and/or exclude individuals' participation in administration of non-invasive sensory stimulation. In some embodiments, monitoring of social aspects is directed at reducing the chance of users and/or individuals participating in a user's therapy from transmitting disease.

In some embodiments, monitoring of social aspects is used at least in part to identify individuals participating in a user's therapy or with potential to participate in a user's therapy, based at least in part on proximity and/or propinquity. In some embodiments, identification of one or more individuals with potential to participate in a user's therapy is directed at identifying individuals to substitute for individuals excluded from participating in therapy. In some embodiments, social monitoring includes one or more communication with one or more user and/or third party. In some embodiments, communication with one or more user and/or third party includes one or more of messages, notifications, chats, interactions directed at determining one or more of: availability, willingness, competency of one or more user and/or third party. In a further exemplary embodiment, scheduling and/or distributing of one or more therapy is responsive to the determining of availability and/or willingness and/or competency of one or more user and/or third party. For example, therapy delivery may be scheduled responsive to a determination that a caregiver collocated or nearby to a user is willing to and/or capable of assisting in the delivery of non-invasive stimulus.

In some embodiments, the present technological solution performs monitoring of activity aspects. In some embodiments, activity aspects include, but are not limited to one or more of: categorization and/or identification and/or recording and/or observation or one or more activities engaged in by one or more user and/or third parties. In some embodiments, activity aspects include one or more of: workload and/or burden and/or project and/or objective and/or responsibility associated with one or more users and/or third party. In some embodiments, monitoring of activity aspects is directed at one or more of: characterizing burden and/or distraction and/or workload and/or responsibility associated with one or more user and/or third party.

In an exemplary embodiment, monitoring of activity aspects is directed at characterizing the congruence and/or compatibility with one or more activity engaged in by one or more user and/or third party with administration of non-invasive sensory stimulation. In an exemplary embodiment, characterizing the congruence and/or compatibility with one or more activity is directed at improving engagement and/or involvement and/or effectiveness and/or reliability of a contribution of one or more user and/or third party to the delivery of non-invasive sensory stimulation.

For example, monitoring of activity aspects may include monitoring or categorizing the tasks or activities that a user is engaged in concurrently or proximate to the delivery of non-invasive sensory stimulation with respect to the level or burden or distraction they impose on the individual engaged in the task, or on others present. In such an example, monitoring of activity is directed at scheduling or configuring therapies so that activities in which users are engaged do not distract from, interfere with, or compromise therapy delivery. For example, users may be engaged in challenging or fatiguing activities or even enjoyable but distracting tasks, during which the administration of non-invasive sensory stimulation would be compromised. In such examples, therapy administration may be rescheduled to avoid periods during or proximate to such activity.

Similarly, monitoring of activity aspects may include monitoring or categorizing the kinds of tasks or activities a caregiver or care partner is engaged in concurrently or proximate to the delivery of non-invasive sensory stimulation to avoid scheduling therapy delivery during periods proximate to caregiver or care partner activities likely to compromise or disrupt the delivery of therapy. Conversely, therapy may be scheduled or configured to avoid disrupting activities in which a person is engaged. For example, in some scenarios, a care partner may be engaged in other tasks or activities that are important to them or their wellbeing, or that impact the effectiveness and persistence of their participation in a patient's care. In such a scenario, monitoring of activity aspects may be directed at identifying and characterizing such activities, so that delivery of therapy, or caregivers' and/or care partners' participation in delivery of therapy, is directed at disrupting or interfering with such activities.

In some embodiments, location monitoring of one or more user and/or third party is performed. In some embodiments, location monitoring includes one or more of: tracking location of one or more individual, tracking proximity of one or first individual to one or more second individual, tracking location histories of one or more individual, determining colocation or co-location histories, contract tracing. In some embodiments location monitoring includes receiving and/or requesting and/or incorporating and/or analyzing and/or processing location information, including but not limited to location and/or location related information acquired from a system service or API or external source.

In an exemplary embodiment, scheduling of one or more therapy or session of non-invasive sensory stimulation or related therapies is responsive, at least in part, to location monitoring of one of one or more user and/or third party, including, but not limited to location and/or co-location history. For example, therapy may be scheduled and/or distributed responsive to identification of periods of colocation and/or proximity of one or more third party with one or more user.

In some embodiments, scenario monitoring of one or more user and/or third party and/or therapy is performed. Scenario monitor may include, for example, one or more of: risk monitoring, scenario identification, scenario categorization, scenario prioritization, scenario formulation. In some embodiments, scenario monitoring incorporates activity and/or social and/or other context information. In some embodiments, scenario monitoring includes predicting one or more of: activity, context, role, relationship, location, responsibility. In some embodiments, scenario monitoring incorporates and/or is responsive to analysis. In some embodiments, scenario monitoring is performed by a separate device operatively coupled to the Neural Stimulation System. In other embodiments, the Neural Stimulation performs scenario monitoring.

In an exemplary embodiment, scenario monitoring determines or assesses likelihood, responsive to observations of activity and/or social presence and/or location monitoring and/or other context monitoring and/or actigraphy, that a user is about to or has engaged in an activity or scenario. For example, scenario monitoring may determine, responsive to departure of one or more care partners in conjunction with observation of activity associated with preparation for sleep that a user is about to go to bed. In some embodiments, therapy distribution and/or dispatch and/or configuration is responsive to scenario monitoring. For example, responsive to determination that a user is about to go to bed, in some embodiments, therapy may be scheduled or proposed to a user or may be configured for pre-sleep dosing and administration.

In some embodiments, weather monitoring associated with one or more user and/or third party and/or therapy is performed. In some embodiments weather monitoring includes one or more of: recording weather proximate to therapy administration, recording weather proximate to user and/or third-party activity, recording weather proximate to assessment, recording weather proximate to other event, recording weather proximate to disease related event. In some embodiments weather monitoring includes correlating one or more weather conditions with one or more aspects of context monitoring and/or one or more aspect of user monitoring and/or one or more aspects of stimulus signal and/or one or more assessment and/or one or more analysis. In some embodiments weather monitoring includes receiving and/or requesting and/or incorporating and/or analyzing and/or processing weather information, including but not limited to weather and/or weather-related information acquired from a system service or API or external source.

In some embodiments, stimulus opportunity monitoring of one or more user and/or third party and/or context and/or scenario is performed. In some embodiments stimulus opportunity monitoring includes one or more of: observing correlations between context monitoring and/or user monitoring and/or other aspects, directed at detecting and/or identifying opportunities to delivery stimulus and/or associated therapies. In some embodiments, stimulus opportunity includes one or more of: available care partners, available devices, device capabilities, third party capabilities, candidate stimulus delivery settings, candidate delivery conditions, third party state, user state.

In some embodiments, stimulus opportunity monitoring is directed at identifying and/or characterizing and/or categorizing one or more routine of one or more user and/or third party. In some embodiments, stimulus opportunity monitoring is directed at identifying and/or characterizing and/or categorizing one or more third party candidates to assist in therapy administration and/or support. In some embodiments, stimulus opportunity monitoring is directed at identifying and/or characterizing and/or categorizing one or more device capable of and/or suitable for delivering therapy. In some embodiments stimulus opportunity monitoring is directed at identifying and/or characterizing and/or categorizing one or more time suitable for therapy delivery. In some embodiments, stimulus opportunity monitoring is directed at identifying and/or characterizing and/or categorizing one or more environment suitable for therapy delivery.

In some embodiments, monitoring of a routine is directed at avoiding disruption of routine. In an exemplary embodiment, stimulus configuration and/or dispatch and/or distribution is directed at preserving a routine detected at least in part by monitoring. For example, monitoring may determine a time of day or location during which a user or their caregiver engages in a hobby, chore, or other activity, and stimulus may be scheduled to occur at times other than those during which such engagement has been observed to occur. Alternatively, monitoring of a routine may be used to determine the best way to incorporate gamma stimulation therapy without disrupting the routine. For example, the Neural Stimulation System may determine that the subject routinely watches a one-hour show and can administer stimulation during that one-hour period.

In some embodiments, the systems and methods of the present disclosure may improve cognitive capacity by improving a user's sleep quality. For example, the systems and methods of the present disclosure may improve cognitive capacity by producing beneficial changes in actigraphy during sleep periods in one or more of: subjects at risk of AD, subjects experiencing cognitive decline, subjects experiencing sleep disruption, subjects diagnosed with AD, subjects diagnosed with MCI, healthy subjects, subjects with sleep pathologies, and subjects with sleep disruptions. In some embodiments, beneficial changes in actigraphy includes reduction in sleep fragmentation. Beneficial changes in actigraphy may include one or more of: increases the frequency of restful periods during sleep periods and/or reduction in the frequency of sleep interruptions during sleep periods. In some embodiments, the present disclosure delivers non-invasive stimulation directed at producing a reduction in sleep fragmentation during night-time sleep of mild to moderate AD patients. In some embodiments, the present disclosure further describes technologies directed at increasing the length of restful periods during sleep and/or reducing the frequency of awakenings during sleep.

In some embodiments, technologies directed at producing beneficial changes in actigraphy are further directed at producing beneficial sleep-related health outcomes. Beneficial sleep-related health outcomes may include one or more of: clearance of brain waste products, mitigation of cognitive deficits, slowing or delay of AD progression, reduction of circadian rhythm disruptions, reduction of microglial aging and activation, reduction in cognitive impairment, reduction in depression symptoms, mitigation of appetite or eating disorders, reduction in agitation, reduction in apathy, reduction in psychosis symptoms (including delusions and hallucinations), reduction in aggression, reduction in behavioral and psychiatric symptoms of dementia, stabilizing and/or preventing the degradation of one or more measures of performance. In some embodiments, mitigated circadian rhythm disruptions include but are not limited to disruptions associated with: AD, MCI, ageing, eating disorders, irregular sleep wake rhythm disorder, depression, anxiety, stress.

Figure 32:
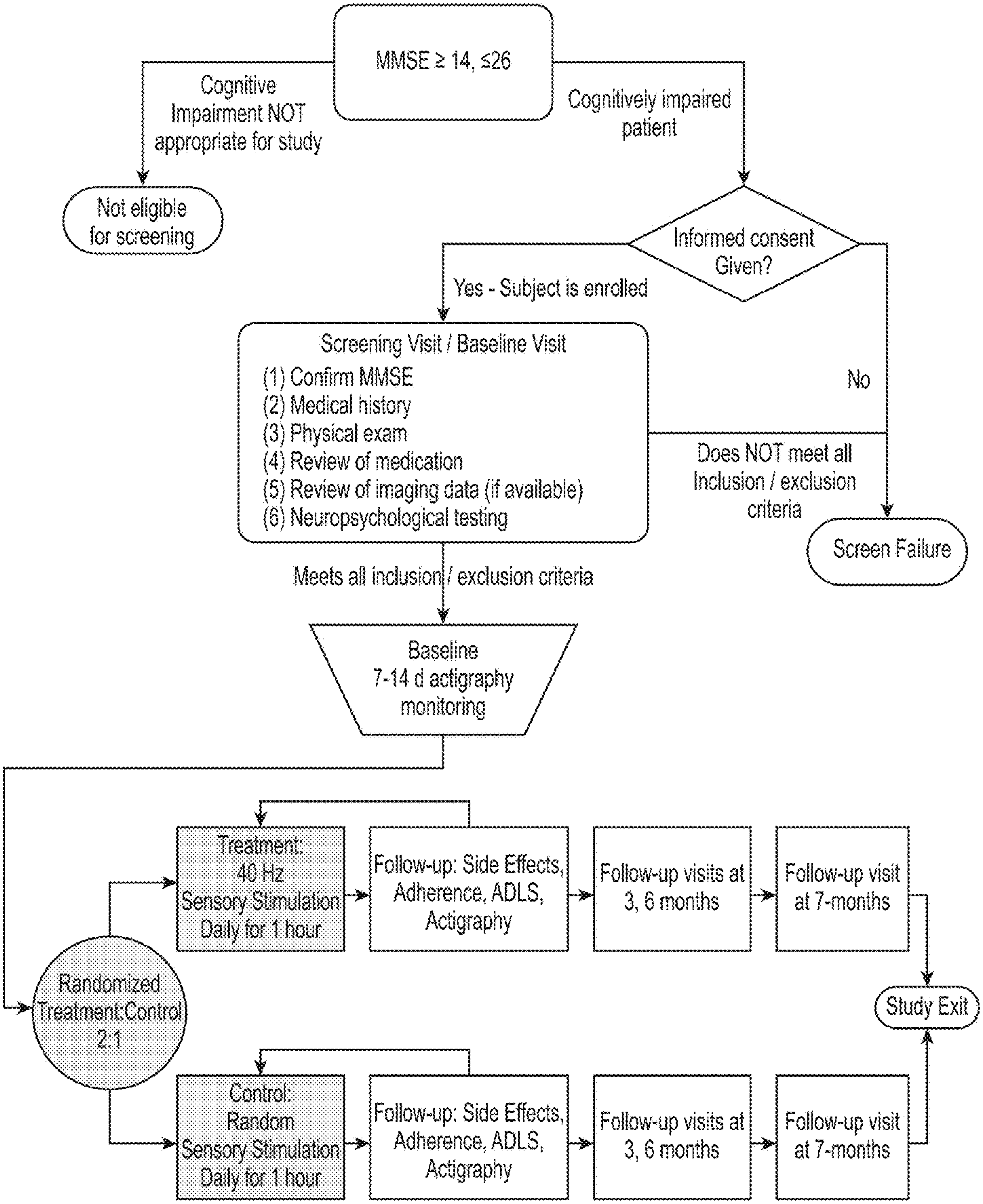
FIG. 32 demonstrates an overview of enrollment, treatment, and control for an exemplary embodiment of non-invasive stimulation improving sleep quality in mild to moderate AD subjects. Treatment was delivered to two thirds of the subjects (12) using 40 Hz frequency audio, and one third of subjects (6, "control") at an alternate frequency.
Figure 33:
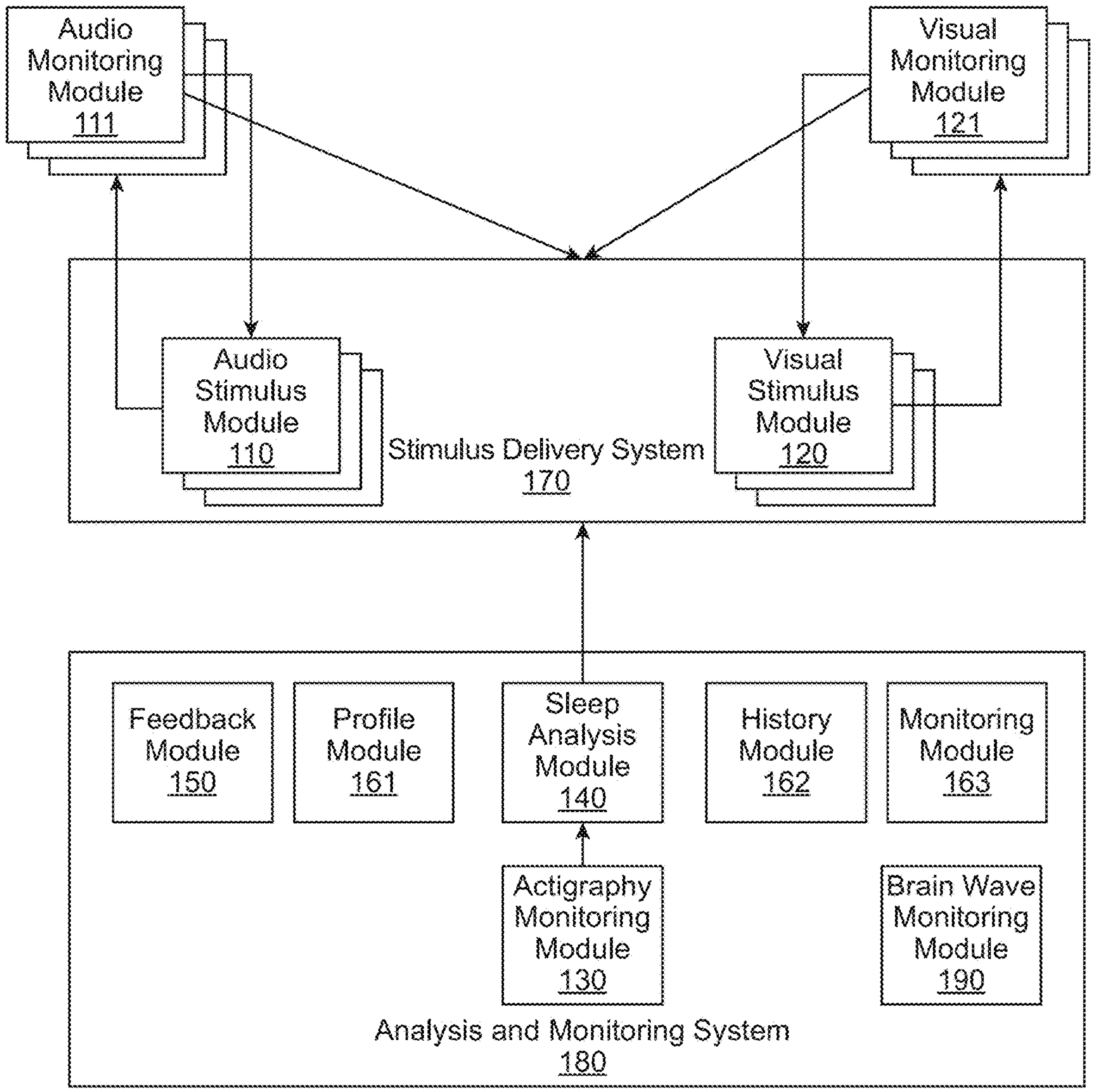
FIG. 33) and Visual Stimulus Module (120.
Figure 34:
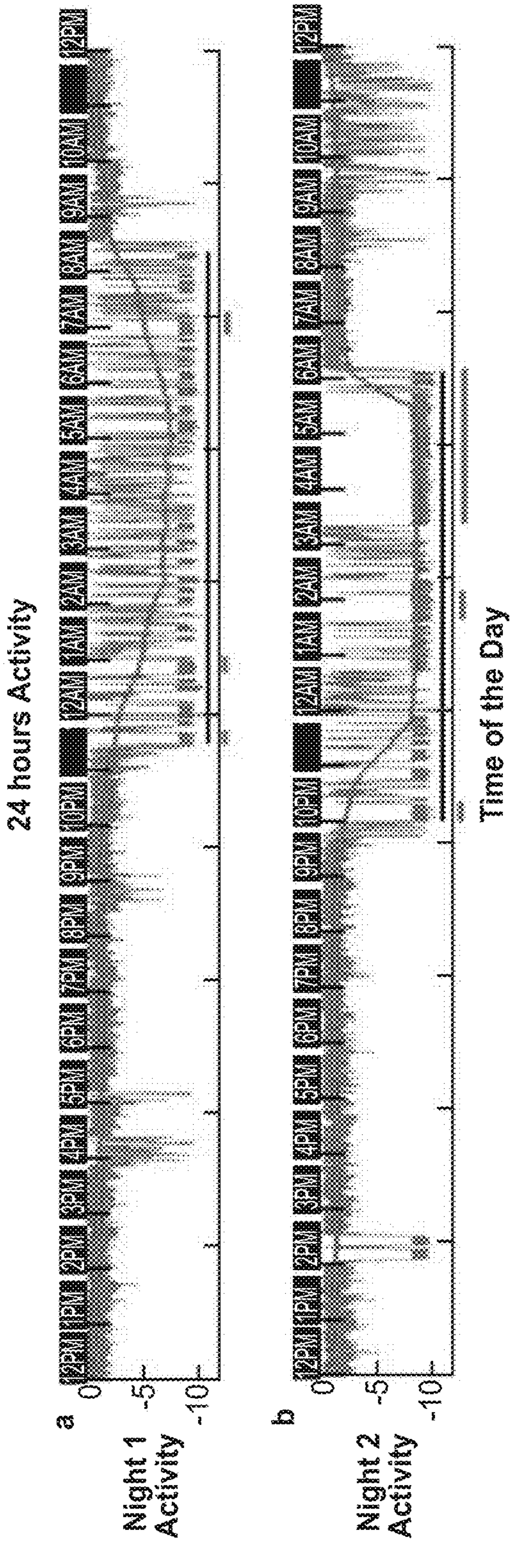
FIG. 34 provides actigraphy data from 24 hours of activity levels (gray bar; 1501, FIG. 37) over two days for a single example patient, centered around 12 AM (indicated by double-sided arrow) along with a median filtered curve (labeled with a dotted arrow; 1507, FIG. 37). The horizontal axis of FIG. 34 shows time of day, and the vertical axis is relative activity recorded on a wrist-worn actigraphic measuring device (arbitrary log scale). Calculated sleep periods (black horizontal lines; see 1508, FIG. 37) along with individual sample rest periods (yellow horizontal lines; see 1509, FIG. 37) are shown: with the top panel (a) showing an exemplary pattern for frequent movements and short rest periods during sleep periods, and the bottom panel (b) showing an exemplary pattern of less frequent movements and longer rest periods during sleep periods.

In some embodiments, sleep, during sleep, or sleep periods may refer to nighttime periods of relative inactivity or periods of frequent rest. In some further embodiments, such periods of relative inactivity or frequent rest refer to those characterized patterns of actigraphy, including but not limited to patterns of actigraphy identified using the methods described in embodiments of the present technological solution. FIG. 32 provides an example of a pattern of actigraphy identified using the methods described herein. FIG. 32 shows twenty-four (24) hours of activity levels (gray; 1501, FIG. 37) over two days for a single example patient, centered around 12 AM (indicated by the thick, gray arrows) along with a median filtered curve (labelled by thin arrows; 1507, FIG. 37). The horizontal axis shows time of day; the vertical axis is relative activity recorded on a wrist-worn actigraphic measuring device (arbitrary log scale). Calculated sleep periods (black horizontal lines; see 1508, FIG. 37) along with individual sample rest periods (yellow horizontal lines; see 1509, FIG. 37) are shown: with (a) showing an exemplary pattern for frequent movements and short rest periods during sleep periods, and (b) showing an exemplary pattern of less frequent movements and longer rest periods during sleep periods. Similarly, FIG. 33 provides exemplary patterns of actigraphy (arbitrary units, see FIG. 34). FIG. 33 provides actigraphy data for over several days (gray; e.g., 1501, FIG. 37), and a smooth curve is superposed. The cutoff line (black line) separates active vs rest periods (e.g., 1505, FIG. 37). The black squares represent initial estimation for the mid-night point (e.g., 1507, FIG. 37), of which a final assessment of the mid-night points will be determined through optimization algorithm e.g., 1508, FIG. 37).

Delivery Methods and Systems

The present disclosure provides a method directed at improving cognitive functioning and/or evoking gamma wave oscillations in a subject, the method comprising non-invasively delivering a signal configured with stimulus program parameters directed at improving cognitive functioning and/or evoking gamma wave oscillations in a subject. In some embodiments, the present disclosure archives sleep quality improvement by enhancing coherence or power of gamma oscillations in at least one brain region of the subject.

In some embodiments the non-invasive signal is delivered through one or more of: visual, auditory, tactile, olfactory stimulation, or bone conduction. In some embodiments combined audio-visual stimulation is delivered for an hour each day for a 3 to 6 month or longer period. In some embodiments, stimulation is delivered for two hours each day. In some embodiments, stimulation is delivered for multiple periods over the course of a day. In some embodiments combined audio-visual stimulation is delivered over an extended open-ended period of time. In some embodiments stimulus is delivered in periods of varying durations. In some embodiments stimulus is delivered responsive to opportunities to effectively deliver stimulus, such opportunities determined by one or more of: monitoring, analysis, user or care giver input, clinician input. In some embodiments, a first stimulus period is delivered through a first apparatus, and a second stimulus period is delivered through a second apparatus. In some embodiments, a first stimulus period and a second stimulus period are delivered through a single apparatus.

In some embodiments, the non-invasive signal is delivered at least in part through glasses, goggles, a mask, or other worn apparatus that provide visual stimulation. In some embodiments, the non-invasive signal evokes gamma wave oscillations to improve sleep.

In some embodiments, the non-invasive signal is delivered at least in part through one or more devices in the user's environment, such as a speaker, lighting fixtures, bed attachment, wall mounted screen, or other household device. In a further embodiment, such devices are controlled by a further device, such as a phone, tablet, or home automation hub, configured to manage the delivery of the non-invasive signal through the one or more devices in the user's environment. In some embodiments such devices may additionally include worn devices.

In some embodiments, the non-invasive signal is delivered at least in part through headphones that provide auditory stimulation. In some embodiments, the present disclosure evokes gamma wave oscillations to improve sleep through headphones that provide auditory stimulation.

In some embodiments, the non-invasive signal is delivered through a combination of visual and auditory stimulation. In some embodiments, the present disclosure evokes gamma wave oscillations to improve sleep through a combination of visual and auditory stimulation.

In some embodiments, the non-invasive signal is delivered through a pair of opaque or partially transparent glasses worn by the subject with illuminating elements on the interior providing a visual signal. In some embodiments, the non-invasive signal is delivered through headphones or earbuds worn by the subject providing an auditory signal. In some embodiments, combined visual and auditory signals are provided by such headphones and glasses worn together at the same time. In some embodiments visual and auditory signals are delivered separately by glasses or headphones worn at different times. An exemplary embodiment includes a pair of glasses, with LEDs on the interior of the glasses providing visual stimulation and headphones providing auditory stimulation.

In some embodiments, subjects control aspects of the stimulus signal directed at achieving one or more of: tolerance, comfort, effectiveness, reduction in fatigue, compliance, adherence. In some embodiments, subjects or third parties can pause, interrupt, or terminate delivery of stimulus. In an exemplary embodiment, subjects and/or third parties can adjust peak audio volume and/or visual intensity of stimulus within a predefined safe operating range using a hand-held controller operably coupled to a stimulation delivery apparatus.

In some embodiments, the non-invasive signal is delivered through vibrotactile stimulation via an article of clothing or body attachment suitable for wearing proximate to or during periods of sleep or rest. In some embodiments such body attachment may include a device providing treatment for a condition of a user during sleep, such as a CPAP device. In some embodiments non-invasive signals may be delivered through the user's nostrils.

In some embodiments, the non-invasive signal is administered at least in part by a device as specified in one or more of US Patents U.S. Pat. No. 10,307,611 B2, U.S. Pat. No. 10,293,177 B2, or U.S. Pat. No. 10,279,192 B2.

In some embodiments, the present disclosure delivers the non-invasive signal through a sleep mask worn over open or closed eyes of a subject. In some embodiments, the present technological solution further provides visual stimulation through closed or partially closed eyelids. In some embodiments, a sleep mask is any device worn by the user proximate to sleep periods. In some embodiments, a sleep mask, may be used in contexts and at times unrelated to sleep periods.

In an exemplary embodiment, a sleep mask with built-in or Bluetooth-paired or other wireless technology-paired or physically paired headphones or earbuds provides the capability for delivering visual stimulation, auditory stimulation, or a combination of the two. In a further exemplary embodiment visual stimulation is automatically provided when the mask is covering the eyes and auditory stimulation is only provided when headphones or earbuds are seated or worn.

In some embodiments, stimulation is delivered by a device that can be worn throughout a subject's sleep period (including but not limited to, for example, a sleep mask embodiment). In a further embodiment, stimulation can be delivered by the device responsive to a user's detected sleep state and/or other information indicative of a user's activity. In an exemplary embodiment, the device delivers stimulation only during periods of detected sleep interruptions, or specific sleep stages, including but not limited to resting before the first period of sleep and/or waking or leaving a sleep area during the night. In some embodiments, stimulation parameters are adjusted responsive to detected sleep state or other monitoring. In an exemplary embodiment, users are offered audio-only stimulation during nighttime periods of sleep interruption. In some embodiments sleep state is detected responsive to one or more of: EEG, information about the location or position of a subject, actigraphy.

In some embodiments, stimulation is delivered to more than one subject present in a space. In an exemplary embodiment, stimulation is delivered to more than one subject in a space through devices present in the space, such devices delivering the same stimulus to all present subjects, or customized stimulus to individual subjects, or a combination thereof.

Monitoring, Feedback, and Motivation.

In some embodiments, the present disclosure also provides for one or more of monitoring improvements in cognitive function and/or neural entrainment, providing feedback to users and third parties relating to these aspects, and motivating users or third parties in the use of the stimulation device or other related activities or therapies. For example, TABLE 1 provides an exemplary testing and monitoring protocol. In TABLE 1, X indicates an office assessment, P indicates a phone assessment, and A indicates an in-home assessment. In some embodiments, an in-home assessment comprises an in-person assessment. In some embodiments, an in-home assessment comprises a video call or a phone call. In some embodiments, the present disclosure executes the exemplary protocol of FIG. 33 in assessing sleep-related conditions. In some embodiments, the present disclosure uses other measures of the effects of non-invasive stimulation. In some embodiments, for example, the present disclosure provides a system that assesses sleep-related conditions using the protocol provided in FIG. 32.

TABLE 1

Exemplary Testing and Monitoring Protocol.

| | Screening/ Baseline ≤12 Weeks | On-going Therapy Sessions (M = months, all visits window + 14 days, 1M = 4 weeks) | | | | | | | | Follow Up |
|---|---|---|---|---|---|---|---|---|---|---|
| Required Testing | from Consent | Initial Tx | 1 M | 2 M | 3 M | 4 M | 5 M | 6 M | Early Term | 7 M[2] |
| MMSE | X | | | | | | | X | X | |
| Medical History | X | | | | | | | | | |
| Physical and Neurological Exam | X | | | | X | | | X | X | X |
| APOE Status Test | X | | | | | | | | | |
| Review Medications | X | | | | X | | | X | X | X |
| NPI[1] | X | | | | X | | | X | X | X |
| ADAS-Cog14 | X | | | | X | | | X | X | X |
| CDR[1] | X | | | | X | | | X | X | X |
| Clock Drawing Test | X | | | | X | | | X | X | X |
| C-SSRS | X | | | | X | | | X | X | X |
| ADL[1] | X | | P | P | X | P | P | X | X | X |
| QOL-AD[1] | X | | P | P | X | P | P | X | X | X |
| Review of Adverse Events | | X | P | P | X | P | P | X | X | X |
| Actigraphy Monitoring | A | | A | A | A | A | A | A | A | A |

TABLE 1-continued

Exemplary Testing and Monitoring Protocol.

| Required Testing | Screening/ Baseline ≤12 Weeks from Consent | On-going Therapy Sessions (M = months, all visits window + 14 days, 1M = 4 weeks) Initial Tx | 1 M | 2 M | 3 M | 4 M | 5 M | 6 M | Early Term | Follow Up 7 M[2] |
|---|---|---|---|---|---|---|---|---|---|---|
| Decision Capacity assessment | X | | | | X | | | X | X | |
| Care partner Capacity Survey (ZBI)[1] | X | | X | X | X | X | X | X | X | X |
| Blinding assessment | | X | | | | | | X | X | |
| EEG assessment (Entrainment) | X | | | | X | | | X | | |
| MRI assessment | X | | | | X | | | X | X[a] | |
| Amyloid PET assessment | X | | | | X | | | X | X[a] | |
| Treatment Sessions (Care Partner Diary) | | X | | | | | | X | | |
| B12, Inflammation panel and Biomarker Sample | X | | | | X | | | X | X | |
| Field Support Home Visits[b] | X | X, A | | | | | | A | A | |
| User Experience Interview[b] | | A | | | | | | A | A | A |

[a]Only if not done within previous 8 weeks.
[b]Done by Cognito Team; visit window does not apply to allow for support as needed throughout the study. Additional Ad Hoc visits may occur; may be done by home visit, video call or telephone call as needed for adequate subject support and data collection.
[1]Includes care partner interview.
[2]7 M Visit only conducted if subject did not continue on to the Extension Phase immediately after the 6 M Visit.

Monitoring

In some embodiments, systems and methods of the present disclosure perform measurements of sleep quality. Measurements of sleep quality may include one or more of: waking durations, time out of bed, motion, body position, eye motion, eyelid status, respiratory sounds, snoring, respiration, heart rate, HRV, respiratory rate, sleep fragmentation. Measurements of sleep quality may include environmental aspects associated with sleep quality including but not limited to one or more of: room noise, room temperature, air circulation, air chemistry, bed temperature, partner sleep attributes, room configuration. Measurements of sleep quality may include other aspects associated with sleep quality, including but not limited to one or more of: alertness tests or self-reports, assessments, surveys, cognitive challenges, physical challenges, task performance, productivity, third party assessment, daily activity, sports performance, appetite, weight gain or loss, hormonal changes, medication use, or other aspects of user performance or wellbeing known or likely to be correlated with sleep quality. Measurements of sleep quality may include measurements taken during sleep or at other times, as appropriate.

Figure 28:
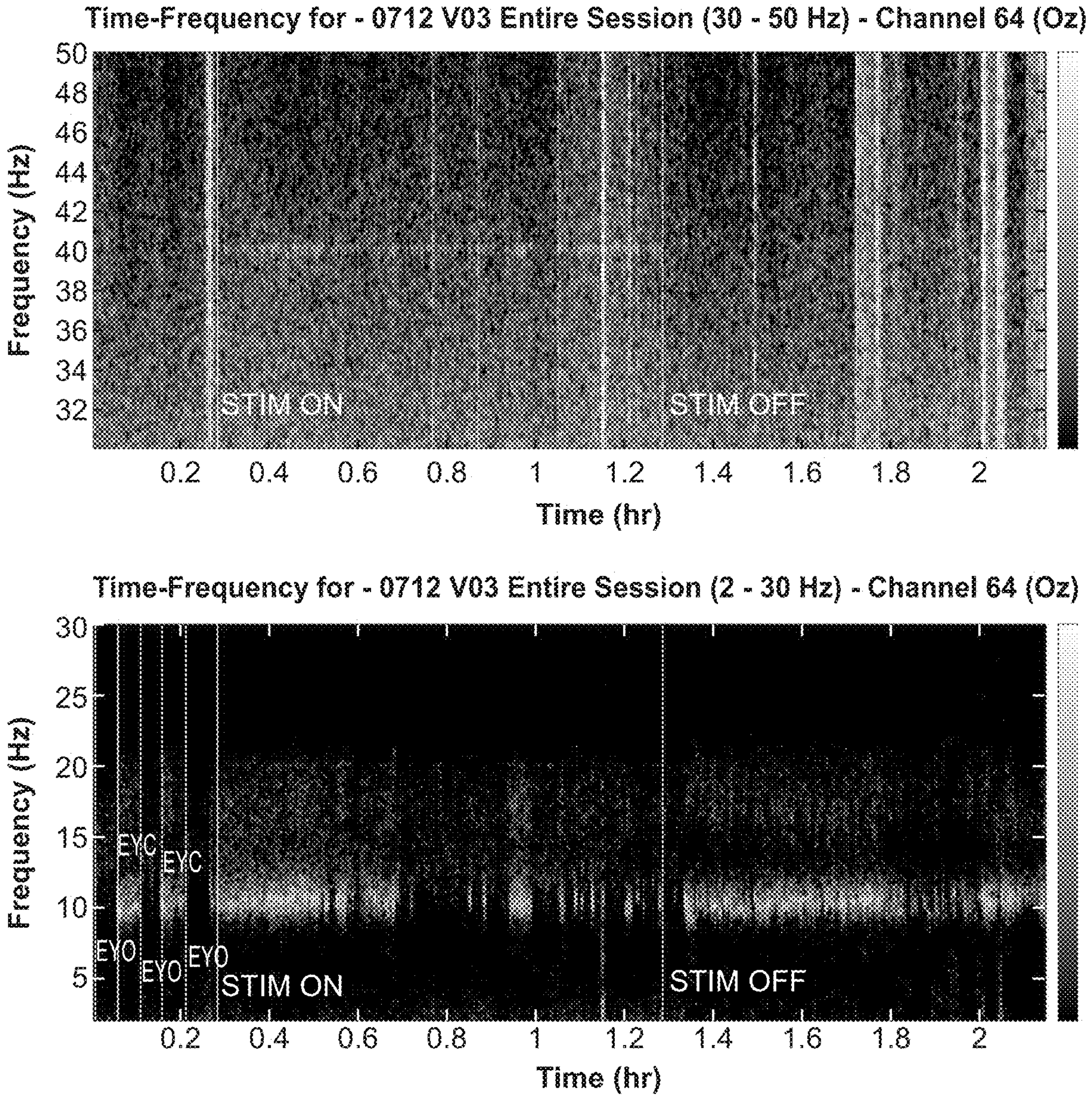
FIG. 28 demonstrates power changes responsive to (1 hr) 40 Hz LED stimulus in an exemplary embodiment showing 40 Hz steady state oscillation and enhanced alpha power during and following stimulus, in a young healthy subject. Both panels illustrate the time-frequency domain decomposition of EEG activity recorded over the occipital pole (Oz, channel-64) before, during and after 40 Hz gamma stimulation. The start and stop of gamma stimulation are marked with STIM ON and STIM OFF boundaries in both panels. The upper panel illustrates enhanced 40 Hz power during stimulation indicating steady-state visually evoked potential (SSVEP). The lower panel shows alpha-power dynamics during eyes-open (EYO) and eyes-closed (EYC) conditions, and the enhanced alpha power both during eyes-open gamma stimulation, as well as following the one-hour 40 Hz gamma stimulation.
Figure 29:
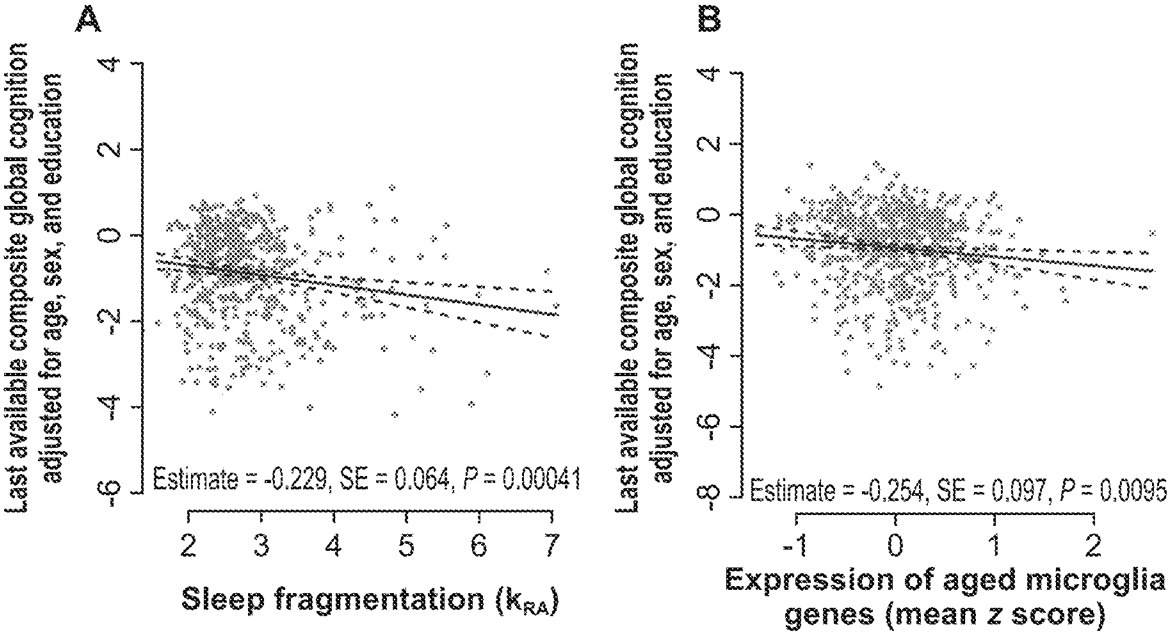
FIG. 29 provides illustrations of the composite global cognitive summary score as a function of average sleep fragmentation (panel A), and composite expression of genes enriched in aged microglia (panel B). The dotted lines show 95% confidence intervals of estimate.
Figure 30:
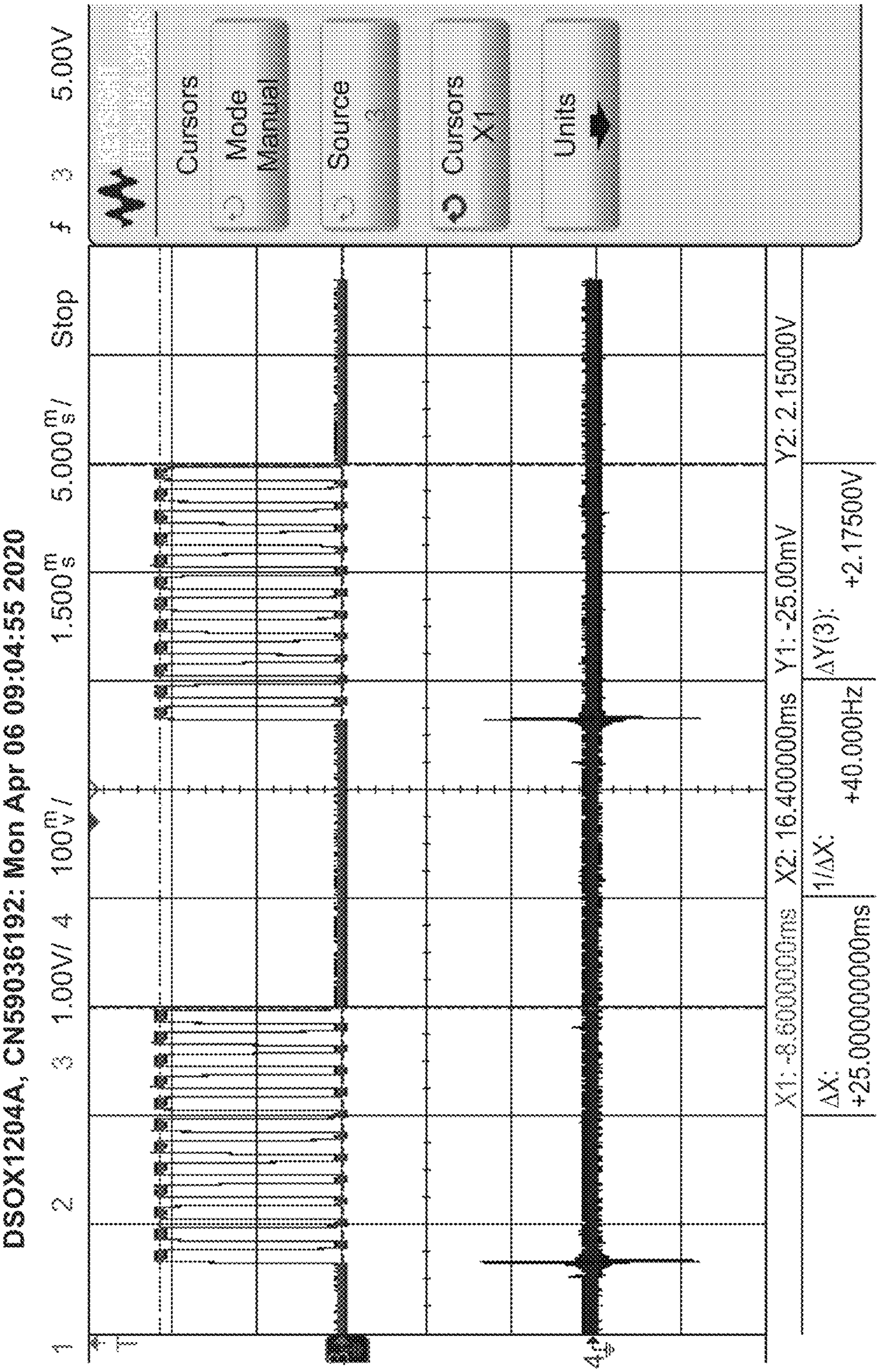
FIG. 30 provides an oscilloscope capture of the visual (upper signal) and audio (lower signal) signals of an exemplary non-invasive sensory stimulus with fs equal to 40 Hz, vd equal to 50%, VD equal to 50%, ft equal to 7,000 Hz, and AD equal to 0.57%.

In some embodiments, monitoring may include measuring of a subject's brain wave parameters, including but not limited to neural activity, gamma entrainment, power in specific frequency bands, attributes of resting quantitative EEG, sensory evoked potentials, steady-state oscillations and induced oscillations, changes in coherence, cross-frequency amplitude coupling, harmonics. In some embodiments, measurement of a subject's brain wave parameters is performed by a module incorporated into a component of the stimulation delivery apparatus. In some embodiments, measurement of a subject's brain wave parameters is performed by a module incorporated into a separate device. In some embodiments, gamma entrainment and/or entrainment at other frequencies is detected by one or more methods (e.g., FIG. 28) and systems described at least in part in U.S. Pat. No. 10,279,192 B2 (e.g., as illustrated there in FIG. 39, by identifying a plurality of neurons in the brain of a subject oscillating at a specific frequency following or during the application of stimulus).

In some embodiments an entrainment score, responsive at least in part to, measurement of gamma entrainment, is computed. In some embodiments, measurements and computations directed at entrainment detection activities are performed according to a schedule (e.g., TABLE 1); in some embodiments, scheduling, timing, and/or other attributes of activities directed at entertainment detection is responsive to one or more of: user input, user state, third party input, third party state, observations of user state or environment. In an exemplary embodiment, a monitoring module implemented in an application running on a device-such as a mobile phone, a tablet, or a similarly-functioning device-aggregates such parameters from connected devices. In further embodiments such connected devices include the stimulation delivery device. In some embodiments, a monitoring module is implemented on the stimulation delivery device. In further embodiments, these measurements are analyzed, possibly along with measures of sleep quality or other parameters that correlate with cognitive functioning. In an exemplary embodiment, analysis of user aspects or context are used in combination with measures of sleep quality or other parameters that correlate with cognitive functioning to identify periods where sleep quality may be affected by that context.

In some embodiments, measurements are taken during sleep; in some embodiments, measurements are taken at other times. In further embodiments, measurements taken at other times may be specifically scheduled to provide the most relevant information (e.g., HRV while resting on waking for sleep quality; alpha wave measurements both during and after stimulation, cognitive assessments during daytime periods of productive wakefulness, etc.). In some embodiments, measurements of sleep quality related parameters may be taken passively; in some embodiments, users may be prompted or scheduled to provide information related to sleep quality (e.g., by completing an assessment task or donning a specific measurement apparatus). In some embodiments, third parties such as a user's caregiver are prompted or scheduled to provide or facilitate the collecting of measurements.

In some embodiments, the present disclosure provides for monitoring sleep interruptions. In an exemplary embodiment, sleep interruptions are detected using actigraphy, such actigraphy provided from one or more devices associated with the user, and either worn or in proximity to the user while sleeping. In a further exemplary embodiment, such actigraphy is provided by sensors incorporated into the stimulation delivery device (c.f. sleep mask) worn by the user throughout their sleep period. In an exemplary embodiment, actigraphy is monitored continuously with a worn actigraphy device, such as a watch with actigraphic measurement capability.

In some embodiments, actigraphic observations include measurement, observation, and/or logging of one or more of: acceleration, gravity, location, position, orientation. In some embodiments, measurements and/or observations are made of one or more body parts. In some embodiments, actigraphic measures are computed from actigraphic observations. In some embodiments, actigraphic measures are responsive to information observed, transmitted, or recorded regarding at least in part: environment, time of day, user self-reports, history, demographic information, diagnosis, device interactions, on-line activity, third party assessment.

In some embodiments, the present technological solution employs monitoring of brain wave parameters to determine stimulus parameters. In an exemplary embodiment, identification of a subject's dominant primary alpha wave frequency is used at least in part to determine the frequency of stimulation applied to the subject. In an exemplary embodiment, a stimulation is applied at four times the subject's dominant primary alpha wave frequency. In some embodiments, stimulation is applied at an integer multiple of the subject's dominant primary alpha wave frequency. In some embodiments, a subject's dominant primary alpha wave frequency may be determined at least in part on one or more of: observations or measurements of a subject's brain wave parameters, demographic information associated with a subject, historical information associated with a subject, profile information associated with a subject.

In some embodiments, the present technological solution employs monitoring of brain wave parameters to categorize a user's risk of developing a neurological condition or to diagnose a neurological condition or disorder. In one embodiment, the present technological solution employs monitoring of brain wave parameters to categorize a user's risk of developing a neurodegenerative disorder, such as MCI or AD, to assess their MCI or AD progression, or to diagnose MCI or AD. In a further embodiment, such categorization is based, at least in part, on detected reductions in the amount of gamma brainwave activity.

In some embodiments, the present technological solution monitors one or more subjects in a space, such monitoring including one or more of: presence in the space, proximity to stimulation delivery devices, levels, and values of stimulus parameters incident on each subject, activity, and behaviors of the subject. In an exemplary embodiment, a subject's presence in a space is observed and recorded. In an exemplary embodiment, the audio or visual characteristics of delivered stimulus is observed and recorded at one or more of: various locations in the space, one or more subject's locations in the space, one or more subject's eyes, one or more subjects' ears. In some embodiments, logs of such monitoring are employed to construct a measure of each subject's aggregate exposure to effective stimulus while in the space.

In some embodiments monitoring information is communicated to a system that contributes to the operation of an automated interaction with a user or third party. In an exemplary embodiment, monitoring information is communicated to a system operating a chat bot interacting with a user or caregiver.

In some embodiments, monitored information includes or is responsive to analysis of monitored information. In some embodiments, monitored information includes or is responsive at least in part to sleep fragmentation analyses from actigraphy and/or comparisons of two or more sleep fragmentation analyses from actigraphy.

Feedback

In some embodiments, the present disclosure provides feedback to users and third parties relating to aspects of the user's sleep quality. In further aspects the disclosure provides such feedback responsive to the delivery of gamma stimulation therapy, or responsive to monitoring or the analysis of monitoring. In some embodiments feedback includes feedback or information about the use of the stimulation device, with or without information about monitoring or analysis.

Figure 36:
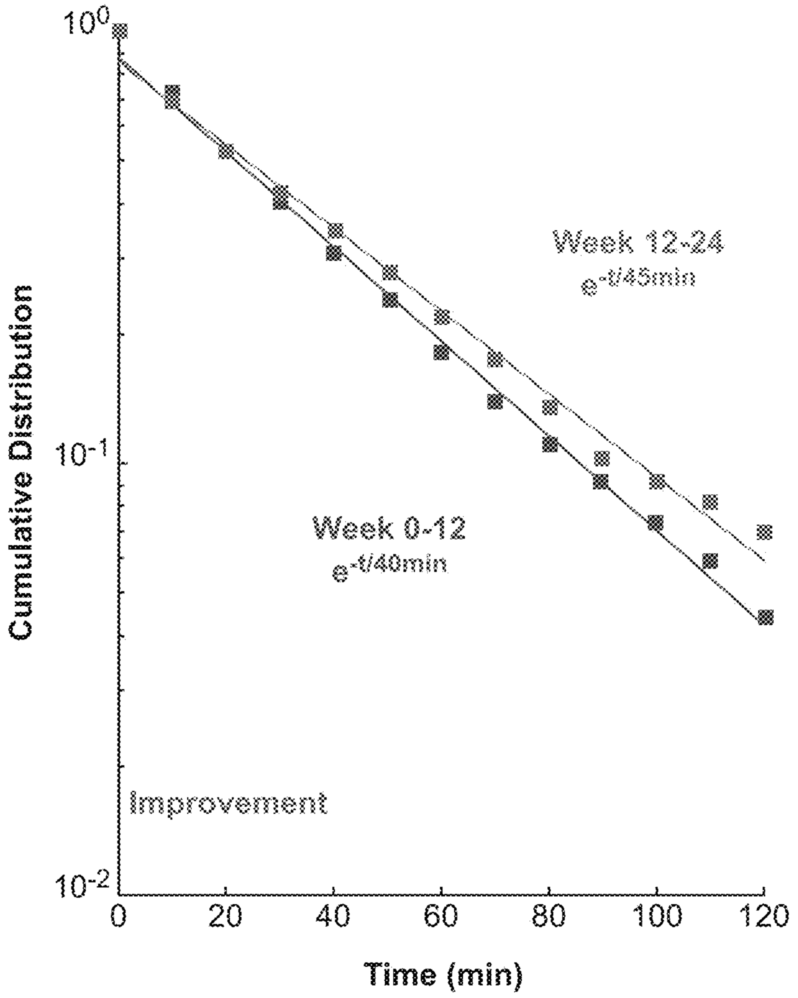
FIG. 36 provides exemplary cumulative distribution of rest periods from a single patient (e.g., 1511, FIG. 37). Data from a first exemplary 12 weeks of treatment (solid line's points, Week 0-12) and a second exemplary 12 weeks of treatment (dashed line's points) is shown. In some embodiments the distribution is characterized by an exponential distribution (e.g., 1512, FIG. 37). In a further embodiment, an increase in the exponential decay constant represents an improvement in sleep quality (e.g., 1513, FIG. 37). In the present example, $tau_2$=45 min, $tau_1$=40 min, and $tau_{diff}$=5 min>0.

In some embodiments, feedback can include reports to the user or to a third party about aspects of the stimulation, including duration, parameters, schedule, etc.; in some embodiments feedback may include values or summaries of values of measurements or monitoring of sleep related parameters; in some embodiments feedback may include information about sleep quality improvement, including the frequency, duration, and distribution of rest periods. In some embodiments third parties may include caregivers, healthcare professionals, providers, insurers, or employers. In some embodiments feedback may be provided on the stimulation device, on a secondary device (such as a phone or tablet), or remotely (e.g., on a console or other device associated with a third party). In some embodiments, one or more of distributions, summary statistics of distributions, or characteristic parameters for fitted distributions, for one or more groups of one or more subjects and/or one or more time periods are compared. In an exemplary embodiment (e.g., FIG. 37), distributions for two groups of subjects are compared and/or distributions within groups over subsequent periods (e.g., 12 weeks) are compared. In some embodiments, distributions for a single patient over two distinct sequential periods (e.g., 12 weeks) are compared. In some embodiments, differences between exponential decay constants are computed as a measure of sleep quality difference between one or more subjects or time periods (e.g., 1513). In an exemplary embodiment, exponential decay constants, $tau_1$ for a first period, and $tau_2$ for a second period, are determined. In a further embodiment $tau_{diff}=tau_2-tau_1$ is computed. In a further embodiment, $tau_{diff}$ is employed as a measure of sleep quality improvement or decline, for example, $tau_{diff}>0$ is reported as sleep quality improvement and/or $tau_{diff}<0$ is reported as sleep quality decline (e.g., FIG. 36). In some embodiments, one or more steps 1501 through 1513 are performed by Actigraphy Monitoring Module 130 (FIG. 33).

In an exemplary embodiment, the user is presented on a personal device connected or paired with the stimulation device (such as a phone or tablet) with a summary of their use of the stimulation device (including one or more of duration of wearing, stimulation applied, parameters, used, etc.), or with a summary of the changes in their sleep quality, or a combination of these.

In an exemplary embodiment, a caregiver is presented on a web dashboard linked to one or more users of one or more stimulation devices, with summaries of the use of the stimulation device (including one or more of duration of wearing, stimulation applied, parameters, used, etc.), or with summaries of the changes in one or more users' sleep quality, or a combination of these.

In some embodiments, monitoring of one or more subjects in a space is employed to provide guidance associated with one or more subjects regarding locations, positions, behaviors, or attitudes within the space. In an exemplary embodiment, subjects are provided with such guidance directed at improving, for one or more subjects, one or more of: the effectiveness of received stimulus, characteristics of received stimulus (e.g., light levels, volume, intensity, frequency, duration, variation, etc.). In some embodiments, such guidance is provided to third parties. In some embodiments, such guidance is provided to subjects.

In some embodiments, monitoring of one or more subjects is used to diagnose a subject with a disease, disorder, or condition. For example, monitoring a subject may include assessing hallmarks of cognitive decline or dementia, changes in fine-motor skills, changes in brainwave activity, sleep fragmentation, or voice or pitch analysis.

In some embodiments, feedback is communicated or presented to one or more stimulus recipients. In some embodiments, feedback is presented in the form of a diagnosis or prescription. In some embodiments, feedback is communicated or presented to a third party, including but not limited to a clinician, delivery facility staff, device operator, device manufacture, therapy component provider, caregiver, payor, provider, employer, family member, researcher, health agency.

In some embodiments, feedback communicated to third parties is modified, processed, filtered, selected, or presented to achieve one or more of: reduction in recipients stress or concerns regarding a stimulus recipient, improvement in outcomes of one or more stimulus recipient, reduction in costs associated with one or more stimulus recipient, compliance with regulations associated with stimulus delivery.

In some embodiments feedback is communicated or presented through a programmatic interaction with a user or third party responsive at least in part to monitored information. In an exemplary embodiment, feedback is communicated by a chatbot or chatbot component interacting with a user or caregiver.

In some embodiments, feedback incorporates or consists of processed or unprocessed monitored information or analysis. In some embodiments, feedback incorporates and/or consists of and/or is responsive at least in part to sleep fragmentation analyses from actigraphy and/or comparisons of two or more sleep fragmentation analyses from actigraphy.

Motivation

In some embodiments, the present disclosure provides for motivating users or third parties in the use of the stimulation device or other related activities or therapies. In further embodiments the disclosure provides such motivation responsive to the delivery of gamma stimulation therapy, or responsive to monitoring or the analysis of monitoring.

Motivation may include instructions on use (or links to instruction on use), reminders or notifications, calendar events, rewards, progress indicators, comparisons with targets or goals, or comparisons with other users or target populations of users or demographic groups. Motivation may include assessments of symptoms and signs of disease progression.

In an exemplary embodiment, users are reminded when they go to bed or shortly before their usual bedtime of progress they have achieved by using the stimulation device shortly before bed in the past; such reminder appearing on one or more of a personal device (e.g., as a notification), the stimulation device (e.g., as a flashing light or audio tone), or other device (e.g., desktop calendar); the content and timing of such reminder further responsive to analysis of times and durations of device use associated with improved sleep quality.

In an exemplary embodiment, users are presented, on a personal device associated with the stimulation device or with the stimulation device's user, with instructions, motivating rewards, prompts, or achievements encouraging their use of the device responsive to the user's history of device uses that have resulted in sleep quality improvement.

In an exemplary embodiment, caregivers are presented, on a web dashboard or console, instructions, or guidance on how to encourage one or more users to use their stimulation devices in context or using methods (e.g., schedules, techniques, environmental conditions, etc.) likely to result in sleep quality improvement. In further exemplary embodiments these ways are prioritized or selected at least in part based on monitoring or analysis of the use of those one or more users, or other users, associated with effective sleep quality improvement.

In some embodiments, motivation is communicated or presented through a programmatic interaction with a user or third party responsive at least in part to monitored information. In an exemplary embodiment, feedback is communicated by a chatbot or chatbot component interacting with a user or caregiver.

In some embodiments, motivation incorporates or consists of feedback. In some embodiments, motivation incorporates and/or consists of and/or is responsive at least in part to sleep fragmentation analyses from actigraphy and/or comparisons of two or more sleep fragmentation analyses from actigraphy.

Analysis

Figure 37:
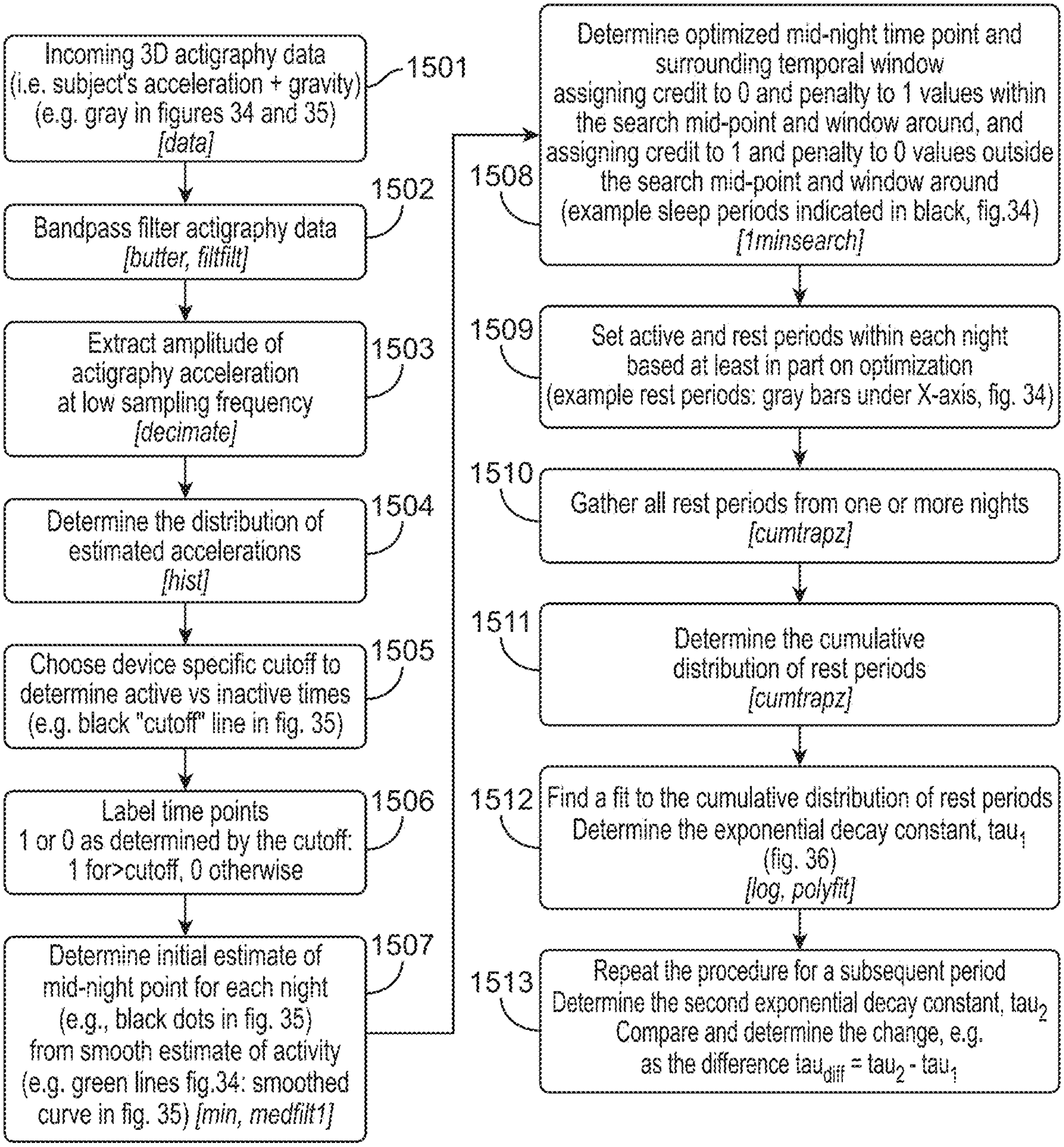
FIG. 37 provides a flowchart of exemplary analysis steps responsive to actigraphy data, provided in some embodiments at least in part by Actigraphy Monitoring Module 130 (FIG. 33). In some embodiments, analysis is directed at determining the cumulative distribution of rest periods for one or more subjects over a period of one or more nighttime sleep periods (1511). In some embodiments analysis is further directed at fitting an exponential distribution to the determined cumulative distribution (1512). In some embodiments, analysis is further directed at computing summary statistics or characteristic parameters for the fitted exponential distribution. In an exemplary embodiment, the exponential decay constant for the fitted exponential distribution is determined (1512.

In some embodiments, beneficial changes in actigraphy are identified by computing statistical measures associated with the distribution of one or more of: sleep fragmentation, rest periods during sleep periods, sleep interruptions during sleep periods (FIG. 37). In an exemplary embodiment, such analysis may include generating a distribution of the durations of rest periods or other measures of sleep fragmentation; in further embodiments such analysis may include comparing these distributions over time, or responsive to varying treatment parameters or patterns of device usage.

Figure 35:
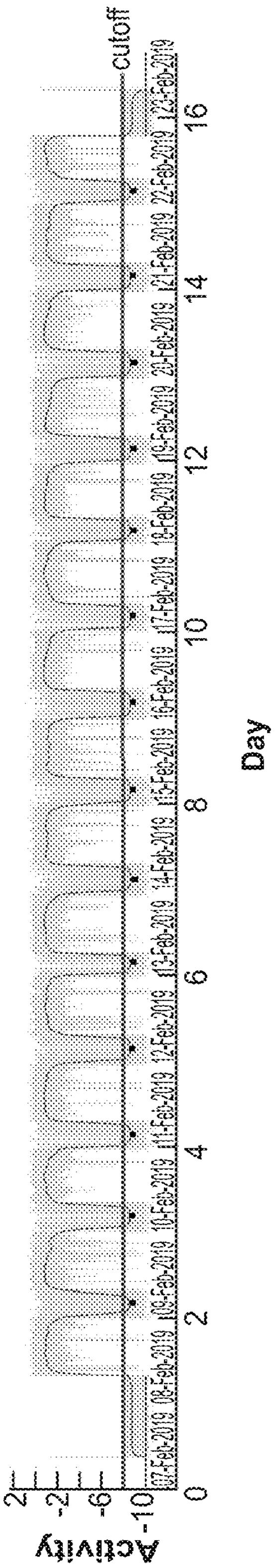
FIG. 35 provides exemplary patterns of actigraphy (arbitrary units, see FIG. 34) over several days showing actigraphy (gray; e.g., 1501, FIG. 37), and a smooth curve is superposed. Cutoff line (black) separates active versus rest periods (e.g., 1505, FIG. 37). Black squares represent initial estimation for the mid-night point (e.g., 1507, FIG. 37). The final assessment of the mid-night points is determined through optimization algorithm (e.g., 1508, FIG. 37).

In some embodiments, the present technological solution includes methods and systems directed at analyzing sleep fragmentation from actigraphy. In some embodiments such methods and systems include collecting and/or receiving actigraphy data for one or more devices associated with one or more subjects over one or more time periods (1501, FIG. 37; e.g., gray in FIG. 34). In some embodiments, such methods and systems further include one or more of: bandpass filtering of at least a portion of such actigraphy data (1502, FIG. 37); extraction of amplitude of at least a portion of such actigraphy data acceleration at one more reduced sampling frequencies (1503, FIG. 37). In some embodiments, such methods and systems further include determination of a distribution of estimated accelerations (1504, FIG. 37). In some embodiments, such methods and systems further include identification of one or more device specific cutoffs distinguishing active vs inactive times based at least in part on device characteristic of actigraphy values associated with device non-use (1505, FIG. 37; e.g., black "cutoff" in FIG. 35), and categorization of actigraphy data based on such distinguishing. In an exemplary embodiment, data points with actigraphy values above values associated with device non-use are assigned a score of 1 while all other data points are assigned a value of 0 (1506, FIG. 375). In some embodiments, such methods and systems include generation of a smoothed estimate of activity from actigraphy data (1507, FIG. 37; e.g., green in FIG. 34). In some embodiments, such methods and systems further include determination of an initial estimated mid-night point for each night from a smooth estimate of activity (1507, FIG. 37; e.g., black dots in FIG. 35). In some embodiments, an initial estimated mid-night point corresponds to the minimum of a smooth estimate of activity over a period from 12:00 PM on consecutive days.

In some embodiments, the present solution further includes methods and systems directed at determining the temporal extent of one or more night time sleep periods (black emphasized periods in FIG. 34), such methods including: an optimization directed at determining an optimized mid-night time point and surrounding temporal window, including: assigning credit to distinguished inactive data points (e.g., those assigned 0 values) and penalty to distinguished active data points (e.g., those assigned 1 values) within an optimized temporal window around an optimized mid-night point, and assigning credit to distinguished active data points and penalty to distinguished inactive data points outside such optimized temporal window (1508, FIG. 37). In some embodiments, the present solution further includes methods and systems directed at identifying active and rest periods (e.g., gray bars in FIG. 34) within each nighttime sleep period (1509, FIG. 37). In an exemplary embodiment, periods with actigraphy values above values associated with device non-use are categorized as active periods while all other data points are categorized as rest periods (1506, FIG. 37). In an exemplary embodiment, rest periods are assigned a value of 1 and active periods are assigned a value of 0.

In some embodiments, the present solution further includes methods and systems directed at characterizing the distribution of identified rest periods, such methods including one or more of: gathering and/or accumulating rest periods from one or more nights or other time periods for one or more subjects or groups of subjects (1510, FIG. 37), determining the cumulative distribution of gathered rest periods (1511, FIG. 37), fitting a statistical distribution to the distribution of gathered rest periods. In some embodiments, such methods and systems further include (1512, FIG. 37): fitting an exponential distribution to the distribution of gathered rest periods, determining the exponential decay constant for a fitted exponential distribution. Some embodiments further include methods directed at determining and/or reporting and/or transmitting a value based at least in part on the determined exponential decay constant for an exponential distribution fit to the cumulative distribution of rest periods for one or more subjects over one or more days and/or other periods (1513, FIG. 37), and/or determining and/or reporting and/or transmitting a value based at least in part on a comparison between exponential decay constants for two or more exponential distributions fit to the cumulative distributions of rest periods for one or more subjects over one or more days and/or other periods (1513, FIG. 37).

In some embodiments, one or more such determined exponential decay constants, comparisons of such constants, functions of such constants, or values responsive to such constants, are reported singly or multiply as a measure of sleep quality, sleep improvement, sleep progress, treatment effectiveness, treatment results, disease progression, and/or other metric of treatment success, failure, effectiveness, or outcome. In an exemplary embodiment, reports responsive to or incorporating a value based on the difference between exponential decay constants for different users or different time periods are reported to users or third parties.

In some embodiments, analysis of sleep fragmentation including characterizing the distribution of identified rest periods is used at least in part to confirm and/or assess and/or report one or more of: beneficial changes in actigraphy during sleep periods, increases the frequency of restful periods during sleep periods, reduction in the frequency of sleep interruptions during sleep periods, improvement and/or maintenance prevention of degradation of sleep-related health outcomes.

In some embodiments, analysis of sleep fragmentation including characterizing the distribution of identified rest periods is used at least in part to determine, adjust, modify, and/or select one or more of: stimulation parameters, stimulation modalities, opportunities for delivering stimulation, goals for reduction in sleep fragmentation, devices for use in stimulation, locations for use in stimulation, environmental adjustments associated with stimulation, user state adjustments associated with stimulation, activities for use in conjunction with stimulation, third party role in stimulation. In some embodiments, such use of analysis of sleep fragmentation to determine, adjust, modify, and/or select is used in conjunction with information responsive to one or more of: user and/or third-party history, location, profile, preferences, diagnosis, task, activity, relationship, assessment, test results, feedback, observation, prognosis, reports, device use history, treatment history. In some embodiments, such use of analysis of sleep fragmentation to determine, adjust, modify, and/or select is used in conjunction with information responsive to one or more of: available stimulation devices, stimulation or other characteristics of available stimulation devices, audio environment information, visual environment information, user context information, third party context information. In an exemplary embodiment, devices and/or opportunities for stimulation and/or parameters associated with effective and/or improved and/or mitigated outcomes as assessed at least in part by patterns in analysis of sleep fragmentation, are presented and/or suggested to users and or third parties.

In some embodiments measured or observed sleep-related parameters are analyzed either locally and/or on a server to compute measures of sleep quality.

In some embodiments, comparison of measures or analysis of sleep quality or sleep fragmentation over time may be used to characterize the progression or risk of sleep-associated disease, such as AD. In some embodiments measures of sleep quality computed by the analysis are used as a measure of AD disease progression, risk, or diagnosis. In an exemplary embodiment, detection of specific levels of sleep fragmentation as determined by the analysis, or changes to those levels over time, are used to identify patients at risk for or in the early stages of AD.

In some embodiments, measured sleep-related and other parameters are aggregated from multiple users to identify population or demographic patterns related to sleep improvement and associations between program parameters or other aspects of stimulation delivery. In some embodiments measured sleep-related and other parameters from a single user are used to identify user-specific patterns.

In some embodiments, identified patterns are used to inform one or more of: the selection of program parameters or values, treatment schedules, motivations, communications with users, caregivers, or healthcare providers, for one or more users or populations of users.

In some embodiments, analysis or results of analysis may be reported to users, care givers, healthcare providers, or other third parties. In an exemplary embodiment, disease progression analysis associated with AD progression is reported to health care providers or caregivers.

Program Parameters and Parameter Values

Figure 31:
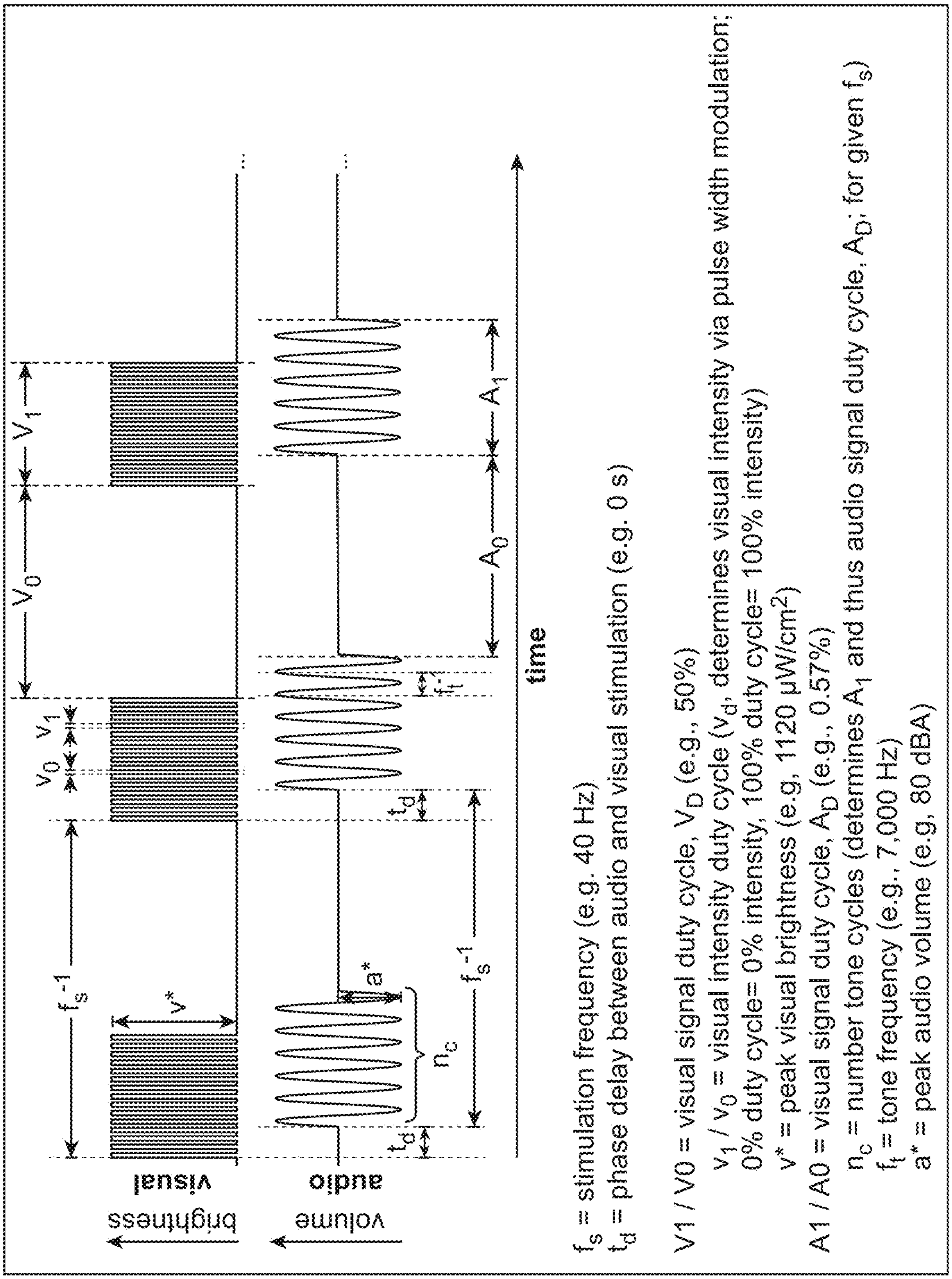
FIG. 31 shows a schematic of some aspects and parameters characterizing stimulus audio and visual components of non-invasive stimulation as delivered respectively by Audio Stimulus Module (110.

In some embodiments, stimulus program parameters are configured with a stimulus frequency (e.g., fs in FIG. 31) of approximately 35 Hz to approximately 45 Hz for both audio and visual signals. In some embodiments, audio and visual signals are offset relative to each other by a delay (e.g., td in FIG. 31). In exemplary embodiment audio and visual signals are synchronized (td=0 s).

In some embodiments, stimulus program parameters are configured with a variety of timing and intensity parameters. In an exemplary embodiment, these parameters include those illustrated in FIG. 31. In some embodiments, these parameters are preconfigured; in some embodiments they are adjusted at least in part by a third party such as a caregiver or healthcare provider; in some embodiments one or more parameters are adjusted responsive to measurements or analysis of one or more of: user context, measured sleep quality related parameters associated with the user, observed, or detected use of the stimulation device. In some embodiments, stimulus parameters are adjusted responsive to detected or analyzed sleep-related AD symptom progression.

In some embodiments, the present disclosure evokes gamma wave oscillations through a variety of frequency and intensity parameters.

In some embodiments, non-invasive stimulation includes one or more of: non-invasive sensory stimulation, non-invasive gamma stimulation, non-invasive gamma sensory stimulation, gamma stimulation therapy, non-invasive gamma stimulation therapy. In some embodiments, non-invasive stimulation is delivered as non-invasive therapy.

In an exemplary embodiment, subjects receive one hour a day non-invasive sensory gamma stimulation therapy. In some embodiments, subjects receive two hours of non-invasive sensory stimulation twice a day. In some embodiments, subjects receive multiple periods of non-invasive stimulation of varying durations and totals over the course of a day. In some embodiments, the timing, distribution of durations, and/or total duration throughout the day are responsive to one or more of: delivered stimulus values, environmental values, observed user state, observed, or inferred effectiveness. In an exemplary embodiment, a subject is delivered brief periods of stimulus throughout a day, at times determined to be suitable for effective stimulus delivery, with a total of all periods responsive at least in part to a cumulative measure of stimulus effectiveness. In some embodiments, stimulus effectiveness is responsive to an entrainment score.

In some embodiments, one or more stimulus parameters or other aspects are responsive at least in part to sleep fragmentation analyses from actigraphy and/or comparisons of two or more sleep fragmentation analyses from actigraphy. In an exemplary embodiment, varying combinations stimulus parameters are used during different time periods and subsequent stimulation parameters are selected at least in part based on comparison of sleep fragmentation analyses from actigraphy among at least some of those periods. In some embodiments, stimulation parameters are selected to optimize, improve, and/or enhance sleep improvement as assessed at least in part by sleep fragmentation analyses from actigraphy.

In some embodiments, the present disclosure delivers 40 Hz non-invasive audio, visual, or combined audio-visual stimulation. In some embodiments stimulus is delivered at one or more stimulation frequencies (e.g., fs in FIG. 31) in the approximate range of 35-45 Hz. In some embodiments, "gamma" refers to frequencies in the range 35-45 Hz. In some embodiments stimulus is delivered based at least in part on a user's detected, reported, or demographically or individually associated or dominant alpha wave frequency.

In some embodiments, specific visual parameters include one or more of: stimulation frequency, intensity (brightness), hue, visual patterns, spatial frequency, contrast, and duty-cycle. In an exemplary embodiment, visual stimulation is provided at a stimulation frequency of 40 Hz, brightness between 0 μW/cm2 to 1120 μW/cm2, and 50% visual signal duty-cycle.

In some embodiments, non-invasive stimulation is delivered as combined visual and auditory stimulation, delivered at 40 Hz frequency. In some embodiments, visual and auditory stimulation is synchronized to begin each cycle simultaneously. In some embodiments, the beginning of each auditory and visual stimulation cycle is offset by a configured time. In some embodiments, visual and auditory signals are delivered at an intensity clearly recognized by subjects and adjusted to their tolerance level.

In some embodiments, at least some of the parameters or characteristics of the non-invasive signal administered to a subject correspond to those specified in one or more of US Patents U.S. Pat. No. 10,307,611 B2, U.S. Pat. No. 10,293,177 B2, or U.S. Pat. No. 10,279,192 B2. In some embodiments, at least some of the parameters or characteristics of the non-invasive signal administered to a subject correspond to those specified in one or more of US Patents U.S. Pat. No. 10,159,816 B2 or U.S. Pat. No. 10,265,497 B2.

In some embodiments specific audio parameters include one or more of: stimulation frequency, intensity (volume), and duty-cycle. In some embodiments, audio frequency is adjusted responsive to a subject's hearing characteristics, for example to frequencies that a subject is better at hearing. In an exemplary embodiment, audio stimulation is provided at an audio tone frequency of 7,000 Hz, volume level between 0 dBA to 80 dBA, and 0.57% audio signal duty-cycle.

Figure 40:
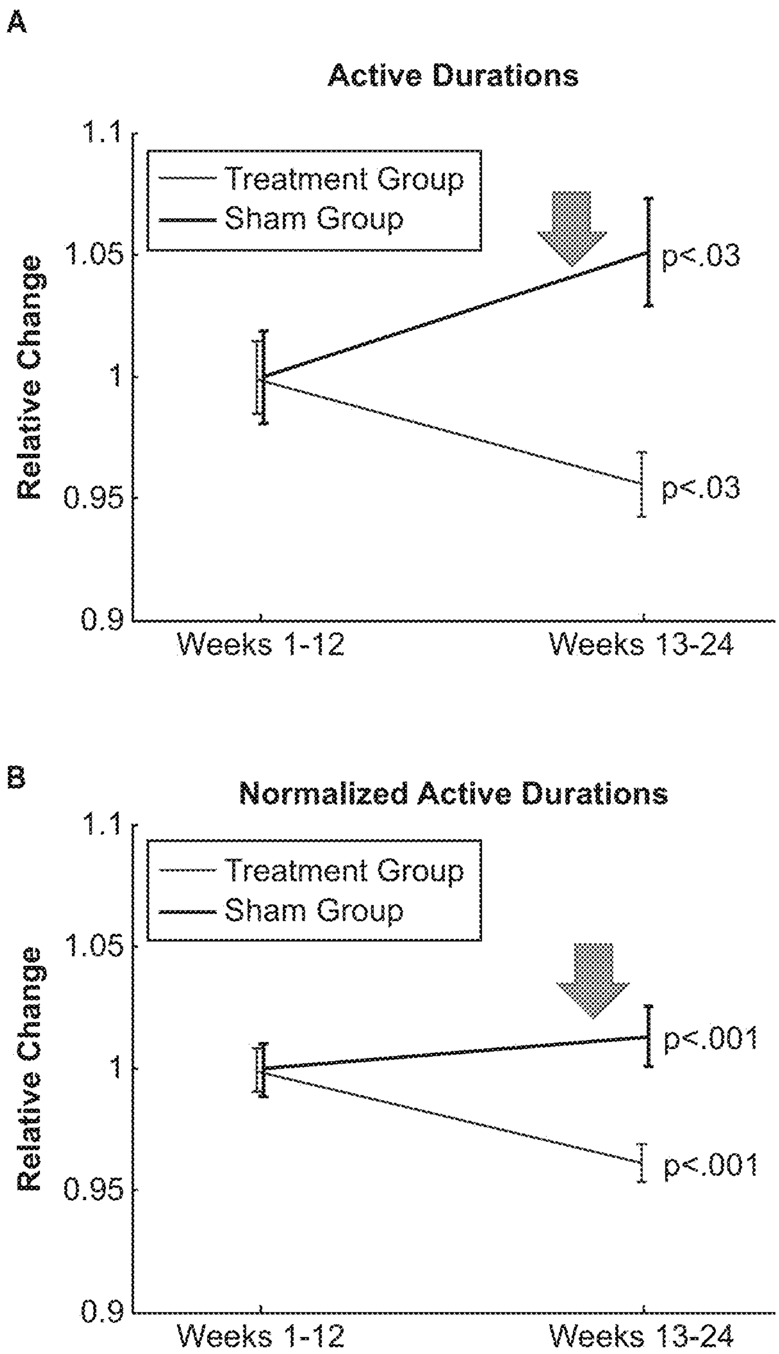
FIG. 40 shows graphs comparing the relative change in active durations, with the Y-axis indicating change relative to Weeks 1-12 during Weeks 13-24.

In some embodiments, non-invasive stimulation parameters are selected directed at evoking gamma wave oscillations in the brains of human subjects. In some embodiments, non-invasive stimulation parameters are selected directed at inducing alpha waves in human subjects (FIG. 40). In some embodiments, the non-invasive stimulation parameters are directed at inducing beta waves in human subjects. In some embodiments, the non-invasive stimulation parameters are directed at inducing beta waves in human subjects. In some embodiments, the non-invasive stimulation parameters are directed at inducing gamma waves in human subjects.

In some embodiments light levels and hue are adjusted to avoid fatiguing the subject. In some embodiments light levels and hue are adjusted to provide motivation to the subject. In some embodiments, parameters to each ear or eye are adjusted in a similar manner. In some embodiments, parameters to each ear or eye are adjusted differently. In an exemplary embodiment, audio, and visual parameters such as tone and hue are varied to provide engagement or motivation to the subject to continue applying the stimulus or monitoring.

Neural Stimulation Via Visual Stimulation

In some embodiments, systems and methods of the present disclosure are directed to controlling frequencies of neural oscillations using visual signals and, in doing so, causing an improvement in sleep quality. The visual stimulation can adjust, control, or otherwise affect the frequency of the neural oscillations to provide beneficial effects to one or more cognitive states or cognitive functions of the brain, or the immune system, while mitigating or preventing adverse consequences on a cognitive state or cognitive function. The visual stimulation can, for example, provide beneficial improvements in sleep quality experienced by a user. The visual stimulation can result in brainwave entrainment that can provide beneficial effects to one or more cognitive states of the brain, cognitive functions of the brain, the immune system, or inflammation. In some cases, the visual stimulation can result in local effect, such as in the visual cortex and associate regions. In some cases, the visual stimulation can result in a more expansive effect and cause alterations in physiology in more than just the nervous system. The brainwave entrainment can, for example, treat sleep abnormalities. Sleep abnormalities, such as sleep fragmentation, have multiple impacts on human physiology, including dysfunction not only in the nervous system, but also impairing body metabolism or immune defense system. The brainwave entrainment can treat disorders, maladies, diseases, inefficiencies, injuries, or other issues related to a cognitive function of the brain, cognitive state of the brain, the immune system, or inflammation.

Neural oscillation occurs in humans or animals and includes rhythmic or repetitive neural activity in the central nervous system. Neural tissue can generate oscillatory activity by mechanisms within individual neurons or by interactions between neurons. Oscillations can appear as either oscillations in membrane potential or as rhythmic patterns of action potentials, which can produce oscillatory activation of post-synaptic neurons. Synchronized activity of a group of neurons can give rise to macroscopic oscillations, which, for example, can be observed by electroencephalography ("EEG"), magnetoencephalography ("MEG"), functional magnetic resonance imaging ("fMRI"), or electrocorticography ("ECoG"). Neural oscillations can be characterized by their frequency, amplitude, and phase. These signal properties can be observed from neural recordings using time-frequency analysis.

For example, an EEG can measure oscillatory activity among a group of neurons, and the measured oscillatory activity can be categorized into frequency bands as follows: delta activity corresponds to a frequency band from 1-4 Hz; theta activity corresponds to a frequency band from 4-8 Hz; alpha activity corresponds to a frequency band from 8-12 Hz; beta activity corresponds to a frequency band from 13-30 Hz; and gamma activity corresponds to a frequency band from 30-70 Hz.

The frequency and presence or activity of neural oscillations can be associated with cognitive states or cognitive functions such as information transfer, perception, motor control and memory. Based on the cognitive state or cognitive function, the frequency of neural oscillations can vary. Further, certain frequencies of neural oscillations can have beneficial effects or adverse consequences on one or more cognitive states or function. However, it may be challenging to synchronize neural oscillations using external stimulus to provide such beneficial effects or reduce or prevent such adverse consequences.

Brainwave entrainment (e.g., neural entrainment or brain entrainment) occurs when an external stimulation of a particular frequency is perceived by the brain and triggers neural activity in the brain that results in neurons oscillating at a frequency corresponding to the particular frequency of the external stimulation. Thus, brain entrainment can refer to synchronizing neural oscillations in the brain using external stimulation such that the neural oscillations occur at a frequency that corresponds to the particular frequency of the external stimulation.

Systems and methods of the present disclosure can provide external visual stimulation to achieve brain entrainment. For example, external signals, such as light pulses or high-contrast visual patterns, can be perceived by the brain. The brain, responsive to observing or perceiving the light pulses, can adjust, manage, or control the frequency of neural oscillations. The light pulses generated at a predetermined frequency and perceived by ocular means via a direct visual field or a peripheral visual field can trigger neural activity in the brain to induce brainwave entrainment. The frequency of neural oscillations can be affected at least in part by the frequency of light pulses. While high-level cognitive function may gate or interfere with some regions being entrained, the brain can react to the visual stimulation at the sensory cortices. Thus, systems and methods of the present disclosure can provide brainwave entrainment using external visual stimulus such as light pulses emitted at a predetermined frequency to synchronize electrical activity among groups of neurons based on the frequency of light pulses. The entrainment of one or more portion or regions of the brain can be observed based on the aggregate frequency of oscillations produced by the synchronous electrical activity in ensembles of cortical neurons. The frequency of the light pulses can cause or adjust this synchronous electrical activity in the ensembles of cortical neurons to oscillate at a frequency corresponding to the frequency of the light pulses.

FIG. 1 is a block diagram depicting a system to perform visual brain entrainment in accordance with an embodiment. The system 100 can include a neural stimulation system ("NSS") 105. The NSS 105 can be referred to as visual NSS 105 or NSS 105. In brief overview, the NSS 105 can include, access, interface with, or otherwise communicate with one or more of a light generation module 110, light adjustment module 115, unwanted frequency filtering module 120, profile manager 125, side effects management module 130, feedback monitor 135, data repository 140, visual signaling component 150, filtering component 155, or feedback component 160. The light generation module 110, light adjustment module 115, unwanted frequency filtering module 120, profile manager 125, side effects management module 130, feedback monitor 135, visual signaling component 150, filtering component 155, or feedback component 160 can each include at least one processing unit or other logic device such as programmable logic array engine, or module configured to communicate with the database repository 150. The light generation module 110, light adjustment module 115, unwanted frequency filtering module 120, profile manager 125, side effects management module 130, feedback monitor 135, visual signaling component 150, filtering component 155, or feedback component 160 can be separate components, a single component, or part of the NSS 105. The system 100 and its components, such as the NSS 105, may include hardware elements, such as one or more processors, logic devices, or circuits. The system 100 and its components, such as the NSS 105, can include one or more hardware or interface component depicted in system 700 in FIGS. 7A and 7B. For example, a component of system 100 can include or execute on one or more processors 721, access storage 728 or memory 722, and communicate via network interface 718.

Still referring to FIG. 1, and in further detail, the NSS 105 can include at least one light generation module 110. The light generation module 110 can be designed and constructed to interface with a visual signaling component 150 to provide instructions or otherwise cause or facilitate the generation of a visual signal, such as a light pulse or flash of light, having one or more predetermined parameter. The light generation module 110 can include hardware or software to receive and process instructions or data packets from one or more module or component of the NSS 105. The light generation module 110 can generate instructions to cause the visual signaling component 150 to generate a visual signal. The light generation module 110 can control or enable the visual signaling component 150 to generate the visual signal having one or more predetermined parameters.

The light generation module 110 can be communicatively coupled to the visual signaling component 150. The light generation module 110 can communicate with the visual signaling component 150 via a circuit, electrical wire, data port, network port, power wire, ground, electrical contacts or pins. The light generation module 110 can wirelessly communicate with the visual signaling component 150 using one or more wireless protocols such as BlueTooth, BlueTooth Low Energy, Zigbee, Z-Wave, IEEE 802.11, WIFI, 3G, 4G, LTE, near field communications ("NFC"), or other short, medium or long range communication protocols, etc. The light generation module 110 can include or access network interface 718 to communicate wirelessly or over a wire with the visual signaling component 150.

The light generation module 110 can interface, control, or otherwise manage various types of visual signaling components 150 in order to cause the visual signaling component 150 to generate, block, control, or otherwise provide the visual signal having one or more predetermined parameters. The light generation module 110 can include a driver configured to drive a light source of the visual signaling component 150. For example, the light source can include a light emitting diode ("LED"), and the light generation module 110 can include an LED driver, chip, microcontroller, operational amplifiers, transistors, resistors, or diodes configured to drive the LED light source by providing electricity or power having certain voltage and current characteristics.

Figure 2A:
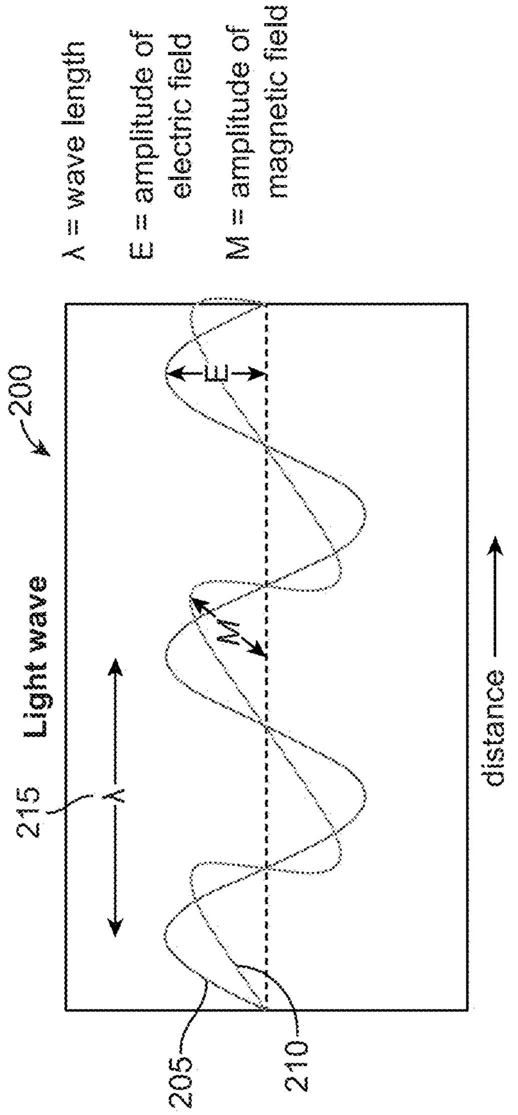
FIGS. 2A-2F illustrate visual stimulation signals that cause neural stimulation in accordance with some embodiments.

In some embodiments, the light generation module 110 can instruct the visual signaling component 150 to provide a visual signal that include a light wave 200 as depicted in FIG. 2A. The light wave 200 can include or be formed of electromagnetic waves. The electromagnetic waves of the light wave can have respective amplitudes and travel orthogonal to one another as depicted by the amplitude of the electric field 205 versus time and the amplitude of the magnetic field 210 versus time. The light wave 200 can have a wavelength 215. The light wave can also have a frequency. The product of the wavelength 215 and the frequency can be the speed of the light wave. For example, the speed of the light wave can be approximately 299,792,458 meters per second in a vacuum.

The light generation module 110 can instruct the visual signaling component 150 to generate light waves having one or more predetermined wavelength or intensity. The wavelength of the light wave can correspond to the visible spectrum, ultraviolet spectrum, infrared spectrum, or some other wavelength of light. For example, the wavelength of the light wave within the visible spectrum range can range from 390 to 700 nanometers ("nm"). Within the visible spectrum, the light generation module 110 can further specify one or more wavelengths corresponding to one or more colors. For example, the light generation module 110 can instruct the visual signaling component 150 to generate visual signals comprising one or more light waves having one or more wavelength corresponding to one or more of ultra-violet (e.g., 10-380 nm); violet (e.g., 380-450 nm), blue (e.g., 450-495 nm), green (e.g., 495-570 nm), yellow (e.g., 570-590 nm), orange (e.g., 590-620 nm), red (e.g., 620-750 nm); or infrared (e.g., 750-1000000 nm). The wavelength can range from 10 nm to 100 micrometers. In some embodiments, the wavelength can be in the range of 380 to 750 nm.

Figure 2B:
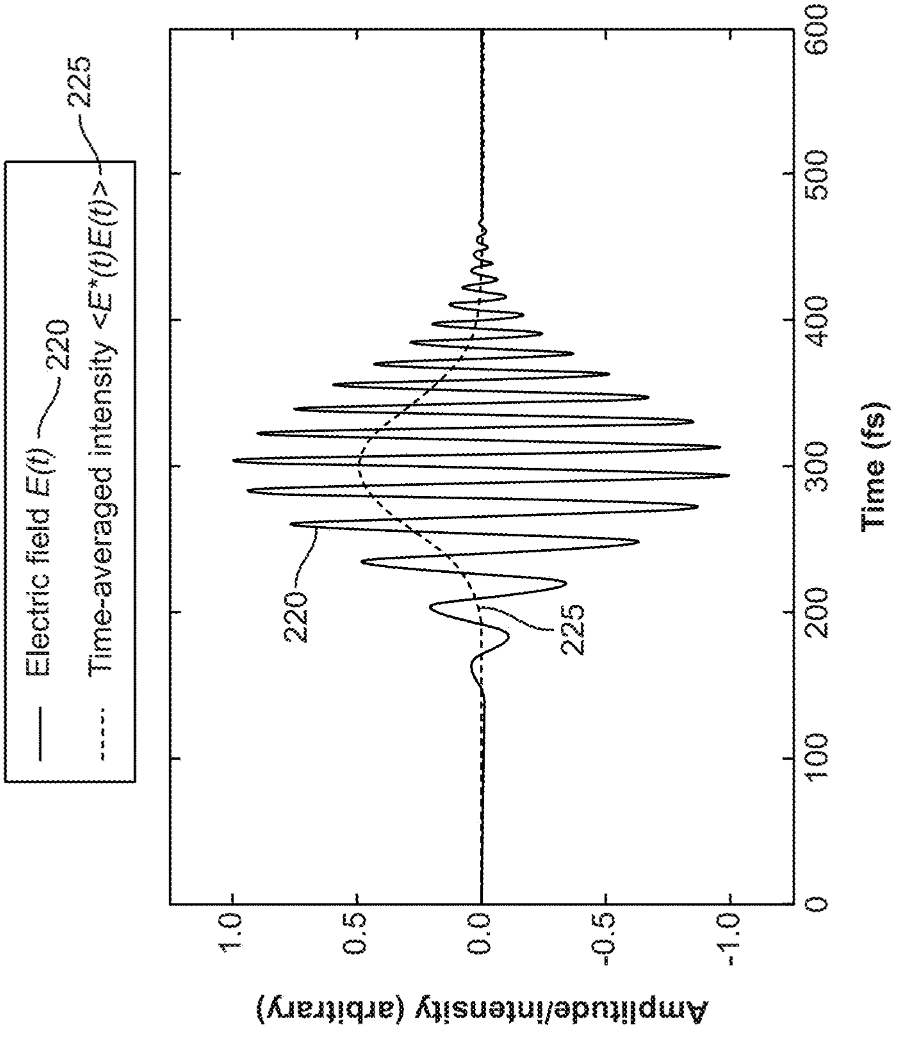

The light generation module 110 can determine to provide visual signals that include light pulses. The light generation module 110 can instruct or otherwise cause the visual signaling component 150 to generate light pulses. A light pulse can refer to a burst of light waves. For example, FIG. 2B illustrates a burst of a light wave. The burst of light wave can refer to a burst of an electric field 250 generated by the light wave. The burst of the electric field 250 of the light wave can be referred to as a light pulse or a flash of light. For example, a light source that is intermittently turned on and off can create bursts, flashes or pulses of light.

Figure 2C:
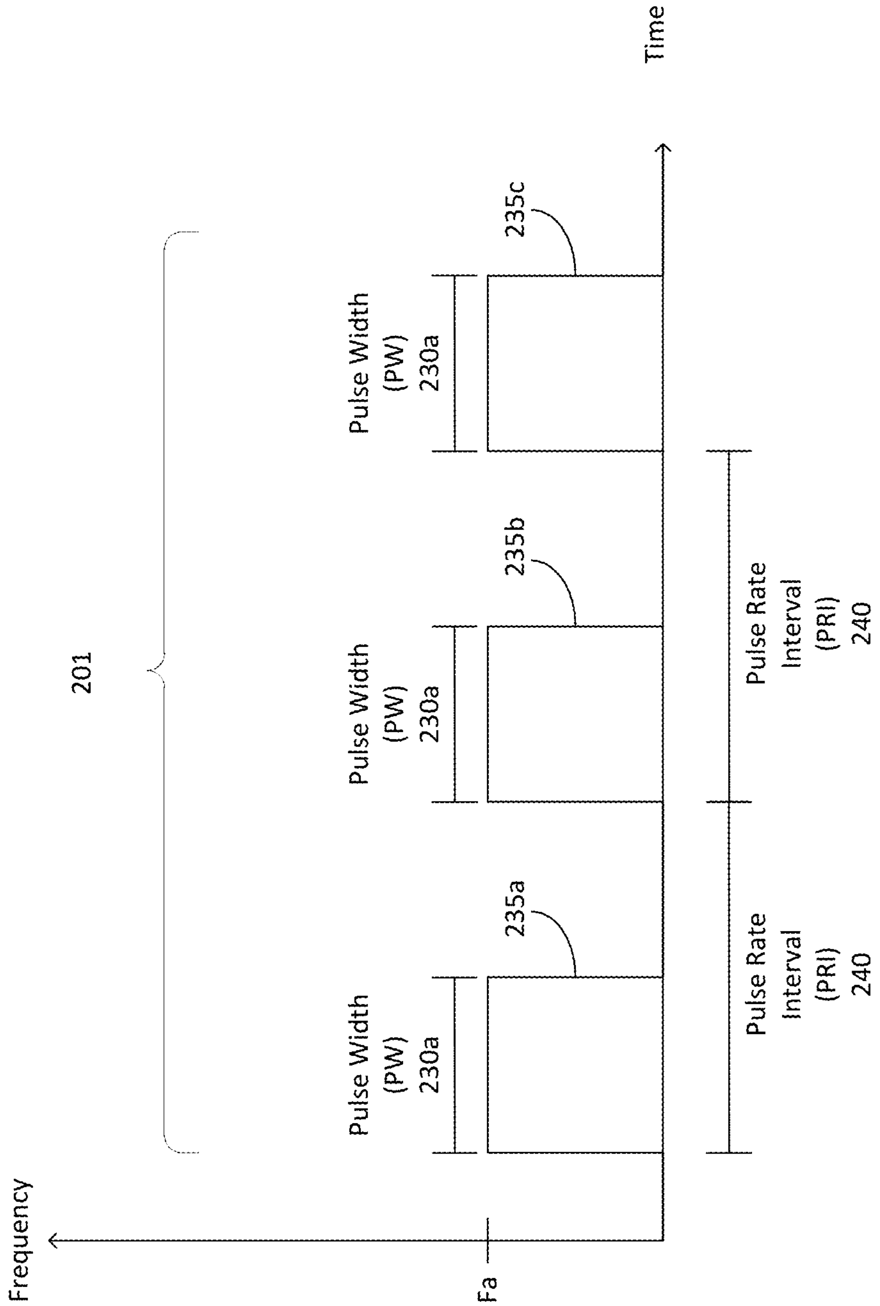

FIG. 2C illustrates pulses of light 235*a-c* in accordance with an embodiment. The light pulses 235*a-c* can be illustrated via a graph in the frequency spectrum where the y-axis represents frequency of the light wave (e.g., the speed of the light wave divided by the wavelength) and the x-axis represents time. The visual signal can include modulations of light wave between a frequency of Fa and frequency different from Fa. For example, the NSS 105 can modulate a light wave between a frequency in the visible spectrum, such as Fa, and a frequency outside the visible spectrum. The NSS 105 can modulate the light wave between two or more frequencies, between an on state and an off state, or between a high power state and a low power state.

In some cases, the frequency of the light wave used to generate the light pulse can be constant at Fa, thereby generating a square wave in the frequency spectrum. In some embodiments, each of the three pulses 235*a-c* can include light waves having a same frequency Fa.

Figure 2D:
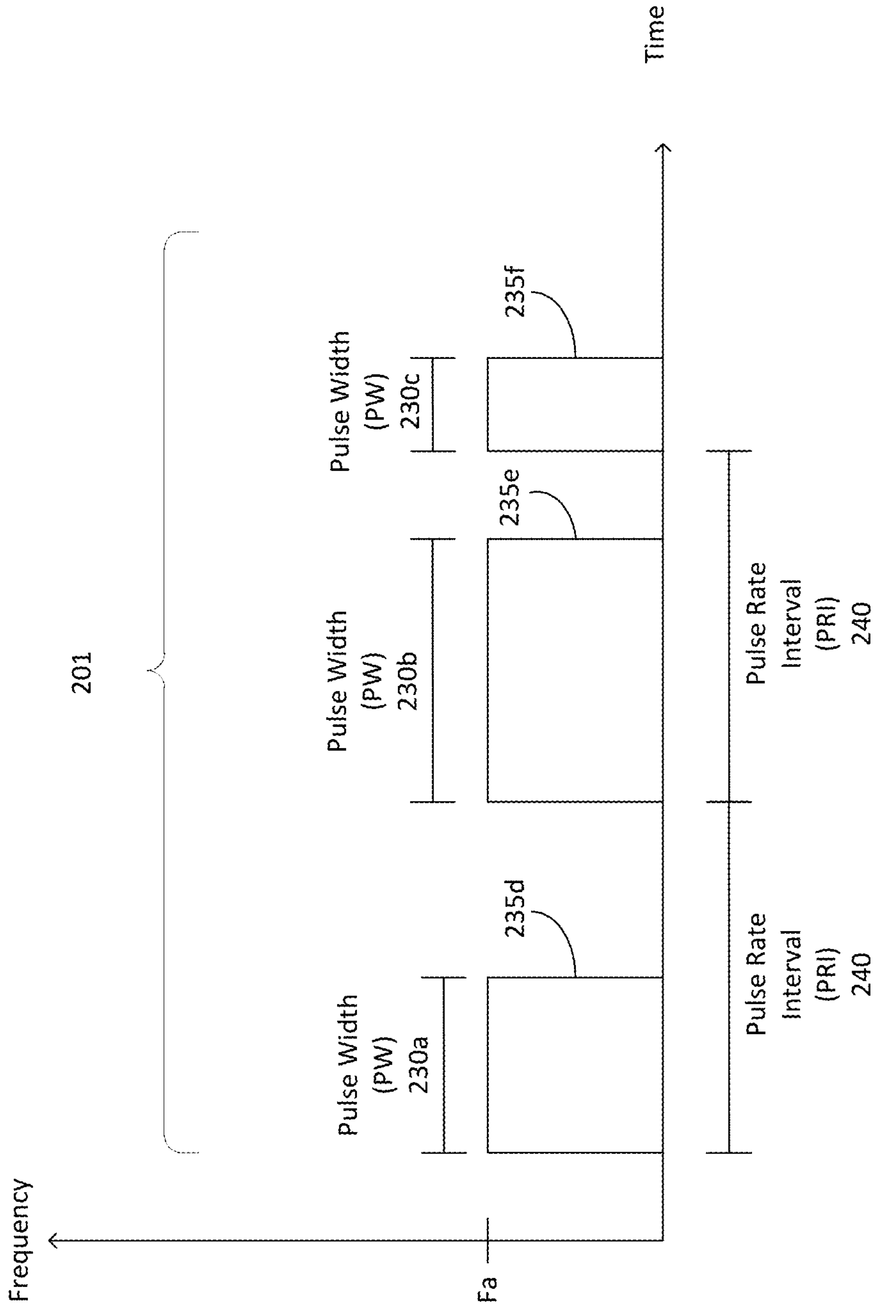

The width of each of the light pulses (e.g., the duration of the burst of the light wave) can correspond to a pulse width 230*a*. The pulse width 230*a* can refer to the length or duration of the burst. The pulse width 230*a* can be measured in units of time or distance. In some embodiments, the pulses 235*a-c* can include lights waves having different frequencies from one another. In some embodiments, the pulses 235*a-c* can have different pulse widths 230*a* from one another, as illustrated in FIG. 2D. For example, a first pulse 235*d* of FIG. 2D can have a pulse width 230*a*, while a second pulse 235*e* has a second pulse width 230*b* that is greater than the first pulse width 230*a*. A third pulse 235*f* can have a third pulse width 230*c* that is less than the second pulse width 230*b*. The third pulse width 230*c* can also be less than the first pulse width 230*a*. While the pulse widths 230*a-c* of the pulses 235*d-f* of the pulse train may vary, the light generation module 110 can maintain a constant pulse rate interval 240 for the pulse train.

The pulses 235*a-c* can form a pulse train having a pulse rate interval 240. The pulse rate interval 240 can be quantified using units of time. The pulse rate interval 240 can be based on a frequency of the pulses of the pulse train 201. The frequency of the pulses of the pulse train 201 can be referred to as a modulation frequency. For example, the light generation module 110 can provide a pulse train 201 with a predetermined frequency corresponding to gamma activity, such as 40 Hz. To do so, the light generation module 110 can determine the pulse rate interval 240 by taking the multiplicative inverse (or reciprocal) of the frequency (e.g., 1 divided by the predetermined frequency for the pulse train). For example, the light generation module 110 can take the multiplicative inverse of 40 Hz by dividing 1 by 40 Hz to determine the pulse rate interval 240 as 0.025 seconds. The pulse rate interval 240 can remain constant throughout the pulse train. In some embodiments, the pulse rate interval 240 can vary throughout the pulse train or from one pulse train to a subsequent pulse train. In some embodiments, the number of pulses transmitted during a second can be fixed, while the pulse rate interval 240 varies.

Figure 2E:
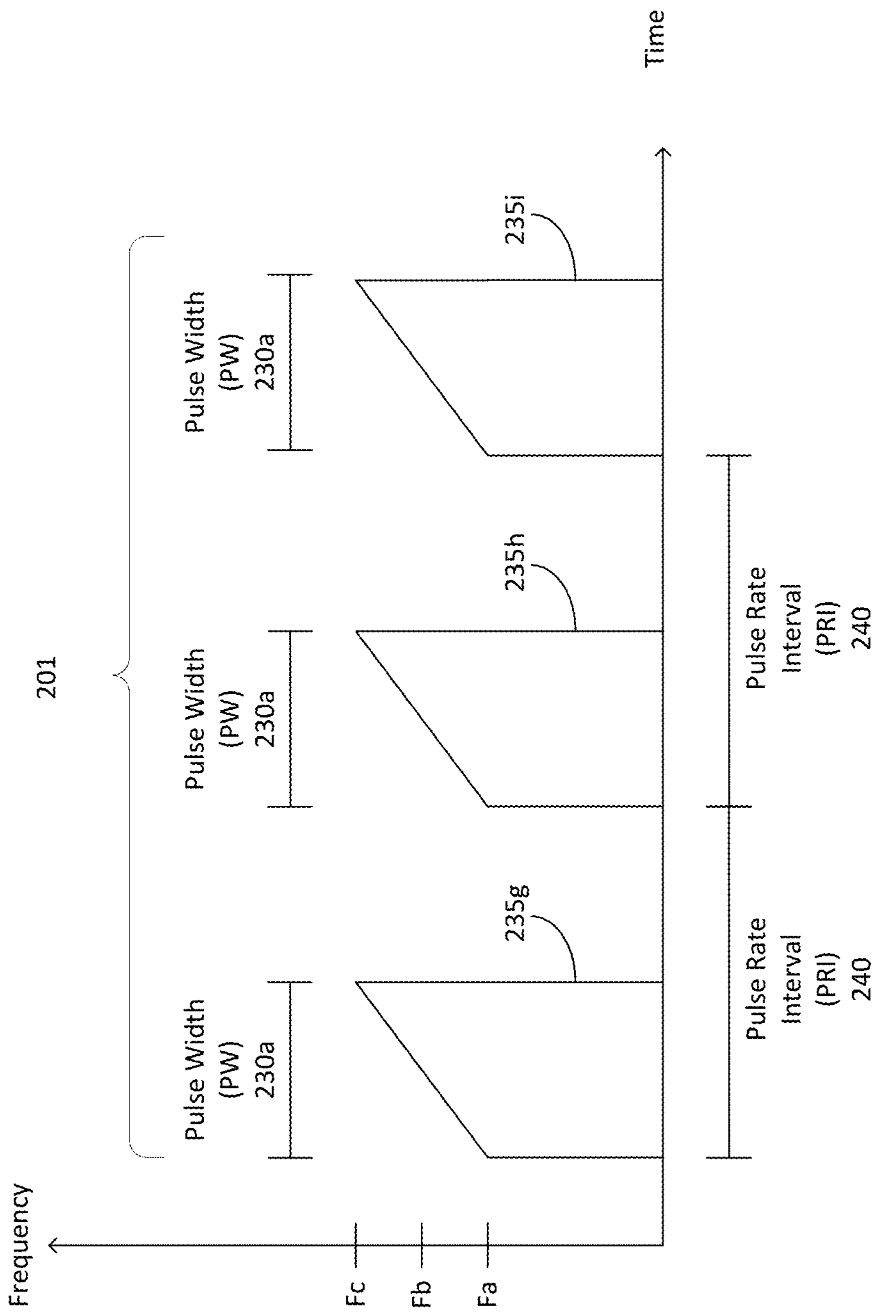

In some embodiments, the light generation module 110 can generate a light pulse having a light wave that varies in frequency. For example, the light generation module 110 can generate up-chirp pulses where the frequency of the light wave of the light pulse increases from the beginning of the pulse to the end of the pulse as illustrated in FIG. 2E. For example, the frequency of a light wave at the beginning of pulse 235*g* can be Fa. The frequency of the light wave of the pulse 235*g* can increase from Fa to Fb in the middle of the pulse 235*g*, and then to a maximum of Fc at the end of the pulse 235*g*. Thus, the frequency of the light wave used to generate the pulse 235*g* can range from Fa to Fc. The frequency can increase linearly, exponentially, or based on some other rate or curve.

Figure 2F:
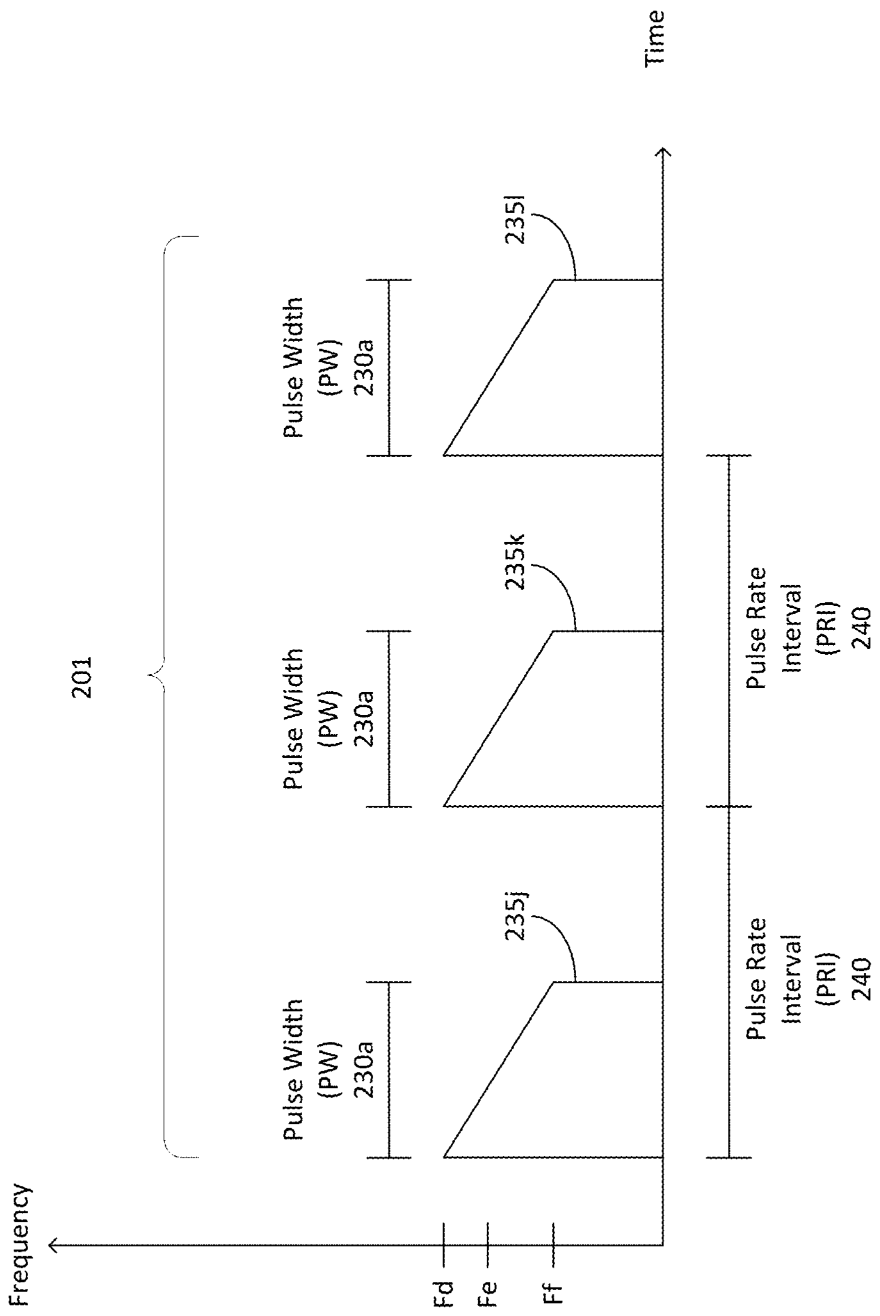

The light generation module 110 can generate down-chirp pulses, as illustrated in FIG. 2F, where the frequency of the light wave of the light pulse decreases from the beginning of the pulse to the end of the pulse. For example, the frequency of a light wave at the beginning of pulse 235*j* can be Fa. The frequency of the light wave of the pulse 235*j* can decrease from Fd to Fe in the middle of the pulse 235*j*, and then to a minimum of Ff at the end of the pulse 235*j*. Thus, the frequency of the light wave used to generate the pulse 235*j* can range from Fa to Ff. The frequency can decrease linearly, exponentially, or based on some other rate or curve.

Visual signaling component 150 can be designed and constructed to generate the light pulses responsive to instructions from the light generation module 110. The instructions can include, for example, parameters of the light pulse such as a frequency or wavelength of the light wave, intensity, duration of the pulse, frequency of the pulse train, pulse rate interval, or duration of the pulse train (e.g., a number of pulses in the pulse train or the length of time to transmit a pulse train having a predetermined frequency). The light pulse can be perceived, observed, or otherwise identified by the brain via ocular means such as eyes. The light pulses can be transmitted to the eye via direct visual field or peripheral visual field.

Figure 3A:
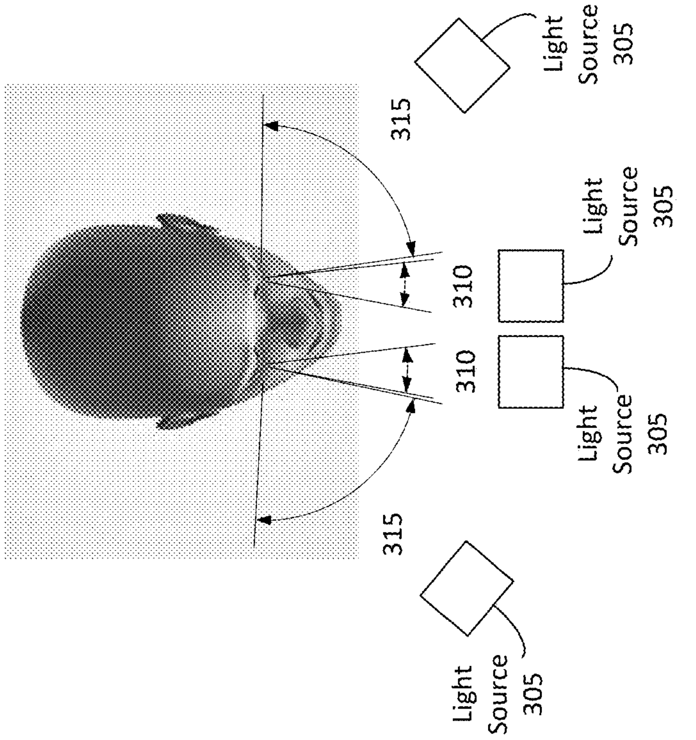
FIGS. 3A-3C illustrate fields of vision in which visual signals can be transmitted for visual brain entrainment in accordance with some embodiments.
Figure 3B:
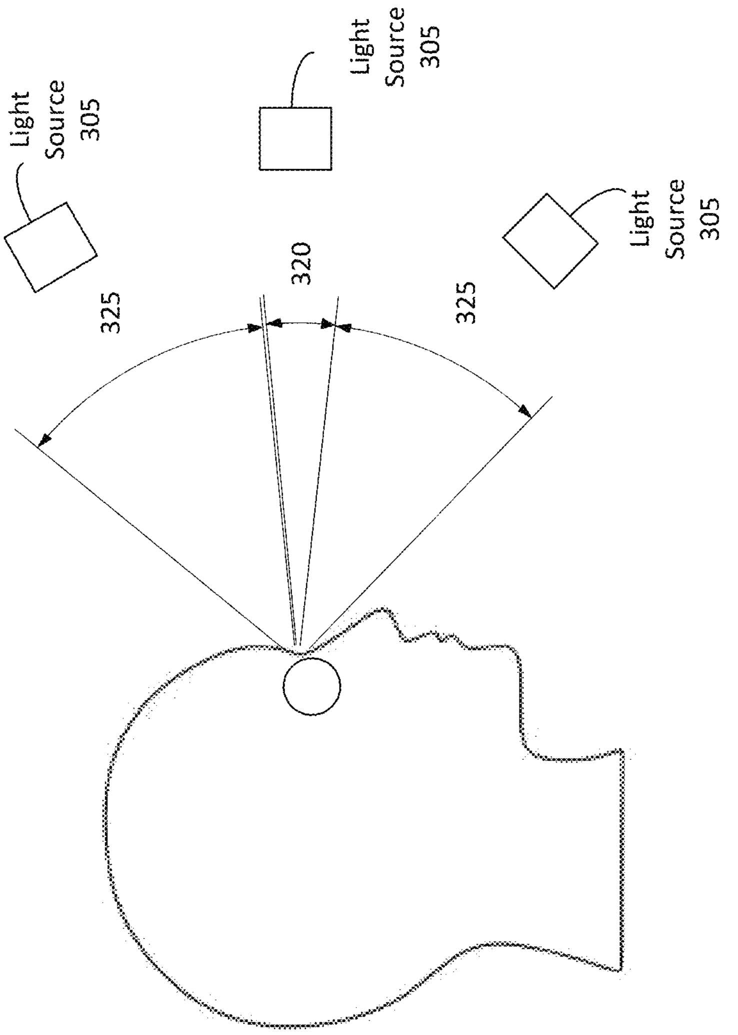
Figure 3C:
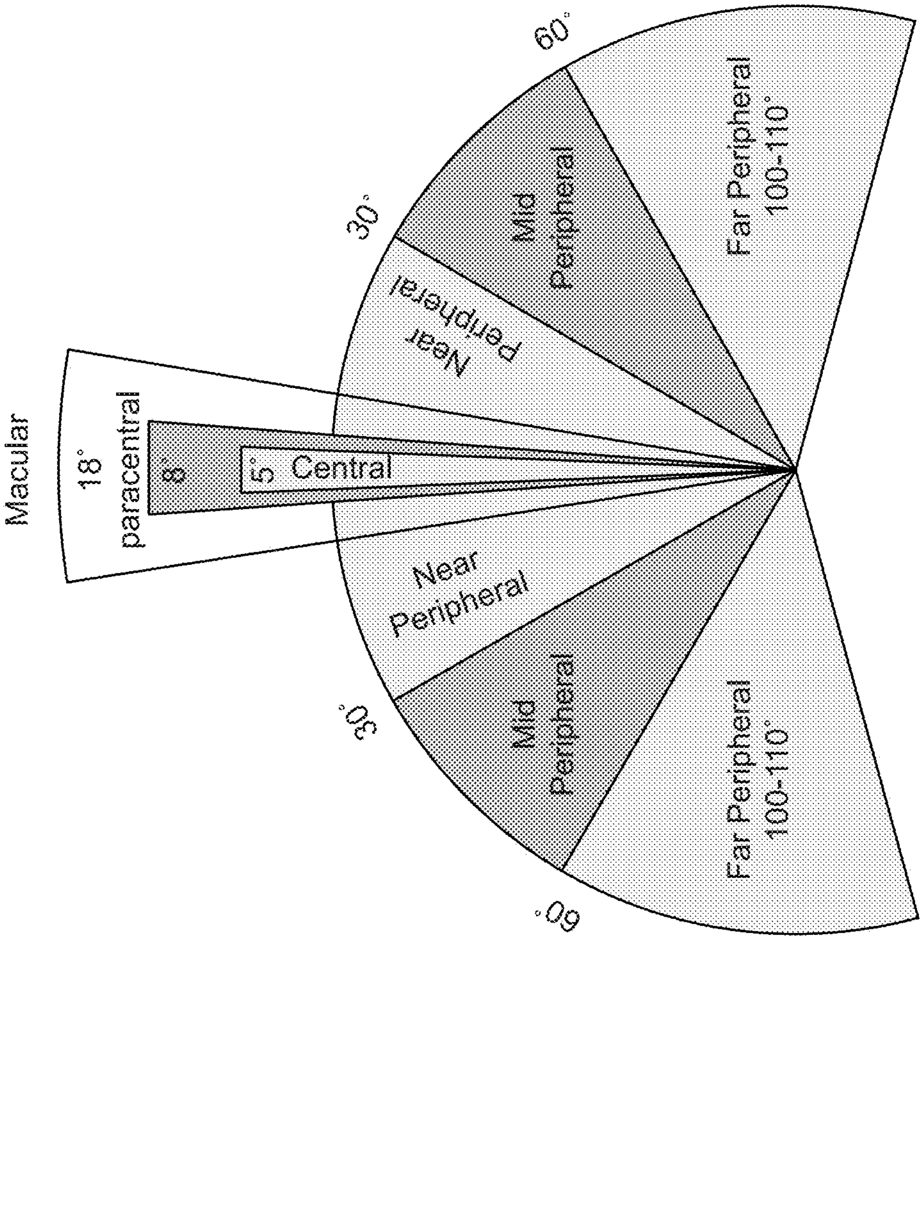

FIG. 3A illustrates a horizontal direct visual field 310 and a horizontal peripheral visual field. FIG. 3B illustrates a vertical direct visual field 320 and a vertical peripheral visual field 325. FIG. 3C illustrates degrees of direct visual fields and peripheral visual fields, including relative distances at which visual signals might be perceived in the different visual fields. The visual signaling component 150 can include a light source 305. The light source 305 can be positioned to transmit light pulses into the direct visual field 310 or 320 of a person's eyes. The NSS 105 can be configured to transmit light pulses into the direct visual field 310 or 320 because this may facilitate brain entrainment as the person may pay more attention to the light pulses. The level of attention can be quantitatively measured directly in the brain, indirectly through the person's eye behavior, or by active feedback (e.g., mouse tracking).

The light source 305 can be positioned to transmit light pulses into a peripheral visual field 315 or 325 of a person's eyes. For example, the NSS 105 can transmit light pulses into the peripheral visual field 315 or 325 as these light pulses may be less distracting to the person who might be performing other tasks, such as reading, walking, driving, etc. Thus, the NSS 105 can provide subtle, on-going visual brain stimulation by transmitting light pulses via the peripheral visual field.

In some embodiments, the light source 305 can be head-worn, while in other embodiments the light source 305 can be held by a subject's hands, placed on a stand, hung from a ceiling, or connected to a chair or otherwise positioned to direct light towards the direct or peripheral visual fields. For example, a chair or externally supported system can include or position the light source 305 to provide the visual input while maintaining a fixed/pre-specified relationship between the subject's visual field and the visual stimulus. The system can provide an immersive experience. For example, the system can include an opaque or partially opaque dome that includes the light source. The dome can positioned over the subject's head while the subject sits or reclines in chair. The dome can cover portions of the subject's visual field, thereby reducing external distractions and facilitating entrainment of regions of the brain.

The light source 305 can include any type of light source or light emitting device. The light source can include a coherent light source, such as a laser. The light source 305 can include a light emitting diode (LED), Organic LED, fluorescent light source, incandescent light, or any other light emitting device. The light source can include a lamp, light bulb, or one or more light emitting diodes of various colors (e.g., white, red, green, blue). In some embodiments, the light source includes a semiconductor light emitting device, such as a light emitting diode of any spectral or wavelength range. In some embodiments, the light source 305 includes a broadband lamp or a broadband light source. In some embodiments, the light source includes a black light. In some embodiments, light source 305 includes a hollow cathode lamp, a fluorescent tube light source, a neon lamp, an argon lamp, a plasma lamp, a xenon flash lamp, a mercury lamp, a metal halide lamp, or a sulfur lamp. In some embodiments, the light source 305 includes a laser, or a laser diode. In some embodiments, light source 305 includes an OLED, PHOLED, QDLED, or any other variation of a light source utilizing an organic material. In some embodiments, light source 305 includes a monochromatic light source. In some embodiments, light source 305 includes a polychromatic light source. In some embodiments, the light source 305 includes a light source emitting light partially in the spectral range of ultraviolet light. In some embodiments, light source 305 includes a device, product or a material emitting light partially in the spectral range of visible light. In some embodiments, light source 305 is a device, product or a material partially emanating or emitting light in the spectral range of the infrared light. In some embodiments, light source 305 includes a device, product or a material emanating or emitting light in the visible spectral range. In some embodiments, light source 305 includes a light guide, an optical fiber or a waveguide through which light is emitted from the light source.

In some embodiments, light source 305 includes one or more mirrors for reflecting or redirecting of light. For example, the mirrors can reflect or redirect light towards the direct visual field 310 or 320, or the peripheral visual field 315 or 325. The light source 305 can include interact with microelectromechanical devices ("MEMS"). The light source 305 can include or interact with a digital light projector ("DLP"). In some embodiments, the light source 305 can include ambient light or sunlight. The ambient light or sunlight can be focused by one or more optical lenses and directed towards the direct visual field or peripheral field. The ambient light or sunlight can be directed by one or more mirrors towards the directed visual field or peripheral visual field.

Figure 4A:
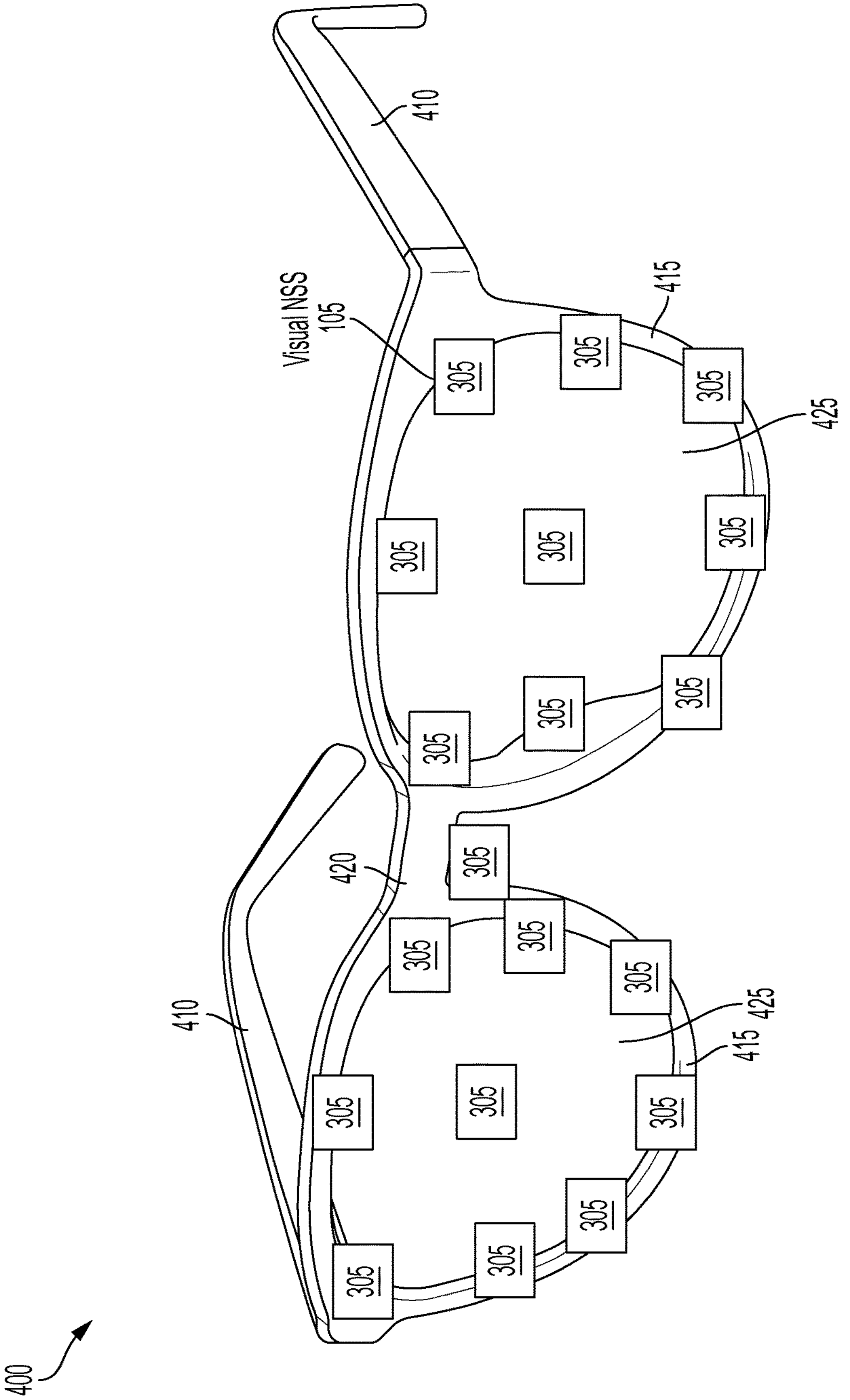
FIGS. 4A-4C illustrate devices configured to transmit visual signals for neural stimulation in accordance with some embodiments.

In cases where the light source is ambient light, the ambient light is not positioned but the ambient light can enter the eye via a direct visual field or peripheral visual field. In some embodiments, the light source 305 can be positioned to direct light pulses towards the direct visual field or peripheral field. For example, one or more light sources 305 can be attached, affixed, coupled, mechanically coupled, or otherwise provided with a frame 400 as illustrated in FIG. 4A. In some embodiments, the visual signaling component 150 can include the frame 400. Additional details of the operation of the NSS 105 in conjunction with the frame 400 including one or more light sources 305 are provided below, in the section labelled as "NSS Operating With A Frame". Thus, the light source can include any type of light source such as an optical light source, mechanical light source, or chemical light source. The light source can include any material or object that is reflective or opaque that can generate, emit, or reflect oscillating patterns of light, such as a fan rotating in front of a light, or bubbles. In some embodiments, the light source can include optical illusions that are invisible, physiological phenomena that are within the eye (e.g., pressing the eyeball), or chemicals applied to the eye.

Systems and Devices Configured for Neural Stimulation Via Visual Stimulation

Referring now to FIG. 4A, the frame 400 can be designed and constructed to be placed or positioned on a person's head. The frame 400 can be configured to be worn by the person. The frame 400 can be designed and constructed to stay in place. The frame 400 can be configured to be worn and stay in place as a person sits, stands, walks, runs, or lays down flat. The light source 305 can be configured on the frame 400 to project light pulses towards the person's eyes during these various positions. In some embodiments, the light source 305 can be configured to project light pulses towards the person's eyes if their eyelids are closed such that the light pulse penetrates the eyelid to be perceived by the retina. The frame 400 can include a bridge 420. The frame 400 can include one or more eye wires 415 coupled to the bridge 420. The bridge 420 can be positioned in between the eye wires 415. The frame 400 can include one or more temples extending from the one or more eye wires 415. In some embodiments, the eye wires 415 can include or hold a lens 425. In some embodiments, the eye wires 415 can include or hold a solid material 425 or cover 425. The lens, solid material, or cover 425 can be transparent, semi-transparent, opaque, or completely block out external light.

One or more light sources 305 can be positioned on or adjacent to the eye wire 415, lens or other solid material 425, or bridge 420. For example, a light source 305 can be positioned in the middle of the eye wire 415 on a solid material 425 in order to transmit light pulses into the direct visual field. In some embodiments, a light source 305 can be positioned at a corner of the eye wire 415, such as a corner of the eye wire 415 coupled to the temple 410, in order to transmit light pulses towards a peripheral field.

The NSS 105 can perform visual brain entrainment via a single eye or both eyes. For example, the NSS 105 can direct light pulses to a single eye or both eyes. The NSS 105 can interface with a visual signaling component 150 that includes a frame 400 and two eye wires 415. However, the visual signaling component 150 may include a single light source 305 configured and positioned to direct light pulses to a first eye. The visual signaling component 150 can further include a light blocking component that keeps out or blocks the light pulses generated from the light source 305 from entering a second eye. The visual signaling component 150 can block or prevent light from entering the second eye during the brain entrainment process.

In some embodiments, the visual signaling component 150 can alternatively transmit or direct light pulses to the first eye and the second eye. For example, the visual signaling component 150 can direct light pulses to the first eye for a first time interval. The visual signaling component 150 can direct light pulses to the second eye for a second time interval. The first time interval and the second time interval can be a same time interval, overlapping time intervals, mutually exclusive time intervals, or subsequent time intervals.

Figure 4B:
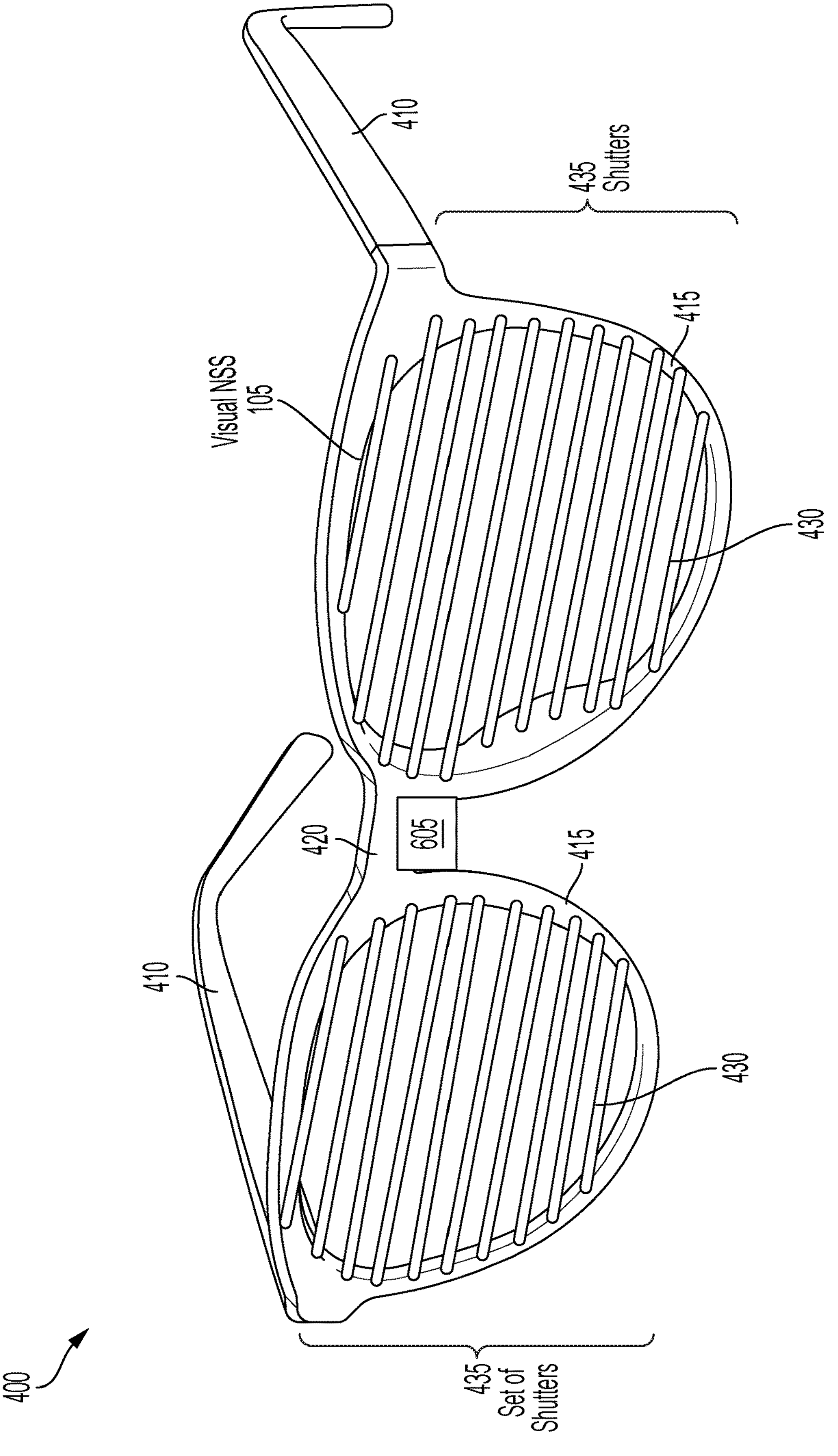

FIG. 4B illustrates a frame 400 comprising a set of shutters 435 that can block at least a portion of light that enters through the eye wire 415. The set of shutters 435 can intermittently block ambient light or sunlight that enters through the eye wire 415. The set of shutters 435 can open to allow light to enter through the eye wire 415, and close to at least partially block light that enters through the eye wire 415. Additional details of the operation of the NSS 105 in conjunction with the frame 400 including one or more shutters 430 are provided below, in the section labelled as "NSS Operating With A Frame".

The set of shutters 435 can include one or more shutter 430 that is opened and closed by one or more actuator. The shutter 430 can be formed from one or more materials. The shutter 430 can include one or more materials. The shutter 430 can include or be formed from materials that are capable of at least partially blocking or attenuating light.

The frame 400 can include one or more actuators configured to at least partially open or close the set of shutters 435 or an individual shutter 430. The frame 400 can include one or more types of actuators to open and close the shutters 435. For example, the actuator can include a mechanically driven actuator. The actuator can include a magnetically driven actuator. The actuator can include a pneumonic actuator. The actuator can include a hydraulic actuator. The actuator can include a piezoelectric actuator. The actuator can include a micro-electromechanical systems ("MEMS").

The set of shutters 435 can include one or more shutter 430 that is opened and closed via electrical or chemical techniques. For example, the shutter 430 or set of shutters 435 can be formed from one or more chemicals. The shutter 430 or set of shutters can include one or more chemicals. The shutter 430 or set of shutters 435 can include or be formed from chemicals that are capable of at least partially blocking or attenuating light.

For example, the shutter 430 or set of shutters 435 can include photochromic lenses configured to filter, attenuate or block light. The photochromic lenses can automatically darken when exposed to sunlight. The photochromic lens can include molecules that are configured to darken the lens. The molecules can be activated by light waves, such as ultraviolet radiation or other light wavelengths. Thus, the photochromic molecules can be configured to darken the lens in response to a predetermined wavelength of light.

The shutter 430 or set of shutters 435 can include electrochromic glass or plastic. Electrochromic glass or plastic can change from light to dark (e.g., clear to opaque) in response to an electrical voltage or current. Electrochromic glass or plastic can include metal-oxide coatings that are deposited on the glass or plastic, multiple layers, and lithium ions that travel between two electrodes between a layer to lighten or darken the glass.

The shutter 430 or set of shutters 435 can include micro shutters. Micro shutters can include tiny windows that measure 100 by 200 microns. The micro shutters can be arrayed in the eye frame 415 in a waffle-like grid. The individual micro shutters can be opened or closed by an actuator. The actuator can include a magnetic arm that sweeps past the micro shutter to open or close the micro shutter. An open micro shutter can allow light to enter through the eye frame 415, while a closed micro shutter can block, attenuate, or filter the light.

The NSS 105 can drive the actuator to open and close one or more shutters 430 or the set of shutters 435 at a predetermined frequency such as 40 Hz. By opening and closing the shutter 430 at the predetermined frequency, the shutter 430 can allow flashes of light to pass through the eye wire 415 at the predetermined frequency. Thus, the frame 400 including a set of shutters 435 may not include or use separate light source coupled to the frame 400, such as a light source 305 coupled to frame 400 depicted in FIG. 4A.

Figure 4C:
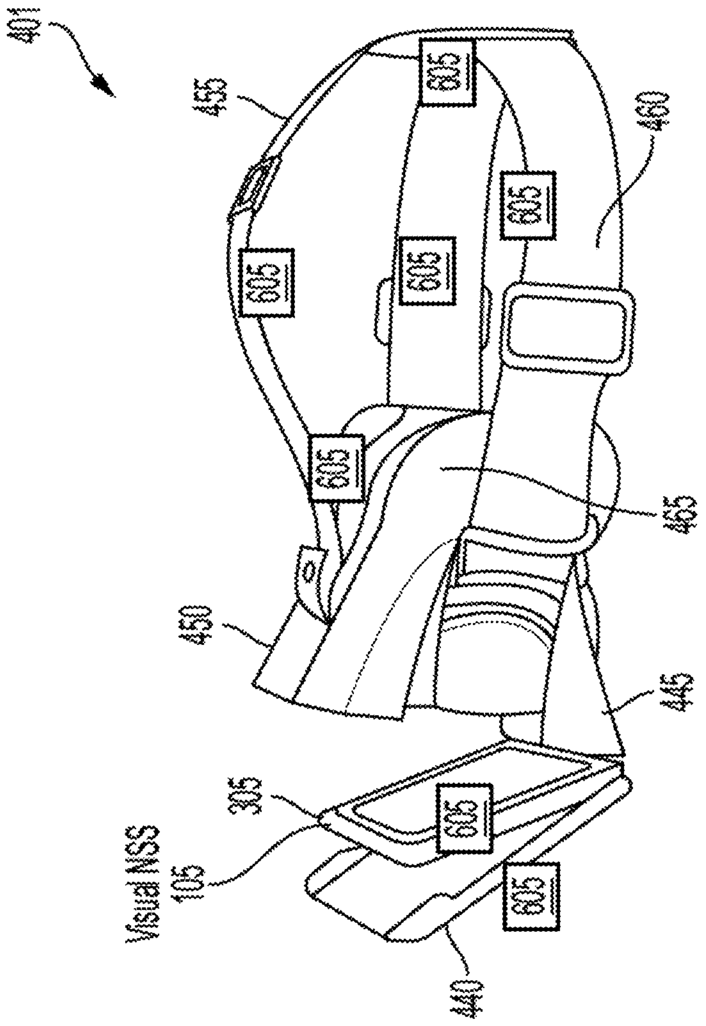

In some embodiments, the visual signaling component 150 or light source 305 can refer to or be included in a virtual reality headset 401, as depicted in FIG. 4C. For example, the virtual reality headset 401 can be designed and constructed to receive a light source 305. The light source 305 can include a computing device having a display device, such as a smartphone or mobile telecommunications device. The virtual reality headset 401 can include a cover 440 that opens to receive the light source 305. The cover 440 can close to lock or hold the light source 305 in place. When closed, the cover 440 and case 450 and 445 can form an enclosure for the light source 305. This enclosure can provide an immersive experience that minimize or eliminates unwanted visual distractions. The virtual reality headset can provide an environment to maximize brainwave entrainment. The virtual reality headset can provide an augmented reality experience. In some embodiments, the light source 305 can form an image on another surface such that the image is reflected off the surface and towards a subject's eye (e.g., a heads up display that overlays on the screen a flickering object or an augmented portion of reality). Additional details of the operation of the NSS 105 in conjunction with the virtual reality headset 401 are provided below, in the section labeled as "Systems And Devices Configured For Neural Stimulation Via Visual Stimulation".

The virtual reality headset 401 includes straps 455 and 460 configured to secure the virtual reality headset 401 to a person's head. The virtual reality headset 401 can be secured via straps 455 and 460 such to minimize movement of the headset 401 worn during physical activity, such as walking or running. The virtual reality headset 401 can include a skull cap formed from 460 or 455.

The feedback sensor 605 can include an electrode, dry electrode, gel electrode, saline soaked electrode, or adhesive-based electrodes.

FIGS. 5A-5D illustrate embodiments of the visual signaling component 150 that can include a tablet computing device 500 or other computing device 500 having a display screen 305 as the light source 305. The visual signaling component 150 can transmit light pulses, light flashes, or patterns of light via the display screen 305 or light source 305.

Figure 5B:
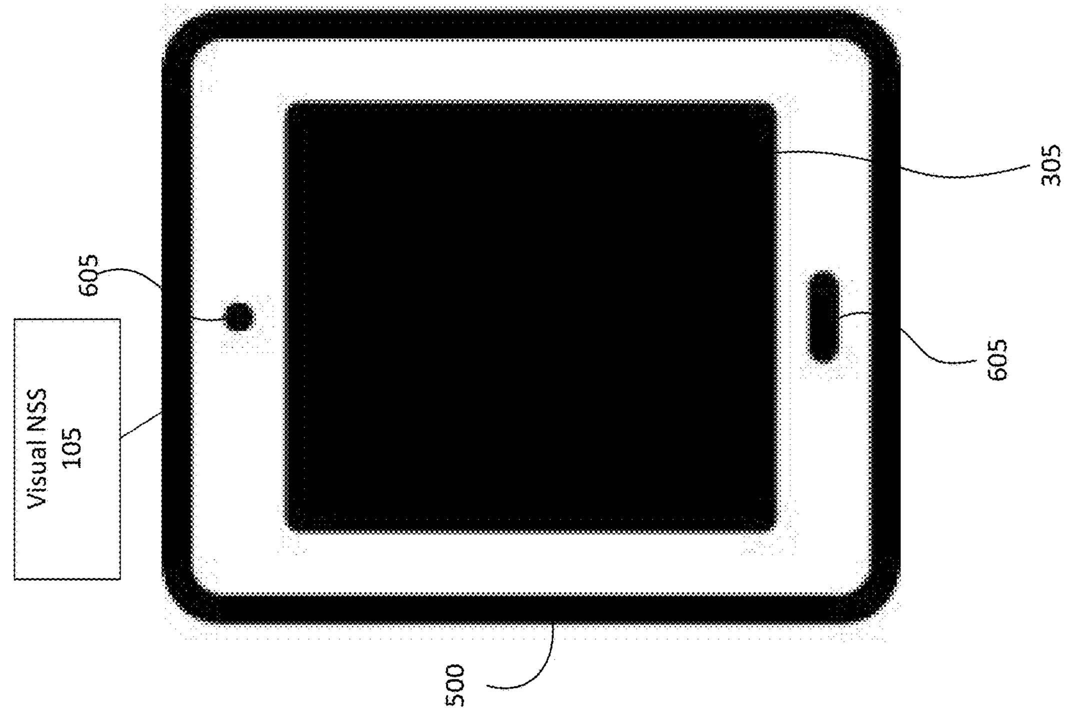
FIGS. 5A-5D illustrate devices configured to transmit visual signals for neural stimulation in accordance with some embodiments.
Figure 5A:
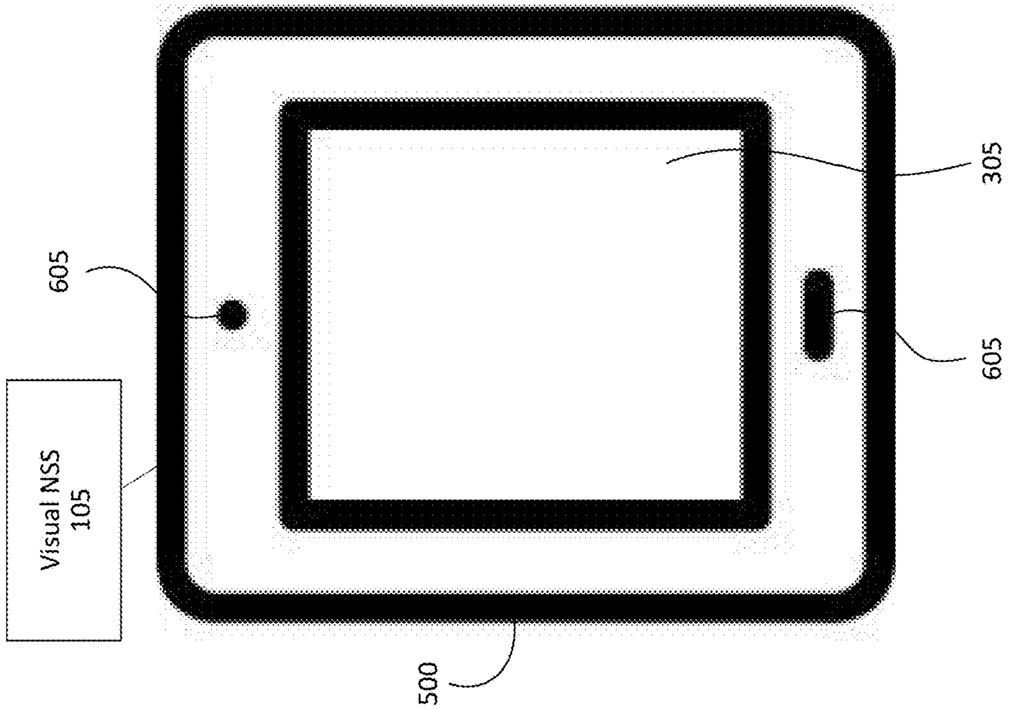

FIG. 5A illustrates a display screen 305 or light source 305 that transmits light. The light source 305 can transmit light comprising a wavelength in the visible spectrum. The NSS 105 can instruct the visual signaling component 150 to transmit light via the light source 305. The NSS 105 can instruct the visual signaling component 150 to transmit flashes of light or light pulses having a predetermined pulse rate interval. For example, FIG. 5B illustrates the light source 305 turned off or disabled such that the light source does not emit light, or emits a minimal or reduced amount of light. The visual signaling component 150 can cause the tablet computing device 500 to enable (e.g., FIG. 5A) and disable (e.g., FIG. 5B) the light source 305 such that flashes of light have a predetermined frequency, such as 40 Hz. The visual signaling component 150 can toggle or switch the light source 305 between two or more states to generate flashes of light or light pulses with the predetermined frequency.

Figure 5D:
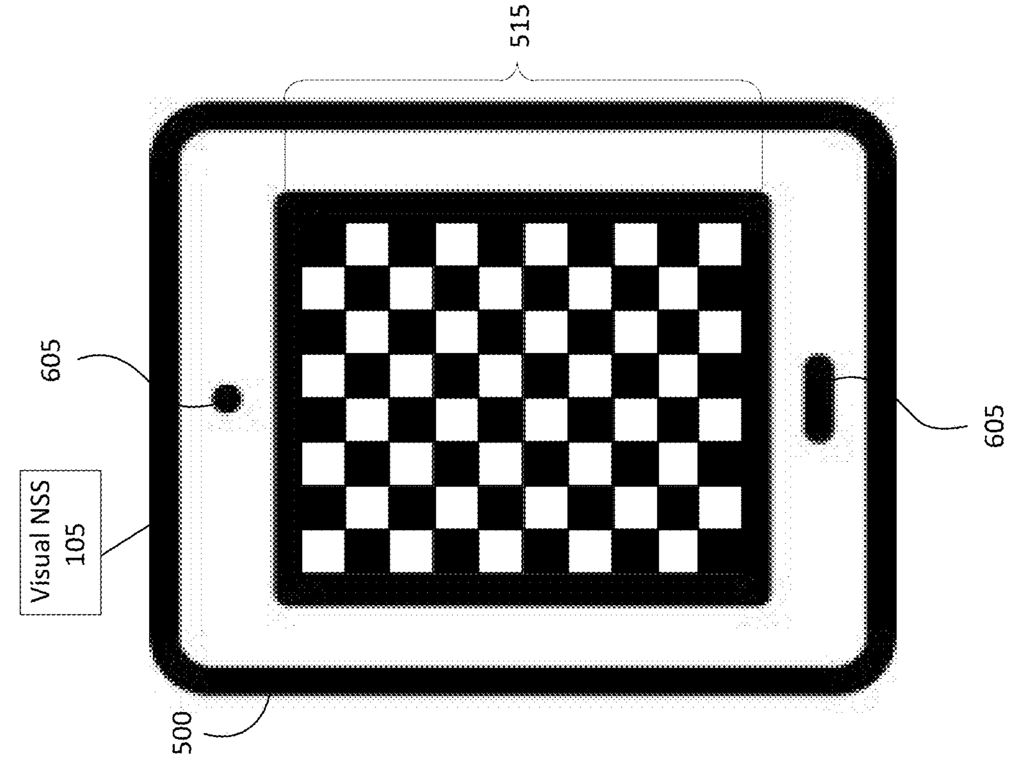
Figure 5C:
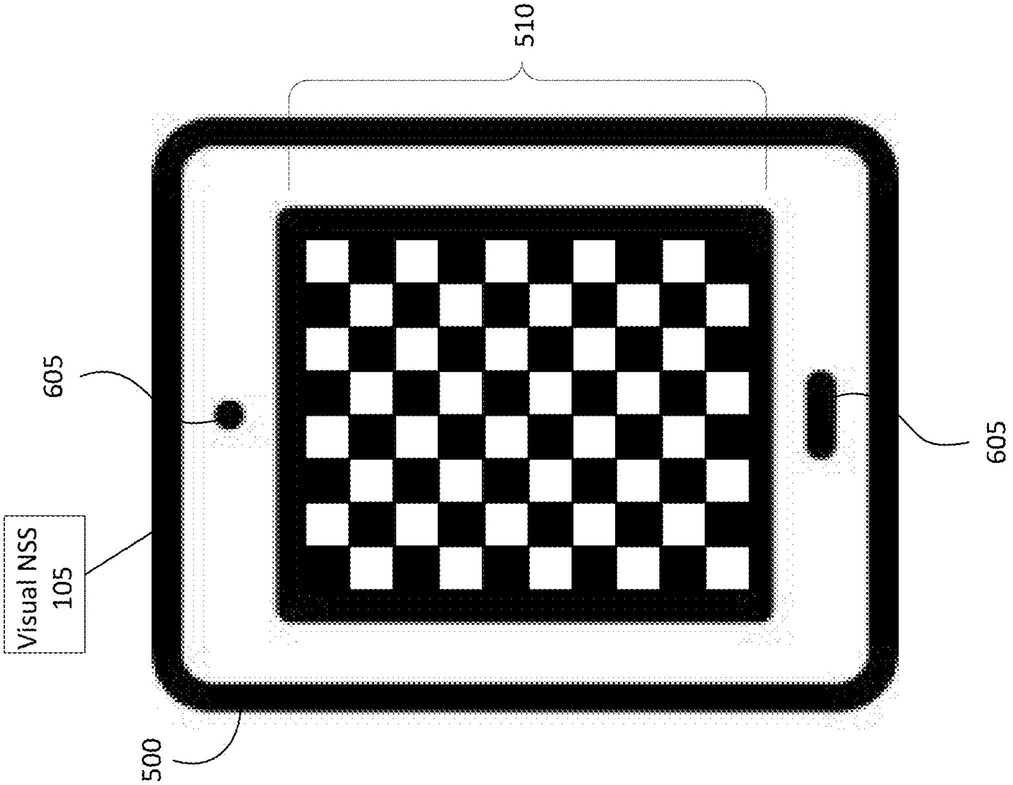

In some embodiments, the light generation module 110 can instruct or cause the visual signaling component 150 to display a pattern of light via display device 305 or light source 305, as depicted in FIGS. 5C and 5D. The light generation module 110 can cause the visual signaling component 150 can flicker, toggle or switch between two or more patterns to generate flashes of light or light pulses. Patterns can include, for example, alternating checkerboard patterns 510 and 515. The pattern can include symbols, characters, or images that can be toggled or adjusted from one state to another state. For example, the color of a character or text relative to a background color can be inverted to cause a switch between a first state 510 and a second state 515. Inverting a foreground color and background color at a predetermined frequency can generate light pulses by way of indicating visual changes that can facilitate adjusting or managing a frequency of neural oscillations. Additional details of the operation of the NSS 105 in conjunction with the tablet 500 are provided below, in the section labeled as "NSS Operating With a Tablet".

In some embodiments, the light generation module 110 can instruct or cause the visual signaling component 150 to flicker, toggle, or switch between images configured to stimulate specific or predetermined portions of the brain or a specific cortex. The presentation, form, color, motion and other aspects of the light or an image based stimuli can dictate which cortex or cortices are recruited to process the stimuli. The visual signaling component 150 can stimulate discrete portions of the cortex by modulating the presentation of the stimuli to target specific or general regions of interest. The relative position in the field of view, the color of the input, or the motion and speed of the light stimuli can dictate which region of the cortex is stimulated.

For example, the brain can include at least two portions that process predetermined types of visual stimuli: the primary visual cortex on the left side of the brain, and the calcarine fissure on the right side of the brain. Each of these two portions can have one or more multiple sub-portions that process predetermined types of visual stimuli. For example, the calcarine fissure can include a sub-portion referred to as area V5 that can include neurons that respond strongly to motion but may not register stationary objects. Subjects with damage to area V5 may have motion blindness, but otherwise normal vision. In another example, the primary visual cortex can include a sub-portion referred to as area V4 that can include neurons that are specialized for color perception. Subjects with damage to area V4 may have color blindness and only perceive objects in shades of gray. In another example, the primary visual cortex can include a sub-portion referred to as area V1 that includes neurons that respond strongly to contrast edges and helps segment the image into separate objects.

Thus, the light generation module 110 can instruct or cause the visual signaling component 150 to form a type of still image or video, or generate a flicker, or toggle between images that configured to stimulate specific or predetermined portions of the brain or a specific cortex. For example, the light generation module 110 can instruct or cause the visual signaling component 150 to generate images of human faces to stimulate a fusiform face area, which can facilitate brain entrainment for subjects having prosopagnosia or face blindness. The light generation module 110 can instruct or cause the visual signaling component 150 to generate images of faces flickering to target this area of the subject's brain. In another example, the light generation module 110 can instruct the visual signaling component 150 to generate images that include edges or line drawings to stimulate neurons of the primary visual cortex that respond strongly to contrast edges.

The NSS 105 can include, access, interface with, or otherwise communicate with at least one light adjustment module 115. The light adjustment module 115 can be designed and constructed to measure or verify an environmental variable (e.g., light intensity, timing, incident light, ambient light, eye lid status, etc.) to adjust a parameter associated with the visual signal, such as a frequency, amplitude, wavelength, intensity pattern or other parameter of the visual signal. The light adjustment module 115 can automatically vary a parameter of the visual signal based on profile information or feedback. The light adjustment module 115 can receive the feedback information from the feedback monitor 135. The light adjustment module 115 can receive instructions or information from a side effects management module 130. The light adjustment module 115 can receive profile information from profile manager 125.

The NSS 105 can include, access, interface with, or otherwise communicate with at least one unwanted frequency filtering module 120. The unwanted frequency filtering module 120 can be designed and constructed to block, mitigate, reduce, or otherwise filter out frequencies of visual signals that are undesired to prevent or reduce an amount of such visual signals from being perceived by the brain. The unwanted frequency filtering module 120 can interface, instruct, control, or otherwise communicate with a filtering component 155 to cause the filtering component 155 to block, attenuate, or otherwise reduce the effect of the unwanted frequency on the neural oscillations.

The NSS 105 can include, access, interface with, or otherwise communicate with at least one profile manager 125. The profile manager 125 can be designed or constructed to store, update, retrieve or otherwise manage information associated with one or more subjects associated with the visual brain entrainment. Profile information can include, for example, historical treatment information, historical brain entrainment information, dosing information, parameters of light waves, feedback, physiological information, environmental information, or other data associated with the systems and methods of brain entrainment.

The NSS 105 can include, access, interface with, or otherwise communicate with at least one side effects management module 130. The side effects management module 130 can be designed and constructed to provide information to the light adjustment module 115 or the light generation module 110 to change one or more parameter of the visual signal in order to reduce a side effect. Side effects can include, for example, nausea, migraines, fatigue, seizures, eye strain, or loss of sight.

The side effects management module 130 can automatically instruct a component of the NSS 105 to alter or change a parameter of the visual signal. The side effects management module 130 can be configured with predetermined thresholds to reduce side effects. For example, the side effects management module 130 can be configured with a maximum duration of a pulse train, maximum intensity of light waves, maximum amplitude, maximum duty cycle of a pulse train (e.g., the pulse width multiplied by the frequency of the pulse train), maximum number of treatments for brainwave entrainment in a time period (e.g., 1 hour, 2 hours, 12 hours, or 24 hours).

The side effects management module 130 can cause a change in the parameter of the visual signal in response to feedback information. The side effect management module 130 can receive feedback from the feedback monitor 135. The side effects management module 130 can determine to adjust a parameter of the visual signal based on the feedback. The side effects management module 130 can compare the feedback with a threshold to determine to adjust the parameter of the visual signal.

The side effects management module 130 can be configured with or include a policy engine that applies a policy or a rule to the current visual signal and feedback to determine an adjustment to the visual signal. For example, if feedback indicates that a patient receiving visual signals has a heart rate or pulse rate above a threshold, the side effects management module 130 can turn off the pulse train until the pulse rate stabilizes to a value below the threshold, or below a second threshold that is lower than the threshold.

The NSS 105 can include, access, interface with, or otherwise communicate with at least one feedback monitor 135. The feedback monitor can be designed and constructed to receive feedback information from a feedback component 160. Feedback component 160 can include, for example, a feedback sensor 605 such as a temperature sensor, heart or pulse rate monitor, physiological sensor, ambient light sensor, ambient temperature sensor, sleep status via actigraphy, blood pressure monitor, respiratory rate monitor, brain wave sensor, EEG probe, electrooculography ("EOG") probes configured to measure the corneo-retinal standing potential that exists between the front and the back of the human eye, accelerometer, gyroscope, motion detector, proximity sensor, camera, microphone, or photo detector.

In some embodiments, a computing device 500 can include the feedback component 160 or feedback sensor 605, as depicted in FIGS. 5C and 5D. For example, the feedback sensor on tablet 500 can include a front-facing camera that can capture images of a person viewing the light source 305.

Figure 6A:
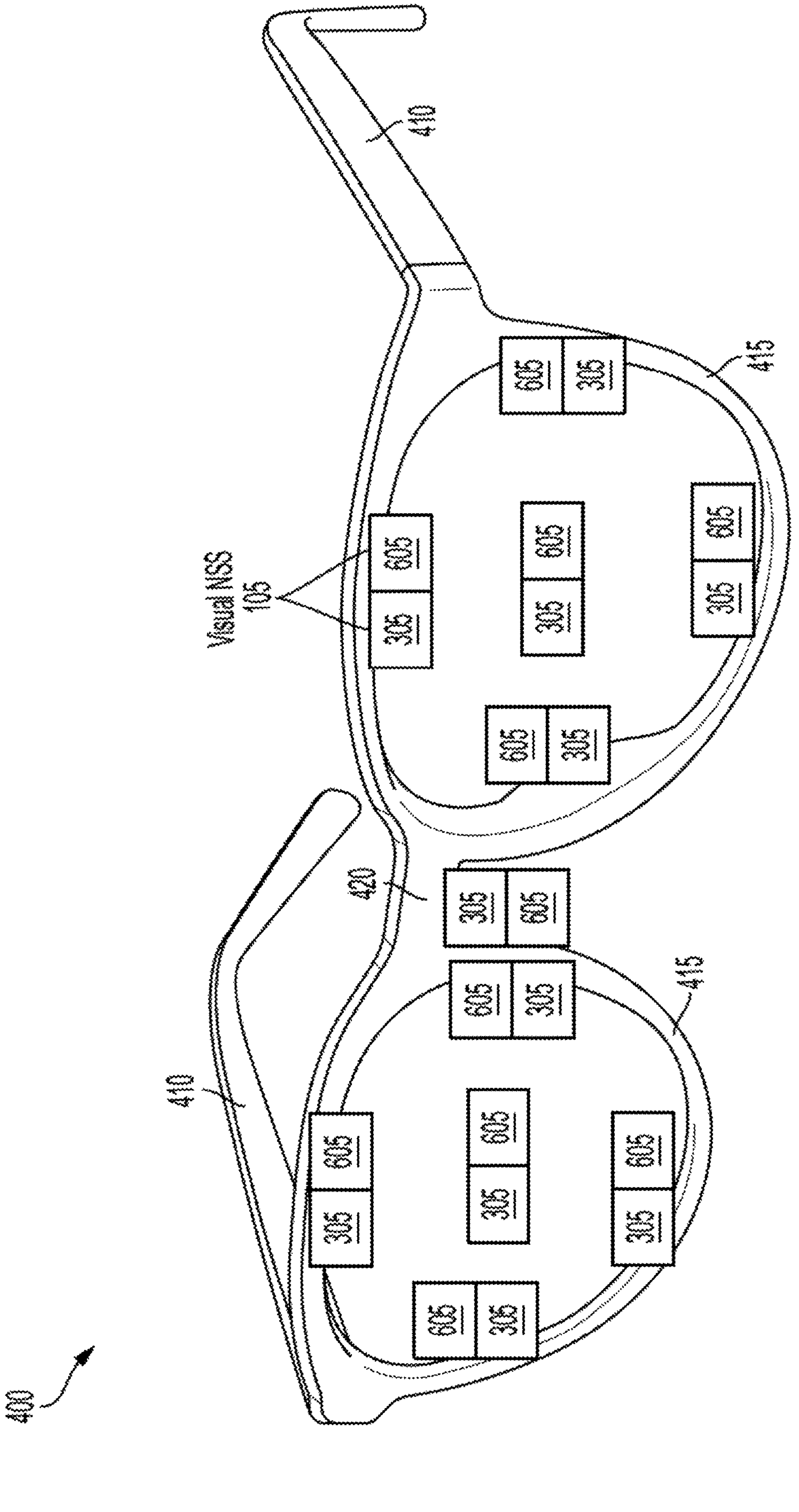
FIGS. 6A AND 6B illustrate devices configured to receive feedback to facilitate neural stimulation in accordance with some embodiments.

FIG. 6A depicts one or more feedback sensors 605 provided on a frame 400. In some embodiments, a frame 400 can include one or feedback sensors 605 provided on a portion of the frame, such as the bridge 420 or portion of the eye wire 415. The feedback sensor 605 can be provided with or coupled to the light source 305. The feedback sensor 605 can be separate from the light source 305.

The feedback sensor 605 can interact with or communicate with NSS 105. For example, the feedback sensor 605 can provide detected feedback information or data to the NSS 105 (e.g., feedback monitor 135). The feedback sensor 605 can provide data to the NSS 105 in real-time, for example as the feedback sensor 605 detects or senses or information. The feedback sensor 605 can provide the feedback information to the NSS 105 based on a time interval, such as 1 minute, 2 minutes, 5 minutes, 10 minutes, hourly, 2 hours, 4 hours, 12 hours, or 24 hours. The feedback sensor 605 can provide the feedback information to the NSS 105 responsive to a condition or event, such as a feedback measurement exceeding a threshold or falling below a threshold. The feedback sensor 605 can provide feedback information responsive to a change in a feedback parameter. In some embodiments, the NSS 105 can ping, query, or send a request to the feedback sensor 605 for information, and the feedback sensor 605 can provide the feedback information in response to the ping, request, or query.

Figure 6B:
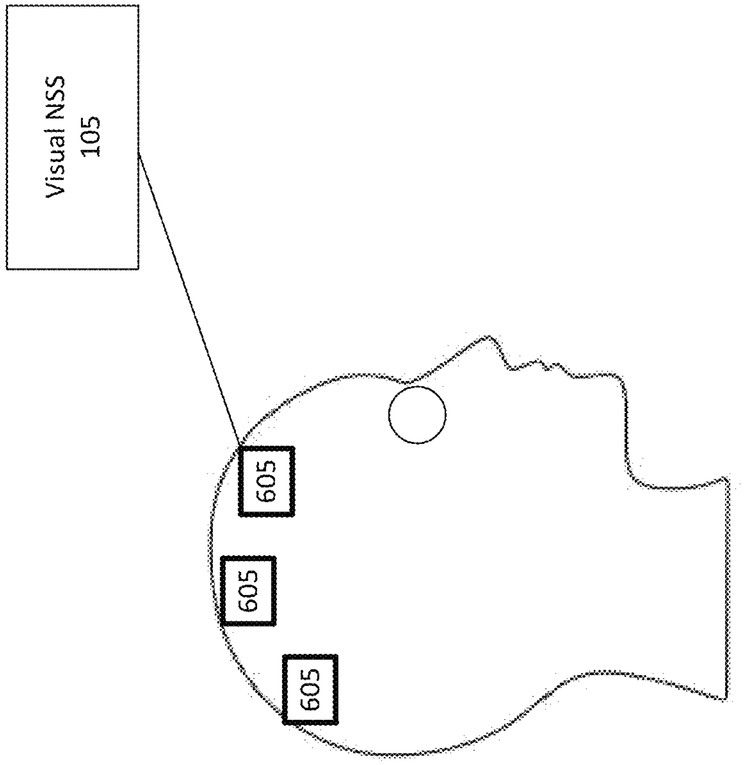

FIG. 6B illustrates feedback sensors 605 placed or positioned at, on, or near a person's head. Feedback sensors 605 can include, for example, EEG probes that detect brain wave activity.

The feedback monitor 135 can detect, receive, obtain, or otherwise identify feedback information from the one or more feedback sensors 605. The feedback monitor 135 can provide the feedback information to one or more component of the NSS 105 for further processing or storage. For example, the profile manager 125 can update profile data structure 145 stored in data repository 140 with the feedback information. Profile manager 125 can associate the feedback information with an identifier of the patient or person undergoing the visual brain stimulation, as well as a time stamp and date stamp corresponding to receipt or detection of the feedback information. The identifier can be indicative of an activity of a subject, a physiological or physical condition of a subject, or a mental condition of a subject. The identifier can also be indicative of a disease, disorder, or condition.

The feedback monitor 135 can detect symptoms of a neurological disease or disorder. For the example, the feedback monitor can be used to evaluate changes in fine motor skills over time or changes in voice pitch or tone. The profile manager 125 can update profile data structure with the feedback information. The profile data structure can be used to assess whether a person is at risk of developing a neurological disorder, whether a person has a neurological disorder, or progression of symptoms of a neurological disorder.

The feedback monitor 135 can determine a level of attention. The level of attention can refer to the focus provided to the light pulses used for brain stimulation. The feedback monitor 135 can determine the level of attention using various hardware and software techniques. The feedback monitor 135 can assign a score to the level of attention (e.g., 1 to 10 with 1 being low attention and 10 being high attention, or vice versa, 1 to 100 with 1 being low attention and 100 being high attention, or vice versa, 0 to 1 with 0 being low attention and 1 being high attention, or vice versa), categorize the level of attention (e.g., low, medium, high), grade the attention (e.g., A, B, C, D, or F), or otherwise provide an indication of a level of attention.

In some cases, the feedback monitor 135 can track a person's eye movement to identify a level of attention. The feedback monitor 135 can interface with a feedback component 160 that includes an eye-tracker. The feedback monitor 135 (e.g., via feedback component 160) can detect and record eye movement of the person and analyze the recorded eye movement to determine an attention span or level of attention. The feedback monitor 135 can measure eye gaze which can indicate or provide information related to covert attention. For example, the feedback monitor 135 (e.g., via feedback component 160) can be configured with electro-oculography ("EOG") to measure the skin electric potential around the eye, which can indicate a direction the eye faces relative to the head. In some embodiments, the EOG can include a system or device to stabilize the head so it cannot move in order to determine the direction of the eye relative to the head. In some embodiments, the EOG can include or interface with a head tracker system to determine the position of the heads, and then determine the direction of the eye relative to the head.

In some embodiments, the feedback monitor 135 and feedback component 160 can determine or track the direction of the eye or eye movement using video detection of the pupil or corneal reflection. For example, the feedback component 160 can include one or more camera or video camera. The feedback component 160 can include an infra-red source that sends light pulses towards the eyes. The light can be reflected by the eye. The feedback component 160 can detect the position of the reflection. The feedback component 160 can capture or record the position of the reflection. The feedback component 160 can perform image processing on the reflection to determine or compute the direction of the eye or gaze direction of the eye.

The feedback monitor 135 can compare the eye direction or movement to historical eye direction or movement of the same person, nominal eye movement, or other historical eye movement information to determine a level of attention. For example, if the eye is focused on the light pulses during the pulse train, then the feedback monitor 135 can determine that the level of attention is high. If the feedback monitor 135 determines that the eye moved away from the pulse train for 25% of the pulse train, then the feedback monitor 135 can determine that the level of attention is medium. If the feedback monitor 135 determines that the eye movement occurred for more than 50% of the pulse train or the eye was not focused on the pulse train for greater than 50%, then the feedback monitor 135 can determine that the level of attention is low.

In some embodiments, the system 100 can include a filter (e.g., filtering component 155) to control the spectral range of the light emitted from the light source. In some embodiments, light source includes a light reactive material affecting the light emitted, such as a polarizer, filter, prism or a photochromic material, or electrochromic glass or plastic. The filtering component 155 can receive instructions from the unwanted frequency filtering module 120 to block or attenuate one or more frequencies of light.

The filtering component 155 can include an optical filter that can selectively transmit light in a particular range of wavelengths or colors, while blocking one or more other ranges of wavelengths or colors. The optical filter can modify the magnitude or phase of the incoming light wave for a range of wavelengths. The optical filter can include an absorptive filter, or an interference or dichroic filter. An absorptive filter can take energy of a photon to transform the electromagnetic energy of a light wave into internal energy of the absorber (e.g., thermal energy). The reduction in intensity of a light wave propagating through a medium by absorption of a part of its photons can be referred to as attenuation.

An interference filter or dichroic filter can include an optical filter that reflects one or more spectral bands of light, while transmitting other spectral bands of light. An interference filter or dichroic filter may have a nearly zero coefficient of absorption for one or more wavelengths. Interference filters can be high-pass, low-pass, bandpass, or band-rejection. An interference filter can include one or more thin layers of a dielectric material or metallic material having different refractive indices.

In an illustrative implementation, the NSS 105 can interface with a visual signaling component 150, a filtering component 155, and a feedback component 160. The visual signaling component 150 can include hardware or devices, such as glass frames 400 and one or more light sources 305. The filtering component 155 can include hardware or devices, such as a feedback sensor 605. The filtering component 155 can include hardware, materials or chemicals, such as a polarizing lens, shutters, electrochromic materials or photochromic materials.

Computing Environment

Figure 7A:
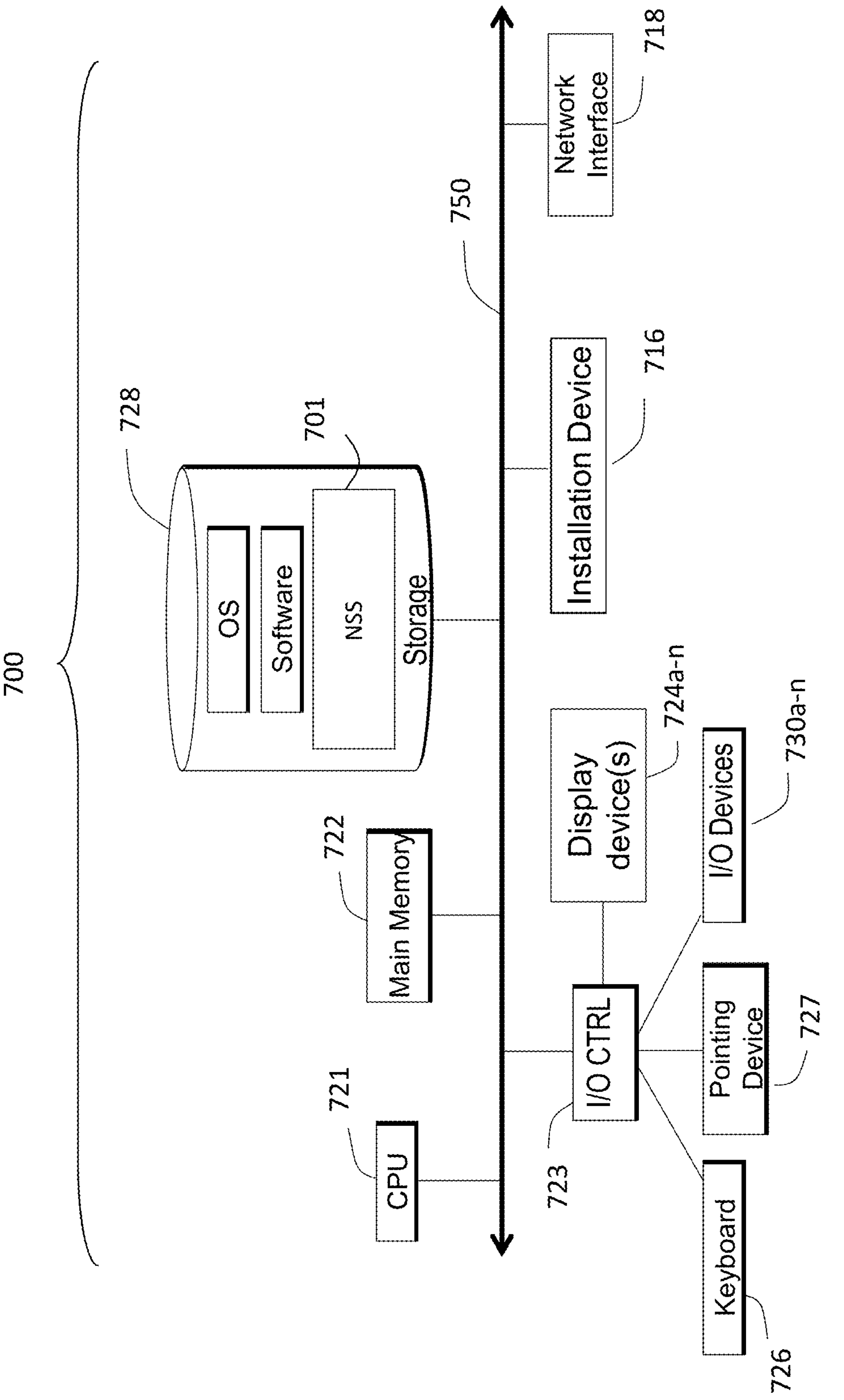
FIGS. 7A and 7B are block diagrams depicting embodiments of computing devices useful in connection with the systems and methods described herein.
Figure 7B:
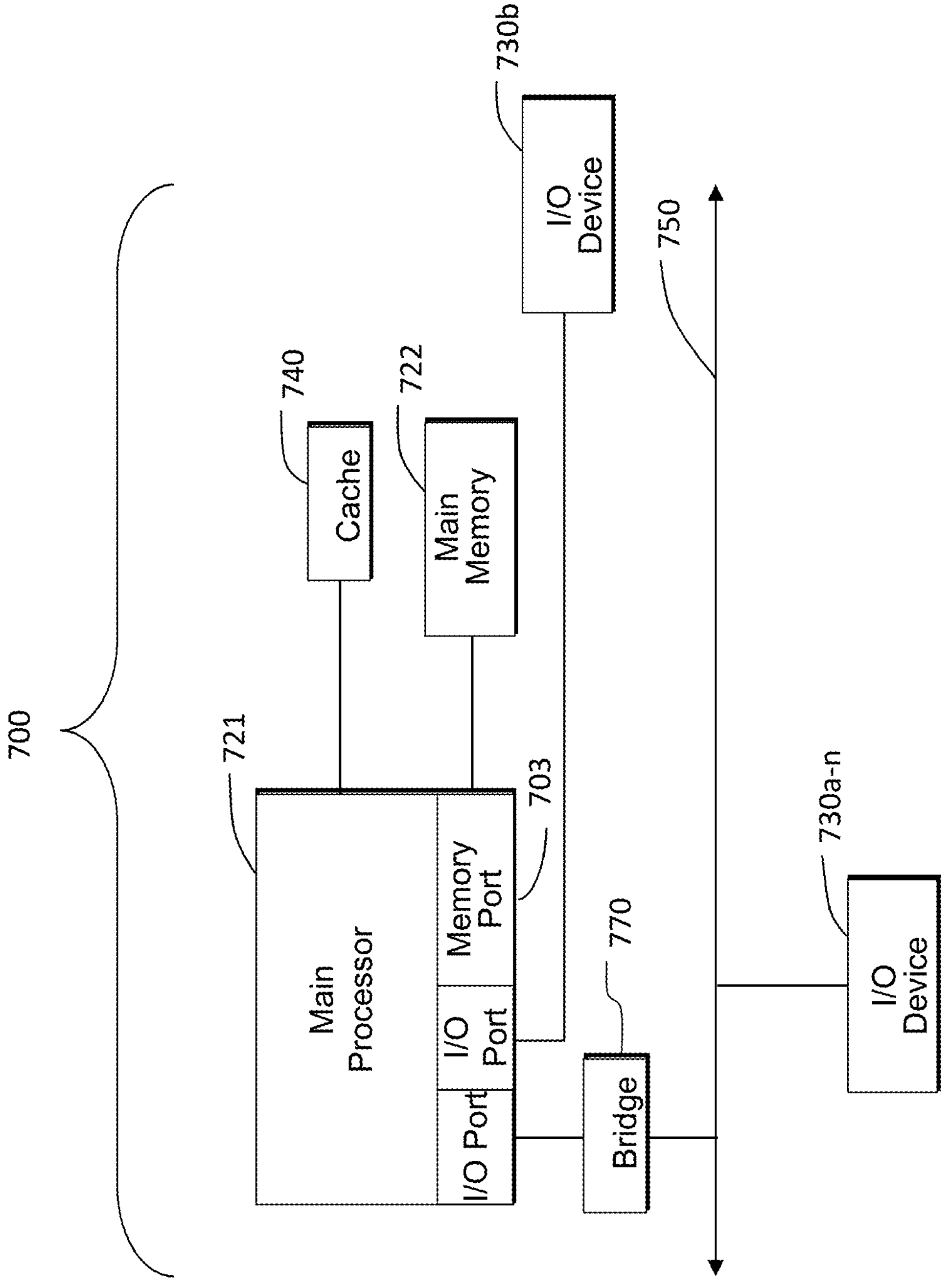

FIGS. 7A and 7B depict block diagrams of a computing device 700. As shown in FIGS. 7A and 7B, each computing device 700 includes a central processing unit 721, and a main memory unit 722. As shown in FIG. 7A, a computing device 700 can include a storage device 728, an installation device 716, a network interface 718, an I/O controller 723, display devices 724*a*-724*n*, a keyboard 726 and a pointing device 727, e.g., a mouse. The storage device 728 can include, without limitation, an operating system, software, and software of a neural stimulation system ("NSS") 701. The NSS 701 can include or refer to one or more of NSS 105, NSS 905, or NSOS 1605. As shown in FIG. 7B, each computing device 700 can also include additional optional elements, e.g., a memory port 703, a bridge 770, one or more input/output devices 730*a*-730*n* (generally referred to using reference numeral 730), and a cache memory 740 in communication with the central processing unit 721.

The central processing unit 721 is any logic circuitry that responds to and processes instructions fetched from the main memory unit 722. In many embodiments, the central processing unit 721 is provided by a microprocessor unit, e.g.: those manufactured by Intel Corporation of Mountain View, California; those manufactured by Motorola Corporation of Schaumburg, Illinois; the ARM processor (from, e.g., ARM Holdings and manufactured by ST, TI, ATMEL, etc.) and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California; or field programmable gate arrays ("FPGAs") from Altera in San Jose, CA, Intel Corporation, Xlinix in San Jose, CA, or MicroSemi in Aliso Viejo, CA, etc. The computing device 700 can be based on any of these processors, or any other processor capable of operating as described herein. The central processing unit 721 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 722 can include one or more memory chips capable of storing data and allowing any storage location to be directly accessed by the microprocessor 721. Main memory unit 722 can be volatile and faster than storage 728 memory. Main memory units 722 can be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 722 or the storage 728 can be non-volatile, e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 722 can be based on any of the above described memory chips, or any other available memory chips capable of operating as described herein. In the embodiment shown in FIG. 7A, the processor 721 communicates with main memory 722 via a system bus 750 (described in more detail below). FIG. 7B depicts an embodiment of a computing device 700 in which the processor communicates directly with main memory 722 via a memory port 703. For example, in FIG. 7B the main memory 722 can be DRDRAM.

FIG. 7B depicts an embodiment in which the main processor 721 communicates directly with cache memory 740 via a secondary bus, sometimes referred to as a backside bus. In other embodiments, the main processor 721 communicates with cache memory 740 using the system bus 750. Cache memory 740 typically has a faster response time than main memory 722 and is typically provided by SRAM, BSRAM, or EDRAM. In the embodiment shown in FIG. 7B, the processor 721 communicates with various I/O devices 730 via a local system bus 750. Various buses can be used to connect the central processing unit 721 to any of the I/O devices 730, including a PCI bus, a PCI-X bus, or a PCI-Express bus, or a NuBus. For embodiments in which the I/O device is a video display 724, the processor 721 can use an Advanced Graphics Port (AGP) to communicate with the display 724 or the I/O controller 723 for the display 724. FIG. 7B depicts an embodiment of a computer 700 in which the main processor 721 communicates directly with I/O device 730*b* or other processors 721' via HYPERTRANSPORT, RAPIDIO, or INFINIBAND communications technology. FIG. 7B also depicts an embodiment in which local busses and direct communication are mixed: the processor 721 communicates with I/O device 730*a* using a local interconnect bus while communicating with I/O device 730*b* directly.

A wide variety of I/O devices 730*a*-730*n* can be present in the computing device 700. Input devices can include keyboards, mice, trackpads, trackballs, touchpads, touch mice, multi-touch touchpads and touch mice, microphones (analog or MEMS), multi-array microphones, drawing tablets, cameras, single-lens reflex camera (SLR), digital SLR (DSLR), CMOS sensors, CCDs, accelerometers, inertial measurement units, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 730*a*-730*n* can include a combination of multiple input or output devices, including, e.g., Microsoft KINECT, Nintendo Wiimote for the WII, Nintendo WII U GAMEPAD, or Apple IPHONE. Some devices 730*a*-730*n* allow gesture recognition inputs through combining some of the inputs and outputs. Some devices 730*a*-730*n* provides for facial recognition which can be utilized as an input for different purposes including authentication and other commands. Some devices 730*a*-730*n* provides for voice recognition and inputs, including, e.g., Microsoft KINECT, SIRI for IPHONE by Apple, Google Now or Google Voice Search.

Additional devices 730*a*-730*n* have both input and output capabilities, including, e.g., haptic feedback devices, touch-screen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touch-screen devices, including, e.g., Microsoft PIXELSENSE or Multi-Touch Collaboration Wall, can have larger surfaces, such as on a table-top or on a wall, and can also interact with other electronic devices. Some I/O devices 730*a*-730*n*, display devices 724*a*-724*n* or group of devices can be augmented reality devices. The I/O devices can be controlled by an I/O controller 721 as shown in FIG. 7A. The I/O controller 721 can control one or more I/O devices, such as, e.g., a keyboard 126 and a pointing device 727, e.g., a mouse or optical pen. Furthermore, an I/O device can also provide storage and/or an installation medium 116 for the computing device 700. In still other embodiments, the computing device 700 can provide USB connections (not shown) to receive handheld USB storage devices. In further embodiments, an I/O device 730 can be a bridge between the system bus 750 and an external communication bus, e.g., a USB bus, a SCSI bus, a FireWire bus, an Ethernet bus, a Gigabit Ethernet bus, a Fibre Channel bus, or a Thunderbolt bus.

In some embodiments, display devices 724*a*-724*n* can be connected to I/O controller 721. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g., stereoscopy, polarization filters, active shutters, or autostereoscopy. Display devices 724*a*-724*n* can also be a head-mounted display (HMD). In some embodiments, display devices 724*a*-724*n* or the corresponding I/O controllers 723 can be controlled through or have hardware support for OPENGL or DIRECTX API or other graphics libraries.

In some embodiments, the computing device 700 can include or connect to multiple display devices 724*a*-724*n*, which each can be of the same or different type and/or form. As such, any of the I/O devices 730*a*-730*n* and/or the I/O controller 723 can include any type and/or form of suitable hardware, software, or combination of hardware and software to support, enable or provide for the connection and use of multiple display devices 724*a*-724*n* by the computing device 700. For example, the computing device 700 can include any type and/or form of video adapter, video card, driver, and/or library to interface, communicate, connect or otherwise use the display devices 724*a*-724*n*. In one embodiment, a video adapter can include multiple connectors to interface to multiple display devices 724*a*-724*n*. In other embodiments, the computing device 700 can include multiple video adapters, with each video adapter connected to one or more of the display devices 724*a*-724*n*. In some embodiments, any portion of the operating system of the computing device 700 can be configured for using multiple displays 724*a*-724*n*. In other embodiments, one or more of the display devices 724*a*-724*n* can be provided by one or more other computing devices 700*a* or 700*b* connected to the computing device 700, via the network 140. In some embodiments, software can be designed and constructed to use another computer's display device as a second display device 724*a* for the computing device 700. For example, in one embodiment, an Apple iPad can connect to a computing device 700 and use the display of the device 700 as an additional display screen that can be used as an extended desktop.

Referring again to FIG. 7A, the computing device 700 can comprise a storage device 728 (e.g., one or more hard disk drives or redundant arrays of independent disks) for storing an operating system or other related software, and for storing application software programs such as any program related to the software for the NSS. Examples of storage device 728 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 728 can be non-volatile, mutable, or read-only. Some storage device 728 can be internal and connect to the computing device 700 via a bus 750. Some storage device 728 can be external and connect to the computing device 700 via a I/O device 730 that provides an external bus. Some storage device 728 can connect to the computing device 700 via the network interface 718 over a network, including, e.g., the Remote Disk for MACBOOK AIR by Apple. Some client devices 700 can not require a non-volatile storage device 728 and can be thin clients or zero clients 202. Some storage device 728 can also be used as an installation device 716, and can be suitable for installing software and programs. Additionally, the operating system and the software can be run from a bootable medium, for example, a bootable CD, e.g., KNOPPIX, a bootable CD for GNU/Linux that is available as a GNU/Linux distribution from knoppix.net.

Computing device 700 can also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc.

Furthermore, the computing device 700 can include a network interface 718 to interface to the network 140 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 700 communicates with other computing devices 700' via any type and/or form of gateway or tunneling protocol e.g., Secure Socket Layer (SSL) or Transport Layer Security (TLS), or the Citrix Gateway Protocol manufactured by Citrix Systems, Inc. of Ft. Lauderdale, Florida. The network interface 118 can comprise a built-in network adapter, network interface card, PCMCIA network card, EXPRESSCARD network card, card bus network adapter, wireless network adapter, USB network adapter, modem or any other device suitable for interfacing the computing device 700 to any type of network capable of communication and performing the operations described herein.

A computing device 700 of the sort depicted in FIG. 7A can operate under the control of an operating system, which controls scheduling of tasks and access to system resources. The computing device 700 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 7000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g., Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, can be used on zero clients or thin clients, including, e.g., CHROMEBOOKS.

The computer system 700 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 700 has sufficient processor power and memory capacity to perform the operations described herein. In some embodiments, the computing device 700 can have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 700 is a gaming system. For example, the computer system 700 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, or an XBOX 360 device manufactured by the Microsoft Corporation of Redmond, Washington, or an OCULUS RIFT or OCULUS VR device manufactured BY OCULUS VR, LLC of Menlo Park, California.

In some embodiments, the computing device 700 is a digital audio player such as the Apple IPOD, IPOD Touch, and IPOD NANO lines of devices, manufactured by Apple Computer of Cupertino, California. Some digital audio players can have other functionality, including, e.g., a gaming system or any functionality made available by an application from a digital application distribution platform. For example, the IPOD Touch can access the Apple App Store. In some embodiments, the computing device 700 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 700 is a tablet e.g., the IPAD line of devices by Apple; GALAXY TAB family of devices by Samsung; or KINDLE FIRE, by Amazon.com, Inc. of Seattle, Washington. In other embodiments, the computing device 700 is an eBook reader, e.g., the KINDLE family of devices by Amazon.com, or NOOK family of devices by Barnes & Noble, Inc. of New York City, New York.

In some embodiments, the communications device 700 includes a combination of devices, e.g., a smartphone combined with a digital audio player or portable media player. For example, one of these embodiments is a smartphone, e.g., the IPHONE family of smartphones manufactured by Apple, Inc.; a Samsung GALAXY family of smartphones manufactured by Samsung, Inc.; or a Motorola DROID family of smartphones. In yet another embodiment, the communications device 700 is a laptop or desktop computer equipped with a web browser and a microphone and speaker system, e.g., a telephony headset. In these embodiments, the communications devices 700 are web-enabled and can receive and initiate phone calls. In some embodiments, a laptop or desktop computer is also equipped with a webcam or other video capture device that enables video chat and video call.

In some embodiments, the status of one or more machines 700 in the network are monitored, generally as part of network management. In one of these embodiments, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

A Method for Neural Stimulation

Figure 8:
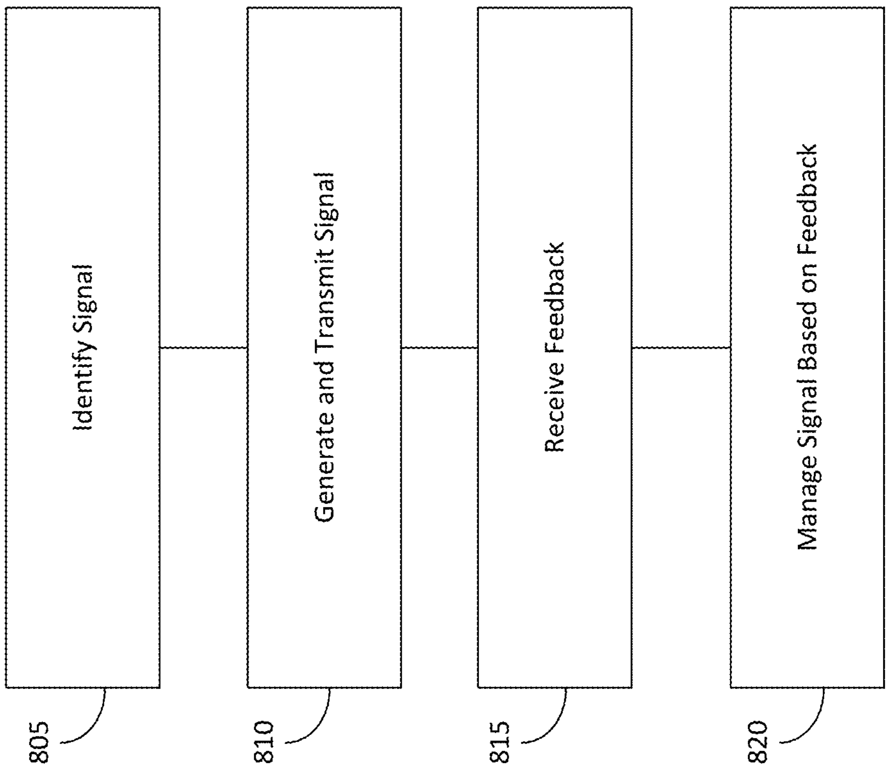
FIG. 8 is a flow diagram of a method of performing neural stimulation using visual stimulation in accordance with an embodiment.

In FIG. 8 is a flow diagram of a method of performing visual brain entrainment in accordance with an embodiment. The method 800 can be performed by one or more system, component, module or element depicted in FIGS. 1-7B, including, for example, a neural stimulation system (NSS). In brief overview, the NSS can identify a visual signal to provide at block 805. At block 810, the NSS can generate and transmit the identified visual signal. At 815 the NSS can receive or determine feedback associated with neural activity, physiological activity, environmental parameters, or device parameters. At 820 the NSS can manage, control, or adjust the visual signal based on the feedback.

NSS Operating with a Frame

The NSS 105 can operate in conjunction with the frame 400 including a light source 305 as depicted in FIG. 4A. The NSS 105 can operate in conjunction with the frame 400 including a light source 30 and a feedback sensor 605 as depicted in FIG. 6A. The NSS 105 can operate in conjunction with the frame 400 including at least one shutter 430 as depicted in FIG. 4B. The NSS 105 can operate in conjunction with the frame 400 including at least one shutter 430 and a feedback sensor 605.

In operation, a user of the frame 400 can wear the frame 400 on their head such that eye wires 415 encircle or substantially encircle their eyes. In some cases, the user can provide an indication to the NSS 105 that the glass frames 400 have been worn and that the user is ready to undergo brainwave entrainment. The indication can include an instruction, command, selection, input, or other indication via an input/output interface, such as a keyboard 726, pointing device 727, or other I/O devices 730*a-n*. The indication can be a motion-based indication, visual indication, or voice-based indication. For example, the user can provide a voice command that indicates that the user is ready to undergo brainwave entrainment.

In some cases, the feedback sensor 605 can determine that the user is ready to undergo brainwave entrainment. The feedback sensor 605 can detect that the glass frames 400 have been placed on a user's head. The NSS 105 can receive motion data, acceleration data, gyroscope data, temperature data, or capacitive touch data to determine that the frames 400 have been placed on the user's head. The received data, such as motion data, can indicate that the frames 400 were picked up and placed on the user's head. The temperature data can measure the temperature of or proximate to the frames 400, which can indicate that the frames are on the user's head. In some cases, the feedback sensor 605 can perform eye tracking to determine a level of attention a user is paying to the light source 305 or feedback sensor 605. The NSS 105 can detect that the user is ready responsive to determining that the user is paying a high level of attention to the light source 305 or feedback sensor 605. For example, staring at, gazing or looking in the direction of the light source 305 or feedback sensor 605 can provide an indication that the user is ready to undergo brainwave entrainment.

Thus, the NSS 105 can detect or determine that the frames 400 have been worn and that the user is in a ready state, or the NSS 105 can receive an indication or confirmation from the user that the user has worn the frames 400 and the user is ready to undergo brainwave entrainment. Upon determining that the user is ready, the NSS 105 can initialize the brainwave entrainment process. In some embodiments, the NSS 105 can access a profile data structure 145. For example, a profile manager 125 can query the profile data structure 145 to determine one or more parameter for the external visual stimulation used for the brain entrainment process. Parameters can include, for example, a type of visual stimulation, an intensity of the visual stimulation, frequency of the visual stimulation, duration of the visual stimulation, or wavelength of the visual stimulation. The profile manager 125 can query the profile data structure 145 to obtain historical brain entrainment information, such as prior visual stimulation sessions. The profile manager 125 can perform a lookup in the profile data structure 145. The profile manager 125 can perform a look-up with a username, user identifier, location information, fingerprint, biometric identifier, retina scan, voice recognition and authentication, or other identifying technique.

The NSS 105 can determine a type of external visual stimulation based on the hardware 400. The NSS 105 can determine the type of external visual stimulation based on the type of light source 305 available. For example, if the light source 305 includes a monochromatic LED that generates light waves in the red spectrum, the NSS 105 can determine that the type of visual stimulation includes pulses of light transmitted by the light source. However, if the frames 400 do not include an active light source 305, but, instead, include one or more shutters 430, the NSS 105 can determine that the light source is sunlight or ambient light that is to be modulated as it enters the user's eye via a plane formed by the eye wire 415.

In some embodiments, the NSS 105 can determine the type of external visual stimulation based on historical brainwave entrainment sessions. For example, the profile data structure 145 can be pre-configured with information about the type of visual signaling component 150.

The NSS 105 can determine, via the profile manager 125, a modulation frequency for the pulse train or the ambient light. For example, NSS 105 can determine, from the profile data structure 145, that the modulation frequency for the external visual stimulation should be set to 40 Hz. Depending on the type of visual stimulation, the profile data structure 145 can further indicate a pulse length, intensity, wavelength of the light wave forming the light pulse, or duration of the pulse train.

In some cases, the NSS 105 can determine or adjust one or more parameter of the external visual stimulation. For example, the NSS 105 (e.g., via feedback component 160 or feedback sensor 605) can determine a level or amount of ambient light. The NSS 105 (e.g., via light adjustment module 115 or side effects management module 130) can establish, initialize, set, or adjust the intensity or wavelength of the light pulse. For example, the NSS 105 can determine that there is a low level of ambient light. Due to the low level of ambient light, the user's pupils may be dilated. The NSS 105 can determine, based on detecting a low level of ambient light, that the user's pupils are likely dilated. In response to determining that the user's pupils are likely dilated, the NSS 105 can set a low level of intensity for the pulse train. The NSS 105 can further use a light wave having a longer wavelength (e.g., red), which may reduce strain on the eyes.

In some embodiments, the NSS 105 can monitor (e.g., via feedback monitor 135 and feedback component 160) the level of ambient light throughout the brainwave entrainment process to automatically and periodically adjust the intensity or color of light pulses. For example, if the user began the brainwave entrainment process when there was a high level of ambient light, the NSS 105 can initially set a higher intensity level for the light pulses and use a color that includes light waves having lower wavelengths (e.g., blue). However, in some embodiments in which the ambient light level decreases throughout the brainwave entrainment process, the NSS 105 can automatically detect the decrease in ambient light and, in response to the detection, adjust or lower the intensity while increasing the wavelength of the light wave. The NSS 105 can adjust the light pulses to provide a high contrast ratio to facilitate brainwave entrainment.

In some embodiments, the NSS 105 (e.g., via feedback monitor 135 and feedback component 160) can monitor or measure physiological conditions to set or adjust a parameter of the light wave. For example, the NSS 105 can monitor or measure a level of pupil dilation to adjust or set a parameter of the light wave. In some embodiments, the NSS 105 can monitor or measure heart rate, pulse rate, blood pressure, body temperature, perspiration, or brain activity to set or adjust a parameter of the light wave.

In some embodiments, the NSS 105 can be preconfigured to initially transmit light pulses having a lowest setting for light wave intensity (e.g., low amplitude of the light wave or high wavelength of the light wave) and gradually increase the intensity (e.g., increase the amplitude of the light wave or decrease the wavelength of the light wave) while monitoring feedback until an optimal light intensity is reached. An optimal light intensity can refer to a highest intensity without adverse physiological side effects, such as blindness, seizures, heart attack, migraines, or other discomfort. The NSS 105 (e.g., via side effects management module 130) can monitor the physiological symptoms to identify the adverse side effects of the external visual stimulation, and adjust (e.g., via light adjustment module 115) the external visual stimulation accordingly to reduce or eliminate the adverse side effects.

In some embodiments, the NSS 105 (e.g., via light adjustment module 115) can adjust a parameter of the light wave or light pulse based on a level of attention. For example, during the brainwave entrainment process, the user may get bored, lose focus, fall asleep, or otherwise not pay attention to the light pulses. Not paying attention to the light pulses may reduce the efficacy of the brainwave entrainment process, resulting in neurons oscillating at a frequency different from the desired modulation frequency of the light pulses.

NSS 105 can detect the level of attention the user is paying to the light pulses using the feedback monitor 135 and one or more feedback component 160. The NSS 105 can perform eye tracking to determine the level of attention the user is providing to the light pulses based on the gaze direction of the retina or pupil. The NSS 105 can measure eye movement to determine the level of attention the user is paying to the light pulses. The NSS 105 can provide a survey or prompt asking for user feedback that indicates the level of attention the user is paying to the light pulses. Responsive to determining that the user is not paying a satisfactory amount of attention to the light pulses (e.g., a level of eye movement that is greater than a threshold or a gaze direction that is outside the direct visual field of the light source 305), the light adjustment module 115 can change a parameter of the light source to gain the user's attention. For example, the light adjustment module 115 can increase the intensity of the light pulse, adjust the color of the light pulse, or change the duration of the light pulse. The light adjustment module 115 can randomly vary one or more parameters of the light pulse. The light adjustment module 115 can initiate an attention seeking light sequence configured to regain the user's attention. For example, the light sequence can include a change in color or intensity of the light pulses in a predetermined, random, or pseudo-random pattern. The attention seeking light sequence can enable or disable different light sources if the visual signaling component 150 includes multiple light sources. Thus, the light adjustment module 115 can interact with the feedback monitor 135 to determine a level of attention the user is providing to the light pulses, and adjust the light pulses to regain the user's attention if the level of attention falls below a threshold.

In some embodiments, the light adjustment module 115 can change or adjust one or more parameter of the light pulse or light wave at predetermined time intervals (e.g., every 5 minutes, 10 minutes, 15 minutes, or 20 minutes) to regain or maintain the user's attention level.

In some embodiments, the NSS 105 (e.g., via unwanted frequency filtering module 120) can filter, block, attenuate, or remove unwanted visual external stimulation. Unwanted visual external stimulation can include, for example, unwanted modulation frequencies, unwanted intensities, or unwanted wavelengths of light waves. The NSS 105 can deem a modulation frequency to be unwanted if the modulation frequency of a pulse train is different or substantially different (e.g., 1%, 2%, 5%, 10%, 15%, 20%, 25%, or more than 25%) from a desired frequency.

For example, the desired modulation frequency for brainwave entrainment can be 40 Hz. However, a modulation frequency of 20 Hz or 80 Hz can hinder brainwave entrainment. Thus, the NSS 105 can filter out the light pulses or light waves corresponding to the 20 Hz or 80 Hz modulation frequency.

In some embodiments, the NSS 105 can detect, via feedback component 160, that there are light pulses from an ambient light source that corresponds to an unwanted modulation frequency of 20 Hz. The NSS 105 can further determine the wavelength of the light waves of the light pulses corresponding to the unwanted modulation frequency. The NSS 105 can instruct the filtering component 155 to filter out the wavelength corresponding to the unwanted modulation frequency. For example, the wavelength corresponding to the unwanted modulation frequency can correspond to the color blue. The filtering component 155 can include an optical filter that can selectively transmit light in a particular range of wavelengths or colors, while blocking one or more other ranges of wavelengths or colors. The optical filter can modify the magnitude or phase of the incoming light wave for a range of wavelengths. For example, the optical filter can be configured to block, reflect or attenuate the blue light wave corresponding to the unwanted modulation frequency. The light adjustment module 115 can change the wavelength of the light wave generated by the light generation module 110 and light source 305 such that the desired modulation frequency is not blocked or attenuated by the unwanted frequency filtering module 120.

NSS Operating with a Virtual Reality Headset

The NSS 105 can operate in conjunction with the virtual reality headset 401 including a light source 305 as depicted in FIG. 4C. The NSS 105 can operate in conjunction with the virtual reality headset 401 including a light source 305 and a feedback sensor 605 as depicted in FIG. 4C. In some embodiments, the NSS 105 can determine that the visual signaling component 150 hardware includes a virtual reality headset 401. Responsive to determining that the visual signaling component 150 includes a virtual reality headset 401, the NSS 105 can determine that the light source 305 includes a display screen of a smartphone or other mobile computing device.

The virtual reality headset 401 can provide an immersive, non-disruptive visual stimulation experience. The virtual reality headset 401 can provide an augmented reality experience. The feedback sensors 605 can capture pictures or video of the physical, real world to provide the augmented reality experience. The unwanted frequency filtering module 120 can filter out unwanted modulation frequencies prior to projecting, displaying or providing the augmented reality images via the display screen 305.

In operation, a user of the frame 401 can wear the frame 401 on their head such that the virtual reality headset eye sockets 465 cover the user's eyes. The virtual reality headset eye sockets 465 can encircle or substantially encircle their eyes. The user can secure the virtual reality headset 401 to the user's headset using one or more straps 455 or 460, a skull cap, or other fastening mechanism. In some cases, the user can provide an indication to the NSS 105 that the virtual reality headset 401 has been placed and secured to the user's head and that the user is ready to undergo brainwave entrainment. The indication can include an instruction, command, selection, input, or other indication via an input/output interface, such as a keyboard 726, pointing device 727, or other I/O devices 730*a-n*. The indication can be a motion-based indication, visual indication, or voice-based indication. For example, the user can provide a voice command that indicates that the user is ready to undergo brainwave entrainment.

In some cases, the feedback sensor 605 can determine that the user is ready to undergo brainwave entrainment. The feedback sensor 605 can detect that the virtual reality headset 401 has been placed on a user's head. The NSS 105 can receive motion data, acceleration data, gyroscope data, temperature data, or capacitive touch data to determine that the virtual reality headset 401 has been placed on the user's head. The received data, such as motion data, can indicate that the virtual reality headset 401 was picked up and placed on the user's head. The temperature data can measure the temperature of or proximate to the virtual reality headset 401, which can indicate that the virtual reality headset 401 is on the user's head. In some cases, the feedback sensor 605 can perform eye tracking to determine a level of attention a user is paying to the light source 305 or feedback sensor 605. The NSS 105 can detect that the user is ready responsive to determining that the user is paying a high level of attention to the light source 305 or feedback sensor 605. For example, staring at, gazing or looking in the direction of the light source 305 or feedback sensor 605 can provide an indication that the user is ready to undergo brainwave entrainment.

In some embodiments, a sensor 605 on the straps 455, straps 460 or eye socket 605 can detect that the virtual reality headset 401 is secured, placed, or positioned on the user's head. The sensor 605 can be a touch sensor that senses or detects the touch of the user's head.

Thus, the NSS 105 can detect or determine that the virtual reality headset 401 has been worn and that the user is in a ready state, or the NSS 105 can receive an indication or confirmation from the user that the user has worn the virtual reality headset 401 and the user is ready to undergo brainwave entrainment. Upon determining that the user is ready, the NSS 105 can initialize the brainwave entrainment process. In some embodiments, the NSS 105 can access a profile data structure 145. For example, a profile manager 125 can query the profile data structure 145 to determine one or more parameter for the external visual stimulation used for the brain entrainment process. Parameters can include, for example, a type of visual stimulation, an intensity of the visual stimulation, frequency of the visual stimulation, duration of the visual stimulation, or wavelength of the visual stimulation. The profile manager 125 can query the profile data structure 145 to obtain historical brain entrainment information, such as prior visual stimulation sessions. The profile manager 125 can perform a lookup in the profile data structure 145. The profile manager 125 can perform a look-up with a username, user identifier, location information, fingerprint, biometric identifier, retina scan, voice recognition and authentication, or other identifying technique.

The NSS 105 can determine a type of external visual stimulation based on the hardware 401. The NSS 105 can determine the type of external visual stimulation based on the type of light source 305 available. For example, if the light source 305 includes a smartphone or display device, the visual stimulation can include turning on and off the display screen of the display device. The visual stimulation can include displaying a pattern on the display device 305, such as a checkered pattern, that can alternate in accordance with the desired frequency modulation. The visual stimulation can include light pulses generated by a light source 305 such as an LED that is placed within the virtual reality headset 401 enclosure.

In cases where the virtual reality headset 401 provides an augmented reality experience, the visual stimulation can include overlaying content on the display device and modulating the overlaid content at the desired modulation frequency. For example, the virtual reality headset 401 can include a camera 605 that captures the real, physical world. While displaying the captured image of the real, physical world, the NSS 105 can also display content that is modulated at the desired modulation frequency. The NSS 105 can overlay the content modulated at the desired modulation frequency. The NSS 105 can otherwise modify, manipulate, modulation, or adjust a portion of the display screen or a portion of the augmented reality to generate or provide the desired modulation frequency.

For example, the NSS 105 can modulate one or more pixels based on the desired modulation frequency. The NSS 105 can turn pixels on and off based on the modulation frequency. The NSS 105 can turn of pixels on any portion of the display device. The NSS 105 can turn on and off pixels in a pattern. The NSS 105 can turn on and off pixels in the direct visual field or peripheral visual field. The NSS 105 can track or detect a gaze direction of the eye and turn on and off pixels in the gaze direction so the light pulses (or modulation) are in the direct vision field. Thus, modulating the overlaid content or otherwise manipulated the augmented reality display or other image provided via a display device in the virtual reality headset 401 can generate light pulses or light flashes having a modulation frequency configured to facilitate brainwave entrainment.

The NSS 105 can determine, via the profile manager 125, a modulation frequency for the pulse train or the ambient light. For example, NSS 105 can determine, from the profile data structure 145, that the modulation frequency for the external visual stimulation should be set to 40 Hz. Depending on the type of visual stimulation, the profile data structure 145 can further indicate a number of pixels to modulate, intensity of pixels to modulate, pulse length, intensity, wavelength of the light wave forming the light pulse, or duration of the pulse train.

In some cases, the NSS 105 can determine or adjust one or more parameter of the external visual stimulation. For example, the NSS 105 (e.g., via feedback component 160 or feedback sensor 605) can determine a level or amount of light in captured image used to provide the augmented reality experience. The NSS 105 (e.g., via light adjustment module 115 or side effects management module 130) can establish, initialize, set, or adjust the intensity or wavelength of the light pulse based on the light level in the image data corresponding to the augmented reality experience. For example, the NSS 105 can determine that there is a low level of light in the augmented reality display because it may be dark outside. Due to the low level of light in the augmented reality display, the user's pupils may be dilated. The NSS 105 can determine, based on detecting a low level of light, that the user's pupils are likely dilated. In response to determining that the user's pupils are likely dilated, the NSS 105 can set a low level of intensity for the light pulses or light source providing the modulation frequency. The NSS 105 can further use a light wave having a longer wavelength (e.g., red), which may reduce strain on the eyes.

In some embodiments, the NSS 105 can monitor (e.g., via feedback monitor 135 and feedback component 160) the level of light throughout the brainwave entrainment process to automatically and periodically adjust the intensity or color of light pulses. For example, if the user began the brainwave entrainment process when there was a high level of ambient light, the NSS 105 can initially set a higher intensity level for the light pulses and use a color that includes light waves having lower wavelengths (e.g., blue). However, as the light level decreases throughout the brainwave entrainment process, the NSS 105 can automatically detect the decrease in light and, in response to the detection, adjust or lower the intensity while increasing the wavelength of the light wave. The NSS 105 can adjust the light pulses to provide a high contrast ratio to facilitate brainwave entrainment.

In some embodiments, the NSS 105 (e.g., via feedback monitor 135 and feedback component 160) can monitor or measure physiological conditions to set or adjust a parameter of the light pulses while the user is wearing the virtual reality headset 401. For example, the NSS 105 can monitor or measure a level of pupil dilation to adjust or set a parameter of the light wave. In some embodiments, the NSS 105 can monitor or measure, via one or more feedback sensor of the virtual reality headset 401 or other feedback sensor, a heart rate, pulse rate, blood pressure, body temperature, perspiration, or brain activity to set or adjust a parameter of the light wave.

In some embodiments, the NSS 105 can be preconfigured to initially transmit, via display device 305, light pulses having a lowest setting for light wave intensity (e.g., low amplitude of the light wave or high wavelength of the light wave) and gradually increase the intensity (e.g., increase the amplitude of the light wave or decrease the wavelength of the light wave) while monitoring feedback until an optimal light intensity is reached. An optimal light intensity can refer to a highest intensity without adverse physiological side effects, such as blindness, seizures, heart attack, migraines, or other discomfort. The NSS 105 (e.g., via side effects management module 130) can monitor the physiological symptoms to identify the adverse side effects of the external visual stimulation, and adjust (e.g., via light adjustment module 115) the external visual stimulation accordingly to reduce or eliminate the adverse side effects.

In some embodiments, the NSS 105 (e.g., via light adjustment module 115) can adjust a parameter of the light wave or light pulse based on a level of attention. For example, during the brainwave entrainment process, the user may get bored, lose focus, fall asleep, or otherwise not pay attention to the light pulses generated via the display screen 305 of the virtual reality headset 401. Not paying attention to the light pulses may reduce the efficacy of the brainwave entrainment process, resulting in neurons oscillating at a frequency different from the desired modulation frequency of the light pulses.

NSS 105 can detect the level of attention the user is paying or providing to the light pulses using the feedback monitor 135 and one or more feedback component 160 (e.g., including feedback sensors 605). The NSS 105 can perform eye tracking to determine the level of attention the user is providing to the light pulses based on the gaze direction of the retina or pupil. The NSS 105 can measure eye movement to determine the level of attention the user is paying to the light pulses. The NSS 105 can provide a survey or prompt asking for user feedback that indicates the level of attention the user is paying to the light pulses. Responsive to determining that the user is not paying a satisfactory amount of attention to the light pulses (e.g., a level of eye movement that is greater than a threshold or a gaze direction that is outside the direct visual field of the light source 305), the light adjustment module 115 can change a parameter of the light source 305 or display device 305 to gain the user's attention. For example, the light adjustment module 115 can increase the intensity of the light pulse, adjust the color of the light pulse, or change the duration of the light pulse. The light adjustment module 115 can randomly vary one or more parameters of the light pulse. The light adjustment module 115 can initiate an attention seeking light sequence configured to regain the user's attention. For example, the light sequence can include a change in color or intensity of the light pulses in a predetermined, random, or pseudo-random pattern. The attention seeking light sequence can enable or disable different light sources if the visual signaling component 150 includes multiple light sources. Thus, the light adjustment module 115 can interact with the feedback monitor 135 to determine a level of attention the user is providing to the light pulses, and adjust the light pulses to regain the user's attention if the level of attention falls below a threshold.

In some embodiments, the light adjustment module 115 can change or adjust one or more parameter of the light pulse or light wave at predetermined time intervals (e.g., every 5 minutes, 10 minutes, 15 minutes, or 20 minutes) to regain or maintain the user's attention level.

In some embodiments, the NSS 105 (e.g., via unwanted frequency filtering module 120) can filter, block, attenuate, or remove unwanted visual external stimulation. Unwanted visual external stimulation can include, for example, unwanted modulation frequencies, unwanted intensities, or unwanted wavelengths of light waves. The NSS 105 can deem a modulation frequency to be unwanted if the modulation frequency of a pulse train is different or substantially different (e.g., 1%, 2%, 5%, 10%, 15%, 20%, 25%, or more than 25%) from a desired frequency.

For example, the desired modulation frequency for brainwave entrainment can be 40 Hz. However, a modulation frequency of 20 Hz or 80 Hz can hinder brainwave entrainment. Thus, the NSS 105 can filter out the light pulses or light waves corresponding to the 20 Hz or 80 Hz modulation frequency. For example, the virtual reality headset 401 can detect unwanted modulation frequencies in the physical, real world and eliminate, attenuate, filter out or otherwise remove the unwanted frequencies providing to generating the or providing the augmented reality experience. The NSS 105 can include an optical filter configured to perform digital signal processing or digital image processing to detect the unwanted modulation frequency in the real world captured by the feedback sensor 605. The NSS 105 can detect other content, image or motion having an unwanted parameter (e.g., color, brightness, contrast ratio, modulation frequency), and eliminate same from the augmented reality experience projected to the user via the display screen 305. The NSS 105 can apply a color filter to adjust the color or remove a color of the augmented reality display. The NSS 105 can adjust, modify, or manipulate the brightness, contrast ratio, sharpness, tint, hue, or other parameter of the image or video displayed via the display device 305.

In some embodiments, the NSS 105 can detect, via feedback component 160, that there is captured image or video content from the real, physical world that corresponds to an unwanted modulation frequency of 20 Hz. The NSS 105 can further determine the wavelength of the light waves of the light pulses corresponding to the unwanted modulation frequency. The NSS 105 can instruct the filtering component 155 to filter out the wavelength corresponding to the unwanted modulation frequency. For example, the wavelength corresponding to the unwanted modulation frequency can correspond to the color blue. The filtering component 155 can include a digital optical filter that can digitally remove content or light in a particular range of wavelengths or colors, while allowing one or more other ranges of wavelengths or colors. The digital optical filter can modify the magnitude or phase of the image for a range of wavelengths. For example, the digital optical filter can be configured to attenuate, erase, replace or otherwise alter the blue light wave corresponding to the unwanted modulation frequency. The light adjustment module 115 can change the wavelength of the light wave generated by the light generation module 110 and display device 305 such that the desired modulation frequency is not blocked or attenuated by the unwanted frequency filtering module 120.

NSS Operating With a Tablet

The NSS 105 can operate in conjunction with the tablet 500 as depicted in FIGS. 5A-5D. In some embodiments, the NSS 105 can determine that the visual signaling component 150 hardware includes a tablet device 500 or other display screen that is not affixed or secured to a user's head. The tablet 500 can include a display screen that has one or more component or function of the display screen 305 or light source 305 depicted in conjunction with FIGS. 4A and 4C. The light source 305 in a tablet can be the display screen. The tablet 500 can include one or more feedback sensor that includes one or more component or function of the feedback sensors depicted in conjunction with FIGS. 4B, 4C and 6A.

The tablet 500 can communicate with the NSS 105 via a network, such as a wireless network or a cellular network. The NSS 105 can, in some embodiments, execute the NSS 105 or a component thereof. For example, the tablet 500 can launch, open or switch to an application or resource configured to provide at least one functionality of the NSS 105. The tablet 500 can execute the application as a background process or a foreground process. For example, the graphical user interface for the application can be in the background while the application causes the display screen 305 of the tablet to overlay content or light that changes or modulates at a desired frequency for brain entrainment (e.g., 40 Hz).

The tablet 500 can include one or more feedback sensors 605. In some embodiments, the tablet can use the one or more feedback sensors 605 to detect that a user is holding the tablet 500. The tablet can use the one or more feedback sensors 605 to determine a distance between the light source 305 and the user. The tablet can use the one or more feedback sensors 605 to determine a distance between the light source 305 and the user's head. The tablet can use the one or more feedback sensors 605 to determine a distance between the light source 305 and the user's eyes.

In some embodiments, the tablet 500 can use a feedback sensor 605 that includes a receiver to determine the distance. The tablet can transmit a signal and measure the amount of time it takes for the transmitted signal to leave the tablet 500, bounce on the object (e.g., user's head) and be received by the feedback sensor 605. The tablet 500 or NSS 105 can determine the distance based on the measured amount of time and the speed of the transmitted signal (e.g., speed of light).

In some embodiments, the tablet 500 can include two feedback sensors 605 to determine a distance. The two feedback sensors 605 can include a first feedback sensor 605 that is the transmitter and a second feedback sensor that is the receiver.

In some embodiments, the tablet 500 can include two or more feedback sensors 605 that include two or more cameras. The two or more cameras can measure the angles and the position of the object (e.g., the user's head) on each camera, and use the measured angles and position to determine or compute the distance between the tablet 500 and the object.

In some embodiments, the tablet 500 (or application thereof) can determine the distance between the tablet and the user's head by receiving user input. For example, user input can include an approximate size of the user's head. The tablet 500 can then determine the distance from the user's head based on the inputted approximate size.

The tablet 500, application, or NSS 105 can use the measured or determined distance to adjust the light pulses or flashes of light emitted by the light source 305 of the tablet 500. The tablet 500, application, or NSS 105 can use the distance to adjust one or more parameter of the light pulses, flashes of light or other content emitted via the light source 305 of the tablet 500. For example, the tablet 500 can adjust the intensity of the light pulses emitted by light source 305 based on the distance. The tablet 500 can adjust the intensity based on the distance in order to maintain a consistent or similar intensity at the eye irrespective of the distance between the light source 305 and the eye. The tablet can increase the intensity proportional to the square of the distance.

The tablet 500 can manipulate one or more pixels on the display screen 305 to generate the light pulses or modulation frequency for brainwave entrainment. The tablet 500 can overlay light sources, light pulses or other patterns to generate the modulation frequency for brainwave entrainment. Similar to the virtual reality headset 401, the tablet can filter out or modify unwanted frequencies, wavelengths or intensity.

Similar to the frames 400, the tablet 500 can adjust a parameter of the light pulses or flashes of light generated by the light source 305 based on ambient light, environmental parameters, or feedback.

In some embodiments, the tablet 500 can execute an application that is configured to generate the light pulses or modulation frequency for brainwave entrainment. The application can execute in the background of the tablet such that all content displayed on a display screen of the tablet are displayed as light pulses at the desired frequency. The tablet can be configured to detect a gaze direction of the user. In some embodiments, the tablet may detect the gaze direction by capturing an image of the user's eye via the camera of the tablet. The tablet 500 can be configured to generate light pulses at particular locations of the display screen based on the gaze direction of the user. In embodiments where direct vision field is to be employed, the light pulses can be displayed at locations of the display screen that correspond to the user's gaze. In embodiments where peripheral vision field is to be employed, the light pulses can be displayed at locations of the displays screen that are outside the portion of the display screen corresponding to the user's gaze.

Neural Stimulation Via Auditory Stimulation

Figure 9:
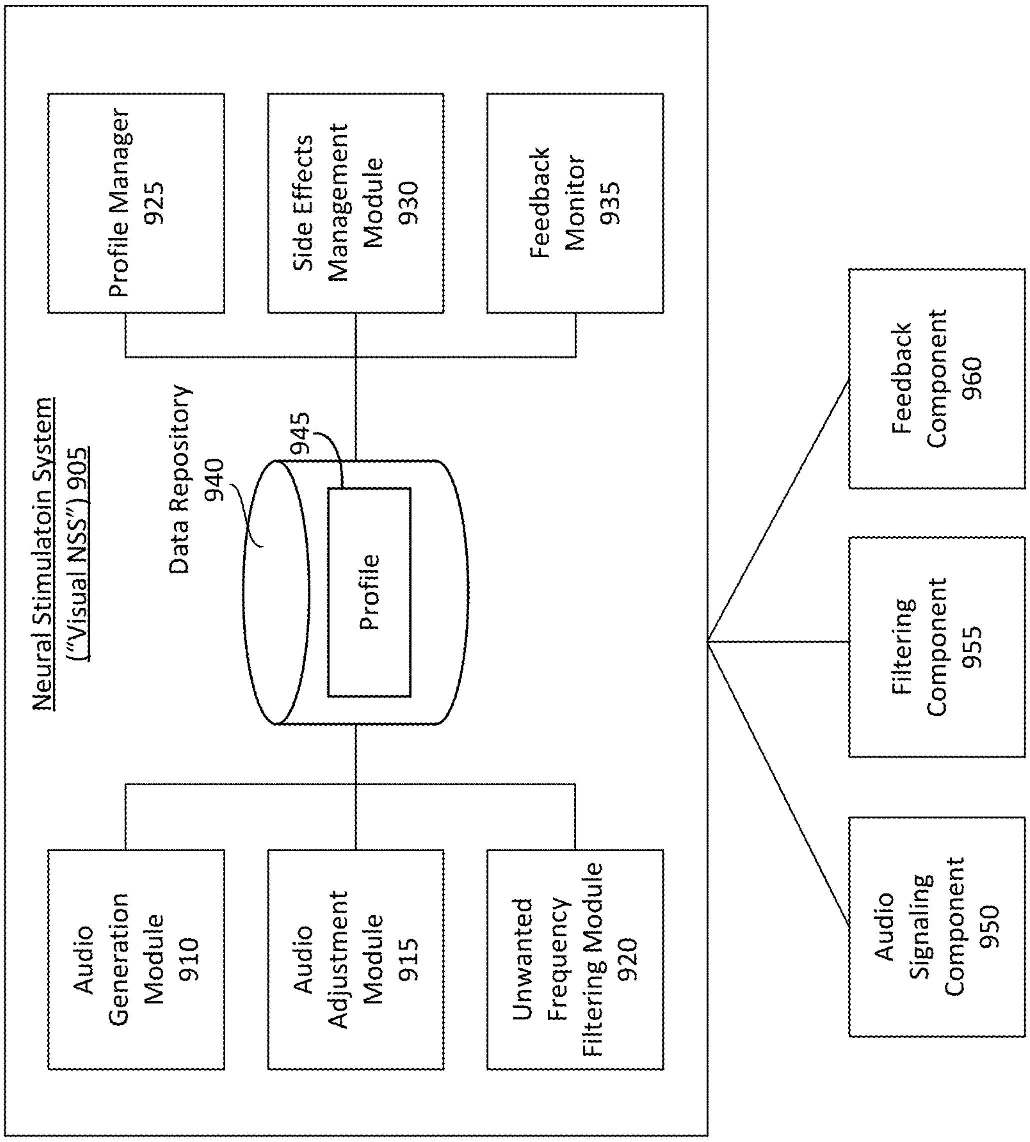
FIG. 9 is a block diagram depicting a system for neural stimulation via auditory stimulation in accordance with an embodiment.

FIG. 9 is a block diagram depicting a system for neural stimulation via auditory stimulation in accordance with an embodiment. The system 900 can include a neural stimulation system ("NSS") 905. The NSS 905 can be referred to as an auditory NSS 905 or NSS 905. In brief overview, the auditory neural stimulation system ("NSS") 905 can include, access, interface with, or otherwise communicate with one or more of an audio generation module 910, audio adjustment module 915, unwanted frequency filtering module 920, profile manager 925, side effects management module 930, feedback monitor 935, data repository 940, audio signaling component 950, filtering component 955, or feedback component 960. The audio generation module 910, audio adjustment module 915, unwanted frequency filtering module 920, profile manager 925, side effects management module 930, feedback monitor 935, audio signaling component 950, filtering component 955, or feedback component 960 can each include at least one processing unit or other logic device such as programmable logic array engine, or module configured to communicate with the database repository 950. The audio generation module 910, audio adjustment module 915, unwanted frequency filtering module 920, profile manager 925, side effects management module 930, feedback monitor 935, audio signaling component 950, filtering component 955, or feedback component 960 can be separate components, a single component, or part of the NSS 905. The system 100 and its components, such as the NSS 905, may include hardware elements, such as one or more processors, logic devices, or circuits. The system 100 and its components, such as the NSS 905, can include one or more hardware or interface component depicted in system 700 in FIGS. 7A and 7B. For example, a component of system 100 can include or execute on one or more processors 721, access storage 728 or memory 722, and communicate via network interface 718.

Still referring to FIG. 9, and in further detail, the NSS 905 can include at least one audio generation module 910. The audio generation module 910 can be designed and constructed to interface with an audio signaling component 950 to provide instructions or otherwise cause or facilitate the generation of an audio signal, such as an audio burst, audio pulse, audio chirp, audio sweep, or other acoustic wave having one or more predetermined parameters. The audio generation module 910 can include hardware or software to receive and process instructions or data packets from one or more module or component of the NSS 905. The audio generation module 910 can generate instructions to cause the audio signaling component 950 to generate an audio signal. The audio generation module 910 can control or enable the audio signaling component 950 to generate the audio signal having one or more predetermined parameters.

The audio generation module 910 can be communicatively coupled to the audio signaling component 950. The audio generation module 910 can communicate with the audio signaling component 950 via a circuit, electrical wire, data port, network port, power wire, ground, electrical contacts or pins. The audio generation module 910 can wirelessly communicate with the audio signaling component 950 using one or more wireless protocols such as BlueTooth, BlueTooth Low Energy, Zigbee, Z-Wave, IEEE 802, WIFI, 3G, 4G, LTE, near field communications ("NFC"), or other short, medium or long range communication protocols, etc. The audio generation module 910 can include or access network interface 718 to communicate wirelessly or over a wire with the audio signaling component 950.

The audio generation module 910 can interface, control, or otherwise manage various types of audio signaling components 950 in order to cause the audio signaling component 950 to generate, block, control, or otherwise provide the audio signal having one or more predetermined parameters. The audio generation module 910 can include a driver configured to drive an audio source of the audio signaling component 950. For example, the audio source can include a speaker, and the audio generation module 910 (or the audio signaling component) can include a transducer that converts electrical energy to sound waves or acoustic waves. The audio generation module 910 can include a computing chip, microchip, circuit, microcontroller, operational amplifiers, transistors, resistors, or diodes configured to provide electricity or power having certain voltage and current characteristics to drive the speaker to generate an audio signal with desired acoustic characteristics.

Figure 10A:
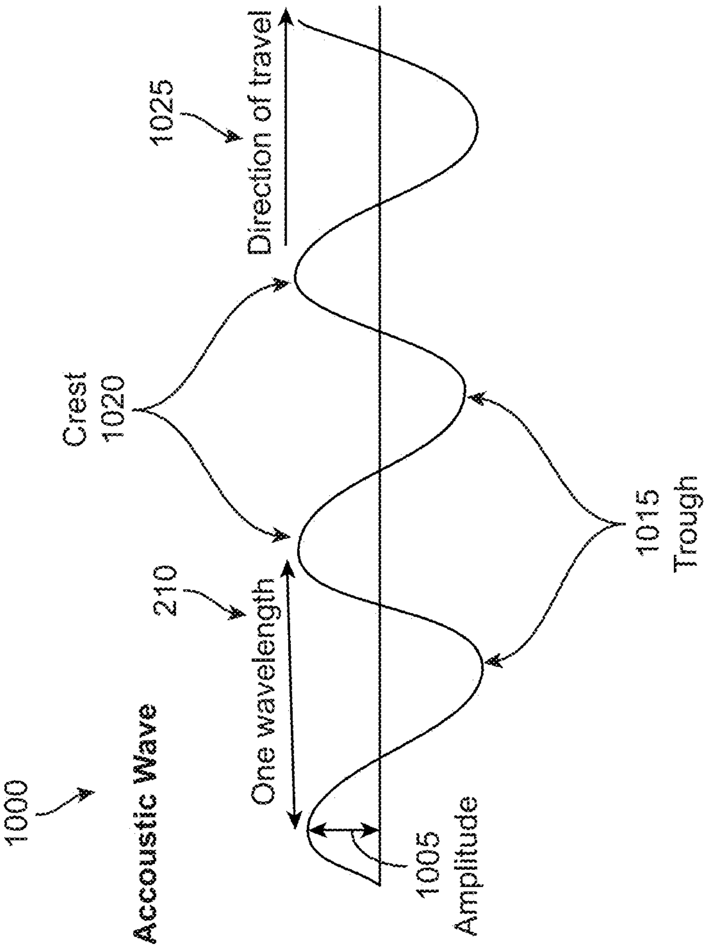
FIG. 10A-10I illustrate audio signals and types of modulations to audio signals used to induce neural oscillations via auditory stimulation in accordance with some embodiments.

In some embodiments, the audio generation module 910 can instruct the audio signaling component 950 to provide an audio signal. For example, the audio signal can include an acoustic wave 1000 as depicted in FIG. 10A. The audio signal can include multiple acoustic waves. The audio signal can generate one or more acoustic waves. The acoustic wave 1000 can include or be formed of a mechanical wave of pressure and displacement that travels through media such as gases, liquids, and solids. The acoustic wave can travel through a medium to cause vibration, sound, ultrasound or infrasound. The acoustic wave can propagate through air, water or solids as longitudinal waves. The acoustic wave can propagate through solids as a transverse wave.

The acoustic wave can generate sound due to the oscillation in pressure, stress, particle displacement, or particle velocity propagated in a medium with internal forces (e.g., elastic or viscous), or the superposition of such propagated oscillation. Sound can refer to the auditory sensation evoked by this oscillation. For example, sound can refer to the reception of acoustic waves and their perception by the brain.

The audio signaling component 950 or audio source thereof can generate the acoustic waves by vibrating a diaphragm of the audio source. For example, the audio source can include a diaphragm such as a transducer configured to inter-convert mechanical vibrations to sounds. The diaphragm can include a thin membrane or sheet of various materials, suspended at its edges. The varying pressure of sound waves imparts mechanical vibrations to the diaphragm which can then create acoustic waves or sound.

The acoustic wave 1000 illustrated in FIG. 10A includes a wavelength 1010. The wavelength 1010 can refer to a distance between successive crests 1020 of the wave. The wavelength 1010 can be related to the frequency of the acoustic wave and the speed of the acoustic wave. For example, the wavelength can be determined as the quotient of the speed of the acoustic wave divided by the frequency of the acoustic wave. The speed of the acoustic wave can be the product of the frequency and the wavelength. The frequency of the acoustic wave can be the quotient of the speed of the acoustic wave divided by the wavelength of the acoustic wave. Thus, the frequency and the wavelength of the acoustic wave can be inversely proportional. The speed of sound can vary based on the medium through which the acoustic wave propagates. For example, the speed of sound in air can be 343 meters per second.

A crest 1020 can refer to the top of the wave or point on the wave with the maximum value. The displacement of the medium is at a maximum at the crest 1020 of the wave. The trough 1015 is the opposite of the crest 1020. The trough 1015 is the minimum or lowest point on the wave corresponding to the minimum amount of displacement.

The acoustic wave 1000 can include an amplitude 1005. The amplitude 1005 can refer to a maximum extent of a vibration or oscillation of the acoustic wave 1000 measured from a position of equilibrium. The acoustic wave 1000 can be a longitudinal wave if it oscillates or vibrates in the same direction of travel 1025. In some cases, the acoustic wave 1000 can be a transverse wave that vibrates at right angles to the direction of its propagation.

The audio generation module 910 can instruct the audio signaling component 950 to generate acoustic waves or sound waves having one or more predetermined amplitude or wavelength. Wavelengths of the acoustic wave that are audible to the human ear range from approximately 17 meters to 17 millimeters (or 20 Hz to 20 kHz). The audio generation module 910 can further specify one or more properties of an acoustic wave within or outside the audible spectrum. For example, the frequency of the acoustic wave can range from 0 to 50 kHz. In some embodiments, the frequency of the acoustic wave can range from 8 to 12 kHz. In some embodiments, the frequency of the acoustic wave can be 10 kHz.

Figure 10B:
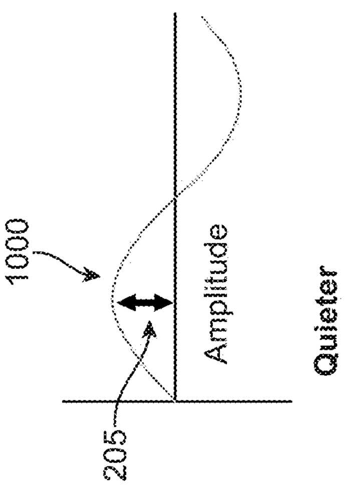
Figure 10C:
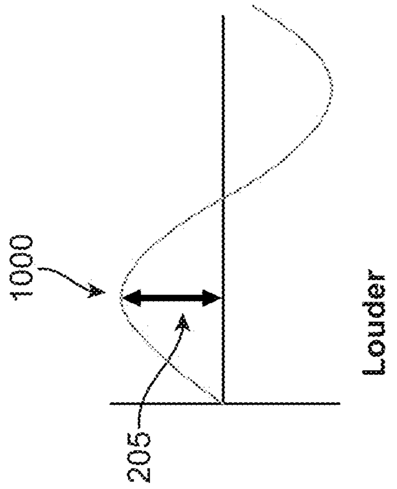

The NSS 905 can modulate, modify, change or otherwise alter properties of the acoustic wave 1000. For example, the NSS 905 can modulate the amplitude or wavelength of the acoustic wave. As depicted in FIG. 10B and FIG. 10C, the NSS 905 can adjust, manipulate, or otherwise modify the amplitude 1005 of the acoustic wave 1000. For example, the NSS 905 can lower the amplitude 1005 to cause the sound to be quieter, as depicted in FIG. 10B, or increase the amplitude 1005 to cause the sound to be louder, as depicted in FIG. 10C.

Figure 10D:
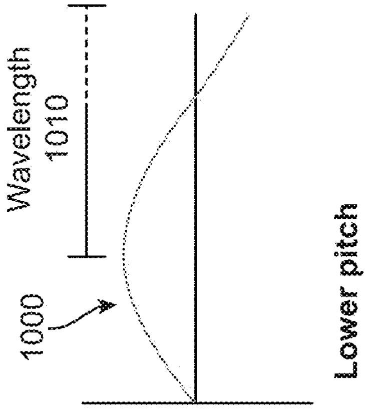
Figure 10E:
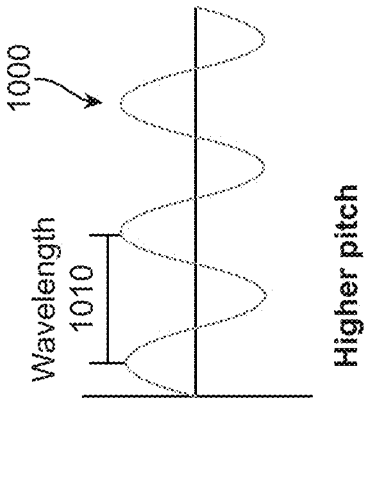

In some cases, the NSS 905 can adjust, manipulate or otherwise modify the wavelength 1010 of the acoustic wave. As depicted in FIG. 10D and FIG. 10E, the NSS 905 can adjust, manipulate, or otherwise modify the wavelength 1010 of the acoustic wave 1000. For example, the NSS 905 can increase the wavelength 1010 to cause the sound to have a lower pitch, as depicted in FIG. 10D, or reduce the wavelength 1010 to cause the sound to have a higher pitch, as depicted in FIG. 10E.

The NSS 905 can modulate the acoustic wave. Modulating the acoustic wave can include modulating one or more properties of the acoustic wave. Modulating the acoustic wave can include filtering the acoustic wave, such as filtering out unwanted frequencies or attenuating the acoustic wave to lower the amplitude. Modulating the acoustic wave can include adding one or more additional acoustic waves to the original acoustic wave. Modulating the acoustic wave can include combining the acoustic wave such that there is constructive or destructive interference where the resultant, combined acoustic wave corresponds to the modulated acoustic wave.

The NSS 905 can modulate or change one or more properties of the acoustic wave based on a time interval. The NSS 905 can change the one or more properties of the acoustic at the end of the time interval. For example, the NSS 905 can change a property of the acoustic wave every 30 seconds, 1 minute, 2 minutes, 3 minutes, 5 minutes, 7 minutes, 10 minutes, or 15 minutes. The NSS 905 can change a modulation frequency of the acoustic wave, where the modulation frequency refers to the repeated modulations or inverse of the pulse rate interval of the acoustic pulses. The modulation frequency can be a predetermined or desired frequency. The modulation frequency can correspond to a desired stimulation frequency of neural oscillations. The modulation frequency can be set to facilitate or cause brainwave entrainment. The NSS 905 can set the modulation frequency to a frequency in the range of 0.1 Hz to 10,000 Hz. For example, the NSS 905 can set the modulation frequency to 0.1 Hz, 1 Hz, 5 Hz, 10 Hz, 20 Hz, 25 Hz, 30 Hz, 31 Hz, 32 Hz, 33 Hz, 34 Hz, 35 Hz, 36 Hz, 37 Hz, 38 Hz, 39 Hz, 40 Hz, 41 Hz, 42 Hz, 43 Hz, 44 Hz, 45 Hz, 46 Hz, 47 Hz, 48 Hz, 49 Hz, 50 Hz, 60 Hz, 70 Hz, 80 Hz, 90 Hz, 100 Hz, 150 Hz, 200 Hz, 250 Hz, 300 Hz, 400 Hz, 500 Hz, 1000 Hz, 2000 Hz, 3000 Hz, 4,000 Hz, 5000 Hz, 6,000 Hz, 7,000 Hz, 8,000 Hz, 9,000 Hz, or 10,000 Hz.

The audio generation module 910 can determine to provide audio signals that include bursts of acoustic waves, audio pulses, or modulations to acoustic waves. The audio generation module 910 can instruct or otherwise cause the audio signaling component 950 to generate acoustic bursts or pulses. An acoustic pulse can refer to a burst of acoustic waves or a modulation to a property of an acoustic wave that is perceived by the brain as a change in sound. For example, an audio source that is intermittently turned on and off can create audio bursts or changes in sound. The audio source can be turned on and off based on a predetermined or fixed pulse rate interval, such as every 0.025 seconds, to provide a pulse repetition frequency of 40 Hz. The audio source can be turned on and off to provide a pulse repetition frequency in the range of 0.1 Hz to 10 kHz or more.

For example, FIGS. 10F-10I illustrates bursts of acoustic waves or bursts of modulations that can be applied to acoustic waves. The bursts of acoustic waves can include, for example, audio tones, beeps, or clicks. The modulations can refer to changes in the amplitude of the acoustic wave, changes in frequency or wavelength of the acoustic wave, overlaying another acoustic wave over the original acoustic wave, or otherwise modifying or changing the acoustic wave.

Figure 10F:
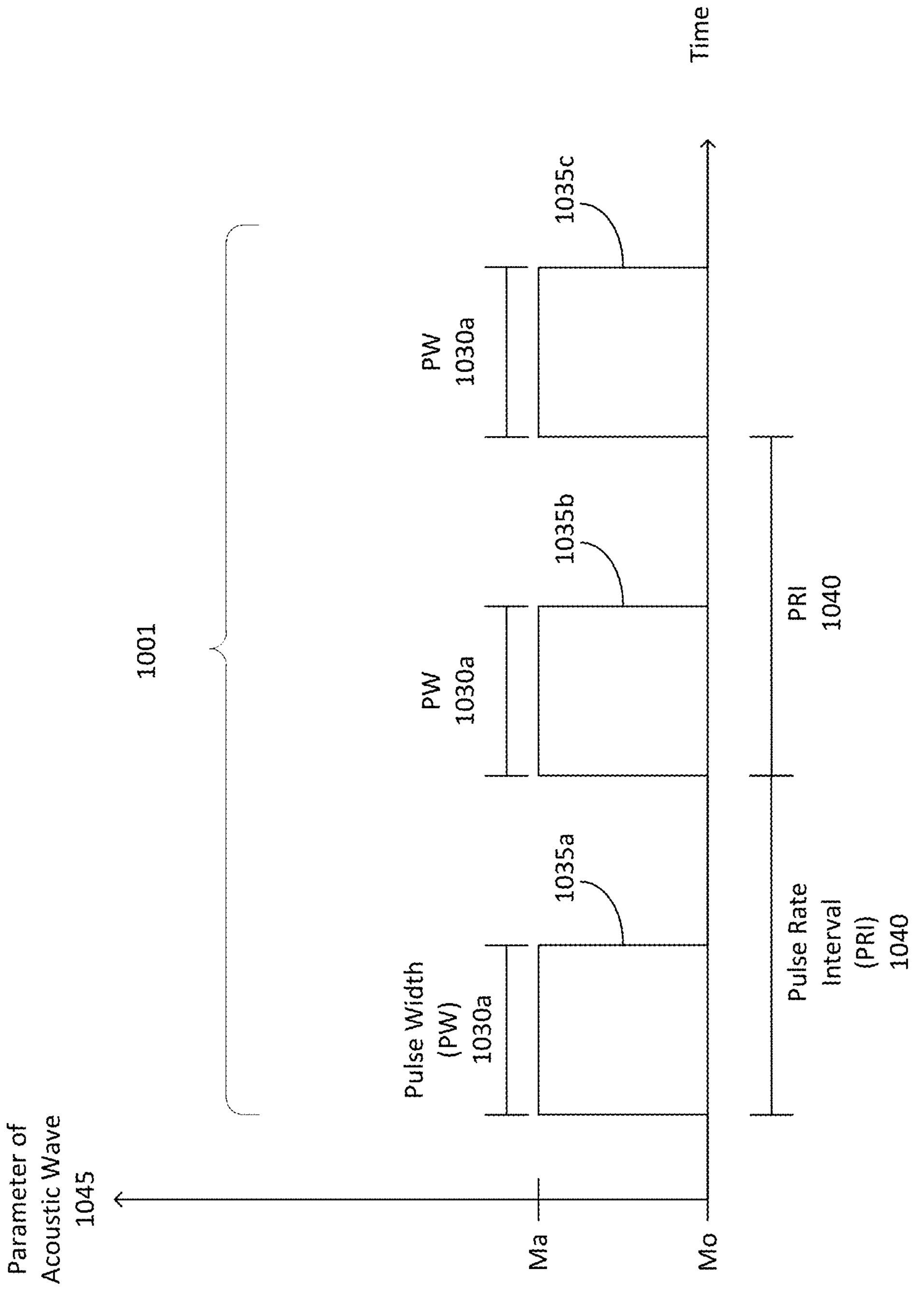

For example, FIG. 10F illustrates acoustic bursts 1035*a-c* (or modulation pulses 1035*a-c*) in accordance with an embodiment. The acoustic bursts 1035*a-c* can be illustrated via a graph where the y-axis represents a parameter of the acoustic wave (e.g., frequency, wavelength, or amplitude) of the acoustic wave. The x-axis can represent time (e.g., seconds, milliseconds, or microseconds).

The audio signal can include a modulated acoustic wave that is modulated between different frequencies, wavelengths, or amplitudes. For example, the NSS 905 can modulate an acoustic wave between a frequency in the audio spectrum, such as Ma, and a frequency outside the audio spectrum, such as Mo. The NSS 905 can modulate the acoustic wave between two or more frequencies, between an on state and an off state, or between a high power state and a low power state.

The acoustic bursts 1035*a-c* can have an acoustic wave parameter with value Ma that is different from the value Mo of the acoustic wave parameter. The modulation Ma can refer to a frequency or wavelength, or amplitude. The pulses 1035*a-c* can be generated with a pulse rate interval (PRI) 1040.

For example, the acoustic wave parameter can be the frequency of the acoustic wave. The first value Mo can be a low frequency or carrier frequency of the acoustic wave, such as 10 kHz. The second value, Ma, can be different from the first frequency Mo. The second frequency Ma can be lower or higher than the first frequency Mo. For example, the second frequency Ma can be 11 kHz. The difference between the first frequency and the second frequency can be determined or set based on a level of sensitivity of the human ear. The difference between the first frequency and the second frequency can be determined or set based on profile information 945 for the subject. The difference between the first frequency Mo and the second frequency Ma can be determined such that the modulation or change in the acoustic wave facilitate brainwave entrainment.

In some cases, the parameter of the acoustic wave used to generate the acoustic burst 1035*a* can be constant at Ma, thereby generating a square wave as illustrated in FIG. 10F.

In some embodiments, each of the three pulses 1035*a-c* can include acoustic waves having a same frequency Ma.

Figure 10G:
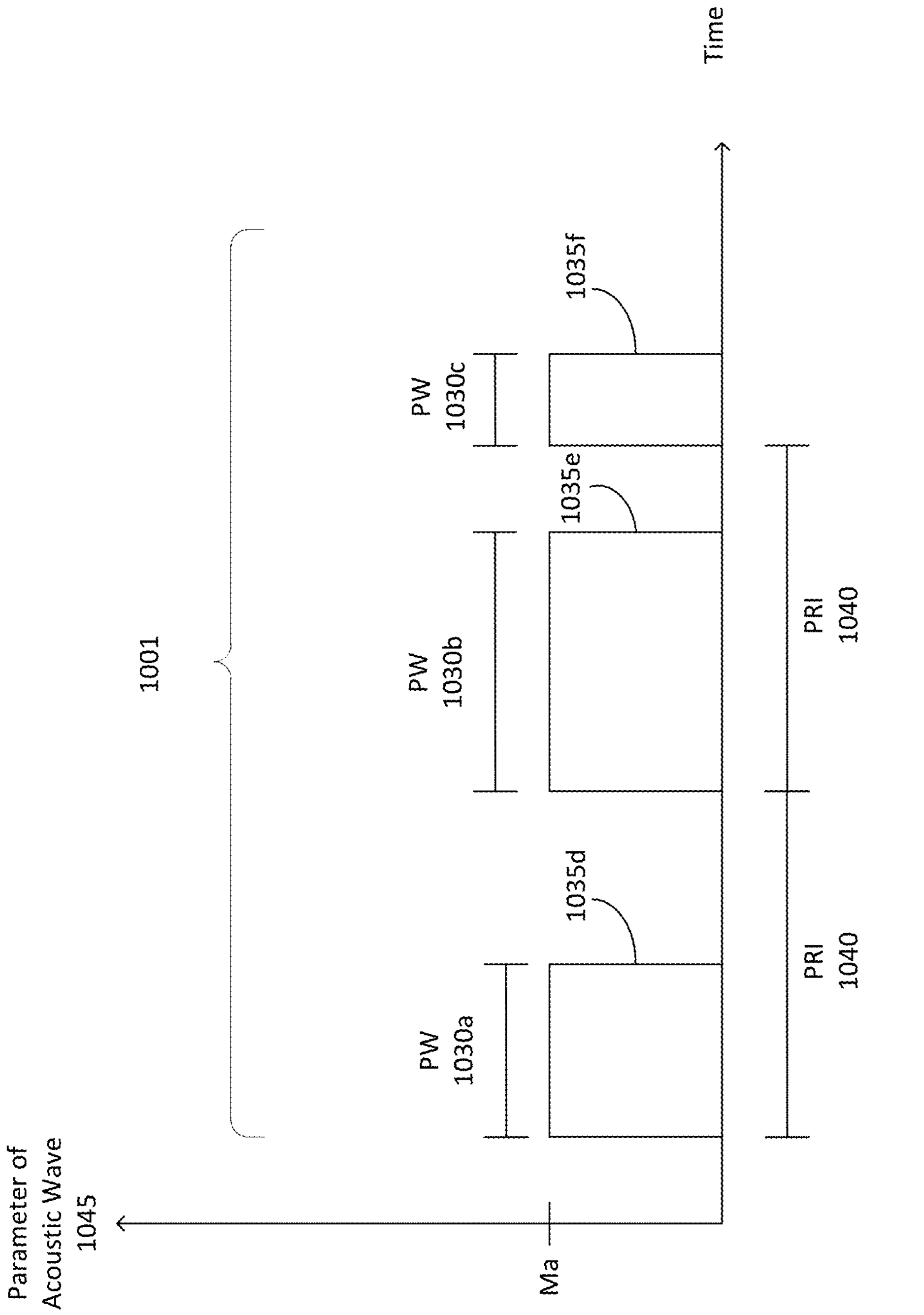

The width of each of the acoustic bursts or pulses (e.g., the duration of the burst of the acoustic wave with the parameter Ma) can correspond to a pulse width 1030*a*. The pulse width 1030*a* can refer to the length or duration of the burst. The pulse width 1030*a* can be measured in units of time or distance. In some embodiments, the pulses 1035*a-c* can include acoustic waves having different frequencies from one another. In some embodiments, the pulses 1035*a-c* can have different pulse widths 1030*a* from one another, as illustrated in FIG. 10G. For example, a first pulse 1035*d* of FIG. 10G can have a pulse width 1030*a*, while a second pulse 1035*e* has a second pulse width 1030*b* that is greater than the first pulse width 1030*a*. A third pulse 1035*f* can have a third pulse width 1030*c* that is less than the second pulse width 1030*b*. The third pulse width 1030*c* can also be less than the first pulse width 1030*a*. While the pulse widths 1030*a-c* of the pulses 1035*d-f* of the pulse train may vary, the audio generation module 910 can maintain a constant pulse rate interval 1040 for the pulse train.

The pulses 1035*a-c* can form a pulse train having a pulse rate interval 1040. The pulse rate interval 1040 can be quantified using units of time. The pulse rate interval 1040 can be based on a frequency of the pulses of the pulse train 201. The frequency of the pulses of the pulse train 201 can be referred to as a modulation frequency. For example, the audio generation module 910 can provide a pulse train 201 with a predetermined frequency, such as 40 Hz. To do so, the audio generation module 910 can determine the pulse rate interval 1040 by taking the multiplicative inverse (or reciprocal) of the frequency (e.g., 1 divided by the predetermined frequency for the pulse train). For example, the audio generation module 910 can take the multiplicative inverse of 40 Hz by dividing 1 by 40 Hz to determine the pulse rate interval 1040 as 0.025 seconds. The pulse rate interval 1040 can remain constant throughout the pulse train. In some embodiments, the pulse rate interval 1040 can vary throughout the pulse train or from one pulse train to a subsequent pulse train. In some embodiments, the number of pulses transmitted during a second can be fixed, while the pulse rate interval 1040 varies.

Figure 10H:
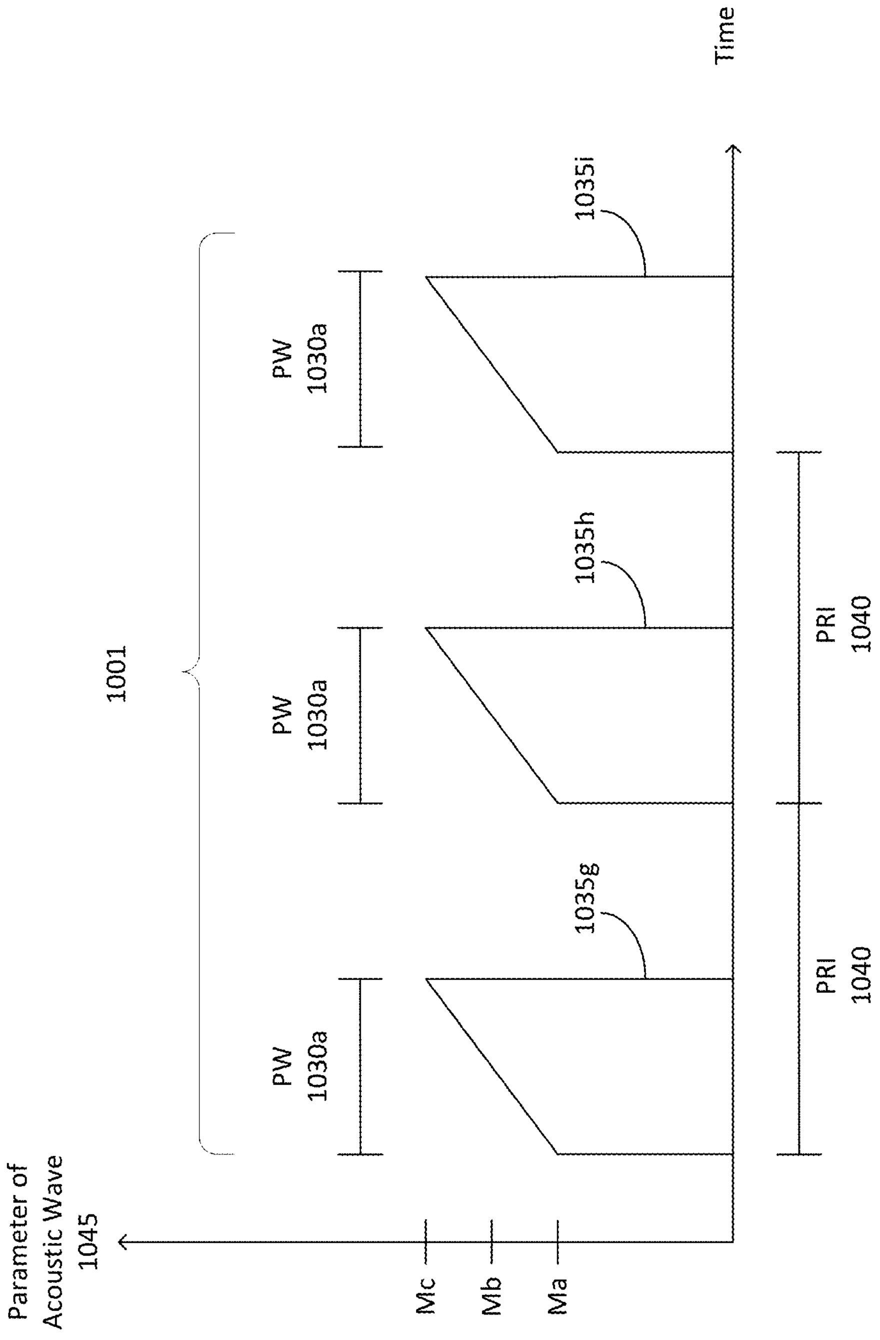

In some embodiments, the audio generation module 910 can generate an audio burst or audio pulse having an acoustic wave that varies in frequency, amplitude, or wavelength. For example, the audio generation module 910 can generate up-chirp pulses where the frequency, amplitude or wavelength of the acoustic wave of the audio pulse increases from the beginning of the pulse to the end of the pulse as illustrated in FIG. 10H. For example, the frequency, amplitude or wavelength of the acoustic wave at the beginning of pulse 1035*g* can be Ma. The frequency, amplitude or wavelength of the acoustic wave of the pulse 1035*g* can increase from Ma to Mb in the middle of the pulse 1035*g*, and then to a maximum of Mc at the end of the pulse 1035*g*. Thus, the frequency, amplitude or wavelength of the acoustic wave used to generate the pulse 1035*g* can range from Ma to Mc. The frequency, amplitude or wavelength can increase linearly, exponentially, or based on some other rate or curve. One or more of the frequency, amplitude or wavelength of the acoustic wave can change from the beginning of the pulse to the end of the pulse.

Figure 10I:
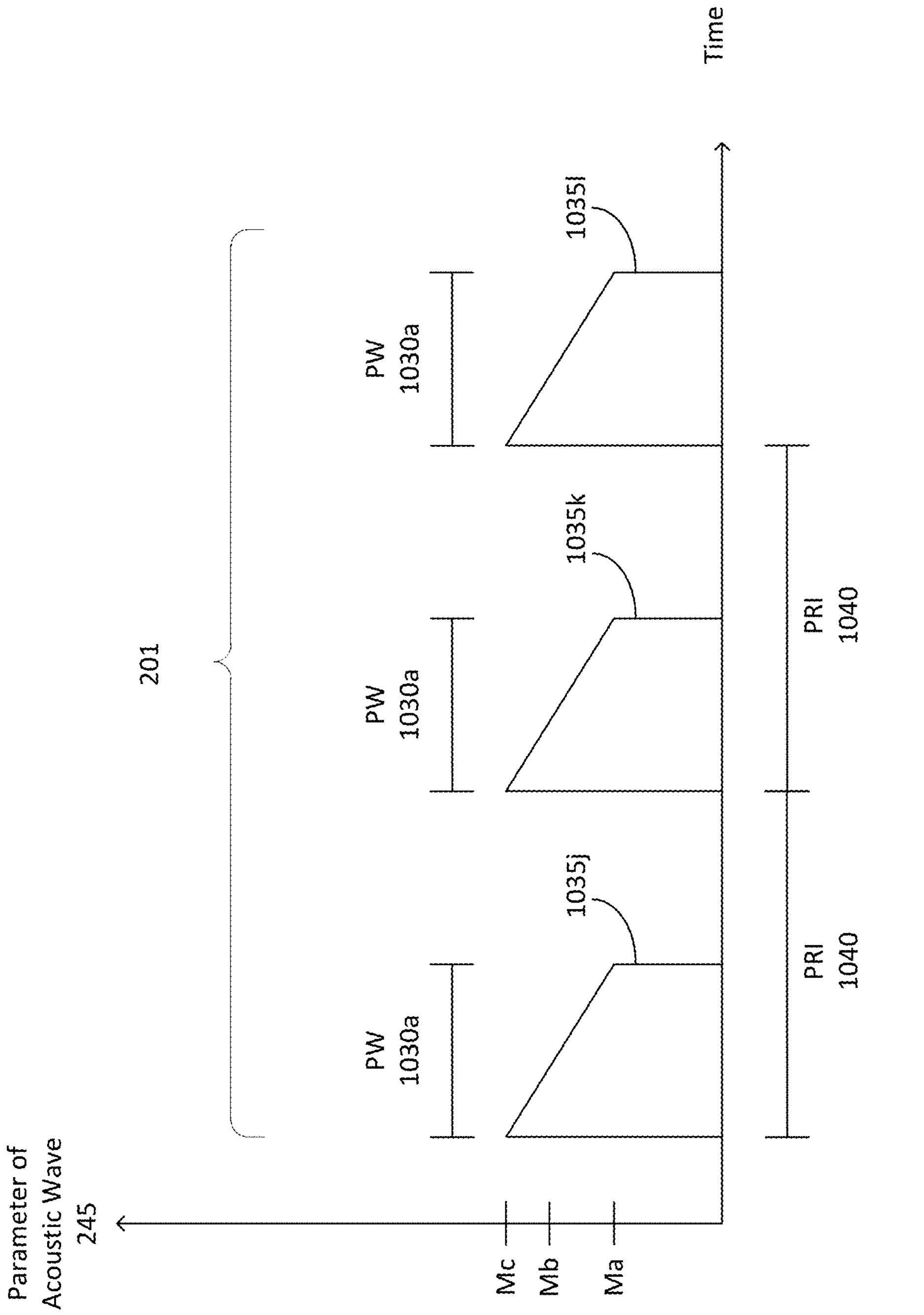

The audio generation module 910 can generate down-chirp pulses, as illustrated in FIG. 10I, where the frequency, amplitude or wavelength of the acoustic wave of the acoustic pulse decreases from the beginning of the pulse to the end of the pulse. For example, the frequency, amplitude or wavelength of an acoustic wave at the beginning of pulse 1035*j* can be Mc. The frequency, amplitude or wavelength of the acoustic wave of the pulse 1035*j* can decrease from Mc to Mb in the middle of the pulse 1035*j*, and then to a minimum of Ma at the end of the pulse 1035*j*. Thus, the frequency, amplitude or wavelength of the acoustic wave used to generate the pulse 1035*j* can range from Mc to Ma. The frequency, amplitude or wavelength can decrease linearly, exponentially, or based on some other rate or curve. One or more of the frequency, amplitude or wavelength of the acoustic wave can change from the beginning of the pulse to the end of the pulse.

In some embodiments, the audio generation module 910 can instruct or cause the audio signaling component 950 to generate audio pulses to stimulate specific or predetermined portions of the brain or a specific cortex. The frequency, wavelength, modulation frequency, amplitude and other aspects of the audio pulse, tone or music based stimuli can dictate which cortex or cortices are recruited to process the stimuli. The audio signaling component 950 can stimulate discrete portions of the cortex by modulating the presentation of the stimuli to target specific or general regions of interest. The modulation parameters or amplitude of the audio stimuli can dictate which region of the cortex is stimulated. For example, different regions of the cortex are recruited to process different frequencies of sound, called their characteristic frequencies. Further, ear laterality of stimulation can have an effect on cortex response since some subjects can be treated by stimulating one ear as opposed to both ears.

Audio signaling component 950 can be designed and constructed to generate the audio pulses responsive to instructions from the audio generation module 910. The instructions can include, for example, parameters of the audio pulse such as a frequency, wavelength or of the acoustic wave, duration of the pulse, frequency of the pulse train, pulse rate interval, or duration of the pulse train (e.g., a number of pulses in the pulse train or the length of time to transmit a pulse train having a predetermined frequency). The audio pulse can be perceived, observed, or otherwise identified by the brain via cochlear means such as ears. The audio pulses can be transmitted to the ear via an audio source speaker in close proximity to the ear, such as headphones, earbuds, bone conduction transducers, or cochlear implants. The audio pulses can be transmitted to the ear via an audio source or speaker not in close proximity to the ear, such as a surround sound speaker system, bookshelf speakers, or other speaker not directly or indirectly in contact with the ear.

Figure 11A:
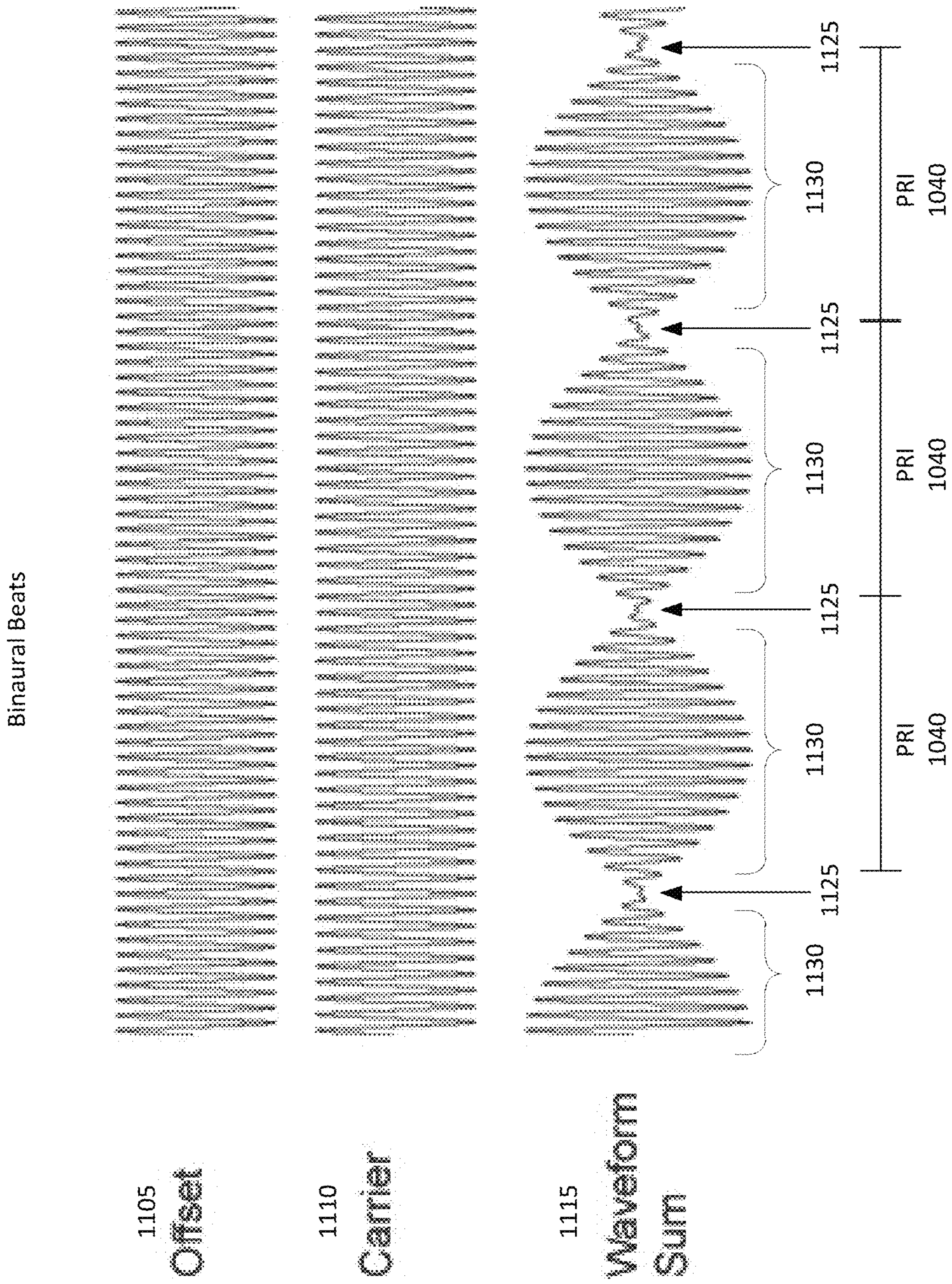
FIG. 11A illustrates audio signals generated using binaural beats, in accordance with an embodiment.

FIG. 11A illustrates audio signals using binaural beats or binaural pulses, in accordance with an embodiment. In brief summary, binaural beats refers to providing a different tone to each ear of the subject. When the brain perceives the two different tones, the brain mixes the two tones together to create a pulse. The two different tones can be selected such that the sum of the tones creates a pulse train having a desired pulse rate interval 1040.

The audio signaling component 950 can include a first audio source that provides an audio signal to the first ear of a subject, and a second audio source that provides a second audio signal to the second ear of a subject. The first audio source and the second audio source can be different. The first ear may only perceive the first audio signal from the first audio source, and the second ear may only receive the second audio signal from the second audio source. Audio sources can include, for example, headphones, earbuds, or bone conduction transducers. The audio sources can include stereo audio sources.

The audio generation component 910 can select a first tone for the first ear and a different second tone for the second ear. A tone can be characterized by its duration, pitch, intensity (or loudness), or timbre (or quality). In some cases, the first tone and the second tone can be different if they have different frequencies. In some cases, the first tone and the second tone can be different if they have different phase offsets. The first tone and the second tone can each be pure tones. A pure tone can be a tone having a sinusoidal waveform with a single frequency.

As illustrated in FIG. 11A, the first tone or offset wave 1105 is slightly different from the second tone 1110 or carrier wave 1110. The first tone 1105 has a higher frequency than the second tone 1110. The first tone 1105 can be generated by a first earbud that is inserted into one of the subject's ears, and the second tone 1110 can be generated by a second earbud that is inserted into the other of the subject's ears. When the auditory cortex of the brain perceives the first tone 1105 and the second tone 1110, the brain can sum the two tones. The brain can sum the acoustic waveforms corresponding to the two tones. The brain can sum the two waveforms as illustrated by waveform sum 1115. Due to the first and second tones having a different parameter (such as a different frequency or phase offset), portions of the waves can add and subtract from another to result in waveform 1115 having one or more pulses 1130 (or beats 1130). The pulses 1130 can be separated by portions 1125 that are at equilibrium. The pulses 1130 perceived by the brain by mixing these two different waveforms together can induce brainwave entrainment.

In some embodiments, the NSS 905 can generate binaural beats using a pitch panning technique. For example, the audio generation module 910 or audio adjustment module 915 can include or use a filter to modulate the pitch of a sound file or single tone up and down, and at the same time pan the modulation between stereo sides, such that one side will have a slightly higher pitch while the other side has a pitch that is slightly lower. The stereo sides can refer to the first audio source that generates and provides the audio signal to the first ear of the subject, and the second audio source that generates and provides the audio signal to the second ear of the subject. A sound file can refer to a file format configured to store a representation of, or information about, an acoustic wave. Example sound file formats can include .mp3, .wav, .aac, .m4a, .smf, etc.

The NSS 905 can use this pitch panning technique to generate a type of spatial positioning that, when listened to through stereo headphones, is perceived by the brain in a manner similar to binaural beats. The NSS 905 can, therefore, use this pitch panning technique to generate pulses or beats using a single tone or a single sound file.

In some cases, the NSS 905 can generate monaural beats or monaural pulses. Monaural beats or pulses are similar to binaural beats in that they are also generated by combining two tones to form a beat. The NSS 905 or component of system 100 can form monaural beats by combining the two tones using a digital or analog technique before the sound reaches the ears, as opposed to the brain combining the waveforms as in binaural beats. For example, the NSS 905 (or audio generation component 910) can identify and select two different waveforms that, when combined, produce beats or pulses having a desired pulse rate interval. The NSS 905 can identify a first digital representation of a first acoustic waveform, and identify a second digital representation of a second acoustic waveform have a different parameter than the first acoustic waveform. The NSS 905 can combine the first and second digital waveforms to generate a third digital waveform different from the first digital waveform and the second digital waveform. The NSS 905 can then transmit the third digital waveform in a digital form to the audio signaling component 950. The NSS 905 can translate the digital waveform to an analog format and transmit the analog format to the audio signaling component 950. The audio signaling component 950 can then, via an audio source, generate the sound to be perceived by one or both ears. The same sound can be perceived by both ears. The sound can include the pulses or beats spaced at the desired pulse rate interval 1040.

Figure 11B:
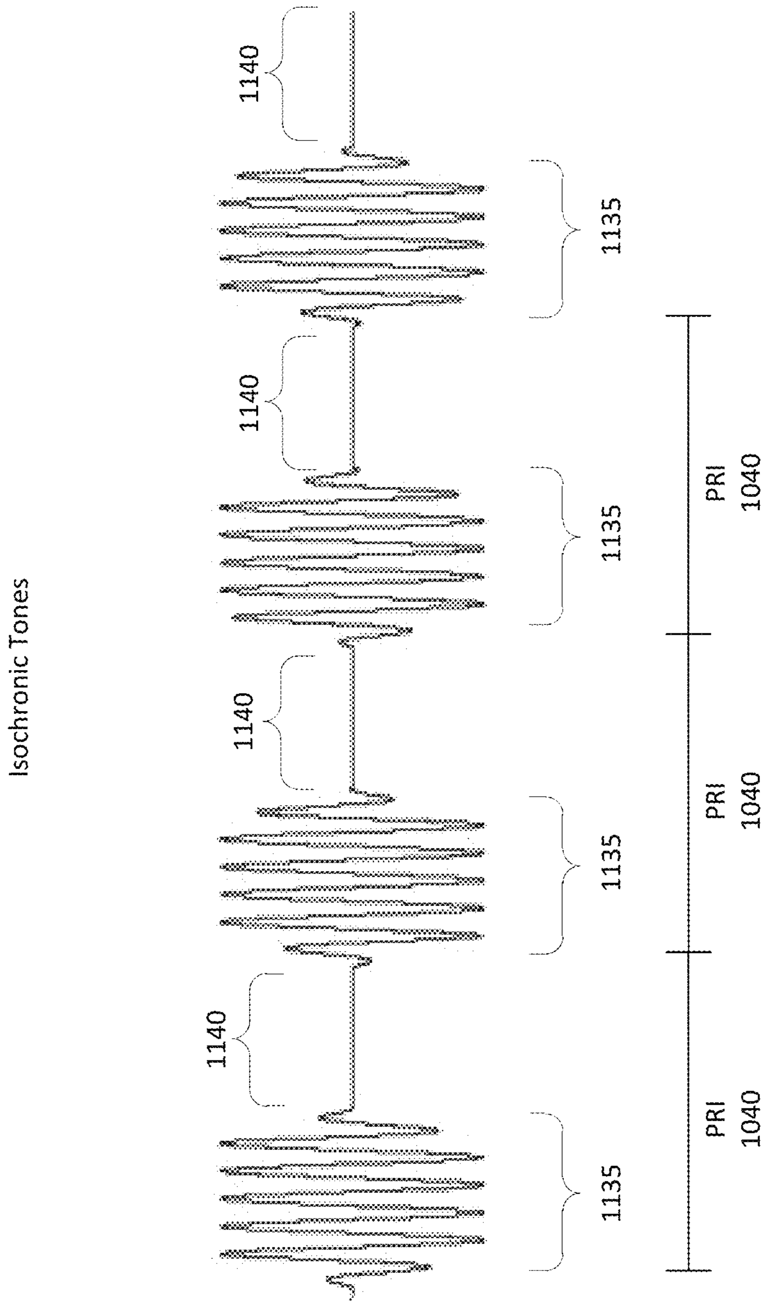
FIG. 11B illustrates acoustic pulses having isochronic tones, in accordance with an embodiment.

FIG. 11B illustrates acoustic pulses having isochronic tones, in accordance with an embodiment. Isochronic tones are evenly spaced tone pulses. Isochronic tones can be created without having to combine two different tones. The NSS 905 or other component of system 100 can create the isochronic tone by turning a tone on and off. The NSS 905 can generate the isochronic tones or pulses by instructing the audio signaling component to turn on and off. The NSS 905 can modify a digital representation of an acoustic wave to remove or set digital values of the acoustic wave such that sound is generated during the pulses 1135 and no sound is generated during the null portions 1140.

By turning on and off the acoustic wave, the NSS 905 can establish acoustic pulses 1135 that are spaced apart by a pulse rate interval 1040 that corresponds to a desired stimulation frequency, such as 40 Hz. The isochronic pulses spaced part at the desired PRI 1040 can induce brainwave entrainment.

Figure 11C:
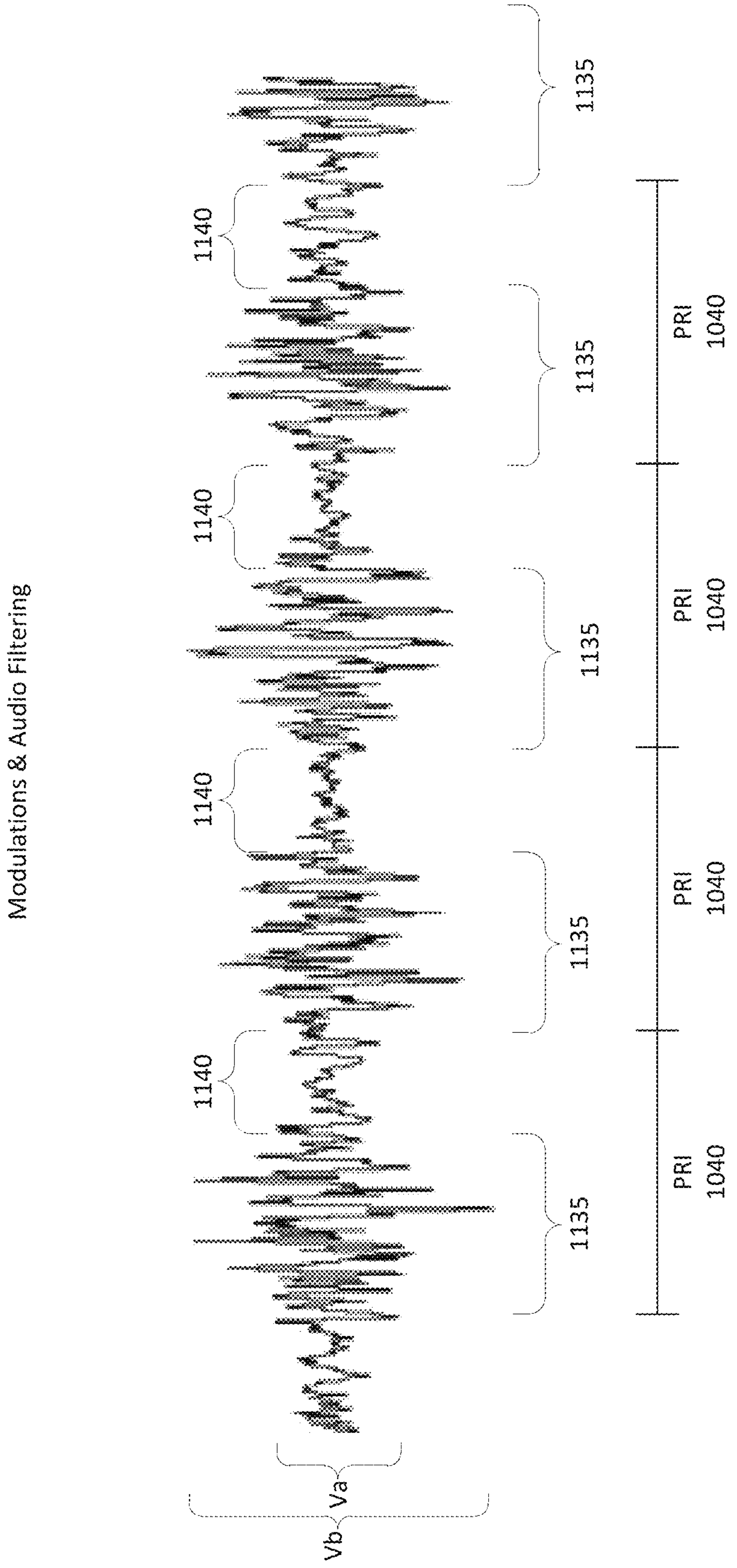
FIG. 11C illustrates audio signals having a modulation technique including audio filters, in accordance with an embodiment.

FIG. 11C illustrates audio pulses generated by the NSS 905 using a sound track, in accordance with an embodiment. A sound track can include or refer to a complex acoustical wave that includes multiple different frequencies, amplitudes, or tones. For example, a sound track can include a voice track, a musical instrument track, a musical track having both voice and musical instruments, nature sounds, or white noise.

The NSS 905 can modulate the sound track to induce brainwave entrainment by rhythmically adjusting a component in the sound. For example, the NSS 905 can modulate the volume by increasing and decreasing the amplitude of the acoustic wave or sound track to create the rhythmic stimulus corresponding to the stimulation frequency for inducing brainwave entrainment. Thus, the NSS 905 can embed, into a sound track acoustic pulses having a pulse rate interval corresponding to the desired stimulation frequency to induce brainwave entrainment. The NSS 905 can manipulate the sound track to generate a new, modified sound track having acoustic pulses with a pulse rate interval corresponding to the desired stimulation frequency to induce brainwave entrainment.

As illustrated in FIG. 11C, pulses 1135 are generated by modulating the volume from a first level Va to a second level Vb. During portions 1140 of the acoustic wave 345, the NSS 905 can set or keep the volume at Va. The volume Va can refer to an amplitude of the wave, or a maximum amplitude or crest of the wave 345 during the portion 1140. The NSS 905 can then adjust, change, or increase the volume to Vb during portion 1135. The NSS 905 can increase the volume by a predetermined amount, such as a percentage, a number of decibels, a subject-specified amount, or other amount. The NSS 905 can set or maintain the volume at Vb for a duration corresponding to a desired pulse length for the pulse 1135.

In some embodiments, the NSS 905 can include an attenuator to attenuate the volume from level Vb to level Va. In some embodiments, the NSS 905 can instruct an attenuator (e.g., an attenuator of audio signaling component 950) to attenuate the volume from level Vb to level Va. In some embodiments, the NSS 905 can include an amplifier to amplify or increase the volume from Va to Vb. In some embodiments, the NSS 905 can instruct an amplifier (e.g., an amplifier of the audio signaling component 950) to amplify or increase the volume from Va to Vb.

Referring back to FIG. 9, the NSS 905 can include, access, interface with, or otherwise communicate with at least one audio adjustment module 915. The audio adjustment module 915 can be designed and constructed to adjust a parameter associated with the audio signal, such as a frequency, amplitude, wavelength, pattern or other parameter of the audio signal. The audio adjustment module 915 can automatically vary a parameter of the audio signal based on profile information or feedback. The audio adjustment module 915 can receive the feedback information from the feedback monitor 935. The audio adjustment module 915 can receive instructions or information from a side effects management module 930. The audio adjustment module 915 can receive profile information from profile manager 925.

The NSS 905 can include, access, interface with, or otherwise communicate with at least one unwanted frequency filtering module 920. The unwanted frequency filtering module 920 can be designed and constructed to block, mitigate, reduce, or otherwise filter out frequencies of audio signals that are undesired to prevent or reduce an amount of such audio signals from being perceived by the brain. The unwanted frequency filtering module 920 can interface, instruct, control, or otherwise communicate with a filtering component 955 to cause the filtering component 955 to block, attenuate, or otherwise reduce the effect of the unwanted frequency on the neural oscillations.

Figure 12A:
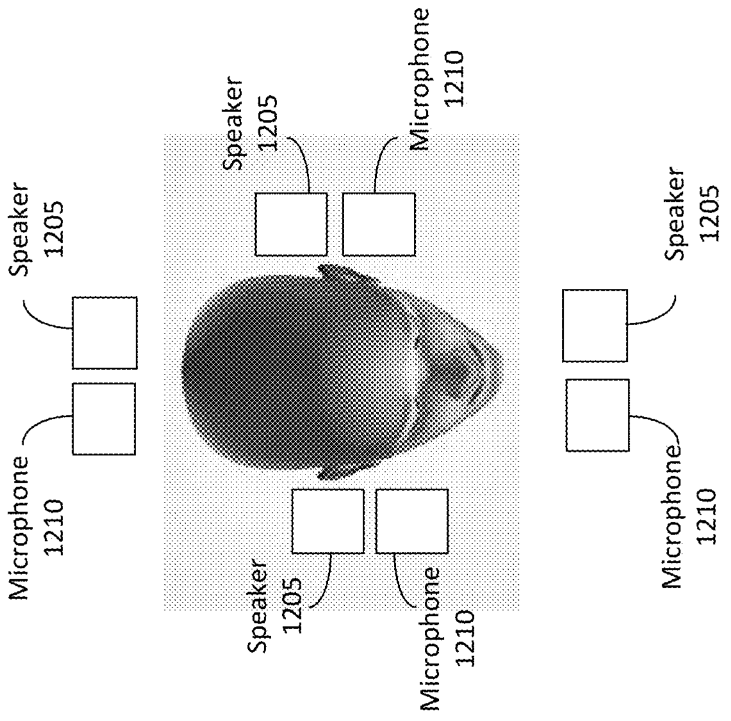
FIGS. 12A-12C illustrate configurations of systems for neural stimulation via auditory stimulation in accordance with some embodiments.
Figure 12B:
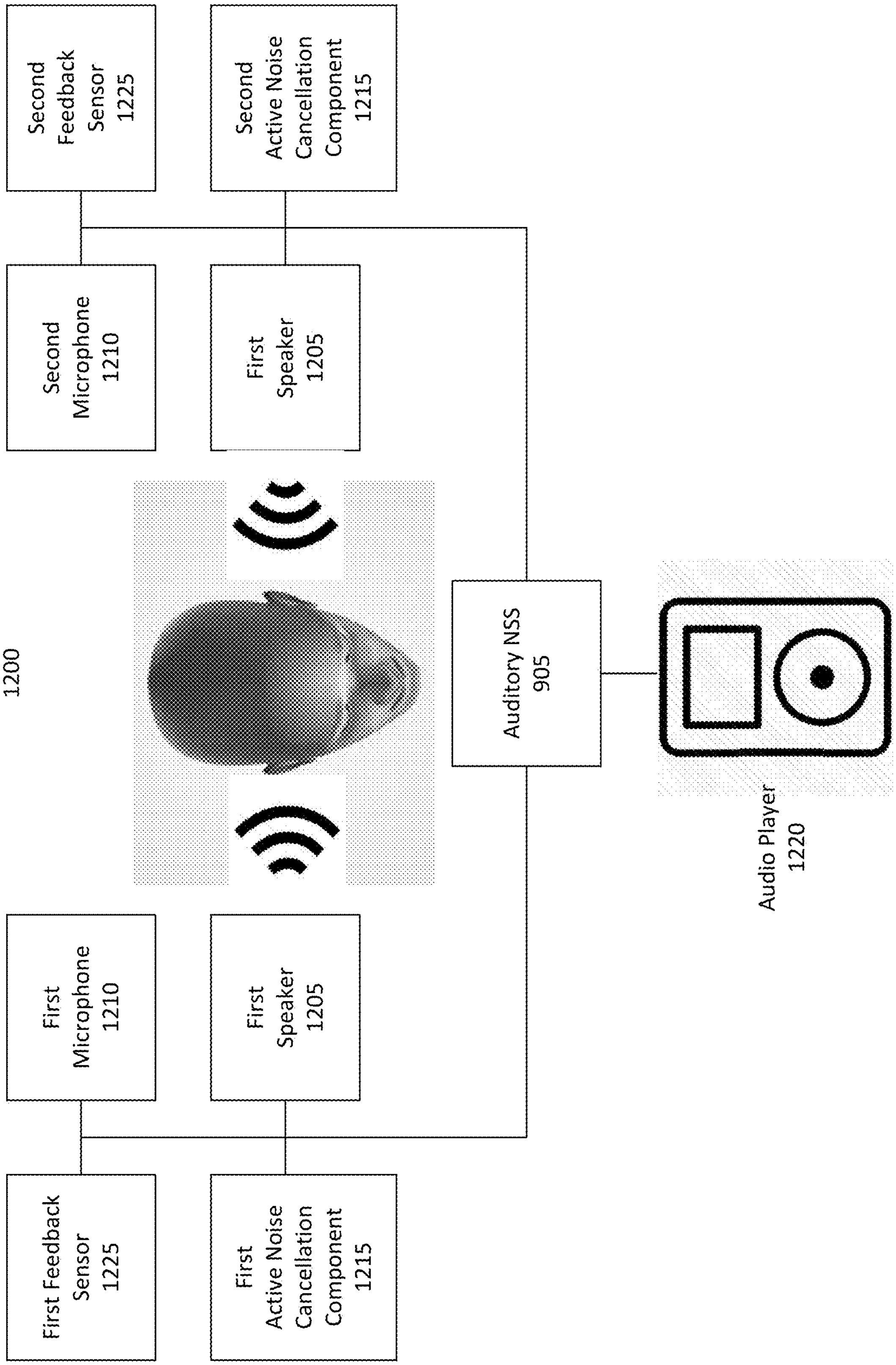
Figure 12C:
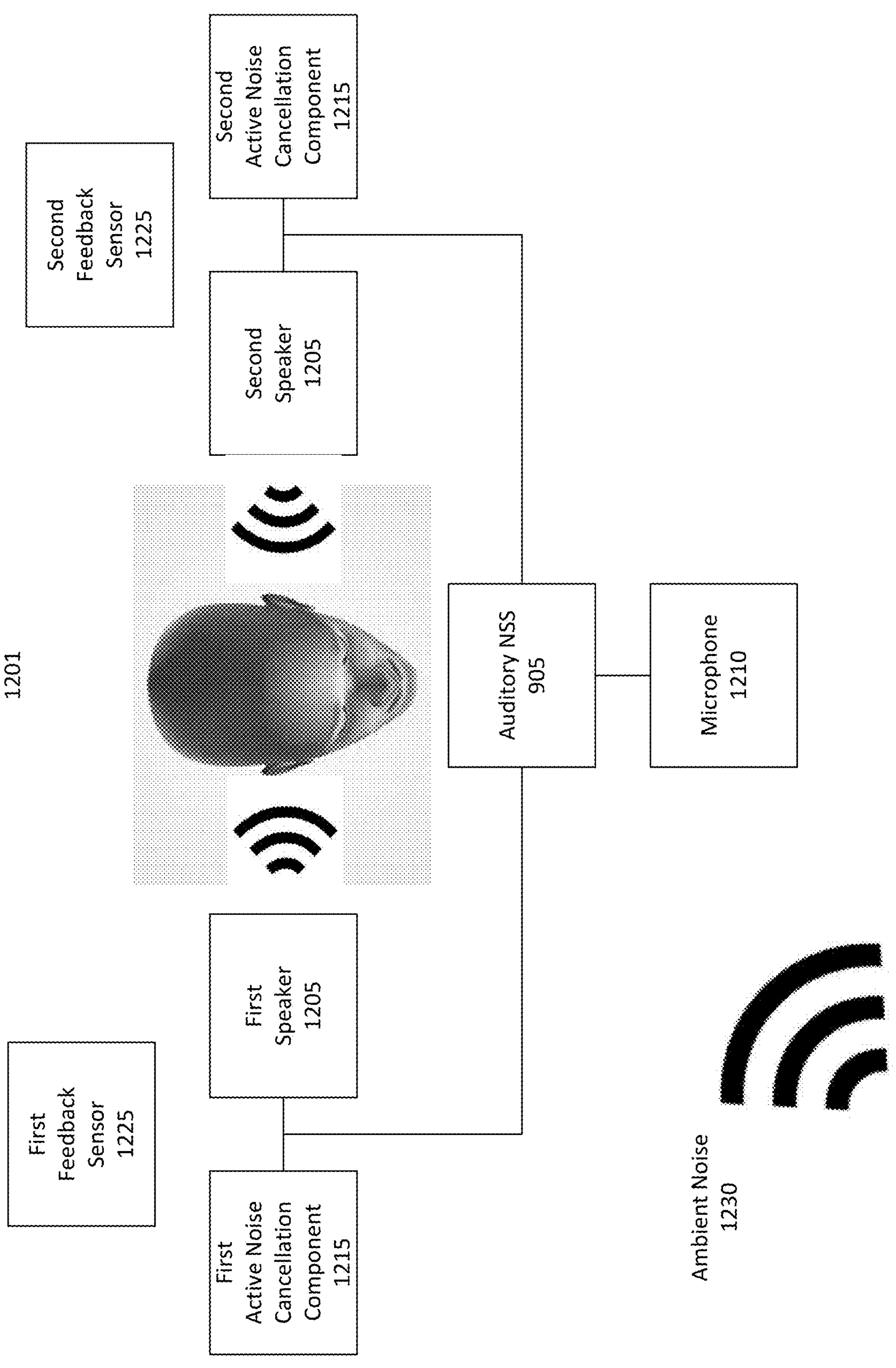

The unwanted frequency filtering module 920 can include an active noise control component (e.g., active noise cancellation component 1215 depicted in FIG. 12B). Active noise control can be referred to or include active noise cancellation or active noise reduction. Active noise control can reduce an unwanted sound by adding a second sound having a parameter specifically selected to cancel or attenuate the first sound. In some cases, the active noise control component can emit a sound wave with the same amplitude but with an inverted phase (or antiphase) to the original unwanted sound. The two waves can combine to form a new wave, and effectively cancel each other out by destructive interference.

The active noise control component can include analog circuits or digital signal processing. The active noise control component can include adaptive techniques to analyze waveforms of the background aural or nonaural noise. Responsive to the background noise, the active noise control component can generate an audio signal that can either phase shift or invert the polarity of the original signal. This inverted signal can be amplified by a transducer or speaker to create a sound wave directly proportional to the amplitude of the original waveform, creating destructive interference. This can reduce the volume of the perceivable noise.

In some embodiments, a noise-cancellation speaker can be co-located with a sound source speaker. In some embodiments, a noise cancellation speaker can be co-located with a sound source that is to be attenuated.

The unwanted frequency filtering module 920 can filter out unwanted frequencies that can adversely impact auditory brainwave entrainment. For example, an active noise control component can identify that audio signals include acoustic bursts having the desired pulse rate interval, as well as acoustic bursts having an unwanted pulse rate interval. The active noise control component can identify the waveforms corresponding to the acoustic bursts having the unwanted pulse rate interval, and generate an inverted phase waveform to cancel out or attenuate the unwanted acoustic bursts.

The NSS 905 can include, access, interface with, or otherwise communicate with at least one profile manager 925. The profile manager 925 can be designed or constructed to store, update, retrieve or otherwise manage information associated with one or more subjects associated with the auditory brain entrainment. Profile information can include, for example, historical treatment information, historical brain entrainment information, dosing information, parameters of acoustic waves, feedback, physiological information, environmental information, or other data associated with the systems and methods of brain entrainment.

The NSS 905 can include, access, interface with, or otherwise communicate with at least one side effects management module 930. The side effects management module 930 can be designed and constructed to provide information to the audio adjustment module 915 or the audio generation module 910 to change one or more parameter of the audio signal in order to reduce a side effect. Side effects can include, for example, nausea, migraines, fatigue, seizures, ear strain, deafness, ringing, or tinnitus.

The side effects management module 930 can automatically instruct a component of the NSS 905 to alter or change a parameter of the audio signal. The side effects management module 930 can be configured with predetermined thresholds to reduce side effects. For example, the side effects management module 930 can be configured with a maximum duration of a pulse train, maximum amplitude of acoustic waves, maximum volume, maximum duty cycle of a pulse train (e.g., the pulse width multiplied by the frequency of the pulse train), maximum number of treatments for brainwave entrainment in a time period (e.g., 1 hour, 2 hours, 12 hours, or 24 hours).

The side effects management module 930 can cause a change in the parameter of the audio signal in response to feedback information. The side effect management module 930 can receive feedback from the feedback monitor 935. The side effects management module 930 can determine to adjust a parameter of the audio signal based on the feedback. The side effects management module 930 can compare the feedback with a threshold to determine to adjust the parameter of the audio signal.

The side effects management module 930 can be configured with or include a policy engine that applies a policy or a rule to the current audio signal and feedback to determine an adjustment to the audio signal. For example, if feedback indicates that a patient receiving audio signals has a heart rate or pulse rate above a threshold, the side effects management module 930 can turn off the pulse train until the pulse rate stabilizes to a value below the threshold, or below a second threshold that is lower than the threshold.

The NSS 905 can include, access, interface with, or otherwise communicate with at least one feedback monitor 935. The feedback monitor can be designed and constructed to receive feedback information from a feedback component 960. Feedback component 960 can include, for example, a feedback sensor 1405 such as a temperature sensor, heart or pulse rate monitor, physiological sensor, ambient noise sensor, microphone, ambient temperature sensor, blood pressure monitor, brain wave sensor, EEG probe, electrooculography ("EOG") probes configured measure the corneo-retinal standing potential that exists between the front and the back of the human eye, accelerometer, gyroscope, motion detector, proximity sensor, camera, microphone, or photo detector.

Systems and Devices Configured for Neural Stimulation Via Auditory Stimulation

FIG. 12A illustrates a system for auditory brain entrainment in accordance with an embodiment. The system 1200 can include one or more speakers 1205. The system 1200 can include one or more microphones. In some embodiments, the system can include both speakers 1205 and microphones 1210. In some embodiments, the system 1200 includes speakers 1205 and may not include microphones 1210. In some embodiments, the system 1200 includes microphones 1210 and may not include speakers 1210.

The speakers 1205 can be integrated with the audio signaling component 950. The audio signaling component 950 can include speakers 1205. The speakers 1205 can interact or communicate with audio signaling component 950. For example, the audio signaling component 950 can instruct the speaker 1205 to generate sound.

The microphones 1210 can be integrated with the feedback component 960. The feedback component 960 can include microphones 1210. The microphones 1210 can interact or communicate with feedback component 960. For example, the feedback component 960 can receive information, data or signals from microphone 1210.

In some embodiments, the speaker 1205 and the microphone 1210 can be integrated together or a same device. For example, the speaker 1205 can be configured to function as the microphone 1210. The NSS 905 can toggle the speaker 1205 from a speaker mode to a microphone mode.

In some embodiments, the system 1200 can include a single speaker 1205 positioned at one of the ears of the subject. In some embodiments, the system 1200 can include two speakers. A first speaker of the two speakers can be positioned at a first ear, and the second speaker of the two speakers can be positioned at the second ear. In some embodiments, additional speakers can be positioned in front of the subject's head, or behind the subject's head. In some embodiments, one or more microphones 1210 can be positioned at one or both ears, in front of the subject's head, or behind the subject's head.

The speaker 1205 can include a dynamic cone speaker configured to produce sound from an electrical signal. The speaker 1205 can include a full-range driver to produce acoustic waves with frequencies over some or all of the audible range (e.g., 60 Hz to 20,000 Hz). The speaker 1205 can include a driver to produce acoustic waves with frequencies outside the audible range, such as 0 to 60 Hz, or in the ultrasonic range such as 20 kHz to 4 GHz. The speaker 1205 can include one or more transducers or drivers to produce sounds at varying portions of the audible frequency range. For example, the speaker 1205 can include tweeters for high range frequencies (e.g., 2,000 Hz to 20,000 Hz), mid-range drivers for middle frequencies (e.g., 250 Hz to 2000 Hz), or woofers for low frequencies (e.g., 60 Hz to 250 Hz).

The speaker 1205 can include one or more types of speaker hardware, components or technology to produce sound. For example, the speaker 1205 can include a diaphragm to produce sound. The speaker 1205 can include a moving-iron loudspeaker that uses a stationary coil to vibrate a magnetized piece of metal. The speaker 1205 can include a piezoelectric speaker. A piezoelectric speaker can use the piezoelectric effect to generate sound by applying a voltage to a piezoelectric material to generate motion, which is converted into audible sound using diaphragms and resonators.

The speaker 1205 can include various other types of hardware or technology, such as magnetostatic loudspeakers, magnetostrictive speakers, electrostatic loudspeakers, a ribbon speaker, planar magnetic loudspeakers, bending wave loudspeakers, coaxial drivers, horn loudspeakers, Heil air motion transducers, or transparent ionic conductions speaker.

In some cases, the speaker 1205 may not include a diaphragm. For example, the speaker 1205 can be a plasma arc speaker that uses electrical plasma as a radiating element. The speaker 1205 can be a thermoacoustic speakers that uses carbon nanotube thin film. The speaker 1205 can be a rotary woofer that includes a fan with blades that constantly change their pitch.

In some embodiments, the speaker 1205 can include a headphone or a pair of headphones, earspeakers, earphones, or earbuds. Headphones can be relatively small speakers as compared to loudspeakers. Headphones can be designed and constructed to be placed in the ear, around the ear, or otherwise at or near the ear. Headphones can include electroacoustic transducers that convert an electrical signal to a corresponding sound in the subject's ear. In some embodiments, the headphones 1205 can include or interface with a headphone amplifier, such as an integrated amplifier or a standalone unit.

In some embodiments, the speaker 1205 can include headphones that can include an air jet that pushes air into the auditory canal, pushing the tympanum in a manner similar to that of a sound wave. The compression and rarefaction of the tympanic membrane through bursts of air (with or without any discernible sound) can control frequencies of neural oscillations similar to auditory signals. For example, the speaker 1205 can include air jets or a device that resembles in-ear headphones that either push, pull or both push and pull air into and out of the ear canal in order to compress or pull the tympanic membrane to affect the frequencies of neural oscillations. The NSS 905 can instruct, configure or cause the air jets to generate bursts of air at a predetermined frequency.

In some embodiments, the headphones can connect to the audio signaling component 950 via a wired or wireless connection. In some embodiments, the audio signaling component 950 can include the headphones. In some embodiments, the headphones 1205 can interface with one or more components of the NSS 905 via a wired or wireless connection. In some embodiments, the headphones 1205 can include one or more components of the NSS 905 or system 100, such as the audio generation module 910, audio adjustment module 915, unwanted frequency filtering module 920, profile manager 925, side effects management module 930, feedback monitor 935, audio signaling component 950, filtering component 955, or feedback component 960.

The speaker 1205 can include or be integrated into various types of headphones. For example, the headphones can include, for example, circumaural headphones (e.g., full size headphones) that include circular or ellipsoid earpads that are designed and constructed to seal against the head to attenuate external noise. Circumaural headphones can facilitate providing an immersive auditory brainwave wave stimulation experience, while reducing external distractions. In some embodiments, headphones can include supra-aural headphones, which include pads that press against the ears rather than around them. Supra-aural headphones may provide less attenuation of external noise.

Both circumaural headphones and supra-aural headphones can have an open back, closed back, or semi open back. An open back leaks more sound and allows more ambient sounds to enter, but provides a more natural or speaker-like sound. Closed back headphones block more of the ambient noise as compared to open back headphones, thus providing a more immersive auditory brainwave stimulation experience while reducing external distractions.

In some embodiments, headphones can include ear-fitting headphones, such as earphones or in-ear headphones. Earphones (or earbuds) can refer to small headphones that are fitted directly in the outer ear, facing but not inserted in the ear canal. Earphones, however, provide minimal acoustic isolation and allow ambient noise to enter. In-ear headphones (or in-ear monitors or canalphones) can refer to small headphones that can be designed and constructed for insertion into the ear canal. In-ear headphones engage the ear canal and can block out more ambient noise as compared to earphones, thus providing a more immersive auditory brainwave stimulation experience. In-ear headphones can include ear canal plugs made or formed from one or more material, such as silicone rubber, elastomer, or foam. In some embodiments, in-ear headphones can include custom-made castings of the ear canal to create custom-molded plugs that provide added comfort and noise isolation to the subject, thereby further improving the immersiveness of the auditory brainwave stimulation experience.

In some embodiments, one or more microphones 1210 can be used to detect sound. A microphone 1210 can be integrated with a speaker 1205. The microphone 1210 can provide feedback information to the NSS 905 or other component of system 100. The microphone 1210 can provide feedback to a component of the speaker 1205 to cause the speaker 1205 to adjust a parameter of audio signal.

The microphone 1210 can include a transducer that converts sound into an electrical signal. The Microphone 1210 can use electromagnetic induction, capacitance change, or piezoelectricity to produce the electrical signal from air pressure variations. In some cases, the microphone 1210 can include or be connected to a pre-amplifier to amplify the signal before it is recorded or processed. The microphone 1210 can include one or more type of microphone, including, for example, a condenser microphone, RF condenser microphone, electret condenser, dynamic microphone, moving-coil microphone, ribbon microphone, carbon microphone, piezoelectric microphone, crystal microphone, fiber optic microphone, laser microphone, liquid or water microphone, microelectromechanical systems ("MEMS") microphone, or speakers as microphones.

The feedback component 960 can include or interface with the microphone 1210 to obtain, identify, or receive sound. The feedback component 960 can obtain ambient noise. The feedback component 960 can obtain sound from the speakers 1205 to facilitate the NSS 905 adjusting a characteristic of the audio signal generated by the speaker 1205. The microphone 1210 can receive voice input from the subject, such as audio commands, instructions, requests, feedback information, or responses to survey questions.

In some embodiments, one or more speakers 1205 can be integrated with one or more microphones 1210. For example, the speaker 1205 and microphone 1210 can form a headset, be placed in a single enclosure, or may even be the same device since the speaker 1205 and the microphone 1210 may be structurally designed to toggle between a sound generation mode and a sound reception mode.

FIG. 12B illustrates a system configuration for auditory brain entrainment in accordance with an embodiment. The system 1200 can include at least one speaker 1205. The system 1200 can include at least microphone 1210. The system 1200 can include at least one active noise cancellation component 1215. The system 1200 can include at least one feedback sensor 1225. The system 1200 can include or interface with the NSS 905. The system 1200 can include or interface with an audio player 1220.

The system 1200 can include a first speaker 1205 positioned at a first ear. The system 1200 can include a second speaker 1205 positioned at a second year. The system 1200 can include a first active noise cancellation component 1215 communicatively coupled with the first microphone 1210. The system 1200 can include a second active noise cancellation component 1215 communicatively coupled with the second microphone 1210. In some cases, the active noise cancellation component 1215 can communicate with both the first speaker 1205 and the second speaker 1205, or both the first microphone 1210 and the second microphone 1210. The system 1200 can include a first microphone 1210 communicatively coupled with the active noise cancellation component 1215. The system 1200 can include a second microphone 1210 communicatively coupled with the active noise cancelation component 1215. In some embodiments, each of the microphone 1210, speaker 1205 and active noise cancellation component can communicate or interface with the NSS 905. In some embodiments, the system 1200 can include a feedback sensor 1225 and a second feedback sensor 1225 communicatively coupled to the NSS 905, the speaker 1205, microphone 1210, or active noise cancellation component 1215.

In operation, and in some embodiments, the audio player 1220 can play a musical track. The audio player 1220 can provide the audio signal corresponding to the musical track via a wired or wireless connection to the first and second speakers 1205. In some embodiments, the NSS 905 can intercept the audio signal from the audio player. For example, the NSS 905 can receive the digital or analog audio signal from the audio player 1220. The NSS 905 can be intermediary to the audio player 1220 and a speaker 1205. The NSS 905 can analyze the audio signal corresponding to the music in order to embed an auditory brainwave stimulation signal. For example, the NSS 905 can adjust the volume of the auditory signal from the audio player 1220 to generate acoustic pulses having a pulse rate interval as depicted in FIG. 11C. In some embodiments, the NSS 905 can use a binaural beats technique to provide different auditory signals to the first and second speakers that, when perceived by the brain, is combined to have the desired stimulation frequency.

In some embodiments, the NSS 905 can adjust for any latency between first and second speakers 1205 such that the brain perceives the audio signals at the same or substantially same time (e.g., within 1 milliseconds, 2 milliseconds, 5 milliseconds, or 10 milliseconds). The NSS 905 can buffer the audio signals to account for latency such that audio signals are transmitted from the speakers at the same time.

In some embodiments, the NSS 905 may not be intermediary to the audio player 1220 and the speaker. For example, the NSS 905 can receive the musical track from a digital music repository. The NSS 905 can manipulate or modify the musical track to embed acoustic pulses in accordance with the desired PRI. The NSS 905 can then provide the modified musical track to the audio player 1220 to provide the modified audio signal to the speaker 1205.

In some embodiments, an active noise cancellation component 1215 can receive ambient noise information from the microphone 1210, identify unwanted frequencies or noise, and generate an inverted phase waveform to cancel out or attenuate the unwanted waveforms. In some embodiments, the system 1200 can include an additional speaker that generates the noise canceling waveform provided by the noise cancellation component 1215. The noise cancellation component 1215 can include the additional speaker.

The feedback sensor 1225 of the system 1200 can detect feedback information, such as environmental parameters or physiological conditions. The feedback sensor 1225 can provide the feedback information to NSS 905. The NSS 905 can adjust or change the audio signal based on the feedback information. For example, the NSS 905 can determine that a pulse rate of the subject exceeds a predetermined threshold, and then lower the volume of the audio signal. The NSS 905 can detect that the volume of the auditory signal exceeds a threshold, and decrease the amplitude. The NSS 905 can determine that the pulse rate interval is below a threshold, which can indicate that a subject is losing focus or not paying a satisfactory level of attention to the audio signal, and the NSS 905 can increase the amplitude of the audio signal or change the tone or music track. In some embodiments, the NSS 905 can vary the tone or the music track based on a time interval. Varying the tone or the music track can cause the subject to pay a greater level of attention to the auditory stimulation, which can facilitate brainwave entrainment.

In some embodiments, the NSS 905 can receive neural oscillation information from EEG probes 1225, and adjust the auditory stimulation based on the EEG information. For example, the NSS 905 can determine, from the probe information, that neurons are oscillating at an undesired frequency. The NSS 905 can then identify the corresponding undesired frequency in ambient noise using the microphone 1210. The NSS 905 can then instruct the active noise cancellation component 1215 to cancel out the waveforms corresponding to the ambient noise having the undesired frequency.

In some embodiments, the NSS 905 can enable a passive noise filter. A pass noise filter can include a circuit having one or more or a resistor, capacitor or an inductor that filters out undesired frequencies of noise. In some cases, a passive filter can include a sound insulating material, sound proofing material, or sound absorbing material.

FIG. 4C illustrates a system configuration for auditory brain entrainment in accordance with an embodiment. The system 401 can provide auditory brainwave stimulation using ambient noise source 1230. For example, system 401 can include the microphone 1210 that detects the ambient noise 1230. The microphone 1210 can provide the detected ambient noise to NSS 905. The NSS 905 can modify the ambient noise 1230 before providing it to the first speaker 1205 or the second speaker 1205. In some embodiments, the system 401 can be integrated or interface with a hearing aid device. A hearing aid can be a device designed to improve hearing.

The NSS 905 can increase or decrease the amplitude of the ambient noise 1230 to generate acoustic bursts having the desired pulse rate interval. The NSS 905 can provide the modified audio signals to the first and second speakers 1205 to facilitate auditory brainwave entrainment.

In some embodiments, the NSS 905 can overlay a click train, tones, or other acoustic pulses over the ambient noise 1230. For example, the NSS 905 can receive the ambient noise information from the microphone 1210, apply an auditory stimulation signal to the ambient noise information, and then present the combined ambient noise information and auditory stimulation signal to the first and second speakers 1205. In some cases, the NSS 905 can filter out unwanted frequencies in the ambient noise 1230 prior to providing the auditory stimulation signal to the speakers 1205.

Thus, using the ambient noise 1230 as part of the auditory stimulation, a subject can observe the surroundings or carry on with their daily activities while receiving auditory stimulation to facilitate brainwave entrainment.

Figure 13:
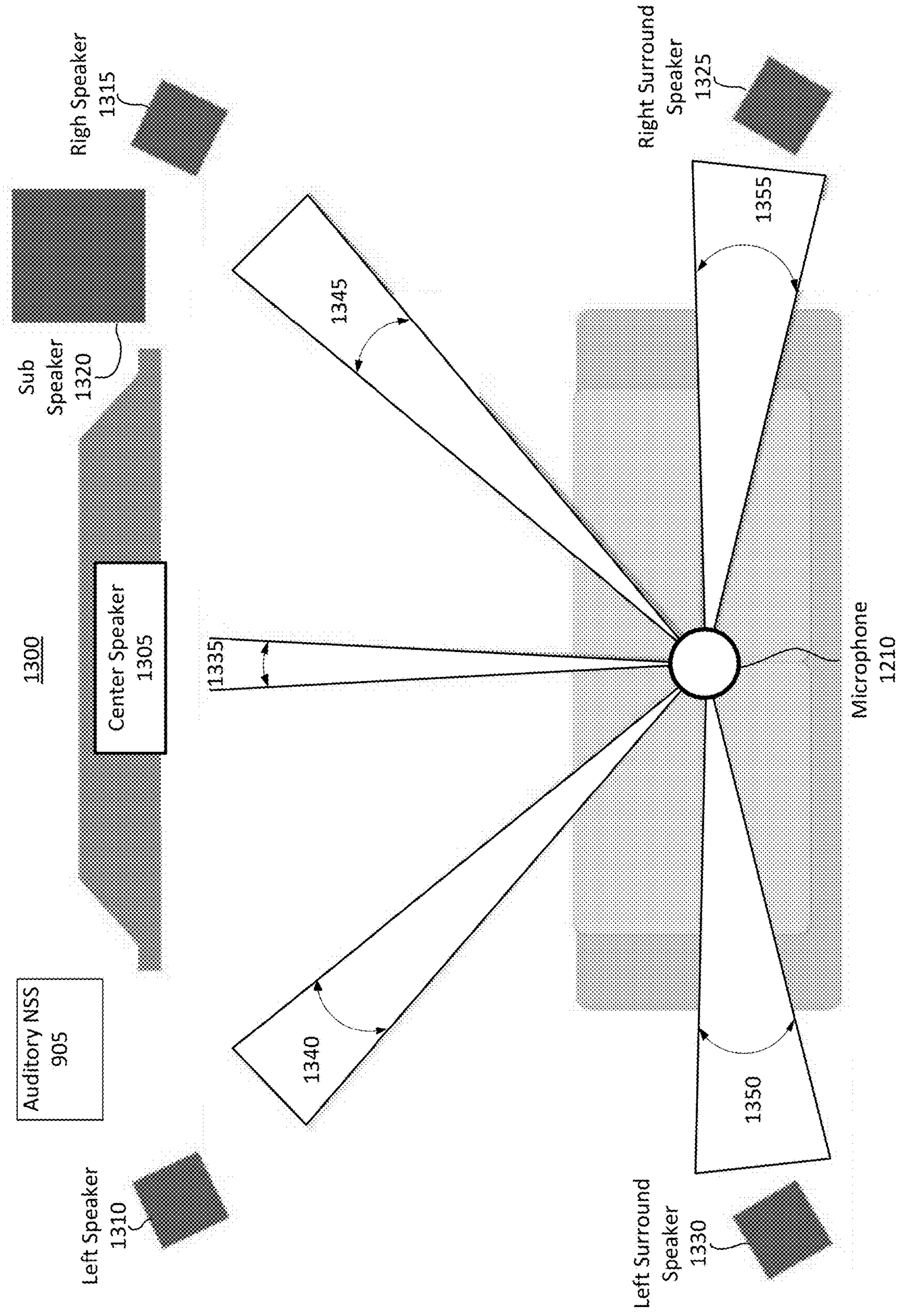
FIG. 13 illustrates a configuration for a system for room-based auditory stimulation for neural stimulation in accordance with an embodiment.

FIG. 13 illustrates a system configuration for auditory brain entrainment in accordance with an embodiment. The system 1300 can provide auditory stimulation for brainwave entrainment using a room environment. The system 1300 can include one or more speakers. The system 1300 can include a surround sound system. For example, the system 1300 includes a left speaker 1310, right speaker 1315, center speaker 1305, right surround speaker 1325, and left surround speaker 1330. System 1300 an include a sub-woofer 1320. The system 1300 can include the microphone 1210. The system 1300 can include or refer to a 5.1 surround system. In some embodiments, the system 1300 can have 1, 2, 3, 4, 5, 6, 7 or more speakers.

When providing auditory stimulation using a surround system, the NSS 905 can provide the same or different audio signals to each of the speakers in the system 1300. The NSS 905 can modify or adjust audio signals provided to one or more of the speakers in system 1300 in order to facilitate brainwave entrainment. For example, the NSS 905 can receive feedback from microphone 1210 and modify, manipulate or otherwise adjust the audio signal to optimize the auditory stimulation provided to a subject located at a position in the room that corresponds to the location of the microphone 1210. The NSS 905 can optimize or improve the auditory stimulation perceived at the location corresponding to microphone 1210 by analyzing the acoustic beams or waves generated by the speakers that propagate towards the microphone 1210.

The NSS 905 can be configured with information about the design and construction of each speaker. For example, speaker 1305 can generate sound in a direction that has an angle of 1335; speaker 1310 can generate sound that travels in a direction having an angle of 1340; speaker 1315 can generate sound that travels in a direction having an angle of 1345; speaker 1325 can generate sound that travels in a direction having an angle of 1355; and speaker 1330 can generate sound that travels in a direction having an angle of 1350. These angles can be the optimal or predetermined angles for each of the speakers. These angles can refer to the optimal angle of each speaker such that a person positioned at location corresponding to microphone 1210 can receive the optimum auditory stimulation. Thus, the speakers in system 1300 can be oriented to transmit auditory stimulation towards the subject.

In some embodiments, the NSS 905 can enable or disable one or more speakers. In some embodiments, the NSS 905 can increase or decrease the volume of the speakers to facilitate brainwave entrainment. The NSS 905 can intercept musical tracks, television audio, movie audio, internet audio, audio output from a set top box, or other audio source. The NSS 905 can adjust or manipulate the received audio, and transmit the adjusted audio signals to the speakers in system 1300 to induce brainwave entrainment.

Figure 14:
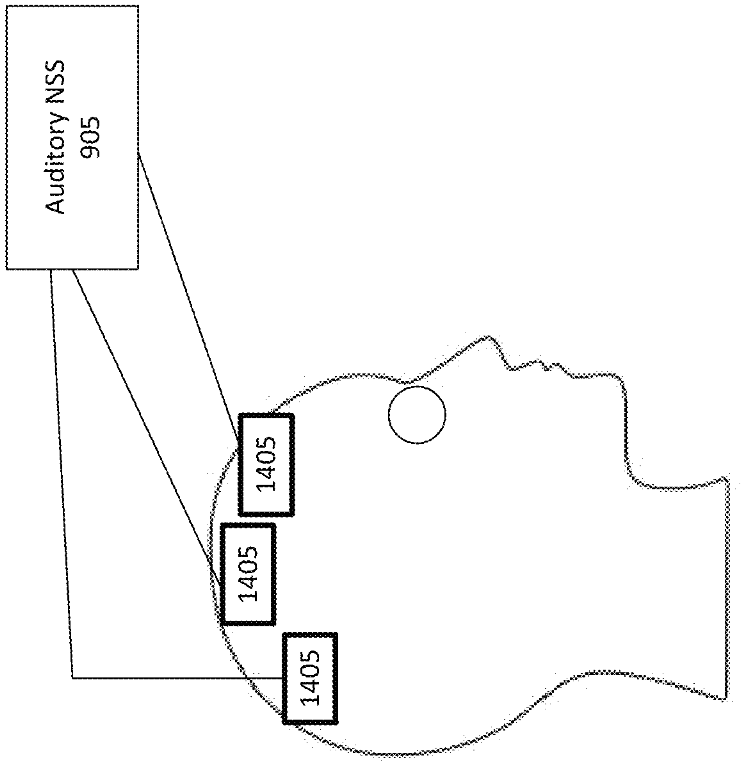
FIG. 14 illustrates devices configured to receive feedback to facilitate neural stimulation via auditory stimulation in accordance with some embodiments.

FIG. 14 illustrates feedback sensors 1405 placed or positioned at, on, or near a person's head. Feedback sensors 1405 can include, for example, EEG probes that detect brain wave activity.

The feedback monitor 935 can detect, receive, obtain, or otherwise identify feedback information from the one or more feedback sensors 1405. The feedback monitor 935 can provide the feedback information to one or more component of the NSS 905 for further processing or storage. For example, the profile manager 925 can update profile data structure 945 stored in data repository 940 with the feedback information. Profile manager 925 can associate the feedback information with an identifier of the patient or person undergoing the auditory brain stimulation, as well as a time stamp and date stamp corresponding to receipt or detection of the feedback information.

The feedback monitor 935 can determine a level of attention. The level of attention can refer to the focus provided to the acoustic pulses used for brain stimulation. The feedback monitor 935 can determine the level of attention using various hardware and software techniques. The feedback monitor 935 can assign a score to the level of attention (e.g., 1 to 10 with 1 being low attention and 10 being high attention, or vice versa, 1 to 100 with 1 being low attention and 100 being high attention, or vice versa, 0 to 1 with 0 being low attention and 1 being high attention, or vice versa), categorize the level of attention (e.g., low, medium, high), grade the attention (e.g., A, B, C, D, or F), or otherwise provide an indication of a level of attention.

In some cases, the feedback monitor 935 can track a person's eye movement to identify a level of attention. The feedback monitor 935 can interface with a feedback component 960 that includes an eye-tracker. The feedback monitor 935 (e.g., via feedback component 960) can detect and record eye movement of the person and analyze the recorded eye movement to determine an attention span or level of attention. The feedback monitor 935 can measure eye gaze which can indicate or provide information related to covert attention. For example, the feedback monitor 935 (e.g., via feedback component 960) can be configured with electro-oculography ("EOG") to measure the skin electric potential around the eye, which can indicate a direction the eye faces relative to the head. In some embodiments, the EOG can include a system or device to stabilize the head so it cannot move in order to determine the direction of the eye relative to the head. In some embodiments, the EOG can include or interface with a head tracker system to determine the position of the heads, and then determine the direction of the eye relative to the head.

In some embodiments, the feedback monitor 935 and feedback component 960 can determine a level of attention the subject is paying to the auditory stimulation based on eye movement. For example, increased eye movement may indicate that the subject is focusing on visual stimuli, as opposed to the auditory stimulation. To determine the level of attention the subject is paying to visual stimuli as opposed to the auditory stimulation, the feedback monitor 935 and feedback component 960 can determine or track the direction of the eye or eye movement using video detection of the pupil or corneal reflection. For example, the feedback component 960 can include one or more camera or video camera. The feedback component 960 can include an infra-red source that sends light pulses towards the eyes. The light can be reflected by the eye. The feedback component 960 can detect the position of the reflection. The feedback component 960 can capture or record the position of the reflection. The feedback component 960 can perform image processing on the reflection to determine or compute the direction of the eye or gaze direction of the eye.

The feedback monitor 935 can compare the eye direction or movement to historical eye direction or movement of the same person, nominal eye movement, or other historical eye movement information to determine a level of attention. For example, the feedback monitor 935 can determine a historical amount of eye movement during historical auditory stimulation sessions. The feedback monitor 935 can compare the current eye movement with the historical eye movement to identify a deviation. The NSS 905 can determine, based on the comparison, an increase in eye movement and further determine that the subject is paying less attention to the current auditory stimulation based on the increase in eye movement. In response to detecting the decrease in attention, the feedback monitor 935 can instruct the audio adjustment module 915 to change a parameter of the audio signal to capture the subject's attention. The audio adjustment module 915 can change the volume, tone, pitch, or music track to capture the subject's attention or increase the level of attention the subject is paying to the auditory stimulation. Upon changing the audio signal, the NSS 905 can continue to monitor the level of attention. For example, upon changing the audio signal, the NSS 905 can detect a decrease in eye movement which can indicate an increase in a level of attention provided to the audio signal.

The feedback sensor 1405 can interact with or communicate with NSS 905. For example, the feedback sensor 1405 can provide detected feedback information or data to the NSS 905 (e.g., feedback monitor 935). The feedback sensor 1405 can provide data to the NSS 905 in real-time, for example as the feedback sensor 1405 detects or senses or information. The feedback sensor 1405 can provide the feedback information to the NSS 905 based on a time interval, such as 1 minute, 2 minutes, 5 minutes, 10 minutes, hourly, 2 hours, 4 hours, 12 hours, or 24 hours. The feedback sensor 1405 can provide the feedback information to the NSS 905 responsive to a condition or event, such as a feedback measurement exceeding a threshold or falling below a threshold. The feedback sensor 1405 can provide feedback information responsive to a change in a feedback parameter. In some embodiments, the NSS 905 can ping, query, or send a request to the feedback sensor 1405 for information, and the feedback sensor 1405 can provide the feedback information in response to the ping, request, or query.

Method for Neural Stimulation Via Auditory Stimulation

Figure 15:
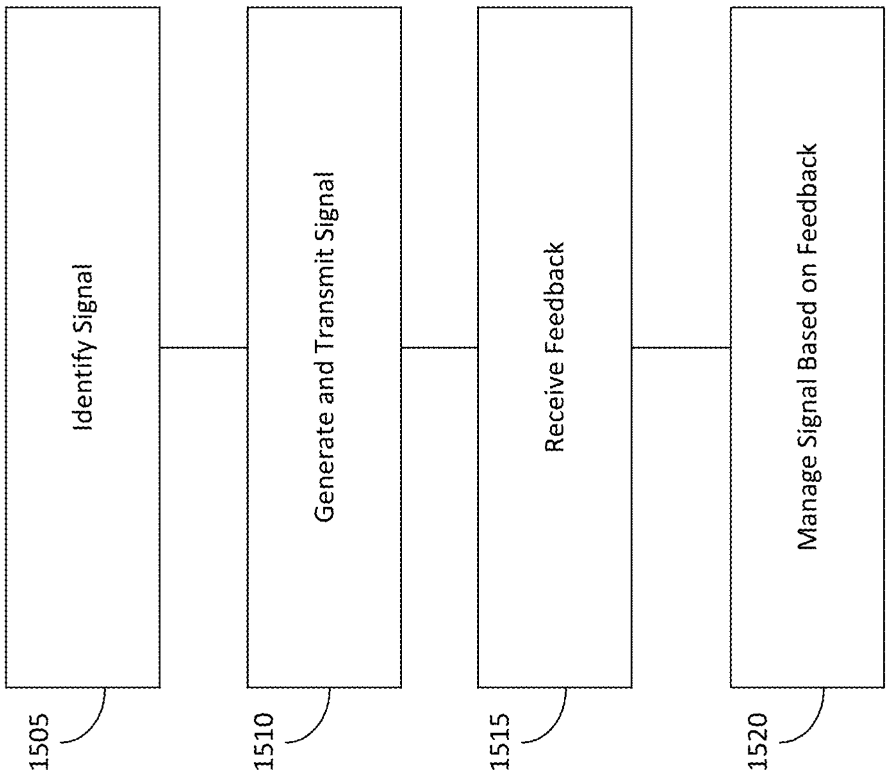
FIG. 15 is a flow diagram of a method of performing auditory brain entrainment in accordance with an embodiment.

FIG. 15 is a flow diagram of a method of performing auditory brain entrainment in accordance with an embodiment. The method 800 can be performed by one or more system, component, module or element depicted in FIGS. 7A, 7B, and 9-14, including, for example, a neural stimulation system (NSS). In brief overview, the NSS can identify an audio signal to provide at block 1505. At block 1510, the NSS can generate and transmit the identified audio signal. At 1515 the NSS can receive or determine feedback associated with neural activity, physiological activity, environmental parameters, or device parameters. At 1520 the NSS can manage, control, or adjust the audio signal based on the feedback.

NSS Operating with Headphones

The NSS 905 can operate in conjunction with the speakers 1205 as depicted in FIG. 12A. The NSS 905 can operate in conjunction with earphones or in-ear phones including the speaker 1205 and a feedback sensor 1405.

In operation, a subject using the headphones can wear the headphones on their head such that speakers or placed at or in the ear canals. In some cases, the subject can provide an indication to the NSS 905 that the headphones have been worn and that the subject is ready to undergo brainwave entrainment. The indication can include an instruction, command, selection, input, or other indication via an input/output interface, such as a keyboard 726, pointing device 727, or other I/O devices 730*a-n*. The indication can be a motion-based indication, visual indication, or voice-based indication. For example, the subject can provide a voice command that indicates that the subject is ready to undergo brainwave entrainment.

In some cases, the feedback sensor 1405 can determine that the subject is ready to undergo brainwave entrainment. The feedback sensor 1405 can detect that the headphones have been placed on a subject's head. The NSS 905 can receive motion data, acceleration data, gyroscope data, temperature data, or capacitive touch data to determine that the headphones have been placed on the subject's head. The received data, such as motion data, can indicate that the headphones were picked up and placed on the subject's head. The temperature data can measure the temperature of or proximate to the headphones, which can indicate that the headphones are on the subject's head. The NSS 905 can detect that the subject is ready responsive to determining that the subject is paying a high level of attention to the headphones or feedback sensor 1405.

Thus, the NSS 905 can detect or determine that the headphones have been worn and that the subject is in a ready state, or the NSS 905 can receive an indication or confirmation from the subject that the subject has worn the headphones and the subject is ready to undergo brainwave entrainment. Upon determining that the subject is ready, the NSS 905 can initialize the brainwave entrainment process. In some embodiments, the NSS 905 can access a profile data structure 945. For example, a profile manager 925 can query the profile data structure 945 to determine one or more parameter for the external auditory stimulation used for the brain entrainment process. Parameters can include, for example, a type of audio stimulation technique, an intensity or volume of the audio stimulation, frequency of the audio stimulation, duration of the audio stimulation, or wavelength of the audio stimulation. The profile manager 925 can query the profile data structure 945 to obtain historical brain entrainment information, such as prior auditory stimulation sessions. The profile manager 925 can perform a lookup in the profile data structure 945. The profile manager 925 can perform a look-up with a username, user identifier, location information, fingerprint, biometric identifier, retina scan, voice recognition and authentication, or other identifying technique.

The NSS 905 can determine a type of external auditory stimulation based on the components connected to the headphones. The NSS 905 can determine the type of external auditory stimulation based on the type of speakers 1205 available. For example, if the headphones are connected to an audio player, the NSS 905 can determined to embed acoustic pulses. If the headphones are not connected to an audio player, but only the microphone, the NSS 905 can determine to inject a pure tone or modify ambient noise.

In some embodiments, the NSS 905 can determine the type of external auditory stimulation based on historical brainwave entrainment sessions. For example, the profile data structure 945 can be pre-configured with information about the type of audio signaling component 950.

The NSS 905 can determine, via the profile manager 925, a modulation frequency for the pulse train or the audio signal. For example, NSS 905 can determine, from the profile data structure 945, that the modulation frequency for the external auditory stimulation should be set to 40 Hz. Depending on the type of auditory stimulation, the profile data structure 945 can further indicate a pulse length, intensity, wavelength of the acoustic wave forming the audio signal, or duration of the pulse train.

In some cases, the NSS 905 can determine or adjust one or more parameter of the external auditory stimulation. For example, the NSS 905 (e.g., via feedback component 960 or feedback sensor 1405) can determine an amplitude of the acoustic wave or volume level for the sound. The NSS 905 (e.g., via audio adjustment module 915 or side effects management module 930) can establish, initialize, set, or adjust the amplitude or wavelength of the acoustic waves or acoustic pulses. For example, the NSS 905 can determine that there is a low level of ambient noise. Due to the low level of ambient noise, subject's hearing may not be impaired or distracted. The NSS 905 can determine, based on detecting a low level of ambient noise, that it may not be necessary to increase the volume, or that it may be possible to reduce the volume to maintain the efficacy of brainwave entrainment.

In some embodiments, the NSS 905 can monitor (e.g., via feedback monitor 935 and feedback component 960) the level of ambient noise throughout the brainwave entrainment process to automatically and periodically adjust the amplitude of the acoustic pulses. For example, if the subject began the brainwave entrainment process when there was a high level of ambient noise, the NSS 905 can initially set a higher amplitude for the acoustic pulses and use a tone that includes frequencies that are easier to perceive, such as 10 kHz. However, in some embodiments in which the ambient noise level decreases throughout the brainwave entrainment process, the NSS 905 can automatically detect the decrease in ambient noise and, in response to the detection, adjust or lower the volume while decreasing the frequency of the acoustic wave. The NSS 905 can adjust the acoustic pulses to provide a high contrast ratio with respect to ambient noise to facilitate brainwave entrainment.

In some embodiments, the NSS 905 (e.g., via feedback monitor 935 and feedback component 960) can monitor or measure physiological conditions to set or adjust a parameter of the acoustic wave. In some embodiments, the NSS 905 can monitor or measure heart rate, pulse rate, blood pressure, body temperature, perspiration, or brain activity to set or adjust a parameter of the acoustic wave.

In some embodiments, the NSS 905 can be preconfigured to initially transmit acoustic pulses having a lowest setting for the acoustic wave intensity (e.g., low amplitude or high wavelength) and gradually increase the intensity (e.g., increase the amplitude of the or decrease the wavelength) while monitoring feedback until an optimal audio intensity is reached. An optimal audio intensity can refer to a highest intensity without adverse physiological side effects, such as deafness, seizures, heart attack, migraines, or other discomfort. The NSS 905 (e.g., via side effects management module 930) can monitor the physiological symptoms to identify the adverse side effects of the external auditory stimulation, and adjust (e.g., via audio adjustment module 915) the external auditory stimulation accordingly to reduce or eliminate the adverse side effects.

In some embodiments, the NSS 905 (e.g., via audio adjustment module 915) can adjust a parameter of the audio wave or acoustic pulse based on a level of attention. For example, during the brainwave entrainment process, the subject may get bored, lose focus, fall asleep, or otherwise not pay attention to the acoustic pulses. Not paying attention to the acoustic pulses may reduce the efficacy of the brainwave entrainment process, resulting in neurons oscillating at a frequency different from the desired modulation frequency of the acoustic pulses.

NSS 905 can detect the level of attention the subject is paying to the acoustic pulses using the feedback monitor 935 and one or more feedback component 960. Responsive to determining that the subject is not paying a satisfactory amount of attention to the acoustic pulses, the audio adjustment module 915 can change a parameter of the audio signal to gain the subject's attention. For example, the audio adjustment module 915 can increase the amplitude of the acoustic pulse, adjust the tone of the acoustic pulse, or change the duration of the acoustic pulse. The audio adjustment module 915 can randomly vary one or more parameters of the acoustic pulse. The audio adjustment module 915 can initiate an attention seeking acoustic sequence configured to regain the subject's attention. For example, the audio sequence can include a change in frequency, tone, amplitude, or insert words or music in a predetermined, random, or pseudo-random pattern. The attention seeking audio sequence can enable or disable different acoustic sources if the audio signaling component 950 includes multiple audio sources or speakers. Thus, the audio adjustment module 915 can interact with the feedback monitor 935 to determine a level of attention the subject is providing to the acoustic pulses, and adjust the acoustic pulses to regain the subject's attention if the level of attention falls below a threshold.

In some embodiments, the audio adjustment module 915 can change or adjust one or more parameter of the acoustic pulse or acoustic wave at predetermined time intervals (e.g., every 5 minutes, 10 minutes, 15 minutes, or 20 minutes) to regain or maintain the subject's attention level.

In some embodiments, the NSS 905 (e.g., via unwanted frequency filtering module 920) can filter, block, attenuate, or remove unwanted auditory external stimulation. Unwanted auditory external stimulation can include, for example, unwanted modulation frequencies, unwanted intensities, or unwanted wavelengths of sound waves. The NSS 905 can deem a modulation frequency to be unwanted if the modulation frequency of a pulse train is different or substantially different (e.g., 1%, 2%, 5%, 10%, 15%, 20%, 25%, or more than 25%) from a desired frequency.

For example, the desired modulation frequency for brainwave entrainment can be 40 Hz. However, a modulation frequency of 20 Hz or 80 Hz can reduce the beneficial effects to cognitive functioning of the brain, a cognitive state of the brain, the immune system, or inflammation that can result from brainwave entrainment at other frequencies, such as 40 Hz. Thus, the NSS 905 can filter out the acoustic pulses corresponding to the 20 Hz or 80 Hz modulation frequency.

In some embodiments, the NSS 905 can detect, via feedback component 960, that there are acoustic pulses from an ambient noise source that corresponds to an unwanted modulation frequency of 20 Hz. The NSS 905 can further determine the wavelength of the acoustic waves of the acoustic pulses corresponding to the unwanted modulation frequency. The NSS 905 can instruct the filtering component 955 to filter out the wavelength corresponding to the unwanted modulation frequency.

Neural Stimulation Via Peripheral Nerve Stimulation

In some embodiments, systems and methods of the present disclosure can provide peripheral nerve stimulation to cause or induce neural oscillations. For example, haptic stimulation on the skin around sensory nerves forming part of or connected to the peripheral nervous system can cause or induce electrical activity in the sensory nerves, causing a transmission to the brain via the central nervous system, which can be perceived by the brain or can cause or induce electrical and neural activity in the brain, including activity resulting in neural oscillations. Similarly, electric currents on or through the skin around sensory nerves forming part of or connected to the peripheral nervous system can cause or induce electrical activity in the sensory nerves, causing a transmission to the brain via the central nervous system, which can be perceived by the brain or can cause or induce electrical and neural activity in the brain, including activity resulting in neural oscillations. The brain, responsive to receiving the peripheral nerve stimulations, can adjust, manage, or control the frequency of neural oscillations. The electric currents can result in depolarization of neural cells, such as due to electric current stimuli such as time-varying pulses. The electric current pulse may directly cause depolarization. Secondary effects in other regions of the brain may be gated or controlled by the brain in response to the depolarization. The peripheral nerve stimulations generated at a predetermined frequency can trigger neural activity in the brain to cause or induce neural oscillations. The frequency of neural oscillations can be based on or correspond to the frequency of the peripheral nerve stimulations, or a modulation frequency associated with the peripheral nerve stimulations. Thus, systems and methods of the present disclosure can cause or induce neural oscillations using peripheral nerve stimulations such as electric current pulses modulated at a predetermined frequency to synchronize electrical activity among groups of neurons based on the frequency of the peripheral nerve stimulations. Brain entrainment associated with neural oscillations can be observed based on the aggregate frequency of oscillations produced by the synchronous electrical activity in ensembles of cortical neurons. The frequency of the modulation of the electric currents, or pulses thereof, can cause or adjust this synchronous electrical activity in the ensembles of cortical neurons to oscillate at a frequency corresponding to the frequency of the peripheral nerve stimulation pulses.

Figure 16A:
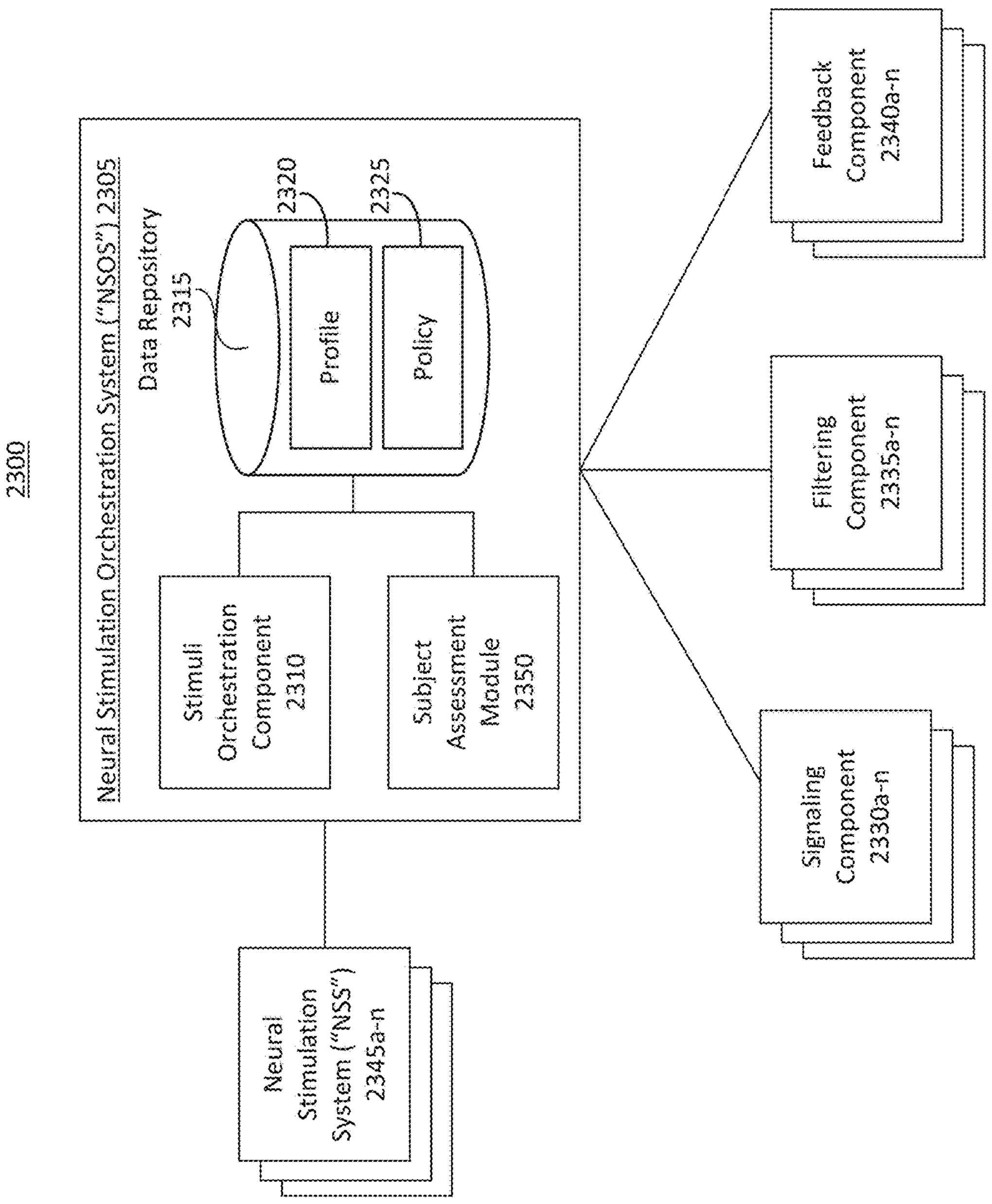
FIG. 16A is a block diagram depicting a system for neural stimulation via peripheral nerve stimulation in accordance with an embodiment.

FIG. 16A is a block diagram depicting a system to perform peripheral nerve stimulation to cause or induce neural oscillations, such as to cause brain entrainment, in accordance with an embodiment. The system 1600 can include a peripheral nerve stimulation system 1605. In brief overview, the peripheral nerve stimulation system (or peripheral nerve stimulation neural stimulation system) ("NSS") 1605 can include, access, interface with, or otherwise communicate with one or more of a nerve stimulus generation module 1610, nerve stimulus adjustment module 1615, profile manager 1625, side effects management module 1630, feedback monitor 1635, data repository 1640, nerve stimulus generator component 1650, shielding component 1655, feedback component 1660, or nerve stimulus amplification component 1665. The nerve stimulus generation module 1610, nerve stimulus adjustment module 1615, profile manager 1625, side effects management module 1630, feedback monitor 1635, nerve stimulus generator component 1650, shielding component 1655, feedback component 1660, or nerve stimulus amplification component 1665 can each include at least one processing unit or other logic device such as programmable logic array engine, or module configured to communicate with the database repository 1650. The nerve stimulus generation module 1610, nerve stimulus adjustment module 1615, profile manager 1625, side effects management module 1630, feedback monitor 1635, nerve stimulus generator component 1650, shielding component 1655, feedback component 1660, or nerve stimulus amplification component 1665 can be separate components, a single component, or part of the NSS 1605. The system 1600 and its components, such as the NSS 1605, may include hardware elements, such as one or more processors, logic devices, or circuits. The system 1600 and its components, such as the NSS 1605, can include one or more hardware or interface component depicted in system 700 in FIGS. 7A and 7B. For example, a component of system 1600 can include or execute on one or more processors 721, access storage 728 or memory 722, and communicate via network interface 718.

Neural Stimulation Via Multiple Modes of Stimulation

Figure 16B:
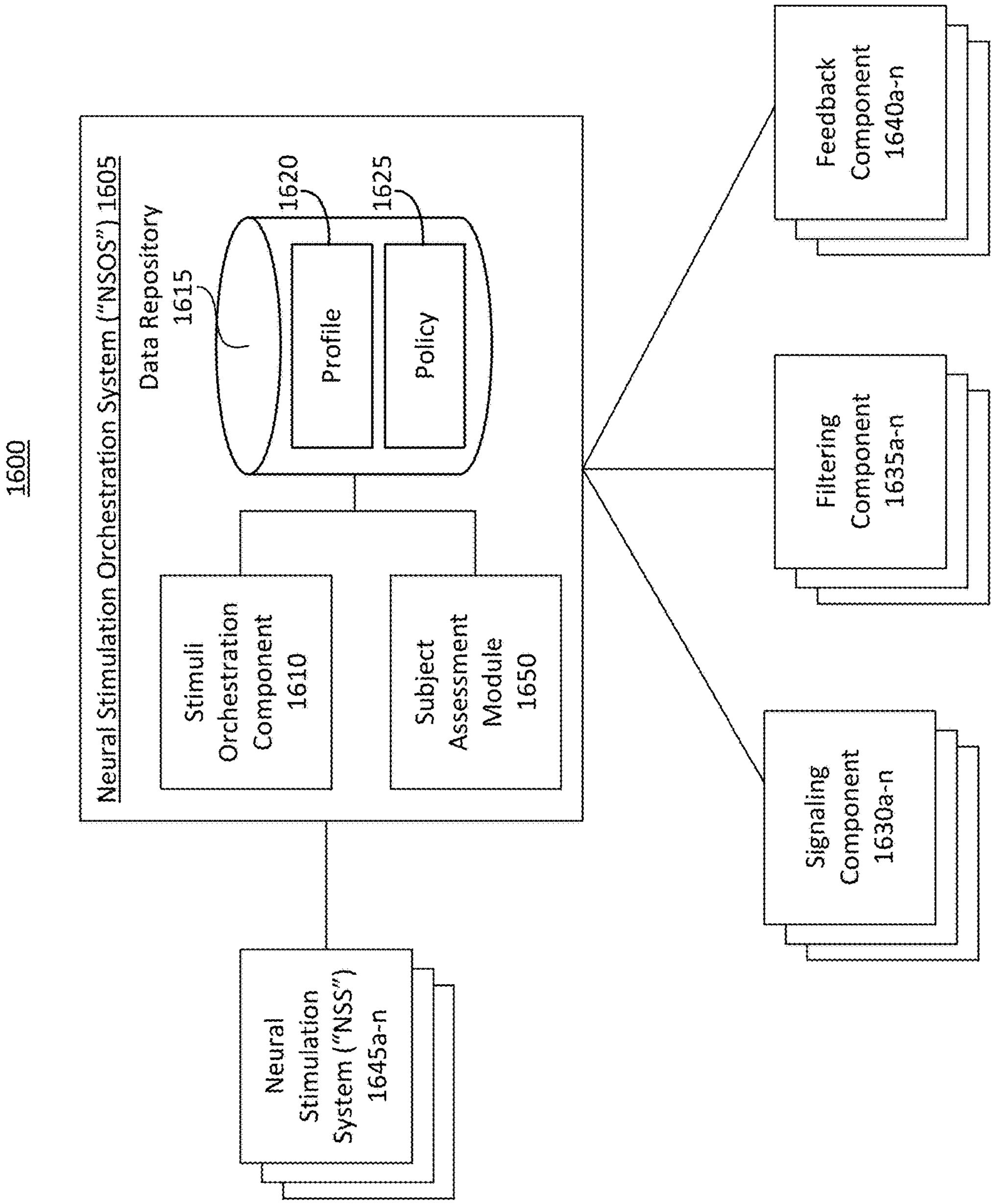
FIG. 16B is a block diagram depicting a system for neural stimulation via multiple modes of stimulation in accordance with an embodiment.

FIG. 16B is a block diagram depicting a system for neural stimulation via multiple modes of stimulation in accordance with an embodiment. The system 1600 can include a neural stimulation orchestration system ("NSOS") 1605. The NSOS 1605 can provide multiple modes of stimulation. For example, the NSOS 1605 can provide a first mode of stimulation that includes visual stimulation, and a second mode of stimulation that includes auditory stimulation. For each mode of stimulation, the NSOS 1605 can provide a type of signal. For example, for the visual mode of stimulation, the NSOS 1605 can provide the following types of signals: light pulses, image patterns, flicker of ambient light, or augmented reality. NSOS 1605 can orchestrate, manage, control, or otherwise facilitate providing multiple modes of stimulation and types of stimulation.

In brief overview, the NSOS 1605 can include, access, interface with, or otherwise communicate with one or more of a stimuli orchestration component 1610, a subject assessment module 1650, a data repository 1615, one or more signaling components 1630*a-n*, one or more filtering components 1635*a-n*, one or more feedback components 1640*a-n*, and one or more neural stimulation systems ("NSS") 1645*a-n*. The data repository 1615 can include or store a profile data structure 1620 and a policy data structure 1625. The stimuli orchestration component 1610 and subject assessment module 1650 can include at least one processing unit or other logic device such as programmable logic array engine, or module configured to communicate with the database repository 1615. The stimuli orchestration component 1610 and subject assessment module 1650 can be a single component, include separate components, or be part of the NSOS 1605. The system 1600 and its components, such as the NSOS 1605, may include hardware elements, such as one or more processors, logic devices, or circuits. The system 1600 and its components, such as the NSOS 1605, can include one or more hardware or interface component depicted in system 700 in FIGS. 7A and 7B. For example, a component of system 1600 can include or execute on one or more processors 721, access storage 728 or memory 722, and communicate via network interface 718. The system 1600 can include one or more component or functionality depicted in FIGS. 1-15, including, for example, system 100, system 900, visual NSS 105, or auditory NSS 905. For example, at least one of the signaling components 1630*a-n* can include one or more component or functionality of visual signaling component 150 or audio signaling component 950. At least one of the filtering components 1635*a-n* can include one or more component or functionality of filtering component 155 or filtering component 955. At least one of the feedback components 1640*a-n* can include one or more component or functionality of feedback component 160 or feedback component 960. At least one of the NSS 1645*a-n* can include one or more component or functionality of visual NSS 105 or auditory NSS 905.

Still referring to FIG. 16B, and in further detail, the NSOS 1605 can include at least stimuli orchestration component 1610. The stimuli orchestration component 1610 can be designed and constructed to perform neural stimulation using multiple modalities of stimulation. The stimuli orchestration component 1610 or NSOS 1605 can interface with at least one of the signaling components 1630*a-n*, at least one of the filtering components 1635*a-n* or at least one of the feedback components 1640*a-n*. One or more of the signaling components 1630*a-n* can be a same type of signaling component or a different type of signaling component. The type of signaling component can correspond to a mode of stimulation. For example, multiple types of signaling components 1630*a-n* can correspond to visual signaling components or auditory signaling components. In some cases, at least one of the signaling components 1630*a-n* includes a visual signaling component 150 such as a light source, LED, laser, tablet computing device, or virtual reality headset. At least one of the signaling components includes an audio signaling component 950, such as headphones, speakers, cochlear implants, or air jets.

One or more of the filtering components 1635*a-n* can be a same type of filtering component or a different type of filtering component. One or more of the feedback components 1640*a-n* can be a same type of feedback component or a different type of feedback component. For example, the feedback components 1640*a-n* can include an electrode, dry electrode, gel electrode, saline soaked electrode, adhesive-based electrodes, a temperature sensor, heart or pulse rate monitor, physiological sensor, ambient light sensor, ambient temperature sensor, sleep status via actigraphy, blood pressure monitor, respiratory rate monitor, brain wave sensor, EEG probe, EOG probes configured measure the corneo-retinal standing potential that exists between the front and the back of the human eye, accelerometer, gyroscope, motion detector, proximity sensor, camera, microphone, or photo detector.

The stimuli orchestration component 1610 can include or be configured with an interface to communicate with different types of signaling components 1630*a-n*, filtering components 1635*a-n* or feedback components 1640*a-n*. The NSOS 1605 or stimuli orchestration component 1610 can interface with system intermediary to one of the signaling components 1630*a-n*, filtering components 1635*a-n*, or feedback components 1640*a-n*. For example, the stimuli orchestration component 1610 can interface with the visual NSS 105 depicted in FIG. 1 or auditory NSS 905 depicted in FIG. 9. Thus, in some embodiments, the stimuli orchestration component 1610 or NSOS 1605 can indirectly interface with at least one of the signaling components 1630*a-n*, filtering components 1635*a-n*, or feedback components 1640*a-n*.

The stimuli orchestration component 1610 (e.g., via the interface) can ping each of the signaling components 1630*a-n*, filtering components 1635*a-n*, and feedback components 1640*a-n* to determine information about the components. The information can include a type of the component (e.g., visual, auditory, attenuator, optical filter, temperature sensor, or light sensor), configuration of the component (e.g., frequency range, amplitude range), or status information (e.g., standby, ready, online, enabled, error, fault, offline, disabled, warning, service needed, availability, or battery level).

The stimuli orchestration component 1610 can instruct or cause at least one of the signaling components 1630*a-n* to generate, transmit or otherwise provide a signal that can be perceived, received or observed by the brain and affect a frequency of neural oscillations in at least one region or portion of a subject's brain. The signal can be perceived via various means, including, for example, optical nerves or cochlear cells.

The stimuli orchestration component 1610 can access the data repository 1615 to retrieve profile information 1620 and a policy 1625. The profile information 1620 can include profile information 145 or profile information 945. The policy 1625 can include a multi-modal stimulation policy. The policy 1625 can indicate a multi-modal stimulation program. The stimuli orchestration component 1610 can apply the policy 1625 to profile information to determine a type of stimulation (e.g., visual or auditory) and determine a value for a parameter for each type of stimulation (e.g., amplitude, frequency, wavelength, color, etc.). The stimuli orchestration component 1610 can apply the policy 1625 to the profile information 1620 and feedback information received from one or more feedback components 1640*a-n* to determine or adjust the type of stimulation (e.g., visual or auditory) and determine or adjust the value parameter for each type of stimulation (e.g., amplitude, frequency, wavelength, color, etc.). The stimuli orchestration component 1610 can apply the policy 1625 to profile information to determine a type of filter to be applied by at least one of the filtering components 1635*a-n* (e.g., audio filter or visual filter) and determine a value for a parameter for the type of filter (e.g., frequency, wavelength, color, sound attenuation, etc.). The stimuli orchestration component 1610 can apply the policy 1625 to profile information and feedback information received from one or more feedback components 1640*a-n* to determine or adjust the type of filter to be applied by at least one of the filtering components 1635*a-n* (e.g., audio filter or visual filter) and determine or adjust the value for the parameter for filter (e.g., frequency, wavelength, color, sound attenuation, etc.).

The NSOS 1605 can obtain the profile information 1620 via a subject assessment module 1650. The subject assessment module 1650 can be designed and constructed to determine, for one or more subjects, information that can facilitate neural stimulation via one or more modes of stimulation. The subject assessment module 1650 can receive, obtain, detect, determine or otherwise identify the information via feedback components 1640*a-n*, surveys, queries, questionnaires, prompts, remote profile information accessible via a network, diagnostic tests, or historical treatments.

The subject assessment module 1650 can receive the information prior to initiating neural stimulation, during neural stimulation, or after neural stimulation. For example, the subject assessment module 1650 can provide a prompt with a request for information prior to initiating the neural stimulation session. The subject assessment module 1650 can provide a prompt with a request for information during the neural stimulation session. The subject assessment module 1650 can receive feedback from feedback component 1640*a-n* (e.g., an EEG probe) during the neural stimulation session. The subject assessment module 1650 can provide a prompt with a request for information subsequent to termination of the neural stimulation session. The subject assessment module 1650 can receive feedback from feedback component 1640*a-n* subsequent to termination of the neural stimulation session.

The subject assessment module 1650 can use the information to determine an effectiveness of a modality of stimulation (e.g., visual stimulation or auditory stimulation) or a type of signal (e.g., light pulse from a laser or LED source, ambient light flicker, or image pattern displayed by a tablet computing device). For example, the subject assessment module 1650 can determine that the desired neural stimulation resulted from a first mode of stimulation or first type of signal, while the desired neural stimulation did not occur or took longer to occur with the second mode of stimulation or second type of signal. The subject assessment module 1650 can determine that the desired neural stimulation was less pronounced from the second mode of stimulation or second type of signal relative to the first mode of stimulation or first type of signal based on feedback information from a feedback component 1640*a-n*.

The subject assessment module 1650 can determine the level of effectiveness of each mode or type of stimulation independently, or based on a combination of modes or types of stimulation. A combination of modes of stimulation can refer to transmitting signals from different modes of stimulation at the same or substantially similar time. A combination of modes of stimulation can refer to transmitting signals from different modes of stimulation in an overlapping manner. A combination of modes of stimulation can refer to transmitting signals from different modes of stimulation in a non-overlapping manner, but within a time interval from one another (e.g., transmit a signal pulse train from a second mode of stimulation within 0.5 seconds, 1 second, 1.5 seconds, 2 seconds, 2.5 seconds, 3 seconds, 5 seconds, 7 seconds, 10 seconds, 12 seconds, 15 seconds, 20 seconds, 30 seconds, 45 seconds, 60 seconds, 1 minute, 2 minutes 3 minutes 5 minutes, 10 minutes, or other time interval where the effect on the frequency of neural oscillation by a first mode can overlap with the second mode).

The subject assessment module 1650 can aggregate or compile the information and update the profile data structure 1620 stored in data repository 1615. In some cases, the subject assessment module 1650 can update or generate a policy 1625 based on the received information. The policy 1625 or profile information 1620 can indicate which modes or types of stimulation are more likely to have a desired effect on neural stimulation, while reducing side effects.

The stimuli orchestration component 1610 can instruct or cause multiple signaling components 1630*a-n* to generate, transmit or otherwise provide different types of stimulation or signals pursuant to the policy 1625, profile information 1620 or feedback information detected by feedback components 1640*a-n*. The stimuli orchestration component 1610 can cause multiple signaling components 1630*a-n* to generate, transmit or otherwise provide different types of stimulation or signals simultaneously or at substantially the same time. For example, a first signaling component 1630*a* can transmit a first type of stimulation at the same time as a second signaling component 1630*b* transmits a second type of stimulation. The first signaling component 1630*a* can transmit or provide a first set of signals, pulses or stimulation at the same time the second signaling component 1630*b* transmits or provides a second set of signals, pulses or stimulation. For example, a first pulse from a first signaling component 1630*a* can begin at the same time or substantially the same time (e.g., 1%, 2%, 3%, 4%, 5%, 6%, 7%, 10%, 15%, 20%) as a second pulse from a second signaling component 1630*b*. First and second pulses can end at the same time or substantially same time. In another example, a first pulse train can be transmitted by the first signaling component 1630*a* at the same or substantially similar time as a second pulse train transmitted by the second signaling component 1630*b*.

The stimuli orchestration component 1610 can cause multiple signaling components 1630*a-n* to generate, transmit or otherwise provide different types of stimulation or signals in an overlapping manner. The different pulses or pulse trains may overlap one another, but may not necessary being or end at a same time. For example, at least one pulse in the first set of pulses from the first signaling component 1630*a* can at least partially overlap, in time, with at least one pulse from the second set of pulses from the second signaling component 1630*b*. For example, the pulses can straddle one another. In some cases, a first pulse train transmitted or provided by the first signaling component 1630*a* can at least partially overlap with a second pulse train transmitted or provided by the second signaling component 1630*b*. The first pulse train can straddle the second pulse train.

The stimuli orchestration component 1610 can cause multiple signaling components 1630*a-n* to generate, transmit or otherwise provide different types of stimulation or signals such that they are received, perceived or otherwise observed by one or more regions or portions of the brain at the same time, simultaneously or at substantially the same time. The brain can receive different modes of stimulation or types of signals at different times. The duration of time between transmission of the signal by a signaling component 1630*a-n* and reception or perception of the signal by the brain can vary based on the type of signal (e.g., visual, auditory), parameter of the signal (e.g., velocity or speed of the wave, amplitude, frequency, wavelength), or distance between the signaling component 1630*a-n* and the nerves or cells of the subject configured to receive the signal (e.g., eyes or ears). The stimuli orchestration component 1610 can offset or delay the transmission of signals such that the brain perceives the different signals at the desired time. The stimuli orchestration component 1610 can offset or delay the transmission of a first signal transmitted by a first signaling component 1630*a* relative to transmission of a second signal transmitted by a second signaling component 1630*b*. The stimuli orchestration component 1610 can determine an amount of an offset for each type of signal or each signaling component 1630*a-n* relative to a reference clock or reference signal. The stimuli orchestration component 1610 can be preconfigured or calibrated with an offset for each signaling component 1630*a-n*.

The stimuli orchestration component 1610 can determine to enable or disable the offset based on the policy 1625. For example, the policy 1625 may indicate to transmit multiple signals at the same time, in which case the stimuli orchestration component 1610 may disable or not use an offset. In another example, the policy 1625 may indicate to transmit multiple signals such that they are perceived by the brain at the same time, in which case the stimuli orchestration component 1610 may enable or use the offset.

In some embodiments, the stimuli orchestration component 1610 can stagger signals transmitted by different signaling components 1630*a-n*. For example, the stimuli orchestration component 1610 can stagger the signals such that the pulses from different signaling components 1630*a-n* are non-overlapping. The stimuli orchestration component 1610 can stagger pulse trains from different signaling components 1630*a-n* such that they are non-overlapping. The stimuli orchestration component 1610 can set parameters for each mode of stimulation or signaling component 1630*a-n* such that the signals they are non-overlapping.

Thus, the stimuli orchestration component 1610 can set parameters for signals transmitted by one or more signaling components 1630*a-n* such that the signals are transmitted in a synchronously or asynchronously, or perceived by the brain synchronously or asynchronously. The stimuli orchestration component 1610 can apply the policy 1625 to available signaling components 1630*a-n* to determine the parameters to set for each signaling component 1630*a-n* for the synchronous or asynchronous transmission. The stimuli orchestration component 1610 can adjust parameters such as a time delay, phase offset, frequency, pulse rate interval, or amplitude to synchronize the signals.

In some embodiments, the NSOS 1605 can adjust or change the mode of stimulation or a type of signal based on feedback received from a feedback component 1640*a-n*. The stimuli orchestration component 1610 can adjust the mode of stimulation or type of signal based on feedback on the subject, feedback on the environment, or a combination of feedback on the subject and the environment. Feedback on the subject can include, for example, physiological information, temperature, attention level, level of fatigue, activity (e.g., sitting, laying down, walking, biking, or driving), vision ability, hearing ability, side effects (e.g., pain, migraine, ringing in ear, or blindness), or frequency of neural oscillation at a region or portion of the brain (e.g., EEG probes). Feedback information on the environment can include, for example, ambient temperature, ambient light, ambient sound, battery information, or power source.

The stimuli orchestration component 1610 can determine to maintain or change an aspect of the stimulation treatment based on the feedback. For example, the stimuli orchestration component 1610 can determine that the neurons are not oscillating at the desired frequency in response to the first mode of stimulation. Responsive to determining that the neurons are not oscillating at the desired frequency, the stimuli orchestration component 1610 can disable the first mode of stimulation and enable a second mode of stimulation. The stimuli orchestration component 1610 can again determine (e.g., via feedback component 1640*a*) that the neurons are not oscillating at the desired frequency in response to the second mode of stimulation. Responsive to determining that the neurons are still not oscillating at the desired frequency, the stimuli orchestration component 1610 can increase an amplitude of the signal corresponding to the second mode of stimulation. The stimuli orchestration component 1610 can determine that the neurons are oscillating at the desired frequency in response to increasing the amplitude of a signal corresponding to the second mode of stimulation.

The stimuli orchestration component 1610 can monitor the frequency of neural oscillations at a region or portion of the brain. The stimuli orchestration component 1610 can determine that neurons in a first region of the brain are oscillating at the desired frequency, whereas neurons in a second region of the brain are not oscillating at the desired frequency. The stimuli orchestration component 1610 can perform a lookup in the profile data structure 1620 to determine a mode of stimulation or type of signal that maps to the second region of the brain. The stimuli orchestration component 1610 can compare the results of the lookup with the currently enabled mode of stimulation to determine that a third mode of stimulation is more likely to cause the neurons in the second region of the brain to oscillate at the desired frequency. Responsive to the determination, the stimuli orchestration component 1610 can identify a signaling component 1630*a-n* configured to generate and transmit signals corresponding to the selected third mode of stimulation, and instruct or cause the identified signaling component 1630*a-n* to transmit the signals.

In some embodiments, the stimuli orchestration component 1610 can determine, based on feedback information, that a mode of stimulation is likely to affect the frequency of neural oscillation, or unlikely to affect the frequency of neural oscillation. The stimuli orchestration component 1610 can select a mode of stimulation from a plurality of modes of stimulation that is most likely to affect the frequency of neural stimulation or result in a desired frequency of neural oscillation. If the stimuli orchestration component 1610 determines, based on the feedback information, that a mode of stimulation is unlikely to affect the frequency of neural oscillation, the stimuli orchestration component 1610 can disable the mode of stimulation for a predetermined duration or until the feedback information indicates that the mode of stimulation would be effective.

The stimuli orchestration component 1610 can select one or more modes of stimulation to conserve resources or minimize resource utilization. For example, the stimuli orchestration component 1610 can select one or more modes of stimulation to reduce or minimize power consumption if the power source is a battery or if the battery level is low. In another example, the stimuli orchestration component 1610 can select one or more modes of stimulation to reduce heat generation if the ambient temperature is above a threshold or the temperature of the subject is above a threshold. In another example, the stimuli orchestration component 1610 can select one or more modes of stimulation to increase the level of attention if the stimuli orchestration component 1610 determines that the subject is not focusing on the stimulation (e.g., based on eye tracking or an undesired frequency of neural oscillations).

Neural Stimulation Via Visual Stimulation and Auditory Stimulation

Figure 17A:
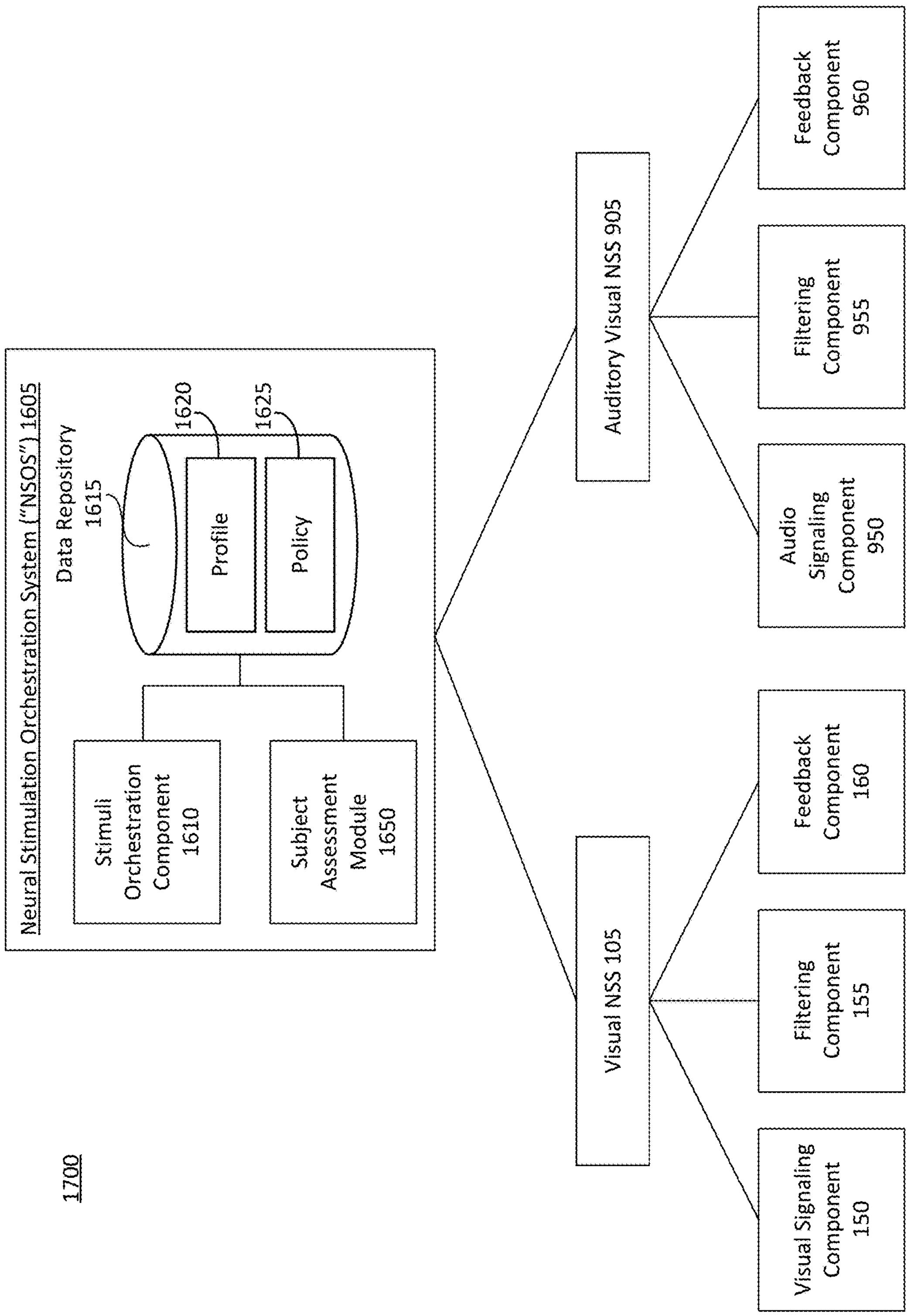
FIG. 17A is a block diagram depicting a system for neural stimulation via visual stimulation and auditory stimulation in accordance with an embodiment.

FIG. 17A is a block diagram depicting an embodiment of a system for neural stimulation via visual stimulation and auditory stimulation. The system 1700 can include the NSOS 1605. The NSOS 1605 can interface with the visual NSS 105 and the auditory NSS 905. The visual NSS 105 can interface or communicate with the visual signaling component 150, filtering component 155, and feedback component 160. The auditory NSS 905 can interface or communicate with the audio signaling component 950, filtering component 955, and feedback component 960.

To provide neural stimulation via visual stimulation and auditory stimulation, the NSOS 1605 can identify the types of available components for the neural stimulation session. The NSOS 1605 can identify the types of visual signals the visual signaling component 150 is configured to generate. The NSOS 1605 can also identify the type of audio signals the audio signaling component 950 is configured to generate. The NSOS 1605 can be configured about the types of visual signals and audio signals the components 150 and 950 are configured to generate. The NSOS 1605 can ping the components 150 and 950 for information about the components 150 and 950. The NSOS 1605 can query the components, send an SNMP request, broadcast a query, or otherwise determine information about the available visual signaling component 150 and audio signaling component 950.

For example, the NSOS 1605 can determine that the following components are available for neural stimulation: the visual signaling component 150 includes the virtual reality headset 401 depicted in FIG. 4C; the audio signaling component 950 includes the speaker 1205 depicted in FIG. 12B; the feedback component 160 includes an ambient light sensor 605, an eye tracker 605 and an EEG probe depicted in FIG. 4C; the feedback component 960 includes a microphone 1210 and feedback sensor 1225 depicted in FIG. 12B; and the filtering component 955 includes a noise cancellation component 1215. The NSOS 1605 can further determine an absence of filtering component 155 communicatively coupled to the visual NSS 105. The NSOS 1605 can determine the presence (available or online) or absence (offline) of components via visual NSS 105 or auditory NSS 905. The NSOS 1605 can further obtain identifiers for each of the available or online components.

The NSOS 1605 can perform a lookup in the profile data structure 1620 using an identifier of the subject to identify one more types of visual signals and audio signals to provide to the subject. The NSOS 1605 can perform a lookup in the profile data structure 1620 using identifiers for the subject and each of the online components to identify one more types of visual signals and audio signals to provide to the subject. The NSOS 1605 can perform a lookup up in the policy data structure 1625 using an identifier of the subject to obtain a policy for the subject. The NSOS 1605 can perform a lookup in the policy data structure 1625 using identifiers for the subject and each of the online components to identify a policy for the types of visual signals and audio signals to provide to the subject.

Figure 17B:
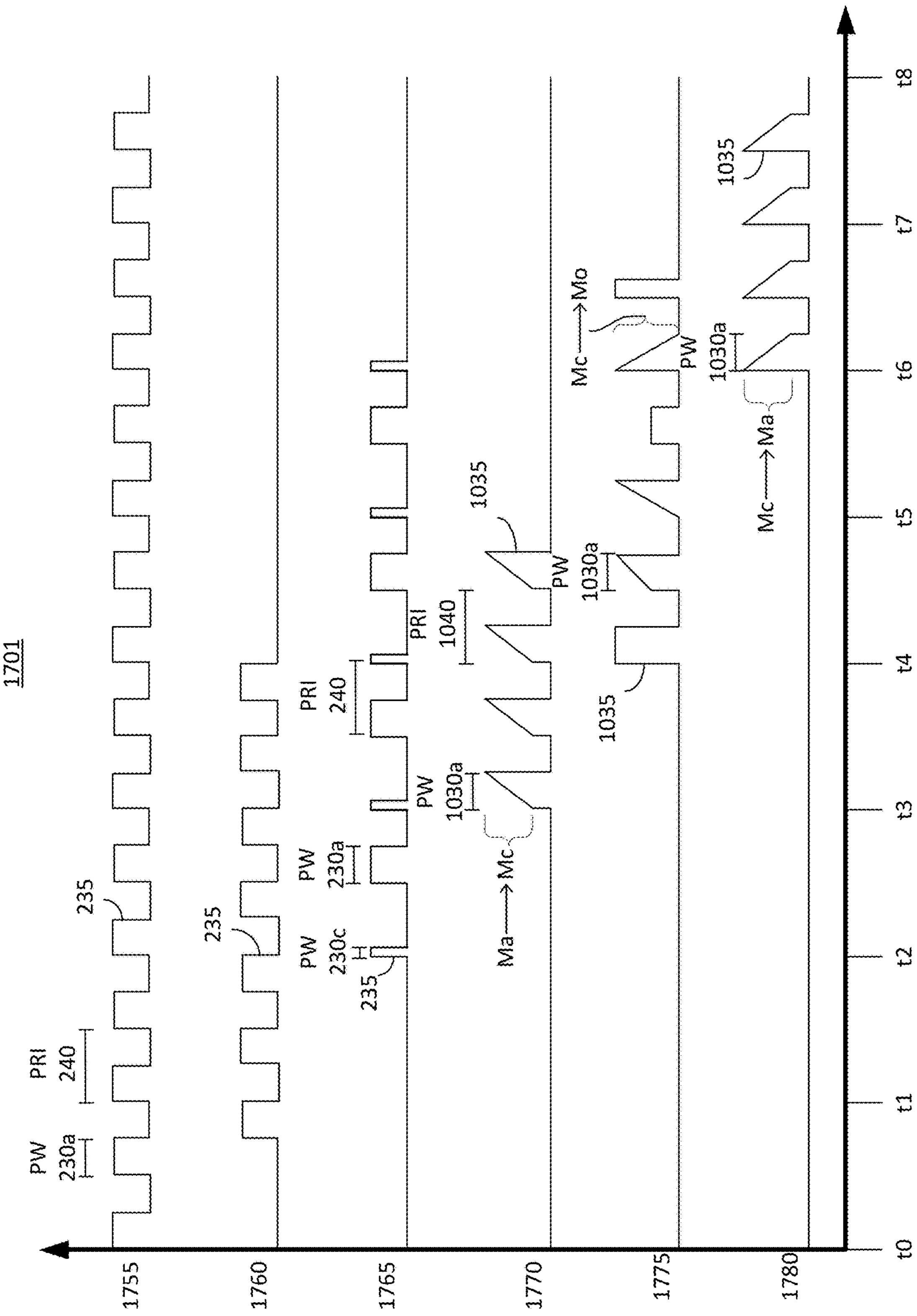
FIG. 17B is a diagram depicting waveforms used for neural stimulation via visual stimulation and auditory stimulation in accordance with an embodiment.

FIG. 17B is a diagram depicting waveforms used for neural stimulation via visual stimulation and auditory stimulation in accordance with an embodiment. FIG. 17B illustrates example sequences or a set of sequences 1701 that the stimuli orchestration component 1610 can generate or cause to be generated by one or more visual signaling components 150 or audio signal components 950. The stimuli orchestration component 1610 can retrieve the sequences from a data structure stored in data repository 1615 of NSOS 1605, or a data repository corresponding to NSS 105 or NSS 905. The sequences can be stored in a table format, such as TABLE 2 below. In some embodiments, the NSOS 1605 can select predetermined sequences to generate a set of sequences for a treatment session or time period, such as the set of sequences in TABLE 2. In some embodiments, the NSOS 1605 can obtain a predetermined or preconfigured set of sequences. In some embodiments, the NSOS 1605 can construct or generate the set of sequences or each sequence based on information obtained from the subject assessment module 1650. In some embodiments, the NSOS 1605 can remove or delete sequences from the set of sequences based on feedback, such as adverse side effects. The NSOS 1605, via subject assessment module 1650, can include sequences that are more likely to stimulate neurons in a predetermined region of the brain to oscillate at a desired frequency.

The NSOS 1605 can determine, based on the profile information, policy, and available components, to use the following sequences illustrated in example TABLE 2 provide neural stimulation using both visual signals and auditory signals.

TABLE 2

Audio and Video Stimulation Sequences

| Sequence Identifier | Mode | Signal Type | Signal Parameter | Stimulation Frequency | Timing Schedule |
|---|---|---|---|---|---|
| 1755 | visual | light pulses from a laser light source | Color: red; Intensity: low; PW: 230a | 40 Hz | {t0:t8) |
| 1760 | visual | checkerboard pattern image from a tablet display screen light source | color: black/white; intensity: high; PW:230a | 40 Hz | {t1:t4} |
| 1765 | visual | modulated ambient light by a frame with actuated shutters | PW: 230c/230a; | 40 Hz | {t2:t6} |
| 1770 | audio | music from headphones or speakers connected to an audio player | amplitude variation from $M_a$ to $M_c$; PW: 1030a | 40 Hz | {t3:15} |

TABLE 2-continued

Audio and Video Stimulation Sequences

| Sequence Identifier | Mode | Signal Type | Signal Parameter | Stimulation Frequency | Timing Schedule |
|---|---|---|---|---|---|
| 1775 | audio | acoustic or audio bursts provided by headphones or speakers | PW: 1030a; frequency variation from $M_c$ to $M_o$; | 39.8 Hz | {t4:{7} |
| 1780 | audio | air pressure generated by a cochlear air jet | PW: 1030a; pressure varies from $M_c$ to $M_a$ | 40 Hz | {t6:18} |

As illustrated in TABLE 2, each waveform sequence can include one or more characteristics, such as a sequence identifier, a mode, a signal type, one or more signal parameters, a modulation or stimulation frequency, and a timing schedule. As illustrated in FIG. 17B and TABLE 2, the sequence identifiers are 1755, 1760, 1765, 1765, 1770, 1775, and 1760.

The stimuli orchestration component 1610 can receive the characteristics of each sequence. The stimuli orchestration component 1610 can transmit, configure, load, instruct or otherwise provide the sequence characteristics to a signaling component 1630*a-n*. In some embodiments, the stimuli orchestration component 1610 can provide the sequence characteristics to the visual NSS 105 or the auditory NSS 905, while in some cases the stimuli orchestration component 1610 can directly provide the sequence characteristics to the visual signaling component 150 or audio signaling component 950.

The NSOS 1605 can determine, from the TABLE 2 data structure, that the mode of stimulation for sequences 1755, 1760 and 1765 is visual by parsing the table and identifying the mode. The NSOS 1605, responsive to determine the mode is visual, can provide the information or characteristics associated with sequences 1755, 1760 and 1765 to the visual NSS 105. The NSS 105 (e.g., via the light generation module 110) can parse the sequence characteristics and then instruct the visual signaling component 150 to generate and transmit the corresponding visual signals. In some embodiments, the NSOS 1605 can directly instruct the visual signaling component 150 to generate and transmit visual signals corresponding to sequences 1755, 1760 and 1765.

The NSOS 1605 can determine, from the TABLE 2 data structure, that the mode of stimulation for sequences 1770, 1775 and 1780 is audio by parsing the table and identifying the mode. The NSOS 1605, responsive to determine the mode is audio, can provide the information or characteristics associated with sequences 1770, 1775 and 1780 to the auditory NSS 905. The NSS 905 (e.g., via the light generation module 110) can parse the sequence characteristics and then instruct the audio signaling component 950 to generate and transmit the corresponding audio signals. In some embodiments, the NSOS 1605 can directly instruct the visual signaling component 150 to generate and transmit visual signals corresponding to sequences 1770, 1775 and 1780.

For example, the first sequence 1755 can include a visual signal. The signal type can include light pulses 235 generated by a light source 305 that includes a laser. The light pulses can include light waves having a wavelength corresponding to the color red in the visible spectrum. The intensity of the light can be set to low. An intensity level of low can correspond to a low contrast ratio (e.g., relative to the level of ambient light) or a low absolute intensity. The pulse width for the light burst can correspond to pulsewidth 230*a* depicted in FIG. 2C. The stimulation frequency can be 40 Hz, or correspond to a pulse rate interval ("PRI") of 0.025 seconds. The first sequence 1655 can run from $t_0$ to $t_8$. The first sequence 1655 can run for the duration of the session or treatment. The first sequence 1655 can run while one or more other sequences are other running. The time intervals can refer to absolute times, time periods, number of cycles, or other event. The time interval from $t_0$ to $t_8$ can be, for example, 1 minute, 2 minutes, 3 minutes, 4 minutes, 5 minutes, 7 minutes, 10 minutes, 12 minutes, 15 minutes, 20 minutes or more or less. The time interval can be cut short or terminated by the subject or responsive to feedback information. The time intervals can be adjusted based on profile information or by the subject via an input device.

The second sequence 1760 can be another visual signal that begins at $t_1$ and ends at $t_4$. The second sequence 1760 can include a signal type of a checkerboard image pattern that is provided by a display screen of a tablet. The signal parameters can include the colors black and white such that the checkerboard alternates black and white squares. The intensity can be high, which can correspond to a high contrast ratio relative to ambient light; or there can be a high contrast between the objects in the checkerboard pattern. The pulse width for the checkerboard pattern can be the same as the pulse width 230*a* as in sequence 1755. Sequence 1760 can begin and end at a different time than sequence 1755. For example, sequence 1760 can begin at $t_1$, which can be offset from to by 5 seconds, 10 seconds, 15 seconds, 20 seconds, 20 seconds, 30 seconds, 1 minute, 2 minutes, 3 minutes, or more or less. The visual signaling component 150 can initiate the second sequence 1760 at $t_1$, and terminate the second sequence at $t_4$. Thus, the second sequence 1760 can overlap with the first sequence 1755.

While pulse trains or sequences 1755 and 1760 can overlap with one another, the pulses 235 of the second sequence 1760 may not overlap with the pulses 235 of the first sequence 1755. For example, the pulses 235 of the second sequence 1760 can be offset from the pulses 235 of the first sequence 1755 such that they are non-overlapping.

The third sequence 1765 can include a visual signal. The signal type can include ambient light that is modulated by actuated shutters configured on frames (e.g., frames 400 depicted in FIG. 4B). The pulse width can vary from 230*c* to 230*a* in the third sequence 1765. The stimulation frequency can still be 40 Hz, such that the PRI is the same as the PRI in sequence 1760 and 1755. The pulses 235 of the third sequence 1765 can at least partially overlap with the pulses 235 of sequence 1755, but may not overlap with the pulses 235 of the sequence 1760. Further, the pulse 235 can refer to block ambient light or allowing ambient light to be perceived by the eyes. In some embodiments, pulse 235 can correspond to blocking ambient light, in which case the laser light pulses 1755 may appear to have a higher contrast ratio. In some cases, the pulses 235 of sequence 1765 can correspond to allowing ambient light to enter the eyes, in which case the contrast ratio for pulses 235 of sequence 1755 may be lower, which may mitigate adverse side effects.

The fourth sequence 1770 can include an auditory stimulation mode. The fourth sequence 1770 can include upchirp pulses 1035. The audio pulses can be provided via headphones or speakers 1205 of FIG. 12B. For example, the pulses 1035 can correspond to modulating music played by an audio player 1220 as depicted in FIG. 12B. The modulation can range from Ma to Mc. The modulation can refer to modulating the amplitude of the music. The amplitude can refer to the volume. Thus, the NSOS 1605 can instruct the audio signaling component 950 to increase the volume from a volume level Ma to a volume level Mc during a duration PW 1030*a*, and then return the volume to a baseline level or muted level in between pulses 1035. The PRI 240 can be 0.025, or correspond to a 40 Hz stimulation frequency. The NSOS 1605 can instruct the fourth sequence 1770 to begin at $t_3$, which overlaps with visual stimulation sequences 1755, 1760 and 1765.

The fifth sequence 1775 can include another audio stimulation mode. The fifth sequence 1775 can include acoustic bursts. The acoustic bursts can be provided by the headphones or speakers 1205 of FIG. 12B. The sequence 1775 can include pulses 1035. The pulses 1035 can vary from one pulse to another pulse in the sequence. The fifth waveform 1775 can be configured to re-focus the subject to increase the subject's attention level to the neural stimulation. The fifth sequence 1775 can increase the subject's attention level by varying parameters of the signal from one pulse to the other pulse. The fifth sequence 1775 can vary the frequency from one pulse to the other pulse. For example, the first pulse 1035 in sequence 1775 can have a higher frequency than the previous sequences. The second pulse can be an upchirp pulse having a frequency that increases from a low frequency to a high frequency. The third pulse can be a sharper upchirp pulse that has frequency that increases from an even lower frequency to the same high frequency. The fifth pulse can have a low stable frequency. The sixth pulse can be a downchirp pulse going from a high frequency to the lowest frequency. The seventh pulse can be a high frequency pulse with a small pulsewidth. The fifth sequence 1775 can being at $t_4$ and end at $t_7$. The fifth sequence can overlap with sequence 1755; and partially overlap with sequence 1765 and 1770. The fifth sequence may not overlap with sequence 1760. The stimulation frequency can be 39.8 Hz.

The sixth sequence 1780 can include an audio stimulation mode. The signal type can include pressure or air provided by an air jet. The sixth sequence can begin at to and end at $t_8$. The sixth sequence 1780 can overlap with sequence 1755, and partially overlap with sequences 1765 and 1775. The sixth sequence 1780 can end the neural stimulation session along with the first sequence 1755. The air jet can provide pulses 1035 with pressure ranging from a high pressure Mc to a low pressure Ma. The pulse width can be 1030*a*, and the stimulation frequency can be 40 Hz.

The NSOS 1605 can adjust, change, or otherwise modify sequences or pulses basd on feedback. In some embodiments, the NSOS 1605 can determine, based on the profile information, policy, and available components, to provide neural stimulation using both visual signals and auditory signals. The NSOS 1605 can determine to synchronize the transmit time of the first visual pulse train and the first audio pulse train. The NSOS 1605 can transmit the first visual pulse train and the first audio pulse train for a first duration (e.g., 1 minute, 2 minutes, or 3 minutes). At the end of the first duration, the NSOS 1605 can ping an EEG probe to determine a frequency of neural oscillation in a region of the brain. If the frequency of oscillation is not at the desired frequency of oscillation, the NSOS 1605 can select a sequence out of order or change the timing schedule of a sequence.

For example, the NSOS 1605 can ping a feedback sensor at $t_1$. The NSOS 1605 can determine, at $t_1$, that neurons of the primary visual cortex are oscillating at the desired frequency. Thus, the NSOS 1605 can determine to forego transmitting sequences 1760 and 1765 because neurons of the primary visual cortex are already oscillating at the desired frequency. The NSOS 1605 can determine to disable sequences 1760 and 1765. The NSOS 1605, responsive to the feedback information, can disable the sequences 1760 and 1765. The NSOS 1605, responsive to the feedback information, can modify a flag in the data structure corresponding to TABLE 2 to indicate that the sequences 1760 and 1765 are disabled.

The NSOS 1605 can receive feedback information at $t_2$. At $t_2$, the NSOS 1605 can determine that the frequency of neural oscillation in the primary visual cortex is different from the desired frequency. Responsive to determining the difference, the NSOS 1605 can enable or re-enable sequence 1765 in order to stimulate the neurons in the primary visual cortex such that the neurons may oscillate at the desired frequency.

Similarly, the NSOS 1605 can enable or disable audio stimulation sequences 1770, 1775 and 1780 based on feedback related to the auditory cortex. In some cases, the NSOS 1605 can determine to disable all audio stimulation sequences if the visual sequence 1755 is successfully affecting the frequency of neural oscillations in the brain at each time period $t_1$, $t_2$, $t_3$, $t_4$, $t_5$, $t_6$, $t_7$, and $t_8$. In some cases, the NSOS 1605 can determine that the subject is not paying attention at $t_4$, and go from only enabling visual sequence 1755 directly to enabling audio sequence 1755 to re-focus a the user using different stimulation mode.

Method for Neural Stimulation Via Visual Stimulation and Auditory Stimulation

Figure 18:
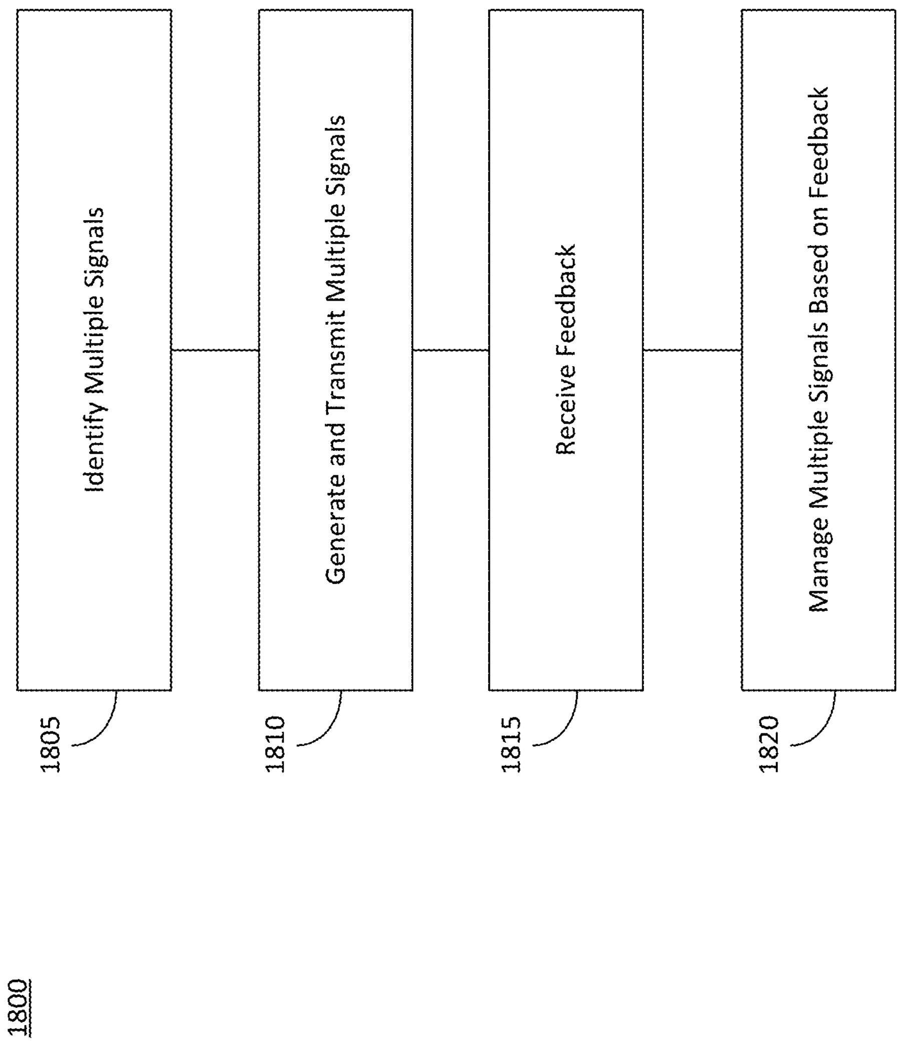
FIG. 18 is a flow diagram of a method for neural stimulation via visual stimulation and auditory stimulation in accordance with an embodiment.

FIG. 18 is a flow diagram of a method for neural stimulation via visual stimulation and auditory stimulation in accordance with an embodiment. The method 180 can be performed by one or more system, component, module or element depicted in FIGS. 1-17B, including, for example, a neural stimulation orchestration component or neural stimulations system. In brief overview, the NSOS can identify multiple modes of signals to provide at block 1805. At block 1810, the NSOS can generate and transmit the identified signals corresponding to the multiple modes. At 1815 the NSOS can receive or determine feedback associated with neural activity, physiological activity, environmental parameters, or device parameters. At 1820 the NSOS can manage, control, or adjust the one or more signals based on the feedback.

While this specification contains many specific implementation details, these should not be construed as limitations on the scope of any inventions or of what can be claimed, but rather as descriptions of features specific to particular embodiments of particular aspects. Certain features described in this specification in the context of separate embodiments can also be implemented in combination in a single embodiment. Conversely, various features described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'.

Thus, particular exemplary embodiments of the subject matter have been described. In some cases, the actions recited in the claims can be performed in a different order and still achieve desirable results. In addition, the processes depicted in the accompanying figures do not necessarily require the particular order shown, or sequential order, to achieve desirable results.

The present technology, including the systems, methods, devices, components, modules, elements or functionality described or illustrated in, or in association with, the figures can treat, prevent, protect against or otherwise affect brain atrophy and disorders, conditions and diseases associated with brain atrophy.

Neural Stimulation System with Sleep-Related Monitoring Modules

FIG. 33 provides a neural stimulation system comprising a stimulus delivery system coupled to an analysis and monitoring system. In some embodiments, the present technological solution comprises a stimulus delivery system which includes one or more of: one or more Audio Stimulus Module (110), one or more Visual Stimulus Module (120). These modules may be in addition to tactile or other stimulus modules (not shown). These modules provide the delivery of audio or visual stimulus at specific parameter values. In some embodiments the values of these parameters are responsive to one or more of: one or more Audio Monitoring Module (111), one or more Visual Monitoring Module (121).

In some embodiments, the present technological solution includes one or more of: one or more Feedback Module (150) collecting, storing, or processing feedback from users or third parties; one or more Profile Module (161) storing and processing profile or demographic information related to one or more users or third parties, or of populations of users or third parties; one or more History Module (162) storing or processing history and logs related to one or more users or third parties, or of populations of users or third parties; one or more Monitoring Module (163), collecting, storing, logging, and/or analysing aspects of one or more users or third parties, including but not limited to: aspects of the environment, state, behavior, input, responses, diagnosis, disease progression, compliance, engagement, mood, adherence. In some embodiments the present technological solution includes one or more Brain Wave Monitoring Module (190) measuring and analysing brain wave activity in one or more users, including but not limited to detecting and characterizing gamma wave power and gamma entrainment.

In some embodiments, the present technological solution includes one or more of: one or more Actigraphy Monitoring Module (130), one or more Sleep Analysis Module (140). In some embodiments, one or more Sleep Analysis Module is responsive, at least in part, to information communicated from one or more Actigraphy Monitoring Module. In some embodiments, a Sleep Analysis Module performs sleep analysis based at least in part on actigraphy information collected at least in part by an Actigraphy Monitoring Module. In some embodiments, Sleep Analysis Module performs one or more analysis steps described in FIG. 37.

In some embodiments, one or more of an Audio Stimulus Module, a Visual Stimulus Module, and/or a Stimulus Delivery System (170) managing or incorporating one or more stimulus modules, may be responsive to one or more of: one or more analysis Analysis and Monitoring System (130) and/or monitoring modules, including but not limited to: one or more Feedback Module (150), one or more Profile Module (161), one or more History Module (162), one or more Monitoring Module (163), one or more Sleep Analysis Module (140), one or more Actigraphy Monitoring Module (130), one or more Brain Wave Monitoring Module (190), and/or one or more Stimulus Delivery System (170) managing or incorporating one or more analysis and monitoring module.

Combination Therapies

In one aspect, the present disclosure provides combination therapies comprising the administration of one or more additional therapeutic regimens in conjunction with methods described herein. In some embodiments, the additional therapeutic regimens are directed to the treatment or prevention of the disease or disorder targeted by methods of the present technology.

In some embodiments, the additional therapeutic regimens comprise administration of one or more pharmacological agents that are used to treat or prevent disorders targeted by methods of the present technology. In some embodiments, methods of the present technology facilitate the use of lower doses of pharmacological agents to treat or prevent targeted disorders.

In some embodiments, the additional therapeutic regimens comprise non-pharmacological therapies that are used to treat or prevent disorders targeted by methods of the present technology such as, but not limited to, cognitive or physical therapeutic regimens.

In some embodiments, a pharmacological agent is administered in conjunction with therapeutic methods described herein. In some embodiments, the pharmacological agent is directed to inducing a relaxed state in a subject administered methods of the present technology. In some embodiments, the pharmacological agent is directed to inducing a heightened state of awareness in a subject administered methods of the present technology. In some embodiments, the pharmacological agent is directed to modulating neuronal and/or synaptic activity. In some embodiments, the agent promotes neuronal and/or synaptic activity. In some embodiments, the agent targets a cholinergic receptor. In some embodiments, the agent is a cholinergic receptor agonist. In some embodiments, the agent is acetylcholine or an acetylcholine derivative. In some embodiments, the agent is an acetylcholinesterase inhibitor.

In some embodiments, the agent inhibits neuronal and/or synaptic activity. In some embodiments, the agent is a cholinergic receptor antagonist. In some embodiments, the agent is an acetylcholine inhibitor or an acetylcholine derivative inhibitor. In some embodiments, the agent is acetylcholinesterase or an acetylcholinesterase derivative.

EXAMPLES

Example 1. Human Clinical Study of Safety, Efficacy, and Results of Treatment Methods and Study Design A clinical study was performed to assess the safety, tolerability, and efficacy of long-term, daily use of gamma sensory stimulation therapy on cognition, functional ability, and biomarkers in a mild-to-moderate AD population via a prospective clinical study. The clinical study was a multi-center, randomized controlled trial evaluating daily gamma sensory stimulation received at home for a 6-month treatment period. Subjects included in the study were adults 50 years and older with a clinical diagnosis of mild to moderate AD (MMSE: 14-26, inclusive), a reliable care partner, and successful tolerance and entrainment screening via EEG. Key exclusion criteria included profound hearing or visual impairment, use of memantine, major psychiatric illness, clinically relevant history of seizure, or contraindication to imaging studies.

Study Participants and Design. A total of 135 patients were assessed for eligibility to participate in the study. Patients were first given a screening EEG, and then split into groups. One group was a sham control group that was not given treatment; the other was a group that was subjected to 1 hour of therapy, which involved subjecting the subject to audio and visual stimulation at a frequency of 40 Hz per day. Of those assessed for eligiblity, 76 were randomized between the active treatment and sham control. Forty-seven of the randomized patients were allocated to the active group and 29 were allocated to the sham group. Of the active group, two patients withdrew prior to therapy and three had no post-baseline efficacy and were not included in the modified intent to treat (mITT) population. In sham group, one patient received active treatment and was not in the sham population. Completers included 33 patients in the active group and 28 in the sham group, with 10 early discontinuations in the active group. Seven of those discontinuations were due to consent withdraw and 23 were attributed to adverse events, whereas in the sham group, only six withdrew consent and one discontinued as a result of adverse events.

The study employed various clinical outcome assessment scales to assess cognitive decline or dysfunction. These included the the Neuropsychiatric Inventory (NPI), Clinical Dementia Rating-Sum of Boxes (CDR-sb), the Clinical Dementia Rating-Global Score (CDR global), the Mini-Mental State Exam (MMSE), the Alzheimer's Disease Assessment Scale-Cognitive Subscale-14 (ADAS-Cog14), and a variation of the Alzheimer's Disease Composite Score (ADCOMS) as optimized for patients with mild or moderate Alzheimer's Disease. NPI examines 12 sub-domains of behavioral functioning: delusions, hallucinations, agitation/aggression, dysphoria, anxiety, euphoria, apathy, disinhibition, irritability/lability, and aberrant motor activity, nighttime behavioral disturbances, and appetite and eating abnormalities. The NPI can be used to screen for multiple types of dementia, and it involves giving the caregiver of a subject the questions and then, based on the answers, rating the frequency of the symptoms, their severity, and the distress the symptoms cause on a three, four, and five-point scale, respectively.

CDR global is calculated based on testing performed for six different cognitive and behavioral domains: memory, orientation, judgment and problem solving, community affairs, home and hobbies performance, and personal care. To test these areas, an informant is given a set of questions about a subject's memory problem, judgment and problem-solving ability of the subject, community affairs of the subject, home life and hobbies of the subject, and personal questions related to the subject. The subject is given another set of questions that includes memory-related questions, orientation-related questions, and questions about judgment and problem-solving ability. The CDR global score is calculated based on the results of those questions, and it is measured using a scale of 0 to 3, with 0 representing no dementia, 0.5 indicating very mild dementia, 1 indicating mild dementia, 2 indicating moderate dementia/cognitive impairment, and 3 indicating severe dementia/cognitive impairment. CDR-sb is a clinical outcome assessment that looks at functional impact of cognitive impairment: memory, executive function, instrumental and basic activities of daily living and assesses them based on interviews with an informant and the patient. The CDR-sb score is based on assessment of items including memory, orientation, judgment and problem solving, community affairs, home and hobbies, and personal care. The CDR-sb is scored from 0 to 18, with higher scores representing greater severity of cognitive and functional impairment.

The MMSE looks at 11 items to assess memory, language, praxis and executive function based on a cognitive assessment of the patient. Items assessed include registration, recall, constructional praxis, attention and concentration, language, orientation time, and orientation place. The MMSE is scaled from 0 to 30, with higher scores representing lower severity of cognitive dysfunction. The ADAS-Cog14 assesses memory, language, praxis and executive function. The score is based on a cognitive assessment of the patient and assesses fourteen items: spoken language, maze, comprehension spoken language, remembering word recognition test instructions, ideational praxis, commands, naming, word finding difficulty, constructional praxis, orientation, digit cancellation, word recognition, word recall, and delayed recall. A score is based on points allocated to each item, and the maximum total score is 90, with higher numbers indicating greater severity of cognitive dysfunction. The Alzheimer's Disease Composite Score (ADCOMS) considers items from all of the above-discussed scores: items from Alzheimer's Disease Assessment Scale-cognitive subscale items, MMSE items, and all of the CDR-sb items. ADCOMS combines portions of the ADAS-cog, Clinical Dementia Rating (CDR) scale, and MMSE that have been shown to change the most over time in people who do not have functional impairment yet. MADCOMS, which was used in the present example, optimizes the scale instead by combining items more significant for mild and moderate dementia.

The study design involved primary efficacy endpoints of MADCOMS, ADAS-cog14, and CDR-sb. Unlike ADCOMS, MADCOMS is optimized for patients with moderate or mild Alzheimer's Disease. These were optimized for AD-specific decline. A separate optimization was done for moderate and mild AD. Secondary efficacy endpoints consisted of ADCS-ADL, ADCOMs (adjusted), MMSE, CDR-global score and the Neuropsychiatric Inventory (NPI). Of the secondary endpoints, ADCS-ADL was measured monthly and MMSE was measured at the last time point.

The efficacy endpoints were analyzed by applying a linear model of analysis and/or a separate means model of analysis. The linear model of analysis involved employing a linear fit model to determine a value at TO based on the difference from baseline in conditions at the end of the study. The seprate means analysis employed estimates of mean values at each assess timepoint, which was either a monthly timepoint or at three and six months after treatment began, depending on the score that was being analyzed. In evaluating MADCOMS composite score, for example, the separate means analysis was applied using mean values that were estimated at three and six months. The linear model was applied by using the estimates of treatment difference at the end of the study and connecting a straight line to 0. Similar models were used for the other efficacy endpoints. FIGS. 20, 21, 22, 23, and 24 show the various linear and separate means models generated for these endpoints.

Figure 25:
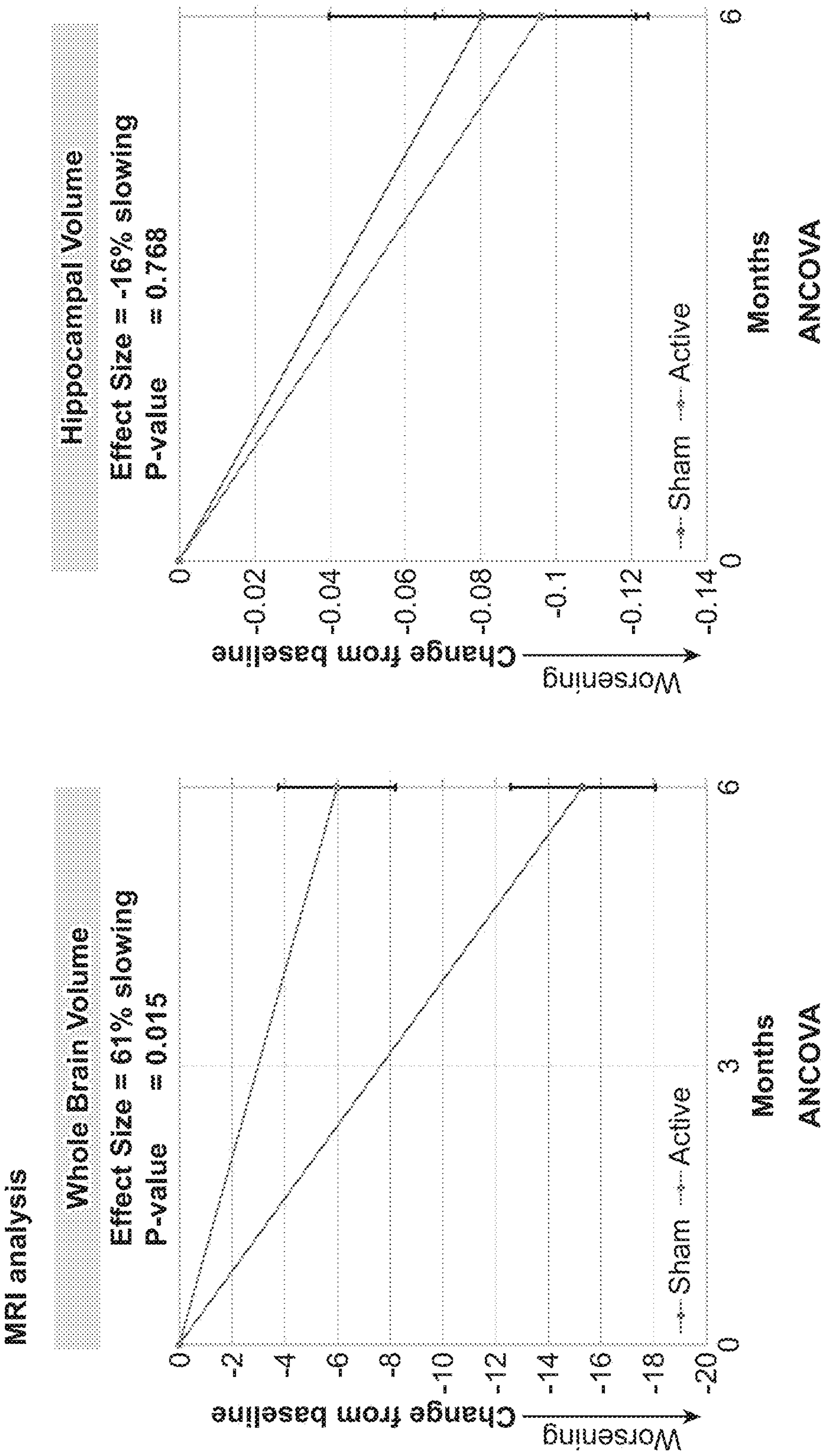
FIG. 25 shows the linear model analysis of magnetic resonance imaging (MRI) results of whole brain volume value, on the left, and hippocampal volume, on the right, after six months of treatment.
Figure 27:
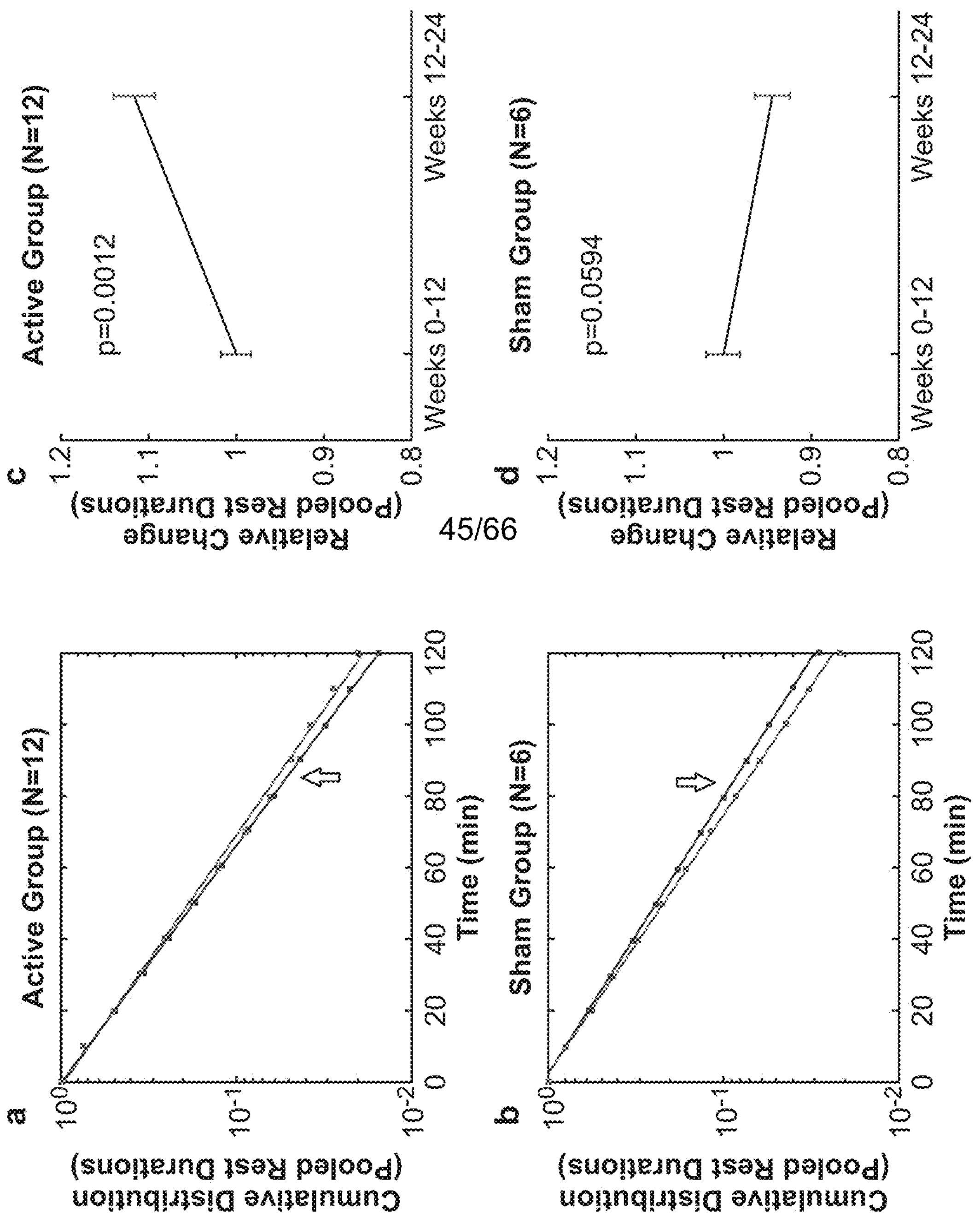
FIG. 27 shows graphs that demonstrate the observed improvement (panels a and b) in sleep quality as measured by a reduction in sleep fragmentation, expressed as a higher frequency longer rest durations, over a 24-week period of exemplary gamma stimulation treatment for a first 12-week period of treatment (indicated by the line closest to the white arrow), and second 12-week period of treatment (indicated by the line furthest from the white arrow), in mild to moderate AD subjects. Panels c and d demonstrate the observed impact of the sham treatment on sleep quality as measured by a reduction in sleep fragmentation.

To assess biomarkers, researches used MRI, volumetric analyses, EEG, Amyloid positron emission tomography (PET), actigraphy, and plasma biomarkers. The study employed structural MRIs, taken before any treatment began and at the end of the sixth months and assessed these for volume-base morphology. Volumetric changes for the hippocampus, lateral ventricles, whole cortex (cerebral cortical gray matter) and whole brain (cerebrum and cerebellum) were determined and the rate of atrophy was compared for active and sham groups using a linear model, as demonstrated in FIG. 25. To analyze for safety and tolerability, researches looked for adverse events and presence of amyloid related imaging abnormalities (ARIA) on MRI. Therapy adherence was also analyzed. Blinding effectiveness for subjects, care partners, and assessors were prospectively analyzed by assessing baseline and follow up ascertainment of whether the care partner, assessor, or patient thought the patient was on active or sham treatment.

Analysis

For the MADCOMS composite scores, both means of analysis demonstrated 35% slowing in decline rate, indicating that the active group progressed less than the placebo arm over the six-month study. When a linear and means analysis were both employed, the sham group was slightly favored, but non-significantly. When these two separate means analyses were applied to the ADAS-cog14 data, both slightly favored the sham group, although not in a statistically significant manner. When CDR-sb results were analyzed, the mean-estimate model found a 28% slowing rate, whereas the linear extraction showed a 26% slowing rate, but the comparisons were not statistically significant.

Of the secondary endpoints, ADCS-ADL was measured monthly and MMSE was measured at the last time point. When analyzing ADCS-ADL values, the first analysis model employed used estimates for each month and showed 84% slowing over the 6-month time period. The linear fit model was again employed, and the same 84% slowing was found. When analyzing MMSE values, an 83% slowing was identified.

Results

Figure 19:
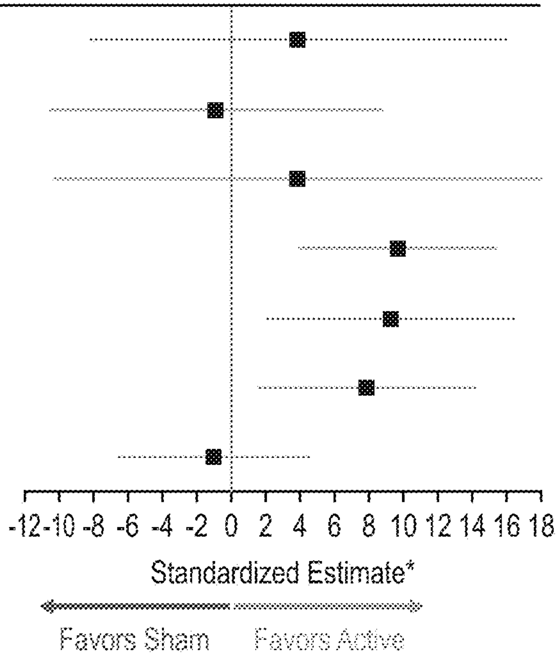
FIG. 19 is an efficacy summary chart for the modified intent to treat (mITT) population, including p-values, difference, confidence intervals (CI), and a standardized estimate of efficacy based on the values.
Figure 20:
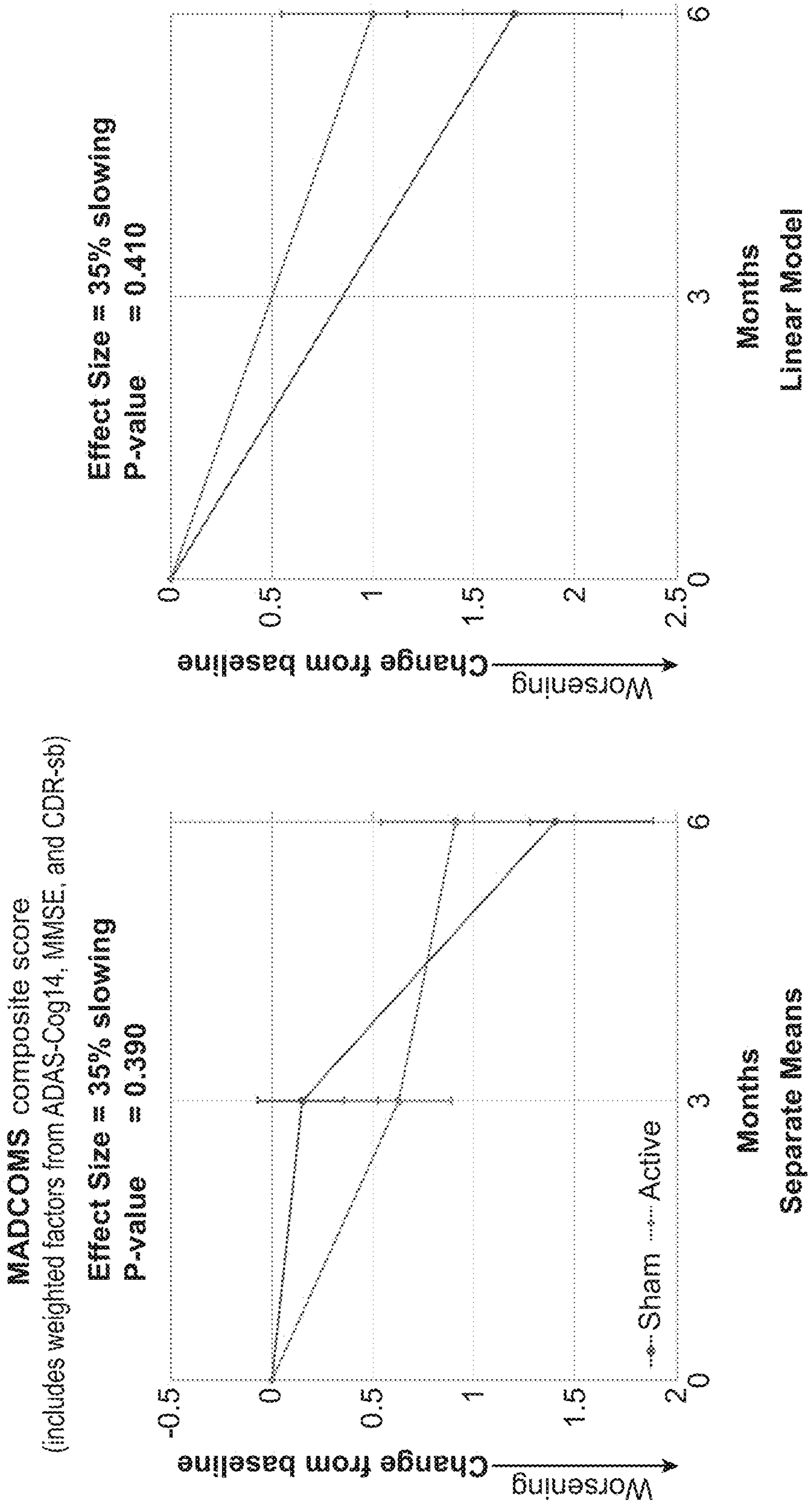
FIG. 20 shows the separate means analysis, on the left, and the linear model analysis, on the right, of the Alzheimer's Disease composite score (ADCOMS) as optimized for mid and moderate Alzheimer's Disease (MADCOMS) for the sham and active treatment groups.
Figure 21:
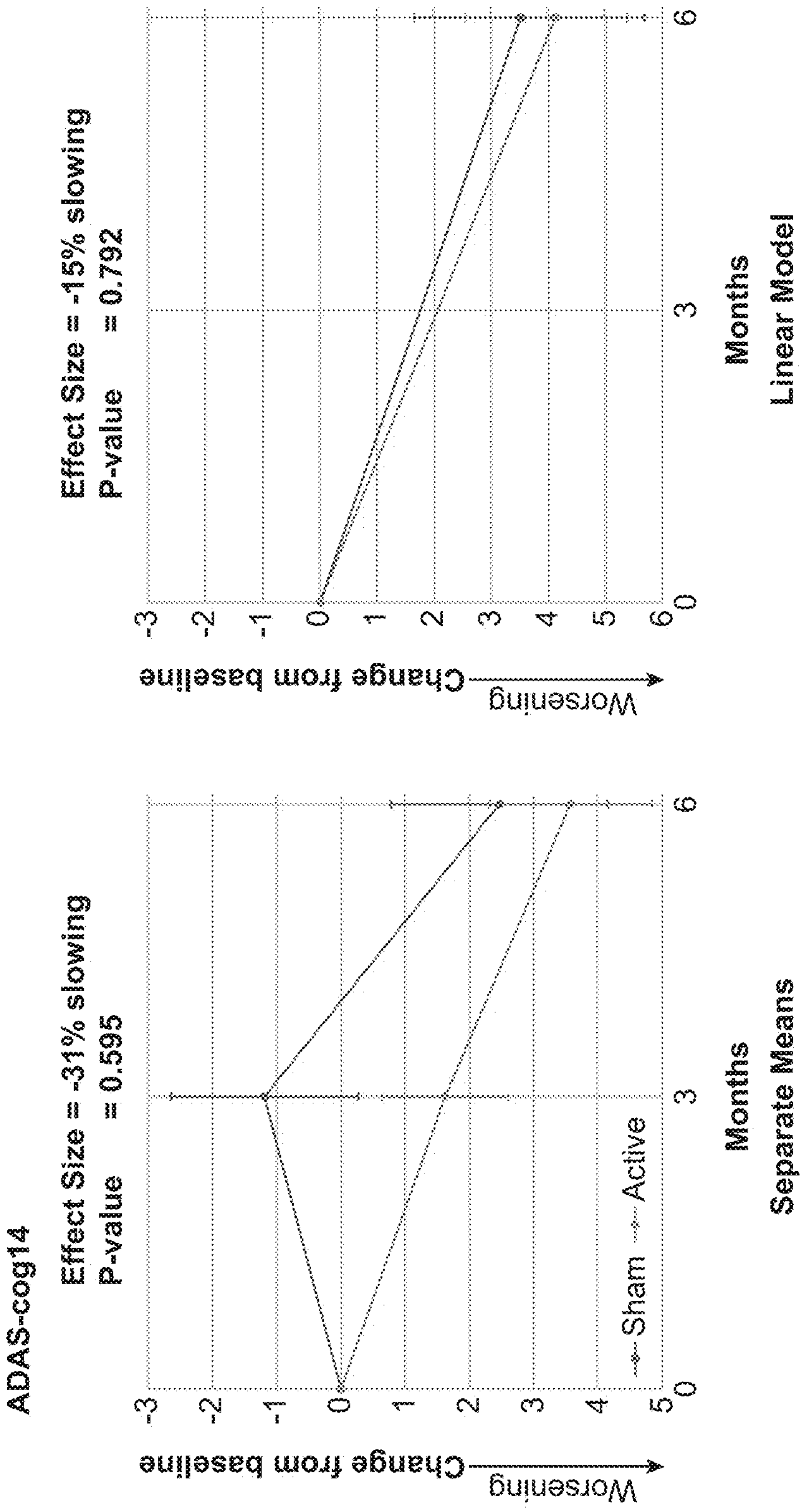
FIG. 21 shows the separate means analysis, on the left, and a linear model analysis, on the right, of the Alzheimer's Disease Assessment Scale-Cognitive Subscale 14 (ADAS-Cog14) values for the sham and active treatment groups.
Figure 22:
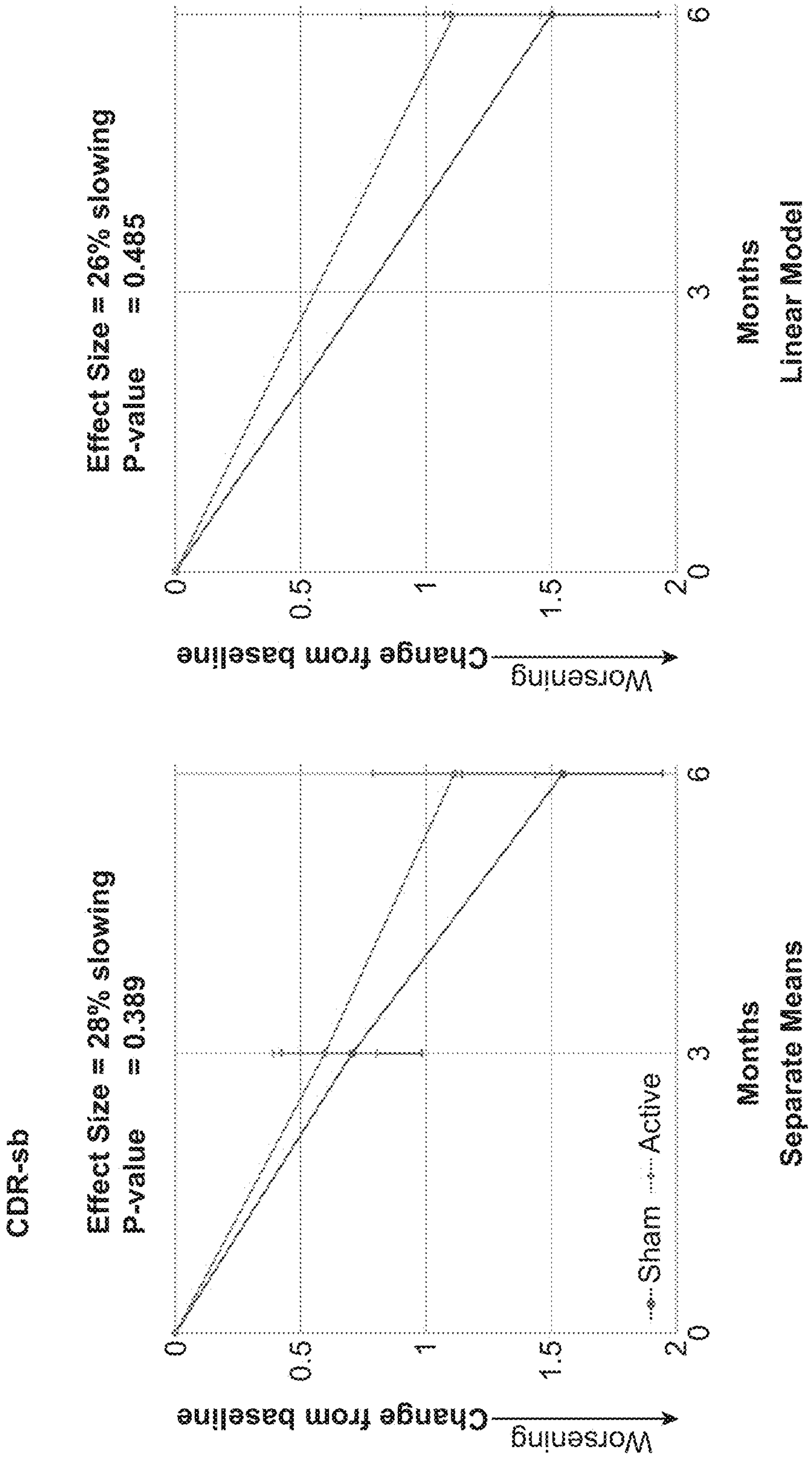
FIG. 22 shows the separate means analysis, on the left, and a linear model analysis, on the right, of the Clinical Dementia Rating Sale Sum of Boxes (CDR-SB) values for the sham and active treatment groups.
Figure 23:
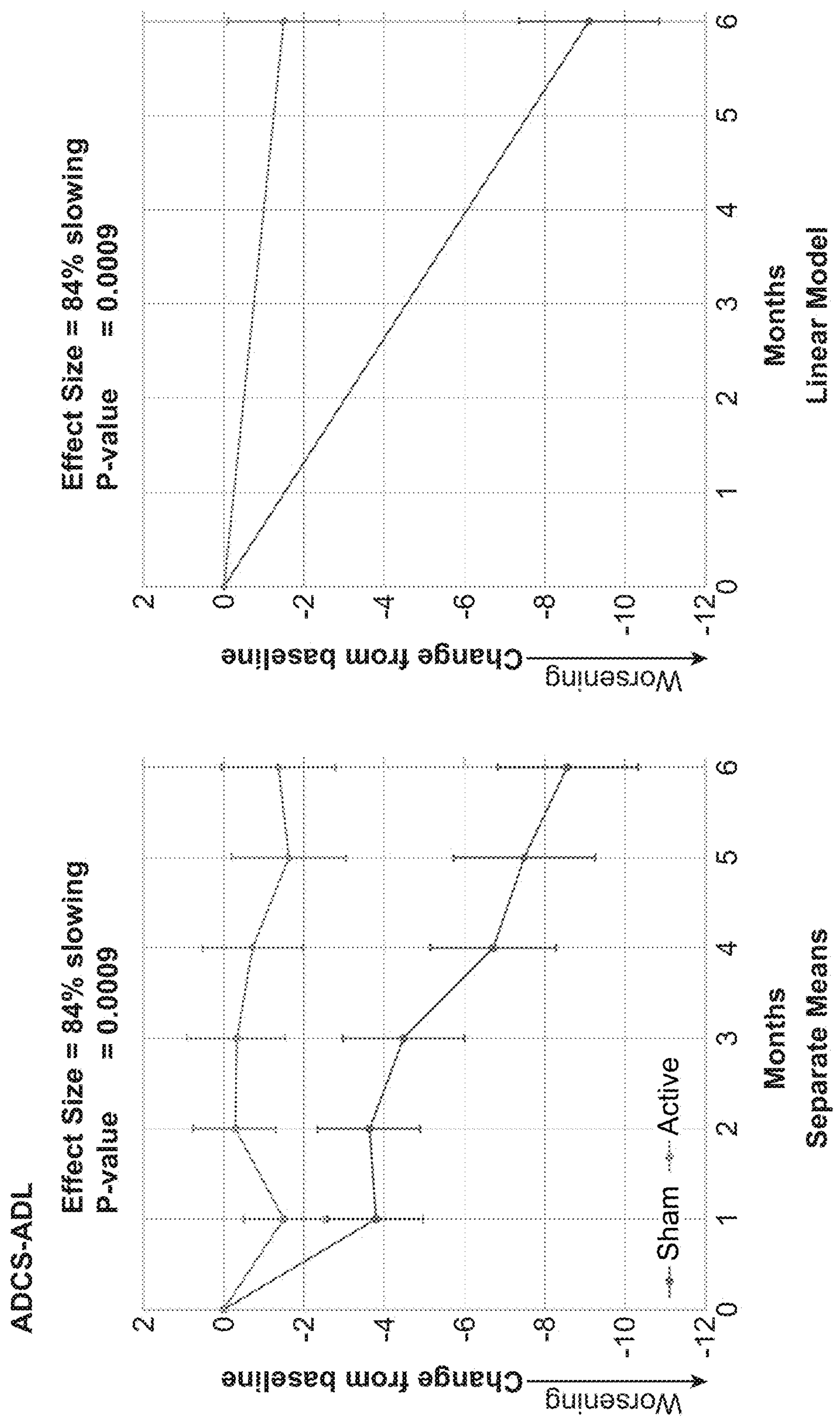
FIG. 23 shows the separate means analysis, on the left, and a linear model analysis, on the right, of the Alzheimer's Disease Cooperative Study-Activities of Daily Living Scale (ADCS-ADL) scores for the sham and active treatment groups.
Figure 24:
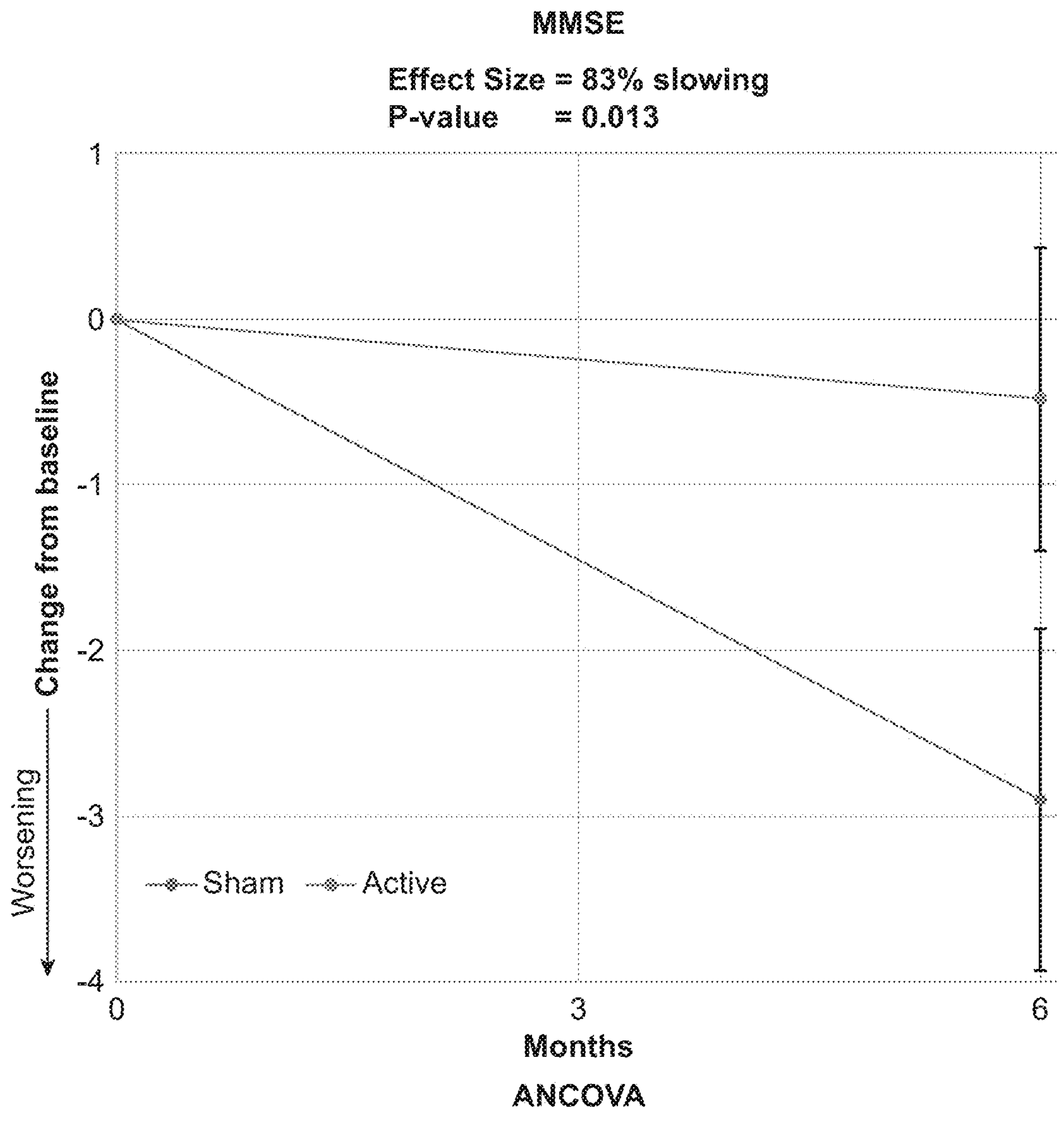
FIG. 24 shows the linear model analysis of the Mini-Mental State Examination (MMSE) score, as measured after six months of treatment (i.e., at the last time point).

FIG. 19 and FIG. 26 summarize the efficacy findings of the study. Following informed consent and screening, a total of 76 subjects were randomized between the active treatment and sham control. The safety population for the study included 74 subjects who received at least one treatment, and the modified intent to treat (mITT) population included a total of 70 subjects, 53 of whom completed the 6-month study, which form the basis for analysis of outcome measures.

Demographic and Baseline Characteristics

In terms of demographic and baseline characteristics of the mITT population, following randomization, the populations were balanced across gender, baseline MMSE, ApoE4 status, activities of daily living (ADL), and PET amyloid standardized uptake value ratio (SUVR) status; imbalances between the two groups were observed in age, ADAS-Cog11, and CDR-sb scores at baseline. Statistical models included covariates for age and MMSE at baseline.

Safety and Tolerability

Non-invasive gamma sensory stimulation was safe and well-tolerated in the mild and moderate AD subjects. The active group had a lower rate of treatment emergent adverse events (TEAE) than the sham group (67% vs 79%).

Treatment related AEs (TRAEs) deemed definitely, probably, and possibly related to the therapy were elevated in the active group versus the sham group (41% vs 32%). One treatment related SAE was noted in the active group for a patient hospitalized for wandering while their care partner was located; this subject discontinued the study subsequently. Of the randomized subjects, withdraw rates were similar between both groups (active 28%, sham 29%) including withdraw rates due to an adverse event (active 7%, sham 7%). TEAEs that occurred more often in the active group are tinnitus, delusions, broken bone. TEAEs that occurred more often in the sham group are upper respiratory infection, confusion, anxiety and dizziness.

Clinical Assessments

Over the treatment period of 6-months, subjects were evaluated in-clinic and via phone visits for cognitive, functional, and biomarker changes on multiple measures.

The primary efficacy endpoints demonstrated effects favoring the active group on the MADCOMS (35% slowing; n.s.) and CDR-sb (27%; n.s.) and favoring the Sham group on the ADAS-cog14 (−15% slowing; n.s.). MADCOMS initially leaned in favor of active group, but the results were not statistically different. ADAS-cog14 was slightly in favor of the sham group but not statistically different. CDR-sb was also in favor of the active group, but the difference was not significant, as shown by the p-values that ranged between 0.39 and 0.7920.

Selected secondary endpoints demonstrated significant effects favoring the treatment (active) group. The active group had significant benefit on functional ability as measured by the ADCS-ADL ($p=0.0009$), which represented an 84% slowing of decline and a treatment difference of 7.59 points over the six-month duration of the trial (FIG. 26). The active group demonstrated significant benefit on the MMSE (ANCOVA $p=0.013$), which represented an 83% slowing in the rate of decline versus the Sham group and a treatment difference of 2.42 points.

Biomarker Changes-MRI

Structural MR imaging was analyzed for volume-base morphometry using an automated image processing pipeline (Biospective, Montreal, Canada). Volumetric changes of the hippocampus, lateral ventricles, whole cortex (cerebral cortical gray matter) and whole brain (cerebrum and cerebellum, no cerebrospinal fluid (CSF)) for each subject were determined; no manual corrections were performed. No significant benefit on hippocampal volume was determined. Statistically-significant benefit favoring the active group ($p=0.0154$) on whole brain volume (WBV) was established, representing a 61% slowing compared to the Sham group progression. The treatment value for the active group was 9.34 cm3.

Conclusions

Gamma sensory stimulation was safe and well tolerated. Two of three primary efficacy outcomes (MADCOMS, CDR-sb) favored the active group but did not reach significance. Selected secondary endpoints demonstrated that active treatment with gamma sensory stimulation therapy led to significant benefits in the ability to perform activities of daily living via the ADCS-ADL and cognition via the MMSE, representing important treatment and management objectives for AD patients. Quantitative MR analysis demonstrated slowing of brain atrophy as measured by whole brain volume in the active group. The combined clinical and biomarker findings suggest beneficial effects of gamma sensory stimulation for AD subjects may be facilitated via differentiated pathways. These surprising results indicates that the gamma sensory stimulation may be used to treat a range of diseases and disorders that cause or are caused by brain atrophy.

Example 2. Human Clinical Study to Determine Efficacy of NSS Treatment for Sleep Abnormalties Methods Study Participants and Design. Patients included in the present interim analysis were clinically diagnosed having mild to moderate AD and were under the care of their care neurologist. Inclusion criteria were age of 55 years or older, MMSE score 14-26 and participation of a caregiver, whereas exclusion criteria included profound hearing or visual impairment, seizure disorder, use of memantine, or implantable, non-MR compatible devices. Patients on therapy with an acetylcholine esterase inhibitor could enroll, but their dosing were maintained the same during the trial. Patients were randomized to receive either 40 Hz simultaneous auditory and visual sensory stimulation by a NSS (treatment group; n=14) or placebo treatment (sham group; n=8).

Neural Stimulation System (NSS). In the present study, the system used for the neural stimulation provided noninvasive sensory stimulation provided visual and audio stimulation to invoke gamma oscillations in a brain region, thereby improvoing sleep. Use of such a system is referred to herein as NSS therapy or NSS treatment. The system logs device usage and stimulation output settings for adherence monitoring. This information is uploaded to a secure cloud server for physician remote monitoring. The present experiment utilized a NSS that included a handheld controller, an eye-set for visual stimulation, and headphones for auditory stimulation that work together to deliver precisely timed, non-invasive stimulation to induce steady-state gamma brainwave activity. The visual stimulation generated by the NSS consisted of precisely timed flashes of visible light from light emitting diodes, and the auditory stimulation consisted of short-duration clicks. The stimuli occured at a pulse repetition frequency of 40 Hz. The on-off periods of the visual stimulation were perceivable by the patient but not disruptive; an individual remained aware of their surroundings and could converse with a care partner during use of the system. The customized stimulation output was determined and verified by a physician based on both patient-reported comfort information and on the patient's quantitative electroencephalography (EEG) response to the stimulation. The NSS was then configured to the determined settings, and all subsequent use would be within this predefined operating range.

Monitoring Sleep Fragmentation with Actigraphy and Signal Processing. Effects of the NSS therapy on sleep fragmentation were determined by continuous monitoring activity of AD patients with a wrist worn actigraphy watch (ActiGraph GT9X), and data was collected daily over a 6-month period. Collected data consisted of raw accelerometer readings in three orthogonal directions recorded at a 30 Hz sampling frequency.

Preprocessing the Data. Accelerometer data from three orthogonal dimensions are filtered with a Butterworth bandpass (0.3-3.5 Hz) filter. The magnitude of the bandpass filtered 3-d accelerometer vector was then down-sampled by a factor of 4. This process is done for all data collected from all patients over the six months period. Two representations of the data were made: (i) a binary representation and (ii) a smooth representation. For the binary representation, all data was pooled together and a histogram in the log scale was obtained. The resulting histogram had a bimodal distribution, one peak corresponding to higher changes in acceleration and hence high activity periods, and the second peak corresponding to lower changes in acceleration and hence rest periods. Taking the location of the minimum between the two peaks as a threshold, acceleration magnitudes higher than the threshold were represented by 1's and acceleration magnitudes smaller than the threshold were represented by 0's. For the smooth representation, a median filter with length of six hours was applied to the down-sampled data to get a smooth estimate of the activity levels.

Extracting Nighttime (Sleep Segment). Individual 24-h data segments were extracted from 12:00 μm midday on a given day to the next day 12:00 μm midday. The data was labeled with the binary representation for an initial estimate of the active-1's and rest-0's periods during the given 24-hour window. This window consisted of three segments: daytime (segment prior to sleep), nighttime (sleep segment) and daytime (segment after sleep). We proposed that the nighttime segment would consist of more 0's than 1's and daytime segments would consist of more 1's than 0's. Therefore, an ideal nighttime model was defined which was built with a function that takes a value 0 within continuous period of duration "L" centered at a time "T" with a value 1 outside this region. Given an initial estimate of L and T, the difference between the ideal nighttime model and the binary representation of movement was computed using a quadratic cost function. In this cost function each mismatch, occurring when the binary value is 1 during nighttime or 0 during daytime, contributes 1, and each match, occurring when the binary value is 0 during nighttime and 1 during daytime, contributes 0. The initial estimate for T was taken to be the time point corresponding to the minimum of the smooth representation mentioned above. Initial estimate for L is set to eight hours. Cost function was minimized using unconstrained nonlinear optimization. This led to the best model estimate for L, the nighttime length, and T, the nighttime mid-point, and allowed us to locate the borders for the three segments (daytime, nighttime, daytime) from the 24-hour window. We then extracted the nighttime segment to evaluate the micro-changes within.

Identification of Rest and Active Durations During Nighttime and Relating Them to Sleep. Within the nighttime segments, periods with all 0's is attributable to lack of movement and periods with all 1's is attributable to movement. However, mapping these periods directly to sleep fragmentation faces the problem that the durations of these periods can range from milliseconds to hours in actigraphy data, whereas analysis of sleep is carried out by classifying non-overlapping epochs of 30 second duration into awake and asleep. To link our actigraphy analysis to the analysis time-scales used in sleep studies, all segments of length N were taken and replaced the values in those segments by the median value over a window of 3N duration centered on the segment. While N=30 s was chosen, it was found that the results were not sensitive to this exact choice. After repeating this process for all short segments, consecutive time points in the nighttime segments corresponding to 0's were identified as rest durations and those corresponding to 1's were identified as active durations.

Determining the Distributions of Rest and Active Durations. Rest durations across all participants were pooled and the quantity P(t)=∫p(w)dw, where p(w) is the probability density function of rest durations between w and w+dw, was examined. P(t) represents the fraction of rest durations that are greater than length t and is referred to as the cumulative distribution function. Similarly, the cumulative distribution of the active durations was also calculated, and distributions of both rest and active durations are displayed in FIG. 39.

Assessment of Functional Ability. Activities of daily living were also assessed at baseline and regular monthly intervals during the 24-week treatment period in the same study population of actigraphy recordings using the clinically established ADCS-ADL scale (Galasko, D., D. Bennett, M. Sano, C. Ernesto, R. Thomas, M. Grundman and S. Ferris (1997). "An inventory to assess activities of daily living for clinical trials in Alzheimer's disease. The Alzheimer's Disease Cooperative Study." Alzheimer Dis Assoc Disord 11 Suppl 2: S33-39. The ADCS-ADL assesses the competence of AD patients in basic and instrumental activities of daily living. The assessments were by a caregiver in questionnaire format or administered by a healthcare professional as a structured interview with the caregiver. The six basic ADL items cover everyday activities, such as eating, personal grooming or dressing, also providing information on level of competence. The 16 instrumental ADL items ask the level of patient's engagement with basic instruments, such as a phone or kitchen appliances. ADCS-ADL has been a critical instrument to standardize assessment in AD clinical trials and is used widely as a functional outcome measures in disease modifying trials.

Assessment Cognitive Function. Subject cognitive function was assessed by the Mini-Mental State Exam (MMSE), which is a widely used instrument of cognitive function in AD patients, it tests patients' orientation, attention, memory, language, and visual-spatial skills.

Statistics. All statistical comparisons were done using Kolmogorov-Smirnov test.

Results

This interim analysis reports results on 22 mild-to-moderate AD subjects who successfully completed the 6-month study. Demographic and clinical characteristics of all patients during the initial assessment are shown in TABLE 3.

TABLE 3

Demographic and Clinical Characteristics of all Patients During the Initial Assessment

| Characteristic | Treatment Group (N = 14) | Sham Group (N = 8) |
|---|---|---|
| Demographics | | |
| Age in years, mean ± sd | 66.5 ± 8.0 | 73.5 ± 6.6 |
| Gender, no (%) | | |
| Female | 10 (71) | 5 (63) |
| Male | 4 (29) | 3 (37) |
| Race and Ethnicity, no (%) | | |
| White | 14 (100) | 8 (100) |
| Hispanic or Latino | 1 (7) | 0 (0) |
| APOE-ε4 Allele Status, no (%) | | |
| 0 copies | 5 (36) | 3 (37.5) |
| 1 copy | 8 (57) | 4 (50) |
| 2 copies | 1 (7) | 1 (12.5) |

TABLE 3-continued

Demographic and Clinical Characteristics of all Patients During the Initial Assessment

| Characteristic | Treatment Group (N = 14) | Sham Group (N = 8) |
|---|---|---|
| Cognitive Assessment | | |
| MMSE score†, mean ± sd | 19.9 ± 2.8 | 18.5 ± 2.7 |
| Functional Assessment | | |
| ADCS-ADL score‡, mean ± sd | 61.7 ± 9.2 | 65.0 ± 10.4 |

†Mini-Mental State Examination (MMSE) scores range between 0-30, higher scores indicating better cognitive performance.

‡Alzheimer's Disease Cooperative Study - Activities of Daily Living (ADCS-ADL) scores range between 0-78, higher scores indicating better functioning.

Data on Safety & Adherence

Figure 38:
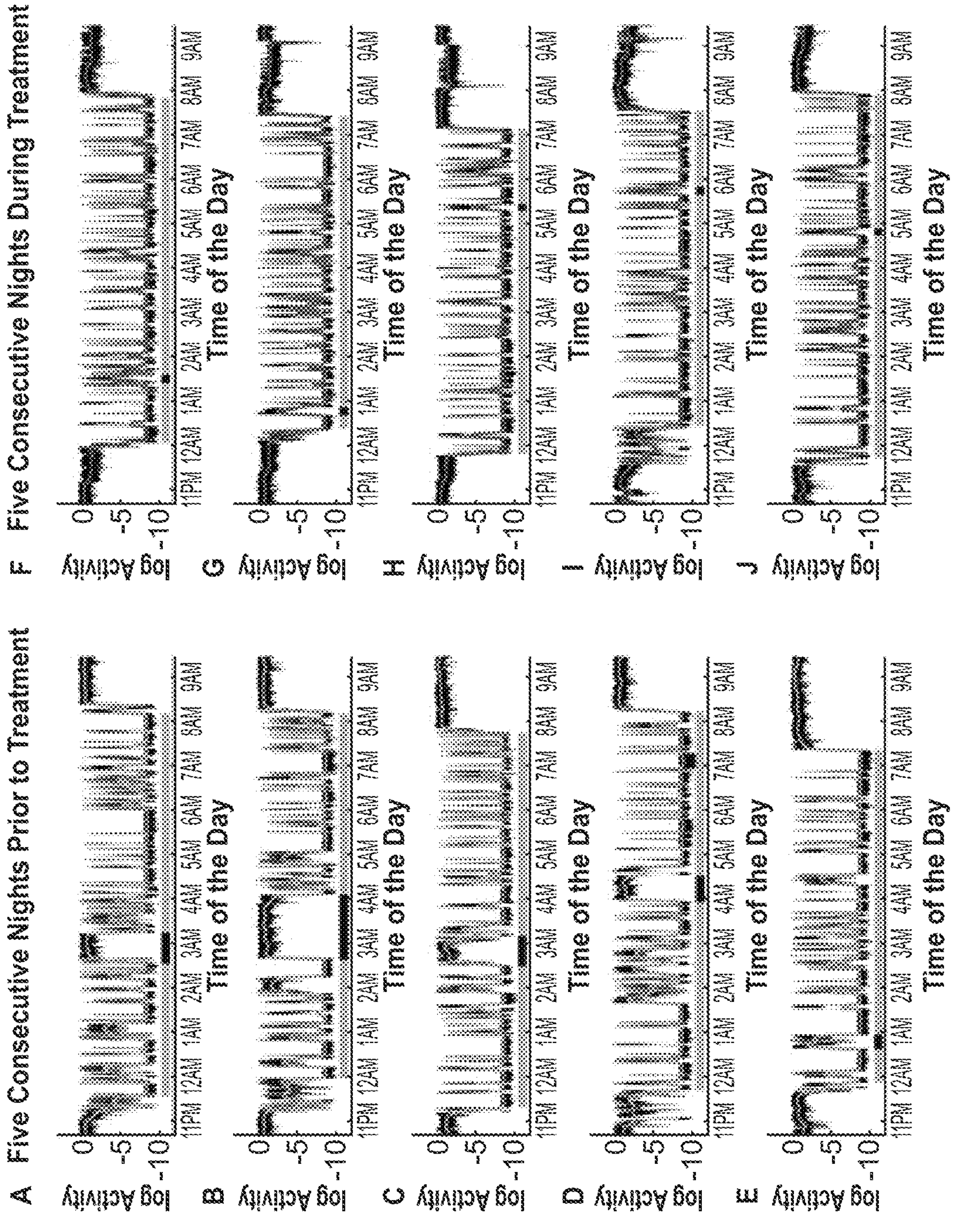
FIG. 38 provides sample actigraphy recordings from a single patient, said sample actigraphy recording demonstrating the effect of gamma stimulation therapy on sleep through recordings taken five consecutive nights prior to treatment, and five consecutive nights following treatment. The dark gray, horizontal bars below the X axis indicate continuous activity periods, with the continuous activity periods appearing significantly higher in the actigraphy recordings taken prior to treatment than the actigraphy recordings taken following treatment.
Figure 39:
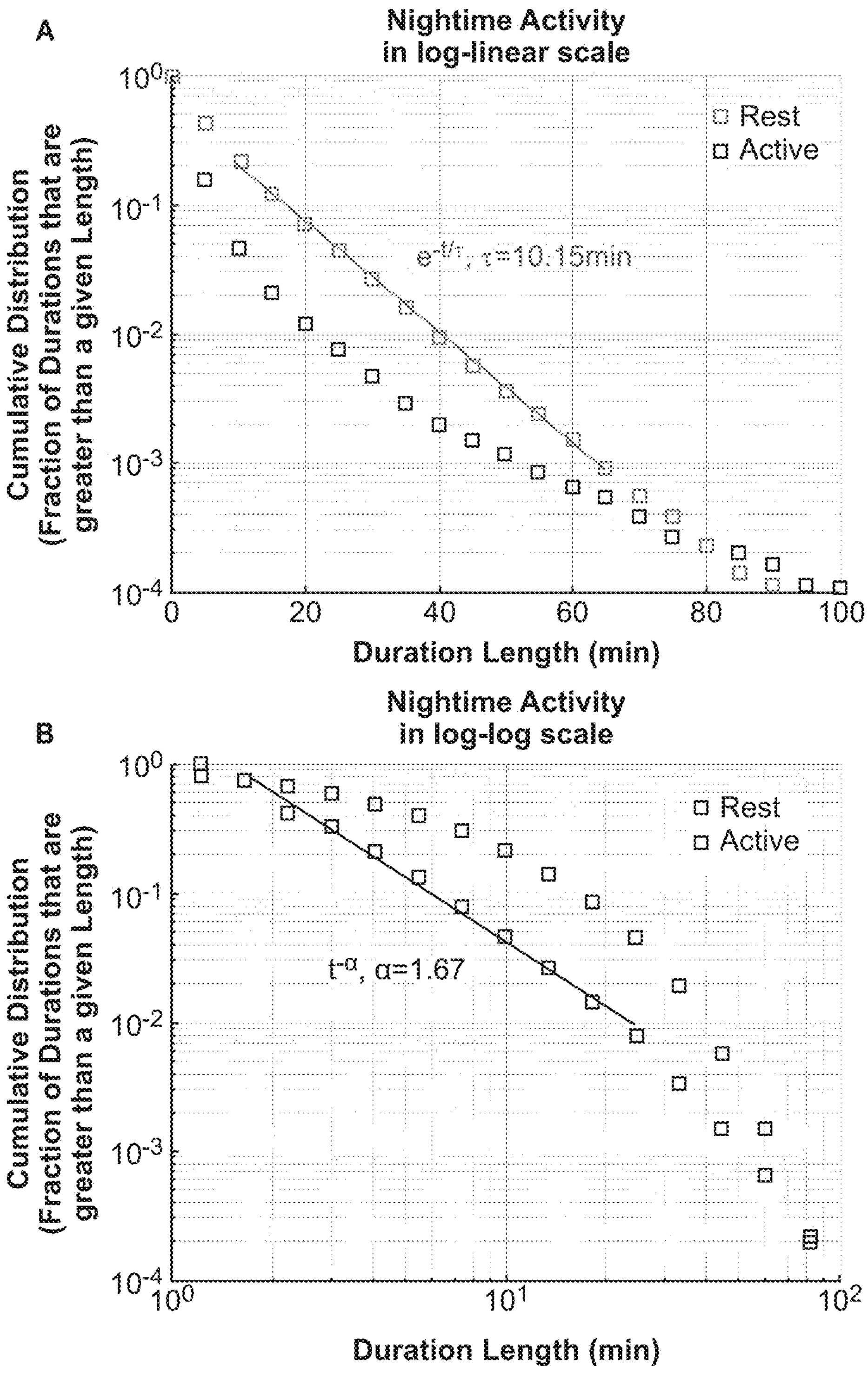
FIG. 39 provides a cumulative distribution of rest and active durations in nighttime based on data pooled from all participants. The black squares indicate active periods, and the gray squares indicate rest periods. Panel A of FIG. 39 shows the cumulative distribution using a log-linear scale, and Panel B of FIG. 39 shows the cumulative distribution using a log-log scale.

Sleep Evaluated by Continuous Actigraphy Recordings. Outcomes from the NSS treatment on sleep were revealed from continually recorded actigraphy data and constructing a nighttime sleep model, which allowed to assess the durations of rest and active periods during sleep. Results from this analysis of a single patient are shown in FIG. 38. FIG. 38 demonstrate nighttime active and rest periods; the level of continuous activity is determined and indicated by the black tracing. Furthermore, intervals were identified as sleep for each night (represented by horizontal light gray bars), and the longest movement periods are indicated by the dark gray bars. All rest and active durations identified by actigraphy data processing were pulled and analyzed from each participant as described in Methods section, and the results were compared to published data of rest and active periods obtained by polysomnography-based sleep analysis. As evidenced by straight-line fits on a log-linear scale, the rest durations follow an exponential distribution, $e\hat{}(-t/\tau)$ with t=10.15 min. In contrast, active durations follow power law distribution (straight-line fit on a log-log scale), $t\hat{}(-\alpha)$ with $\alpha$=1.67 (FIG. 39). As demonstrated by FIG. 39, the cumulative distributions for pooled, nighttime, rest (gray) and active (black) durations show exponential and power law distributions, respectively. The X axes of FIG. 39 show the nighttime durations. The Y axes show the cumulative distributions obtained from 14736 hours of data from 23 patients and the solid lines show the best straight-line fits. Such exponential and power law behaviors have been observed in sleep studies of healthy subjects (Lo, C. C., N. A. L.A., S. Havlin, P. C. Ivanov, T. Penzel, J. H. Peter and H. E. Stanley (2002). "Dynamics of Sleep-Wake Transitions During Sleep." Europhys. Lett. 57 (5): 625-631; Lo, C. C., T. Chou, T. Penzel, T. E. Scammell, R. E. Strecker, H.-E. Stanley and P. C. Ivanov (2004). "Common scale-invariant patterns of sleep-wake transitions across mammalian species." PNAS 101 (50): 17545-17548; Lo, C. C., R. P. Bartsch and P. C. Ivanov (2013). "Asymmetry and Basic Pathways in Sleep-Stage Transitions." Europhys Lett 102 (1): 10008.). These authors analyzed nighttime sleep and awake states as obtained from polysomnographic recordings of healthy subjects and found that cumulative distribution of sleep state durations is characterized by an exponential distribution whereas those of awake state durations were characterized with a power law distribution. Thus, the exponential decay constant as $\tau$=10.9 min for light sleep, $\tau$=12.3 min for deep sleep, $\tau$=9.9 min for REM sleep durations and the power law exponent as $\alpha$=1.1 for awake durations were reported (Lo, Bartsch et al. 2013). It was found that the nighttime rest and active durations, estimated from actigraphy recordings of Alzheimer's disease patients show the same behavior as polysomnographic recordings of healthy subjects. Similarities in the form of the distributions between the results of the experiments described herein and previous work suggest that nighttime rest and active durations as assessed by actigraphy are analogous to sleep and awake states as assessed by polysomnography and that the effect of therapy on sleep may be indirectly assessed through its effect on active and rest durations.

Effects of NSS Treatment on Sleep Quality Determined by Continuous Actigraphy Recordings. Effects of NSS treatment on sleep were determined by comparing the distribution of the length of nighttime uninterrupted rest durations in the first and the second 12-week periods of the study (FIG. 40). Only subjects who wore the actigraphy device for at least six weeks during both the first and last 12-week period were used for assessing efficacy of NSS treatment on sleep (N=7 Treatment, N=6 Sham). To avoid subjects with more data dominating comparisons across periods, the first six weeks of available data closest to the study start and the last six weeks closest to the study end were considered for each subject. Actigraphy recordings from a single patient in the treatment group are shown in FIG. 38, displaying during 5 subsequent nights prior and during treatment period. The X-axis of FIG. 38 shows the time of day, and the Y-axis shows the activity level (in log scale). The black tracings represent the continuous activity levels and the light gray horizontal bars represent the intervals identified as sleep in each night. The dark gray horizontal bars represent the longest movement periods within each night. The letters A through E correspond to five consecutive nights prior to treatment. The imposed curve shows a smooth (median filtered) activity level, with long movement intervals observed. Letters F through J correspond to five consecutive nights during treatment period. The imposed curve shows a smooth (median filtered) activity level. Compared to the pre-treatment period, patient showed fewer and shorter movement periods during treatment. In overall, nighttime active durations were significantly ($p<0.03$) reduced in the treatment group, whereas active durations were significantly ($p<0.03$) increased in patients of the sham group. Comparison of between treatment and sham groups were also done using normalized nighttime active durations. This normalization is done by dividing each active duration by the duration of the corresponding nighttime period. This measure eliminates potential variation in length of total sleep duration impacting numbers or durations of active periods. This analysis further confirmed opposite changes in nighttime active durations between treatment and sham groups. Changes in normalized active periods between the first and second 12-weeks period showed a significant ($p<0.001$) reduction in patients of the treatment group, in contrast to a significant increase ($p<0.001$) in patients of the sham group (FIG. 40). These findings demonstrate a reduction in nighttime active durations in response to NSS treatment, leading to reduction in sleep fragmentation and improvement in sleep quality, while the opposite can be assessed in the sham group.

Effects of NSS Treatment on Sleep Quality Determined by Continuous Actigraphy Recordings. MMSE changes were different in the treatment (n=13) and sham (n=8) groups. Initial assessment showed an MMSE value of 19.9±2.9, which did not change significantly during the duration of the treatment, showing an MMSE value of 19.3±3.4, measured at week 24. In contrast, the sham group showed the expected a significant decline in MMSE scored: initial score of 18.5±2.7 dropped to 16.8±5.7 ($p<0.05$).

Figure 41:
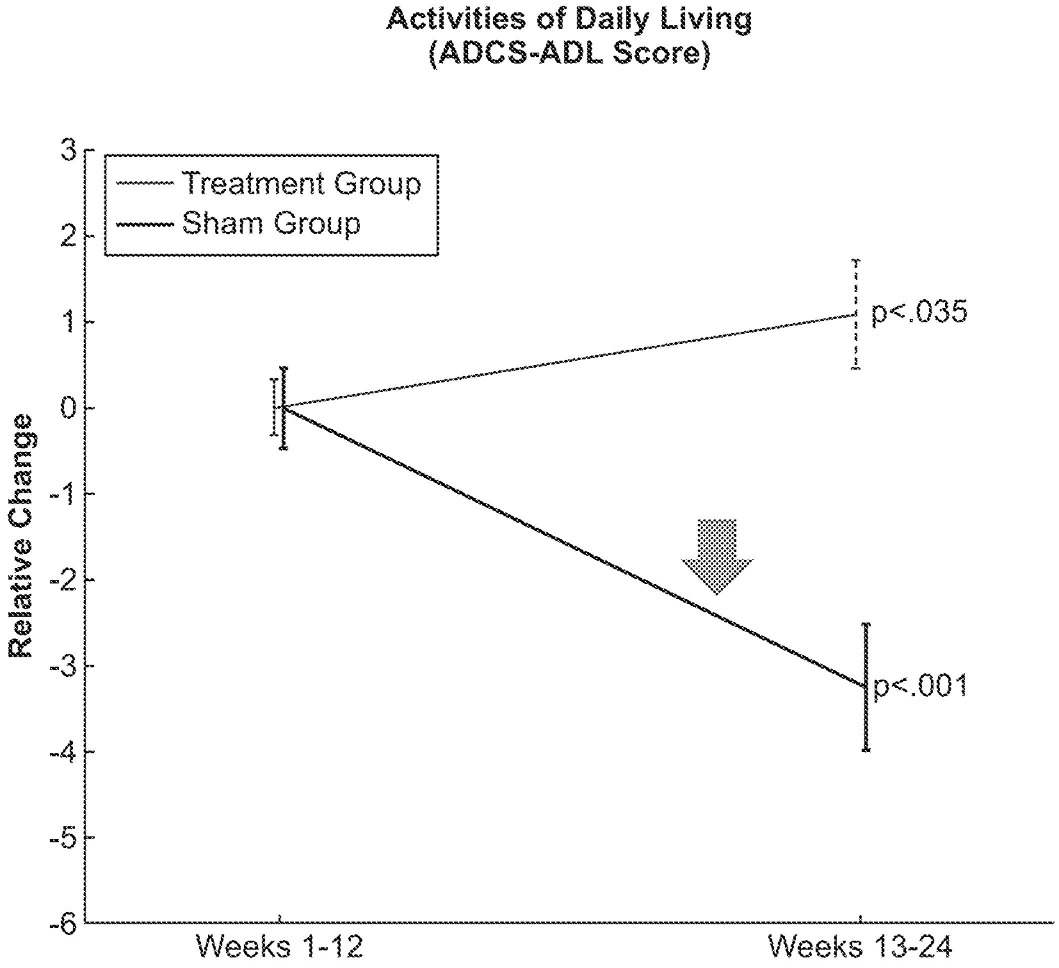
FIG. 41 shows the effect of gamma stimulation therapy on maintenance of daytime activities, as assessed by Activities of Daily Living (ADCS-ADL) scope. The graph shows that changes in daytime activities significantly improved in the treatment group and declined in the sham group. The X-axis compares the period from Week 1-12 and the period from Week 13-24. The Y-axis demonstrates the change in ADCS-ADL score during Weeks 13-24 relative to Weeks 1-12.
Figure 42:
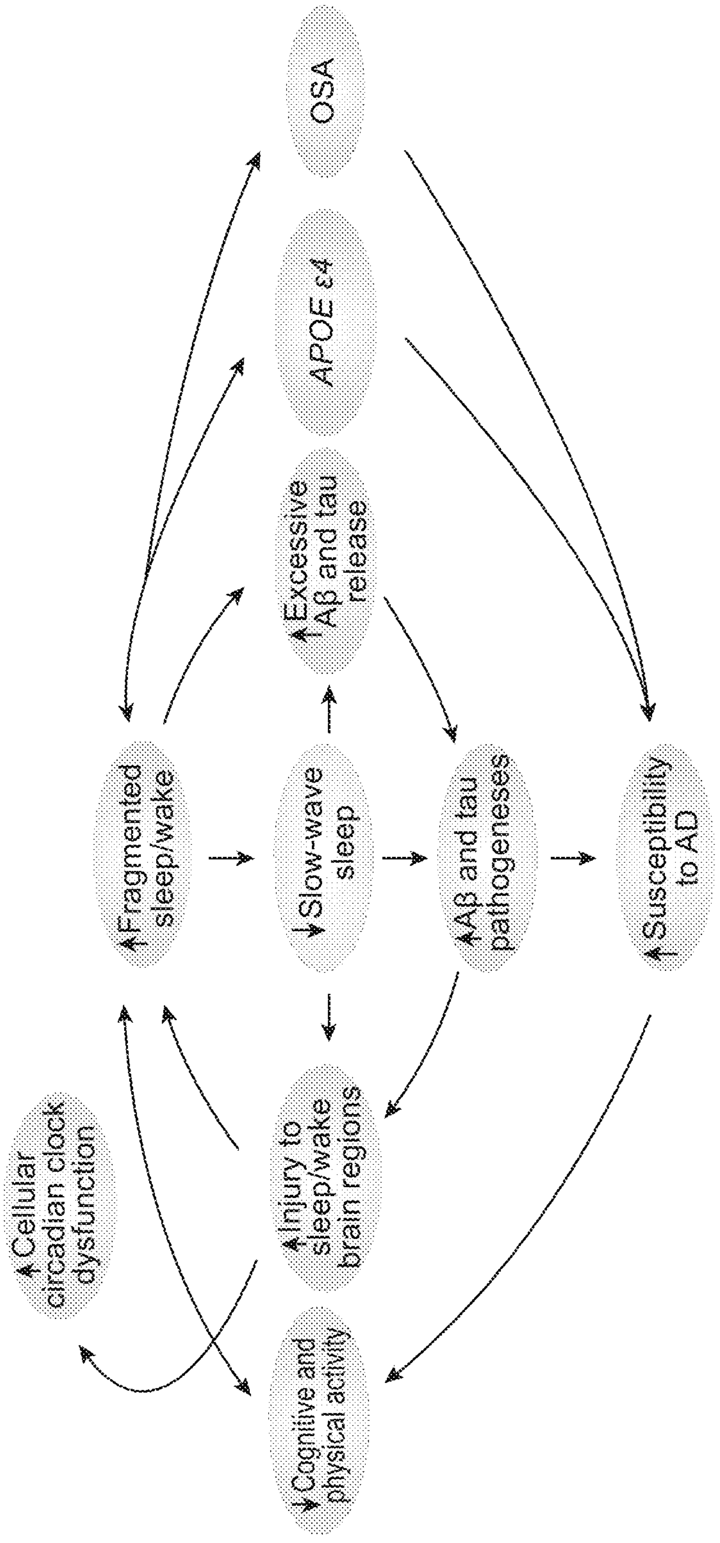
FIG. 42 provides a flow chart demonstrating the proposed relationship between Alzheimer's disease and sleep dysfunction. This was adapted from Wang, C. and D. M. Holtzman (2020). "Bidirectional relationship between sleep and Alzheimer's disease: role of amyloid, tau, and other factors." Neuropsychopharmacology 45 (1): 104-120.
Figure 43:
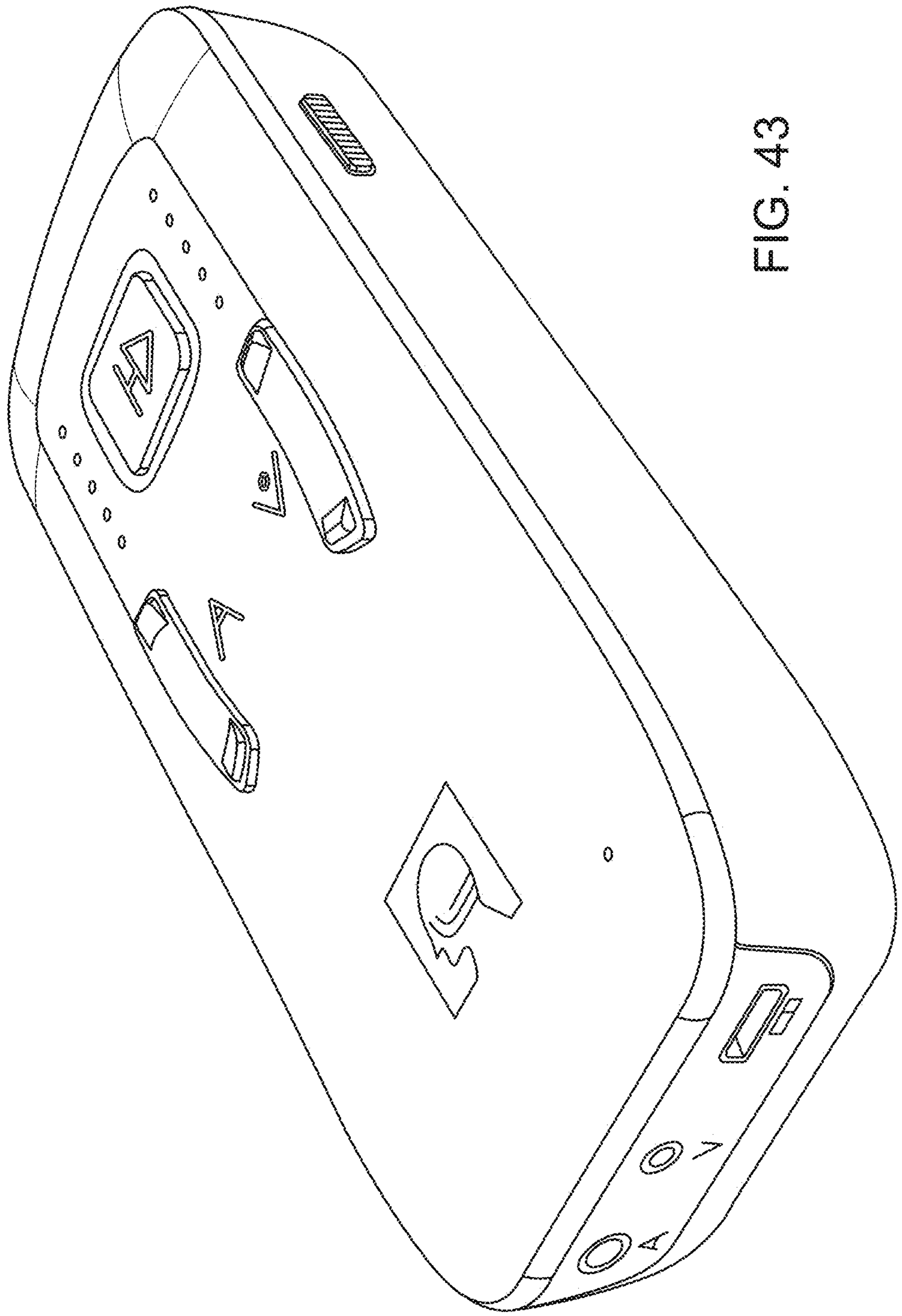
FIG. 43 provides an exemplary embodiment of a handheld controller for adjusting parameters of the stimulus delivered by an operably coupled stimulus apparatus.

Maintenance of Functional Ability Assessed by ADCS-ADL. Effects of NSS treatment on patients' the ability to perform activities of daily living were assessed at baseline and regular monthly intervals during the 24-week treatment period using the clinically proven ADCS-ADL scale via structured interview with care partner. Average ADCS-ADL scores were calculated from the first 12-week and second 12-week periods in both treatment (n=14) and sham (n=8) groups (FIG. 41). The ADCS-ADL is a well-established instrument for testing function of mild to moderate AD patients, and numerous clinical trials have reported a significant decline in the ADCS-ADL scores in this patient population over a 6-month period (Loy, C. and L. Schneider (2006). "Galantamine for Alzheimer's disease and mild cognitive impairment." Cochrane Database Syst Rev (1): CD001747; Peskind, E. R., S. G. Potkin, N. Pomara, B. R. Ott, S. M. Graham, J. T. Olin and S. McDonald (2006). "Memantine treatment in mild to moderate Alzheimer disease: a 24-week randomized, controlled trial." Am J Geriatr Psychiatry 14 (8): 704-715). In our study, each patient in the sham group showed a decline in ADCS-ADL scores, resulting in this patient group significant ($p<0.001$), approximately 3 points decline over the trail period. In contrast, 9 out of 14 patients in the treatment group maintained or even showed improvement in their ADCS-ADL scores. Therefore, the average ADSC-ADL score in the treatment group significantly ($p<0.035$) increased during the treatment period. Accordingly, FIG. 41 demonstrates that changes in daytime activities showed a significant improvement in the treatment group and a significant decline in the sham group.

Discussion

This interim analysis of the Overture trial (NCT03556280) demonstrates a beneficial outcome of daily use of the NSS therapy over a six-month period in mild to moderate AD patients: NSS treatment resulted in improved sleep quality and maintained quality of daily living as compared to subjects in the control arm of the study.

Results, based on the collected actigraphy data over a 6-month period, demonstrate that NSS therapy can reduce sleep fragmentation, leading to significantly reduced active periods during night in mild to moderate AD patients. In contrast, patients in the sham group did not show improvement in sleep characteristics. Given the well-recognized architecture of human physiological sleep, consisting subsequent periods of different NREM stages starting from superficial to deep slow wave sleep and REM sleep period in a strictly subsequent order, it is obvious that sleep fragmentation can dramatically disrupts sleep architecture and consequently effectiveness of sleep. Sleep fragmentation, as a symptom of sleep disorders have multiple impact on human physiology, including dysfunction not only in the nervous system, but also overall health by impairing body metabolism or immune defense system. Nevertheless, decremental cognitive impacts of sleep abnormalities are particularly worrisome in MCI and AD patients. Therefore, application of NSS therapy offers novel intervention for in AD patients for improving sleep quality. Available clinical data revealed that this therapy is safe and can be applied daily in an extended period of time in patients. Considering that sleep disorders are contributing to impaired function and cognition, effective treatments for improving sleep quality potentially have multiple benefits in MCI and AD patients.

The clinical benefits of NSS therapy on sleep is particularly relevant, since pathomechanisms underlying sleep dysfunction in MCI and AD patients are not well understood, therefore developing specific sleep therapies are not feasible currently. AD-related pathological proteins, such as Aβ- and tau-oligomers are known to disrupt sleep, though their mode of action is unknown. From an early stage of the disease brainstem ascending neurons considered to play in role in sleep-wake regulation, including cholinergic, serotoninergic and norepinephrine neurons show profound degeneration (Smith, M. T., C. S. McCrae, J. Cheung, J. L. Martin, C. G. Harrod, J. L. Heald and K. A. Carden (2018). "Use of Actigraphy for the Evaluation of Sleep Disorders and Circadian Rhythm Sleep-Wake Disorders: An American Academy of Sleep Medicine Systematic Review, Meta-Analysis, and GRADE Assessment." J Clin Sleep Med 14 (7): 1209-1230; Tiepolt, S., M. Patt, G. Aghakhanyan, P. M. Meyer, S. Hesse, H. Barthel and O. Sabri (2019). "Current radiotracers to image neurodegenerative diseases." EJNMMI Radiopharm Chem 4 (1): 17; Kang, S. S., X. Liu, E. H. Ahn, J. Xiang, F. P. Manfredsson, X. Yang, H. R. Luo, L. C. Liles, D. Weinshenker and K. Ye (2020). "Norepinephrine metabolite DOPEGAL activates AEP and pathological Tau aggregation in locus coeruleus." The Journal of Clinical Investigation 130 (1): 422-437). Similarly, suprachiasmatic nucleus containing neurons playing the key role in regulating circadian rhythms also shows neurodegeneration early in the disease Van Erum, J., D. Van Dam and P. P. De Deyn (2018). "Sleep and Alzheimer's disease: A pivotal role for the suprachiasmatic nucleus." Sleep Med Rev 40:17-27). There are only limited treatment options for sleep abnormalities in MCI and AD patients, and pharmacological treatments currently include antidepressant, antihistamines, anxiolytics, and sedative-hypnotic drugs such as benzodiazepines (Vitiello, M. V. and S. Borson (2001). "Sleep disturbances in patients with Alzheimer's disease: epidemiology, pathophysiology and treatment." CNS Drugs 15 (10): 777-796; Deschenes, C. L. and S. M. McCurry (2009). "Current treatments for sleep disturbances in individuals with dementia." Curr Psychiatry Rep 11 (1): 20-26; Ooms, S. and Y. E. Ju (2016). "Treatment of Sleep Disorders in Dementia." Curr Treat Options Neurol 18 (9): 40). Some of the most frequently used anxiolytics/sedative-hypnotic drugs in the general clinical practice are GABAA positive allosteric modulators, which are contraindicated in MCI and AD patients due to their negative effects on cognitive function, interference with motor behavior and addiction-forming profile. Recently, suvorexant, an orexin receptor antagonist has been approved as a sleep medication for AD patients having clinically diagnosed insomnia. The main effects of suvorexant are a prolonged total sleep time and delayed wake after sleep onset, without impacting sleep fragmentation or altering sleep architecture (Herring, W. J., P. Ceesay, E. Snyder, D. Bliwise, K. Budd, J. Hutzelmann, J. Stevens, C. Lines and D. Michelson (2020). "Polysomnographic assessment of suvorexant in patients with probable Alzheimer's disease dementia and insomnia: a randomized trial." Alzheimers Dement 16 (3): 541-551). Non-pharmacological treatments include behavioral measures such as sleep hygiene education, exercise regimens, and reduction of noise during sleeping hours. Bright light therapy is one of the non-pharmacologic modalities that offers recommendations from the American Academy of Sleep Medicine for use in sleep disturbances due to circadian disorders. Clinical tests of light therapy in AD patients resulted in conflicting findings (Ouslander, J.G., Connell, B.R., Bliwise, D.L., Endeshaw, Y., Griffiths, P. and Schnelle, J.F. (2006). "A Nonpharmacological Intervention to Improve Sleep in Nursing Home Patients: Results of a Controlled Clinical Trial." Journal of the American Geriatrics Society. 54:38-47; Deschenes et al., 2009), and currently no approved device or therapeutic intervention exists.

The current findings demonstrate a beneficial effect of NSS therapy in mild to moderate AD patients, prolonging nighttime undisturbed restful periods, indicating a reduced sleep fragmentation. There are no proved therapies for reducing sleep fragmentation which could improve sleep quality in MCI or AD patients, and frequently used sedative-hypnotic drugs are decremental on the physiological architecture of sleep. Having monthly interviews with patients and caregivers about everyday activities and sleep habits, there was not an indication that NSS treatment leads to daytime sleepiness or grogginess, which are typical side effects of most sleep medication, including the orexin receptor antagonist suvorexant. Furthermore, in the present trial clinically diagnosed sleep abnormality such as insomnia has not been a requirement, consequently beneficial effects of NSS treatment are not limited to AD patients suffering from clinically recognized sleep problems.

The present findings demonstrate that NSS treatment not only improves sleep quality but also helps to maintain functional ability reflected in activity of daily living in mild to moderate AD patients. Although some pharmacological treatments, such as the acetylcholine esterase inhibitor donepezil, delay decline in activity of daily living, currently there are no approved non-pharmacological therapies achieving this effect. Based on scientific and clinical observations demonstrating a close relationship between sleep quality and activity of daily living, it can be presumed that improving sleep quality in AD patients would provide multiple benefits: better sleep will enhance patients' daytime performance, including cognitive function, and reduce daytime sleepiness. In line with this hypothesis, patients on NSS treatment maintained functional activity as reflected by their unchanged ADSC-ADL score over the six-month treatment period. In contrast, ADSC scores of sham group patients dropped similarly to changes of placebo group patients in clinical trials (Doody, R. S., R. Raman, M. Farlow, T. Iwatsubo, B. Vellas, S. Joffe, K. Kieburtz, F. He, X. Sun, R. G. Thomas, P. S. Aisen, C. Alzheimer's Disease Cooperative Study Steering, E. Siemers, G. Sethuraman, R. Mohs and G. Semagacestat Study (2013). "A phase 3 trial of semagacestat for treatment of Alzheimer's disease." N Engl J Med 369 (4): 341-350; Doody, R. S., R. G. Thomas, M. Farlow, T. Iwatsubo, B. Vellas, S. Joffe, K. Kieburtz, R. Raman, X. Sun, P. S. Aisen, E. Siemers, H. Liu-Seifert, R. Mohs, C. Alzheimer's Disease Cooperative Study Steering and G. Solanezumab Study (2014). "Phase 3 trials of solanezumab for mild-to-moderate Alzheimer's disease." N Engl J Med 370 (4): 311-321). Even though the close relationship between sleep and daily activity is well documented, it is unknown at present whether improved sleep quality is the main factor contributing to the maintenance of ADSC-ADL scores in NSS treated patients, or improvement in sleep and continuation of functional ability are unrelated positive outcomes from the therapy.

Currently, the underlying mechanisms of improved sleep and maintained functional ability of AD patients in response to GSS treatment are not known. Preclinical studies indicate that 40 Hz sensory stimulation reverses Aβ and tau pathologies leading to improved cognitive function in transgenic mice (Iaccarino, Singer et al. 2016; Adaikkan, C., S. J. Middleton, A. Marco, P. C. Pao, H. Mathys, D. N. Kim, F. Gao, J. Z. Young, H. J. Suk, E. S. Boyden, T. J. McHugh and L. H. Tsai (2019). "Gamma Entrainment Binds Higher-Order Brain Regions and Offers Neuroprotection." Neuron 102 (5): 929-943 e928; Martorell, Paulson et al. 2019). Although human AD-related biomarker studies are in progress, at the moment it is unknown if the same biochemical and neuroimmunology mechanisms are activated in AD patients as identified in mice. The bidirectional interaction between sleep and disease progression (Wang and Holtzman 2020) supports the notion that improved sleep in response to GSS treatment could also slow down disease progression.

Conclusion

The present study's findings indicate that NSS treatment helps maintain everyday activity and quality of life of AD patients. Since measurements of both sleep fragmentation and ADCS-ADL were determined in the same patient cohort, the datas suggest a positive treatment effect of maintaining ability to complete daily activities in patients having improved sleep quality. NSS treatment consists of a non-invasive sensory stimulation; with exceptional safety profile, its long-term, chronic application is feasible. Expanded and longer trials will uncover additional clinical benefits and potentially disease-modifying properties of NSS treatment.

Example 3. Randomized Controlled Trial with Greater Amount of Participants

Background

An additional randomized controlled trial was performed, with patients maintaining the same methods and inclusion criteria as the interim analysis of the trial disclosed herein, in EXAMPLE 2. This trial involved a greater number of participants than that which was subject to the interim analysis.

Methods

Patients with mild-to-moderate AD (MMSE 14-26, inclusive; n-74) were randomized to receive either 40 Hz non-invasive audio-visual stimulation or sham stimulation over a 6-month period. Functional abilities of patients were measured by Alzheimer's Disease Cooperative Study-Activities of Daily Living (ADCS-ADL) scale at baseline and every four weeks during the study and follow-up period. Sleep quality was assessed from nighttime activities of a subgroup of patients (n=7 in treatment, n=6 in sham groups) who were monitored continuously via a wrist worn actigraphy watch throughout the 6-month period.

Results

The sham group contained 19 patients, and the treatment group contained 33 patients. Adjusted ADCS-ADL scores from beginning and the end of the trial were compared in patients who completed the trial. Over the 6-month period, patients in the sham group (n=19) showed the expected decline, a 5.40-point drop in ADCS-ADL scores, whereas patients in the treatment group (n=33) receiving therapy exhibited only a 0.57-point decline. Changes in ADCS-ADL scores were statistically significant between the sham and treatment groups (P<0.01). Nighttime active durations in the treatment group were significantly (p<0.03) reduced in the second 3 months compared to the first 3-months but such durations increased in the sham group. To evaluate the impact on active durations, normalization is done by dividing duration of each active period by the duration of the matching entire nighttime period. Analysis of normalized active durations by the corresponding nighttime period of each patient further confirmed opposite changes in nighttime active durations between treatment and sham groups (p<0.001), with the treatment group experiencing reduced nighttime active durations, and the sham group experiencing increased nighttime active durations.

Conclusion

This trial confirmed that patients in gamma stimulation therapy maintained their activities of daily living and showed an improved sleep quality over a 6-month treatment period; two outcome measures, functional ability and sleep quality known to be strongly linked in AD. Maintenance of functional ability represents an important treatment and management goal for AD patients, reducing formal and informal care, and delaying time to institutionalization.

Example 4. Randomized Controlled Trial to Evaluate Impact on a Non-Patient Population Background Participants will be recruited using social media advertisements and selected randomly. Criteria will simply include willingness and availability to participate in a six month trial. Information will be collected on each individual to generate a profile associated with the individual.

Methods

Participants will be recruited using social media advertisements and selected randomly. Criteria will simply include willingness and availability to participate in a six-month trial. Information will be collected on each individual to generate a profile associated with the individual.

Participants will be randomized into two groups, with a 2:1 ratio of treatment group to control group. Within the treatment group, subjects will remain blinded and receive a neural stimulation orchestration system device which outputs sensory stimulation at a 40 Hz frequency. Within the control group, subjects will remain blinded and receive a neural stimulation orchestration system device which outputs sensory stimulation at a random distribution of time around a mean of 35 Hz. Throughout the study, subjects will wear actigraphy watches. These watches will monitor any sleep fragmentation or disturbances experienced by a participant. Cognitive tests, or assessments, will be performed on each subject before neural stimulation orchestration devices are distributed to establish a baseline. These tests will be repeated on bimonthly basis, and the study will conclude after six months. Each assessment is of general cognitive functions, which pertain to both healthy individuals and individuals that have experienced or are at risk of experiencing cognitive deficits, including clinical patient populations. Such suitable tests include those that test any specific functions of a range of cognitions in cognitive or behavioral studies, including tests for perceptive abilities, reaction and other motor functions, visual acuity, long-term memory, working memory, short-term memory, logic, decision-making, and the like.

The following cognitive tests will be used: Visual Short-term memory; Spatial Working Memory; N-back; Stroop Task; Attention Blink; Task Switch; Trials A&B; Flanker Task; Visual Search Task; Perceptual Motor Speed; Basic Processing Speed; Digit Span. These tests are described as follows:

Visual Short-term memory (VSTM). In the visual short-term memory task, individuals are briefly presented with four color patches presented at the center of the screen and are asked to remember the colors. Following a short delay, a single color patch is shown and the individual is asked whether the color was one of those presented or not. For example, on a given trial an individual can be briefly presented with color patches in blue, red, green and yellow and asked to remember them. If they were then shown the color purple, they would respond no match because the color purple was not in the presented and remembered set. This test measures the ability to remember visual information in the short-term.

Spatial Working Memory (SPWM). In the spatial working memory task, one to three objects are briefly flashed on the screen and then disappear, and individuals are asked to remember the locations of each of the objects. After a brief delay, a single object appears on the screen and the participant responds to whether or not the object is in the same location as one of the objects being remembered. This task measures the ability to remember visuospatial information in the short-term.

N-back. In the N-back task individuals are presented with a continuous stream of letters at the center of the screen and are asked to respond whether the letter presented on the current trial matches the one presented on the previous trial. For example, an individual can see the letter W followed by the letter S, and then would be asked to respond to whether the W and S match identity or not. This test measures how well participants can hold and manipulate information in short-term memory. In another version of this task, individuals are presented with a continuous stream of letters at the center of the screen and are asked to respond whether the letter presented on the current trial matches the one presented two trials ago.

Stroop Task. In the Stroop task individuals are asked to name the color of a written word presented at the center of the screen as quickly as possible. The word can either be a color-word (e.g., the word red written in either green or red) or a non-color word (e.g., the word cat written in red). The ability to focus attention is assessed by seeing how much an incorrect color/word combination (e.g., the word red written in green) slows an individual's reaction time. This task provides a measure of how well an individual can control attention and executive function processes.

Attention Blink. In the Attentional Blink task an individual views a stream of letters presented rapidly at the center of the screen and is asked to search the stream for either one or two pre-defined target letters. On trials in which there are two targets, detecting the first target interferes with the ability of an individual to detect the second target, and the extent of this interference is used to assess attention function.

Task Switch. In the task-switch task, individuals see a digit (e.g., 1-10) at the center of the screen, and the digit appears on a color patch. Depending on the color of the patch, the individual has to respond to either the parity (e.g., high vs. low) of the number or whether the number is odd or even. Importantly, on each trial the color patch is either the same color as the previous trial, resulting in participants performing the same task from trial to trial, or a different color than the previous trial, resulting in a switch in the task. For example, on a given trial an observer can see the number two on a pink color patch. On this trial, the individual would perform the parity judgment task. On the following trial, if the color patch stays the same the individual would continue to perform the parity task. However, if the color patch changes color, this signals that the individual should switch and perform the odd/even task on this trial. This task measures the ability to rapidly switch tasks, a subset of executive function.

Trails A&B. In the Trails task, individuals are to connect dots in sequence as quickly as possible using their finger. In trails A, individuals are asked to connect dots 120 in sequence. In trails B, individuals are asked to connect many more dots or dots 110 and A-J in sequence, alternating between numbers and letters. This test measures how quickly individuals can search for and sequentially process information from the within a category (Trails A) or between categories (Trails B). The Trails test measures of attention and executive function.

Flanker Task. In the flanker task, individuals are presented with a display containing several objects. One of the objects, the target, is always presented at the center of the screen, and participants are asked to identify which of two target types the item is. The target is flanked on both sides by distractor objects that are either identical to the target on a given trial or not. For example, participants can view a display containing multiple arrows. One arrow, the target, will be presented at the center of the screen and participants' task is to report whether the arrow is pointing to the left or to the right. This arrow is surrounded on both sides by arrows that are pointing in either the same or different directions. This task assesses how well individuals can focus attention on relevant and ignore irrelevant visual information, providing a measure of attention and executive function.

Visual Search Task. In the Visual Search Task, individuals are presented with an array of objects and are asked to find a target object as quickly as possible. For example, an individual can be told to search for a particular color box with a gap in the top or bottom, and report the location (top or bottom) of the gap. This task assesses how quickly an individual can find and identify basic visual information, a subset of attention function.

Perceptual Motor Speed (PMS). In this task, individuals are presented with a schematic face and are asked to press a button as soon as possible in response to a happy face, and withhold their response to a sad face. The ability to withhold a response to sad faces provides a measure of executive function, and the speed with which responses to happy faces are made provides a measure of processing speed.

Basic Processing Speed. In this task, individuals monitor a blank screen, and after a variable delay a small circle appears at the center of the screen. Participants are asked to press a button as quickly as possible when they see the circle appear. This task measures basic visual processing speed.

Digit Span. In this task observers see strings of two to eight numbers, and are asked to remember their identities and their order. After the strings are removed from the screen, participants need to type as many of the numbers as they can remember. This test provides a measure of verbal short-term memory.

Participants will be given a list of activities to participate in. Each activity will involve a different type of cognitive processing. All study participants will be divided into six groups, with each group comprising an equal amount of control and treatment group members. Each participant will be instructed to reflect on their performance during each activity and record any observations in a journal. Participants will also be asked to record information about their sleep quality, mood, and energy levels in this journal.

The neural stimulation system will provide visual stimulation for one hour per use. One group will use the neurostimulation system for one hour prior to engaging in a selected group of activities, a second group will use the neurostimulation system during engagement in the selected group of activities, and a third group will use the neurostimulation system before, during, and after engaging in the selected group of activities. The fourth group will use the neurostimulation system both during and prior to engaging in the selected group of activities. The fifth group will use the system both prior to engaging in the activities and after engaging in the activities. The sixth group will use the system during and after engaging in the activities.

The impact of the stimulation on a particular group of activities will be measured by participants' self-assessment journals and the results of each cognitive test-based assessment. The impact will be compared for each of the six groups. Profile information obtained in the beginning of the study for each individual will be used to inform differences or discrepancies in response within each group.

The amount of time between use of the neural stimulation system and the start or end of an activity will be held constant within each group. Groups of activities will vary each month and will be rotated so that each participant, by the end of the trial, has engaged in the same activities as the others. Some activities will simulate a learning environment, with subjects being given a definite, supervised period to learn a particular subject and then tested on their ability to recall the learned material. Other activities will involve physical movement and coordination, such as an athletic activity, while some activities will require a participant to operate a vehicle. Some activities will require little physical movement, such as rest or meditation. At the completion of the six months, each group will have participated in the same activities.

Results

Based on the benefits of gamma entrainment seen in the studies involving patients with AD, such as slowing dementia or brain atrophy and improving sleep, it is predicted that the subjects in the treatment group will experience a slight improvement in cognitive capacity. Further, it is predicted that groups receiving neurostimulation during a particular activity will demonstrate the best improvement. Statistical analysis of these results can be used to inform the policy used by the feedback monitor in determining whether to generate an output signal that causes the stimulus-emitting component of the present invention to provide gamma-inducing sensory stimulus to a subject, thereby promoting gamma oscillations.

Example 5. White Matter Atrophy and Myelination

Objectives

The present study evaluated whether gamma sensory stimulation for a 6-month period could affect white matter atrophy and myelination in patients on AD spectrum.

Methods and Materials

The neuroimaging data used in this study is collected in Cognito Therapeutics' Overture, a randomized, placebo-controlled feasibility study (NCT03556280) in patients (age of 50 years or older and Mini-Mental State Examination (MMSE) 14-26) on AD spectrum. In this study, participants in the active treatment arm received 1-hour daily, at-home, 40 Hz simultaneous auditory-visual sensory stimulation for a 6-month period while the placebo arm subjects received sham stimulation. Structural magnetic resonance imaging (MRI) data was acquired at baseline, month 3 and month 6 visits using 1.5 Tesla MRI. 38 participants (25 Treatment and 13 Placebo) who fulfilled the requirement of sufficient T1w image quality were included in the analysis. Volume assessments on multiple white matter structures were done using T1 MRI, and myelination assessments were done using T1w/T2w ratio. One treatment group and one placebo group participant were excluded from myelination analysis owing to T2w image quality. Patient characteristics at baseline are summarized in TABLE 4. Bayesian linear mixed effects modeling was used to assess the changes from baseline. Changes in white matter volume and myelination were compared between treatment group and placebo group participants after 6 months of treatment.

TABLE 4

Demographic and clinical characteristics of the treatment and the placebo group participants at baseline.

| | Treatment (n = 25) | Placebo (n = 13) | p-value |
|---|---|---|---|
| Age in years, mean ± SD | 68.36 ± 7.69 | 76.62 ± 9.97 | 0.02 |
| Sex (Male/Female) | 7(Male)/ 18(Female) | 8(Male)/ 5(Female) | 0.10 |
| MMSE score, mean ± SD | 20.64 ± 3.15 | 19.77 ± 3.27 | 0.44 |
| ADCS-ADL scale, mean ± SD | 64.88 ± 7.95 | 66.23 ± 10.83 | 0.70 |
| Number (%) of APOE ε4 positive | 13(52.00%) | 7(53.85%) | 1 |

Abbreviations: MMSE, Mini-Mental State Exam; ADCS-ADL, Alzheimer's Disease Cooperative Study—Activities of Daily Living; APOE, apolipoprotein E Therapy Device. The device used in this study is a gamma sensory stimulation device developed by Cognito Therapeutics, Inc. It consists of a handheld controller, an eye-set for visual stimulation and headphones for auditory stimulation. All the components work in synchrony to provide precisely timed non-invasive 40 Hz stimulation to evoke steady-state gamma brainwave activity. Prior to study, a physician determines the tolerable range of stimulus parameters for the participant. During the therapy, participants can also adjust the brightness of the visual stimulation and the volume of the auditory stimulation using push buttons on the controller. If assistance is needed, they can communicate with a care partner. The device captures usage information and adherence data. All the information is uploaded to a secured cloud server for remote monitoring.

MRI Data Acquisition. In Overture feasibility study, structural magnetic resonance imaging (MRI) data were acquired at Baseline, month 3 and month 6 using 1.5 Tesla MRI scanner. The study adopted a ADNI1 comparable standardized MRI scan protocol. For T1w, it included 1.25×1.25 mm in-plane spatial resolution, 1.2 mm thickness, TR 2400 ms and TE 3.65 ms for Siemens Espree scanner, 0.94×0.94 mm in-plane spatial resolution, 1.2-mm thickness, TR ~3.9 ms and TE 1.35 ms in General Electric scanner Signa HDxt and 0.94×0.94 mm in-plane spatial resolution, 1.2-mm thickness, TR 9.5 ms and TE ~3.6 or 4 ms in Philips Ingenia scanner or Philips Achieva scanner. For T2w, it included 1×1 mm in-plane spatial resolution, 4 mm thickness, TR 3000 ms and TE 96 ms for Siemens and GE scanners and 1×1 mm in-plane spatial resolution, 4 mm thickness, TR 3000 ms and TE 92 ms for Philips scanner (Jack et al. 2008).

Image Analysis. The FreeSurfer pipeline is used to process and automatically parcellate TI MRI into predefined cortical structures and segment the volume into predefined subcortical structures (Dale et al., 1999; Fischl et al., 2001; Fischl et al., 2008; Fischl et al., 2002; Fischl et al., 1999a; Fischl et al., 1999b; Ségonne et al., 2005; Desikan et al., 2006). Here, we focus on total 52 white matter structures to assess volumetric changes and evaluate myelin content.

Myelin Sensitive Imaging. A non-invasive myelin-sensitive imaging was employed by using T1w/T2w ratio to acquire a myelin-reflecting contrast (Glasser and Van Essen, 2011; Glasser et al., 2014, 2016). This process included co-registration of the T2w images to the T1w images using rigid transformation, inhomogeneity correction for both T1w and T2w images and linear calibration of image intensity using non-brain tissue masks to create T1w/T2w ratio images corresponding to myelin content (Ganzetti et al., 2014, 2015). T1w/T2w ratio was processed using MRTool (v. 1.4.3, https://www.nitrc.org/projects/mrtool/), the toolbox implemented in the SPM12 software (University College London, London, UK, http://www.fil.ion.ucl.ac.uk/spm).

Statistical Methods. Demographic and biomarker data of the treatment group participants and the placebo group participants were compared using two-sample T tests for numerical data or chi-square tests for categorical data. For efficacy analysis, a Bayesian linear mixed effects model was used to assess the changes in the volumetric data and myelination for each of the white matter structures. Fixed effects of the model include total intracranial volume, baseline MMSE score, baseline age, visit (as number of days from the start of the treatment), group, baseline MRI measures (volume for white matter atrophy assessment and sum of T1w/T2w ratio for myelination assessment), group-visit interaction and baseline MRI measures-visit interaction. Random effects of the model include subject and site information. The Kenward-Roger approximation of the degrees of freedom was used. For volumetric analysis, volume change (% change from baseline) and for myelination analysis, sum of T1w/T2w ratio change (% change from baseline) were assessed for each studied white matter structure. All statistical analyses were conducted using R (R version 4.1.1).

Results

With respect to baseline levels, it was observed that the treatment group demonstrated a 0.17±1.08% increase and the placebo group demonstrated a −2.54±1.38% decrease in total cerebral white matter volume after a 6-month period. The difference between these two groups was statistically significant ($p<0.038$). See FIG. 44.

Figure 44:
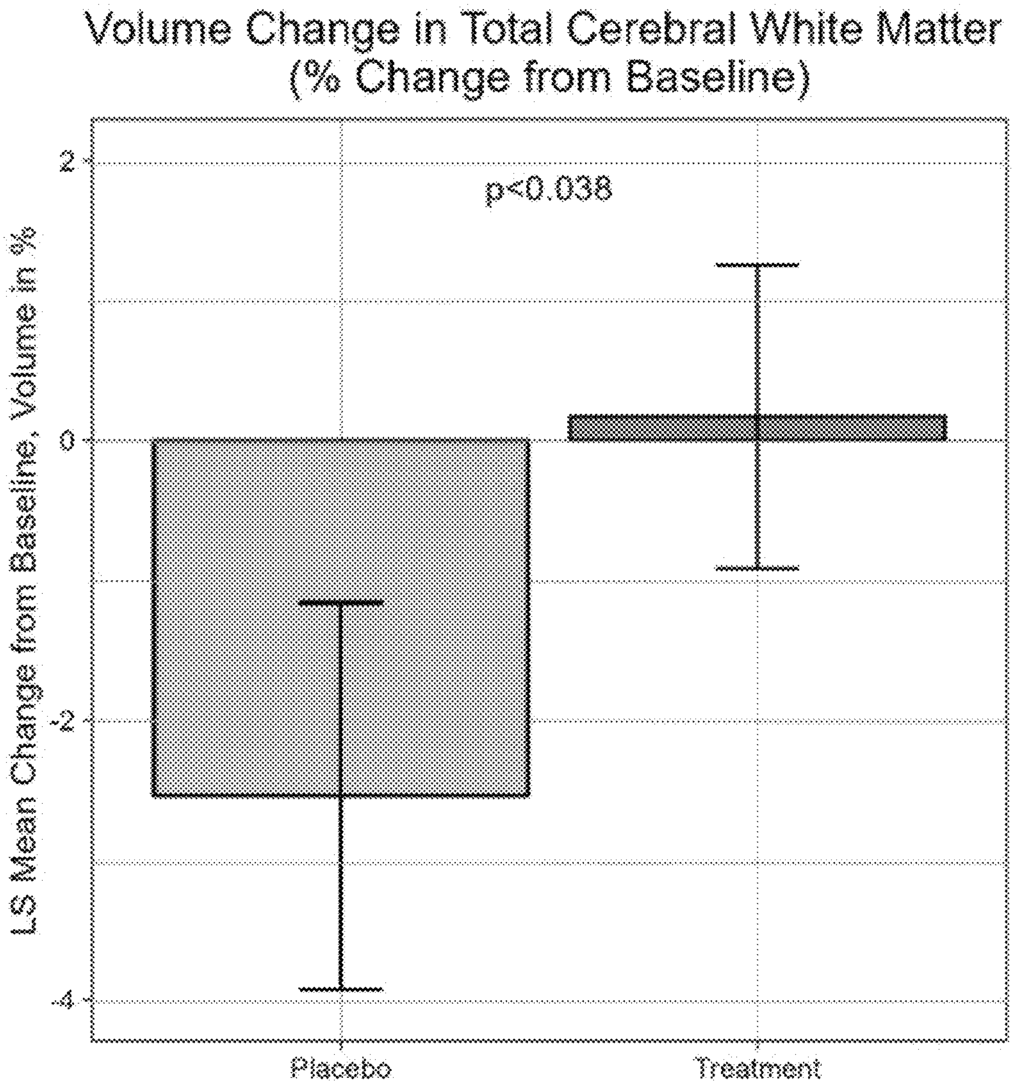
FIG. 44 provides the results on matter volume change from baseline (%) for treatment and control groups who received 40 Hz gamma sensory stimulation therapy and sham sensory stimulation therapy, respectively, for a 6-month period. The dark gray boxes correspond to the Treatment group participants, and the the light gray boxes correspond to the Placebo group participants. Error bars indicate standard error (SE).

FIG. 44 provides white matter volume change from baseline (%) after 40 Hz gamma sensory stimulation therapy for a 6-month period favours the treatment group. LS Mean volume changes for the total cerebral white matter show the significant difference ($p<0.038$) between the Treatment group participants (dark gray) and the Placebo group participants (light gray), favouring the Treatment group. Error bars indicate SE.

Figure 45:
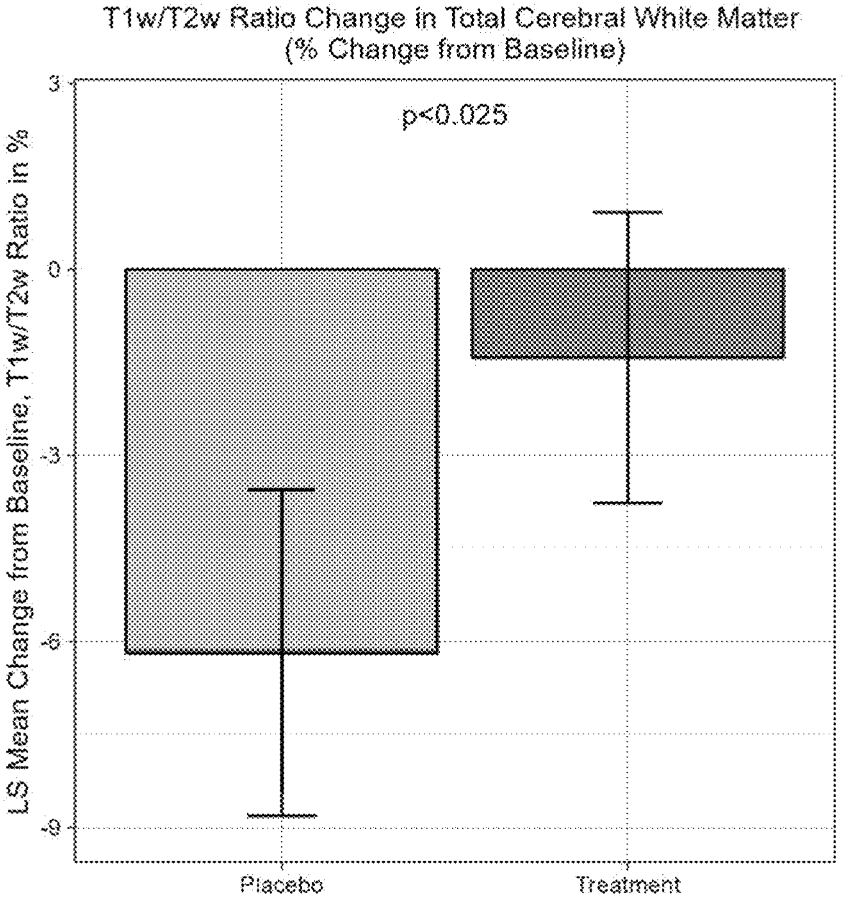
FIG. 45 provides the T1-weighted image to T2-weighted images (T1w/T2w) ratio change in white matter (% change from baseline) for Placebo group participants (light gray) and Treatment group participants (dark gray) after receiving sham and 40 Hz gamma sensory stimulation therapy, respectively, for a 6-month period.

It was also observed that the treatment group demonstrated a-1.42±2.35% decrease and the placebo group demonstrated a −6.19±2.63% decrease in myelination as assessed by summing the ratio of T1 weighted (T1w) and T2 weighted (T2w) intensities across the MRI images. This difference was also statistically significant ($p<0.025$) between groups. See FIG. 45. FIG. 45 provides T1w/T2w ratio change in white matter (% change from baseline) after 40 Hz gamma sensory stimulation therapy for a 6-month period favours the treatment group. LS Mean sum of T1w/T2w ratio changes for the total cerebral white matter show the significant difference ($p<0.025$) between the Treatment group participants (dark gray) and the Placebo group participants (light gray), favouring the Treatment group. Error bars indicate SE.

Figure 46A:
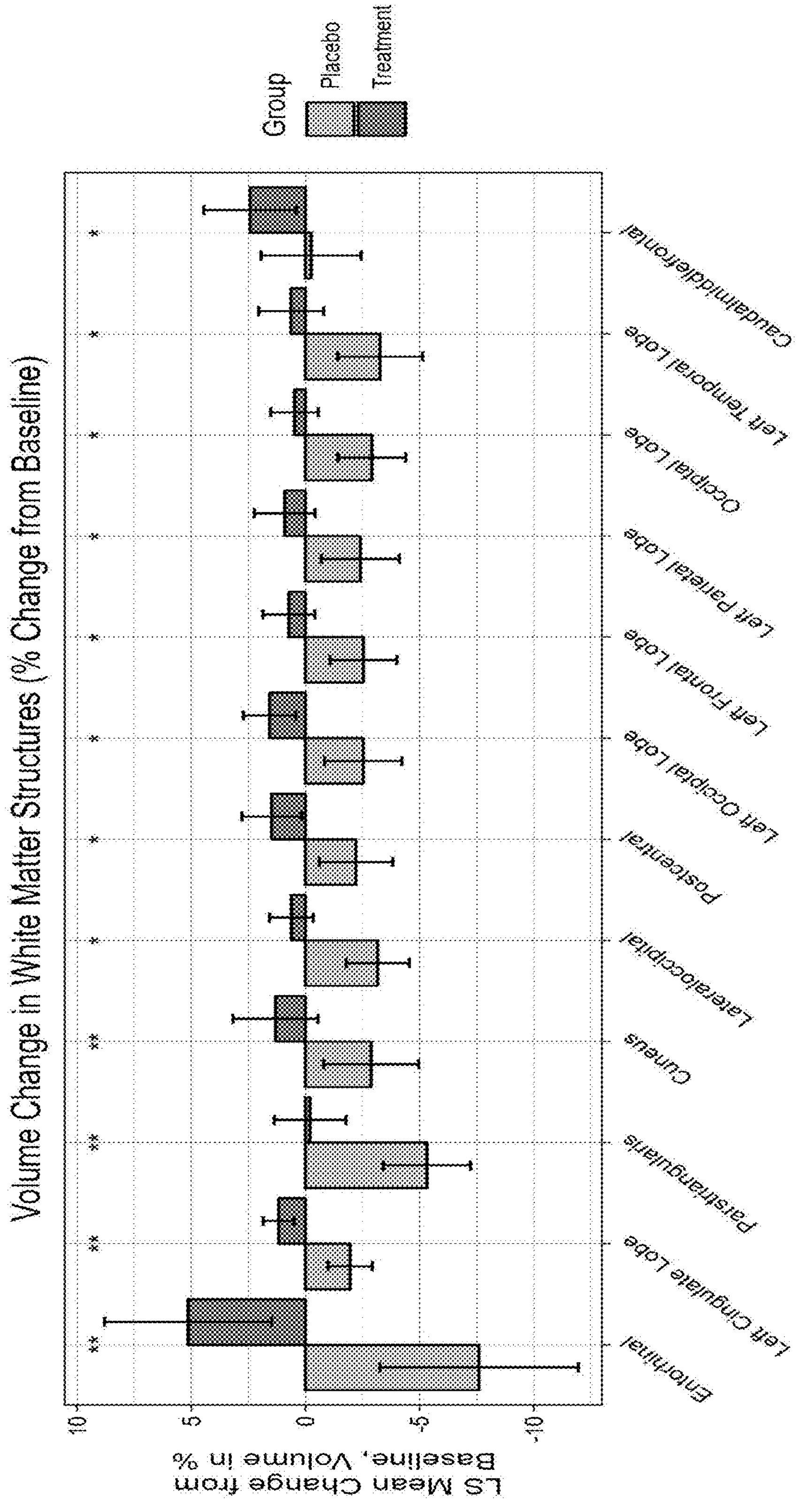
FIGS. 46A and 46B provide measurements of volume change in white matter structures as a percent change relative to baseline. The Treatment group participants are indicated by dark gray and the Placebo group participants' results are indicated in light gray.

Next, the structures that respond to treatment the most, in volume and myelin-reflecting T1w/T2w ratio changes among 52 white matter structures, were examined. All statistically significant changes favored the treatment group. Compared to the placebo group, significant ($p<0.05$) attenuation in volume loss was identified in 12 of 52 structures: the entorhinal region, left cingulate lobe, parstriangularis region, cuneus region, lateral occipital region, postcentral region, left occipital lobe, left frontal lobe, left parietal lobe, occipital lobe, left temporal lobe and caudal middle frontal region (sorted in ascending order by p value) for the treatment group after 6 months of treatment (FIG. 46A). Forty Hz gamma sensory stimulation therapy administered over a 6-month period most significantly reduced white matter atrophy in entorhinal region. The treatment group demonstrated a 5.14±3.66% (0.08±0.06 $cm^3$) increase, while the placebo group demonstrated a −7.60±4.35% (−0.13±0.07 $cm^3$) decrease in volume. The difference between these two groups was statistically significant ($p<0.002$). The treatment also trended in the direction of preventing volume loss ($0.05\leq p<0.1$) in the precentral region, paracentral region, lingual region, fusiform region, frontal lobe, rostral anterior cingulate region, inferior temporal region, right occipital lobe, parietal lobe, rostral middle frontal, precuneus region, medial orbitofrontal region and temporal lobe (sorted in ascending order by p value) (FIG. 46B).

Figure 46B:
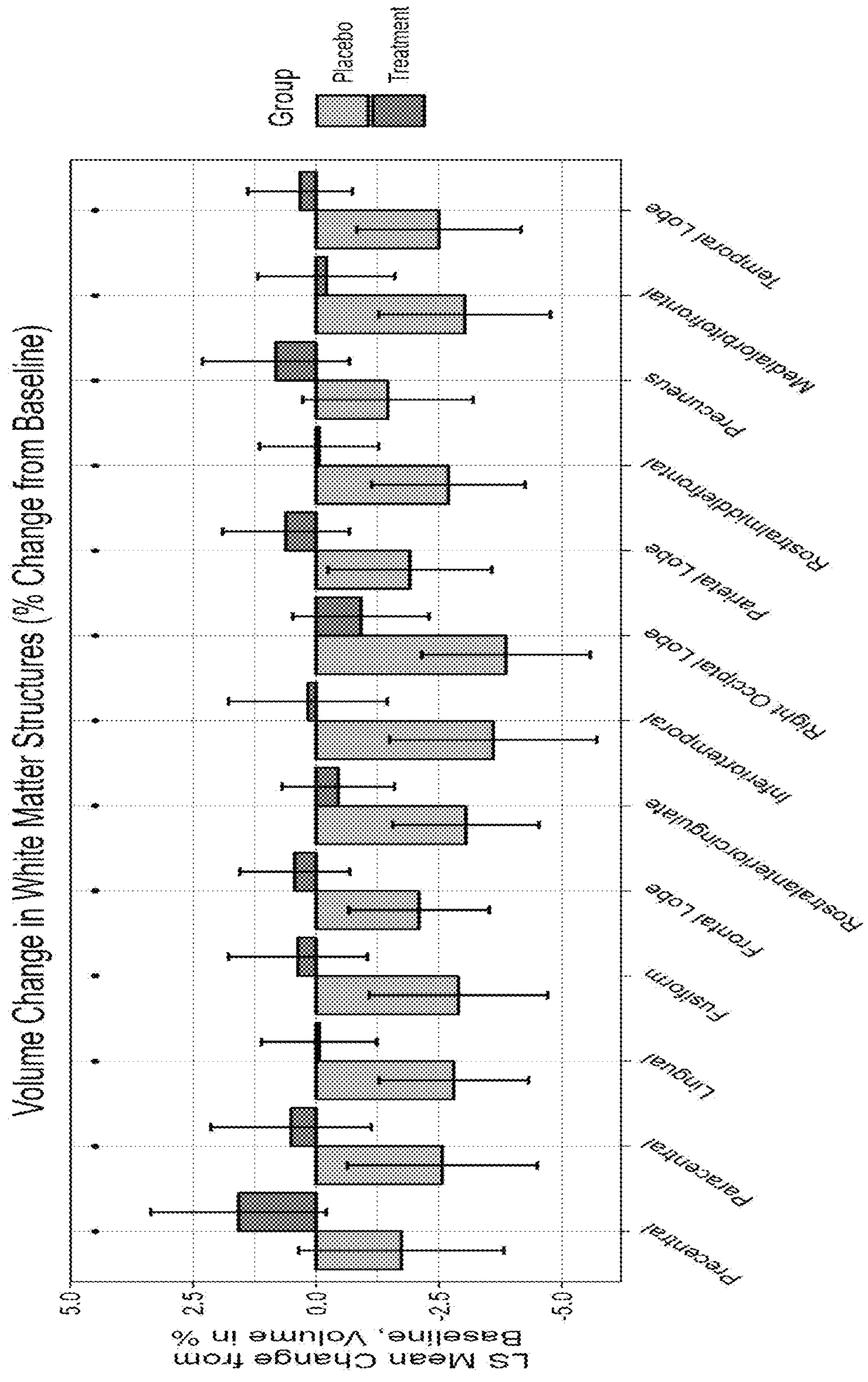

FIG. 46A and FIG. 46B provide white matter structures volume change from baseline (%) after 40 Hz gamma sensory stimulation therapy for a 6-month period favours the treatment group. LS Mean volume changes for the white matter structures (FIG. 46A, sorted in ascending order by p value) show the significant difference ($p<0.05$) between the Treatment group participants (dark gray) and the Placebo group participants (light gray), favouring the treatment group. FIG. 46B (sorted in ascending order by p value) shows LS Mean volume changes for the white matter structures with the marginal difference ($0.05\leq p<0.1$) between the Treatment group participants (dark gray) and the Placebo group participants (light gray), favouring the Treatment group. Error bars indicate SE. * $p<0.05$, ** for $p<0.01$, and · for $0.05<p<0.1$.

Compared to the placebo group, significantly less myelin damage (T1w/T2w ratio) was observed in entorhinal region, parstriangularis region, postcentral region, left parietal lobe, lateral occipital region, paracentral region, rostral middle frontal region, supramarginal region, precentral region, parietal lobe, right occipital lobe, fusiform region, occipital lobe, left frontal lobe, cuneus region, precuneus region, inferior parietal region, frontal lobe, lingual region, left occipital lobe, left temporal lobe, right parietal lobe and parsorbitalis region (FIG. 47A, white matter structures sorted in ascending order by p value), indicating significant differences ($p<0.05$) between the treatment group and the placebo group. Within the 52 studied white matter structures, the most significant myelin-reflecting T1w/T2w ratio change was also in the entorhinal region. The treatment group participants exhibit a +2.78±4.97% increase from baseline on sum of T1w/T2w ratio while the placebo group participants exhibit a −10.59±5.63% decrease from baseline on sum of T1w/T2w ratio ($p<0.003$), suggesting that 40 Hz gamma sensory stimulation therapy for a 6-month period may significantly protect myelin damage in this brain region. The treatment may also trend towards slowing down demyelination ($0.05\leq p<0.1$) in right frontal lobe, caudal middle frontal region, rostral anterior cingulate region, superior frontal region, temporal lobe, medial orbitofrontal region, posterior cingulate region, superior parietal region, left cingulate lobe, superior temporal region, cingulate lobe and temporal pole region (FIG. 47B, white matter structures sorted in ascending order by p value).

Figure 47A:
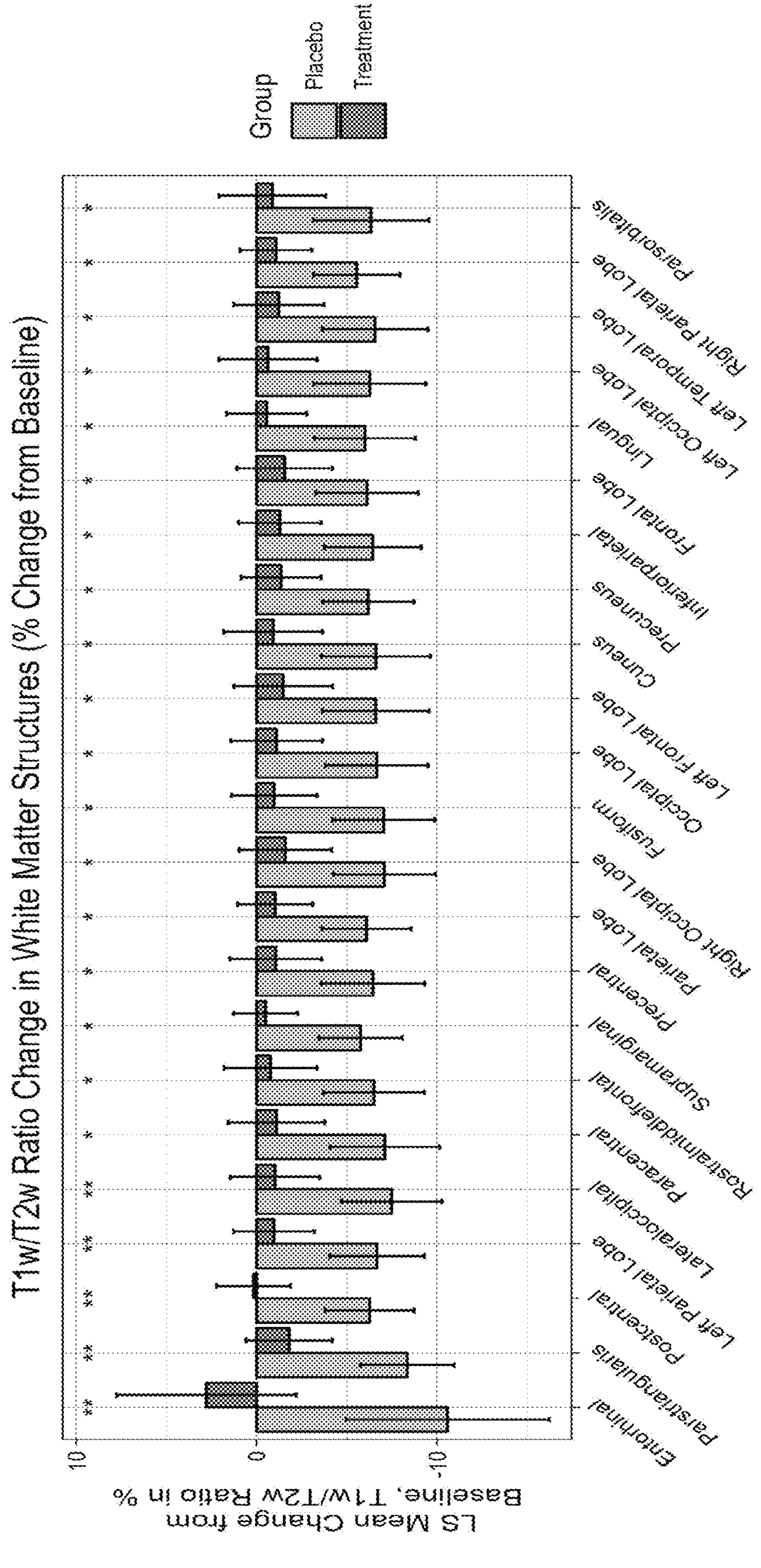
FIGS. 47A and 47B provide the T1w/T2w ratio change in white matter structures (% change from baseline) for Placebo and Treatment group participants after receiving sham and 40 Hz gamma sensory stimulation therapy, respectively, for a 6-month period favours the treatment group.
Figure 47B:
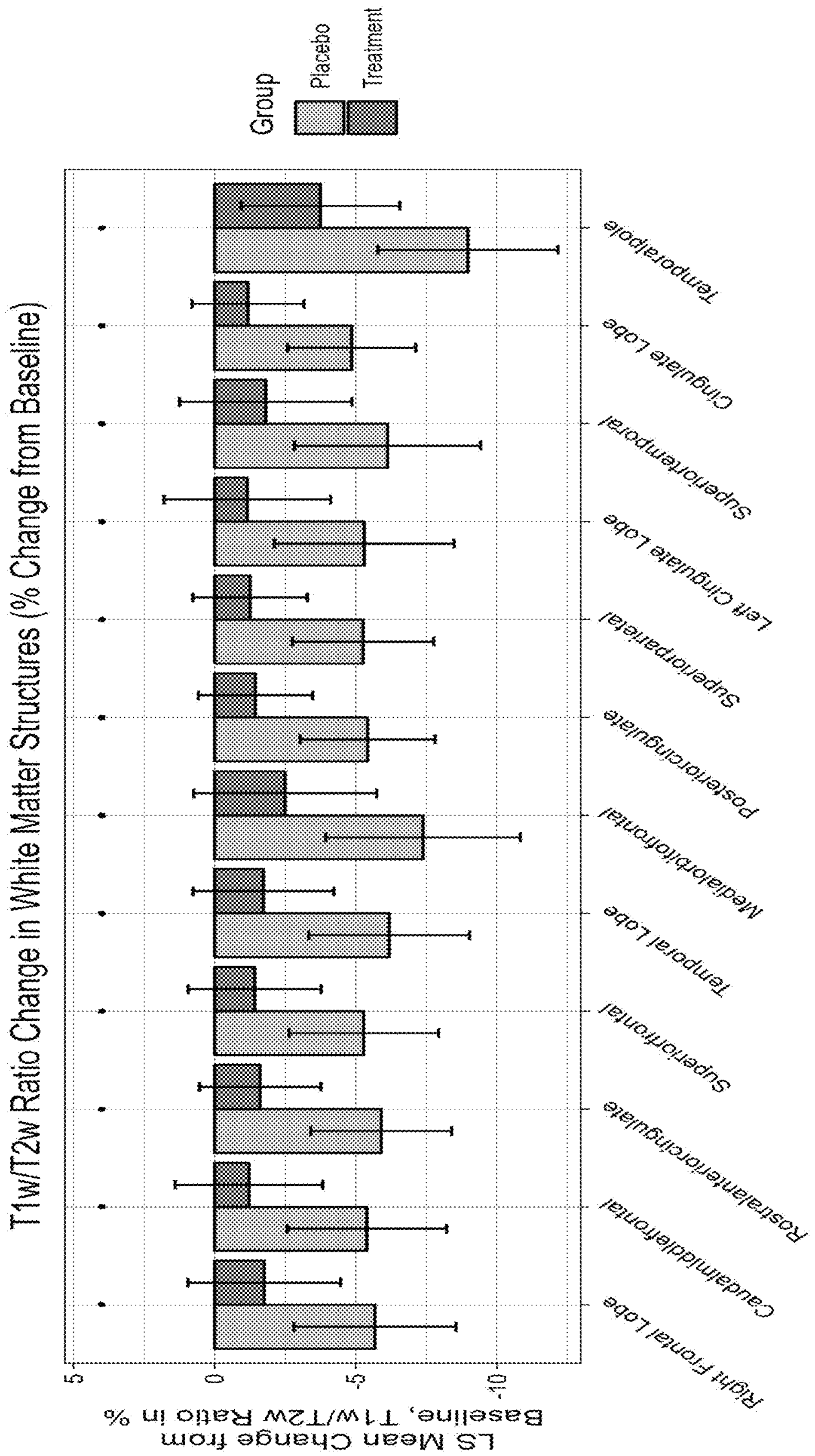

FIGS. 47A and 47B provide T1w/T2w ratio change in white matter structures (% change from baseline) after 40 Hz gamma sensory stimulation therapy for a 6-month period favours the treatment group. LS Mean sum of T1w/T2w ratio changes in the white matter structures (Panel A, sorted in ascending order by p value) shows the significant difference ($p<0.05$) between the Treatment group participants (dark gray) and the Placebo group participants (light gray), favouring the treatment group. Panel B (sorted in ascending order by p value) shows LS Mean sum of T1w/T2w ratio changes in the white matter structures with the marginal difference ($0.05 \leq p < 0.1$) between the Treatment group participants (dark gray) and the Placebo group participants (light gray), favouring the Treatment group. Error bars indicate SE. * $p<0.05$, ** for $p<0.01$, and · for $0.05<p<0.1$.

These results suggest that 40 Hz gamma sensory stimulation therapy for a 6-month period may reduce white matter atrophy and the changes are accompanied by significantly less demyelination in the treatment group compared to placebo group.

Conclusions

Administration of 40 Hz gamma sensory stimulation for a 6-month period led to beneficial effects on total and regional white matter volume along with reduction in myelin damage. Among all white matter structures analyzed, the most significant changes were observed in the entorhinal region: The treatment group demonstrated a 5.14±3.66% increase, while the placebo group demonstrated a −7.60±4.35% decrease in volume. The difference between these two groups was statistically significant ($p<0.002$). The treatment group demonstrated a 2.78+4.97% increase and the placebo group demonstrated a −10.59±5.63% decrease in the myelin-reflecting T1w/T2w measurements. This difference was also statistically significant ($p<0.003$) between groups.

All white matter structures with statistically significant changes were in the treatment group and the most significant change was in the entorhinal region. Given its afferent connections to the hippocampus and the entorhinal cortex, and its relevance in AD pathology, reduction in white matter atrophy and myelin damage in entorhinal region may play an important role to prevent disease progression.

What is claimed is:

1. A method comprising:

(i) identifying a physical activity being performed by a subject; and (ii) administering sensory stimulation to said subject during said physical activity to induce gamma oscillations in a brain region of said subject, wherein said physical activity comprises exposure to water.

2. The method of claim 1, wherein said subject has a disease or disorder associated with white brain matter atrophy, demyelination, or a combination thereof.

3. The method of claim 2, further comprising administering one or more of an active agent to treat said disease or disorder.

4. The method of claim 1, wherein said sensory stimulation comprises mechanical stimulation, auditory stimulation, visual stimulation, or any combination thereof.

5. The method of claim 1, wherein said sensory stimulation comprises a frequency of between 10 and 100 Hertz.

6. The method of claim 1, wherein said method further comprises performing, by said subject, a one or more cognitive processes during said physical activity, wherein said administering said sensory stimulation to said subject causes a change in said one or more cognitive processes.

7. The method of claim 6, wherein said one or more cognitive processes comprises one or more executive functions.

8. The method of claim 7, wherein said one or more executive functions comprises emotional control, cognitive flexibility, goal-directed persistence, metacognition, organization, planning or prioritization, response inhibition, stress tolerance, sustained attention, task initiation, time management, working memory, or any combination thereof.

9. The method of claim 6, wherein said one or more cognitive processes comprise memory encoding, memory consolidation, memory recall, perception, attention, knowledge formation, problem solving, concept formation, pattern recognition, association, decision making, motor coordination, task planning, language expression, language comprehension, or any combination thereof.

10. The method of claim 1, wherein said administering said sensory stimulation comprises slowing neurodegeneration in said subject.

11. The method of claim 1, wherein said administering said sensory stimulation causes a change in a behavior of said subject, wherein said behavior comprises neurotic behavior, anxious behavior, depressive behavior, addictive behavior, food-seeking behavior, sleeping behavior, or any combination thereof.

12. The method of claim 1, wherein said administering comprises improving a cognitive skill.

13. The method of claim 12, wherein said cognitive skill comprises: perceptual reasoning, sustained attention, selective attention, divided attention, long-term memory, working memory, logic and reasoning, auditory processing, visual processing, visual-motor planning and processing, visual spatial planning and processing, auditory memory, visual memory, task planning, task sequencing, task initiation, task completion, visual encoding and decoding, auditory encoding and decoding, sensory encoding and decoding, language expression, language comprehension, processing speed, cognitive control, cognitive inhibition, declarative memory, procedural memory, episodic memory, auditory memory, visual memory, semantic memory, or autobiographical memory, or any combination thereof.

14. The method of claim 12, wherein said cognitive skill comprises visual processing speed, language processing speed, auditory processing speed, motor processing speed, or any combination thereof.

15. The method of claim 1, wherein said method further comprises:

(i) identifying an additional activity being performed by said subject; and (ii) administering said sensory stimulation to said subject during said additional activity to induce gamma oscillations in said brain region of said subject, wherein said additional activity comprises meditating, sleeping, reading, consuming a substance, or any combination thereof.

16. The method of claim 15, wherein said substance comprises a stimulant or a depressant.

17. The method of claim 1, wherein said physical activity comprises bathing.

18. The method of claim 1, wherein said physical activity comprises showering.

19. The method of claim 1, wherein administering said sensory stimulation comprises turning on a source of water, said source of water capable of causing water pressure to fluctuate, thereby administering said sensory stimulation to said subject during said physical activity.

20. The method of claim 1, wherein said physical activity comprises bathing or showering.

* * * * *